United States Patent
Dickson, Jr. et al.

(10) Patent No.: US 7,410,988 B2
(45) Date of Patent: Aug. 12, 2008

(54) 2-AMIDO-THIAZOLE-BASED COMPOUNDS EXHIBITING ATP-UTILIZING ENZYME INHIBITORY ACTIVITY, AND COMPOSITIONS, AND USES THEREOF

(75) Inventors: John K. Dickson, Jr., Apex, NC (US); Carl Nicholas Hodge, Los Gatos, CA (US); Jose Serafin Mendoza, Chapel Hill, NC (US); Ke Chen, Chapel Hill, NC (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 11/202,927

(22) Filed: Aug. 11, 2005

(65) Prior Publication Data

US 2006/0052416 A1 Mar. 9, 2006

Related U.S. Application Data

(60) Provisional application No. 60/608,834, filed on Sep. 10, 2004, provisional application No. 60/601,266, filed on Aug. 13, 2004.

(51) Int. Cl.
*A61K 31/426* (2006.01)
*C07D 277/28* (2006.01)

(52) U.S. Cl. ..................... 514/371; 548/195
(58) Field of Classification Search ................ 548/195, 548/240; 514/371
See application file for complete search history.

(56) References Cited

U.S. PATENT DOCUMENTS

| | | | |
|---|---|---|---|
| 5,189,049 A | 2/1993 | Frehel et al. | |
| 5,314,889 A | 5/1994 | Boigegrain et al. | |
| 5,380,736 A | 1/1995 | Boigegrain et al. | |
| 5,670,534 A | 9/1997 | Animati et al. | |
| 5,741,796 A | 4/1998 | Hartman et al. | |
| 6,114,365 A | 9/2000 | Pevarello et al. | |
| 6,242,196 B1 | 6/2001 | Spiegelman et al. | |
| 6,596,746 B1 | 7/2003 | Das et al. | |
| 6,696,567 B2 | 2/2004 | Blumenkopf et al. | |
| 2004/0053973 A1 | 3/2004 | Ohkawa et al. | |
| 2004/0063946 A1 | 4/2004 | Ohkawa et al. | |
| 2004/0110797 A1 | 6/2004 | Munchhof et al. | |
| 2004/0122016 A1* | 6/2004 | Cao et al. | 514/252.05 |
| 2005/0065198 A1 | 3/2005 | Weinstein | |
| 2007/0281919 A1 | 6/2007 | Fontaine et al. | |

FOREIGN PATENT DOCUMENTS

| | | |
|---|---|---|
| EP | 154190 | 2/1985 |
| EP | 1364949 A1 | 11/2003 |
| JP | 07-149745 | 6/1995 |
| JP | 09-235278 | 9/1997 |
| JP | 10-287634 | 10/1998 |
| JP | 2002-053566 | 2/2002 |
| JP | 2003-053566 | 2/2003 |
| WO | WO 96/16650 | 6/1996 |
| WO | WO 97/24119 | 7/1997 |
| WO | WO 00/62778 | 10/2000 |
| WO | WO 01/10865 A1 | 2/2001 |
| WO | WO 01/23382 A1 | 4/2001 |
| WO | WO 01/46165 A2 | 6/2001 |
| WO | WO 01/74811 A2 | 10/2001 |
| WO | WO01/81298 | 11/2001 |
| WO | WO 02/100433 A1 | 12/2002 |
| WO | WO 02/101007 A2 | 12/2002 |
| WO | WO 03/007945 A1 | 1/2003 |
| WO | WO 03/048140 A1 | 6/2003 |
| WO | WO 03/050090 A1 | 6/2003 |
| WO | WO 03/062215 A1 | 7/2003 |
| WO | WO 03/066630 A2 | 8/2003 |
| WO | WO 2004/002481 A1 | 1/2004 |
| WO | WO 2004/013141 A1 | 2/2004 |
| WO | WO2004/033439 A1 | 4/2004 |
| WO | WO 2004/037250 A1 | 5/2004 |
| WO | WO 2004/041813 A1 | 5/2004 |
| WO | WO 2004041813 A1 * | 5/2004 |
| WO | WO2004/058255 A1 | 7/2004 |
| WO | WO 2004/071447 A2 | 8/2004 |
| WO | WO 2005040161 A1 * | 5/2005 |

OTHER PUBLICATIONS

Patani et al. "Bioisosterism: A Rational Approach to Drug Design" Chemical Reviews, 1996, vol. 96, pp. 3147-3176.*
Foster, J. Estelle et al., "Kinetic and mechanistic analyses of new classes of inhibitors of two-component signal transduction systems using a coupled assay containing HpkA-DrrA from Thermotoga maritima," Microbiology (2004) 150: 885-896.
Miwatashi, Seiji et al., "Synthesis and Biological Activities of 4-Phenyl-5-pyridyl-1,3-thiazole Derivatives as p38 MAP Kinase Inhibitors," Chem. Pharm. Bull. (2005) 53(4): 410-418.
International Search Report and Written Opinion mailed Jun. 8, 2006, in counterpart PCT Application No. PCT/US05/28549.
Sasho, S. et al., "Preparation and Formulation of Thiazole Derivatives as Cell Adhesion Inhibitors" *Database WPI Week* Abstract AN 1997-255535 (JP 09087282)), London:Derwent Publications Ltd.199723 (Mar. 31, 1997).

* cited by examiner

*Primary Examiner*—Kamal Saeed
*Assistant Examiner*—Joseph R. Kosack
(74) *Attorney, Agent, or Firm*—Christopher J. Walsh

(57) ABSTRACT

2-Amido-4-substituted-aryl-thiazole-based compounds exhibiting ATP-utilizing enzyme inhibitory activity, methods of using compounds exhibiting ATP-utilizing enzyme inhibitory activity, and compositions comprising compounds exhibiting ATP-utilizing enzyme inhibitory activity, are disclosed.

25 Claims, No Drawings

2-AMIDO-THIAZOLE-BASED COMPOUNDS EXHIBITING ATP-UTILIZING ENZYME INHIBITORY ACTIVITY, AND COMPOSITIONS, AND USES THEREOF

This application claims the benefit of U.S. Provisional Patent Application No. 60/608,834, filed Sep. 10, 2004; and of U.S. Provisional Patent Application No. 60/601,266, filed Aug. 13, 2004. Each of those applications is incorporated herein by reference for all purposes.

ATP-utilizing enzymes catalyze the transfer of a phosphate group from an adenosine triphosphate (ATP) molecule to a biomolecule such as a protein or carbohydrate. Examples of ATP-utilizing enzymes include, but are not limited to, synthetases, ligases, and kinases.

Protein kinases encompass a large family of functionally and structurally related enzymes that are responsible for the control of a wide variety of cellular processes including signal transduction, metabolism, transcription, cell cycle progression, cytoskeletal rearrangement and cell movement, apoptosis, and differentiation. In general, protein kinases control protein activity by catalyzing the addition of a negatively charged phosphate group from a phosphate-containing molecule such as cyclic adenosine monophosphate (cAMP), adenosine diphosphate (ADP), and ATP, to other proteins. Protein phosphorylation in turn can modulate or regulate the functioning of a target protein. Protein phosphorylation is known to play a role in intercellular communication during development, in physiological responses and in homeostasis, and in the functioning of the nervous and immune systems.

The unregulated phosphorylation of proteins is known to be a cause of, or associated with the etiology of major diseases, such as Alzheimer's disease, stroke, diabetes, obesity, inflammation, cancer, and rheumatoid arthritis. Deregulated protein kinase activity and over-expression of protein kinases has been implicated in the pathophysiology of a number of important human disorders. Furthermore, genetic mutations in protein kinases are implicated in a number of disorders and many toxins and pathogens exert their effects by altering the phosphorylation of intracellular proteins.

ATP-utilizing enzymes, such as protein kinases, therefore, represent a broad class of pharmacological targets of interest for the treatment of human disease. The identification and development of compounds that selectively inhibit the functioning of ATP-utilizing enzymes is therefore of considerable interest.

AKT/protein kinase B (PKB) is a pivotal kinase in the phosphatidylinositol 3'-OH kinase (PI3K)/AKT pathway that regulates cell survival and apoptosis, or programmed cell death (Kauffmann-Zeh et al., Nature 385:544-548 (1997); Hemmings, Science, 275:628-630 (1997); Dudek et al., Science 275:661-665 (1997)). The PI3K/AKT pathway is activated by numerous factors, including growth factors such as platelet-derived growth factor and insulin-like growth factor-1, and this activation involves the induction of PI3K activity to increase the levels of its product phosphatidylinositol (3,4,5)-triphosphate (PIP3) and the subsequent recruitment of AKT to the PIP3-enriched membrane via its plekstrin homology (PH) domain (Hemmings Science, 277:534 (1997). AKT is subsequently activated via phosphorylation, and the two regulatory sites are Thr308 and Ser473. The tumor suppressor PTEN is a protein and lipid phosphatase that negatively regulates the PI3K/AKT pathway by removing the 3'phosphate of PIP3. There are three isoforms of AKT, AKT1 (PKB alpha), AKT2 (PKB beta) and AKT3(PKB gamma).

Numerous lines of evidence has linked the PI3K/AKT pathway to human diseases, particularly cancer (Vivanco and Sawyers, Nature Rev. Cancer 2:489-501 (2002); Luo et al., Cancer Cell 4:257-262 (2003); Vivanco and Sawyer, 2002 Nature Rev. Drug Disc. 2, 489-501; Bellacosa et al., Canc. Biol. Therapy, 3, 268-275 (2004)). AKTs are differentially overexpressed in a number of human tumors (Sun et al., Am. J. Pathol. 159:431-437 (2001); Yuan et al., Oncogene 19:2324-2330 (2000); Nakatani et al., J. Biol. Chem. 274: 21528-21532 (1999)) and AKT1 and AKT2 have been shown to be amplified in several cancer types (Staal, Proc. Natl. Acad. Sci. USA 84:5034-5037 (1987); Nicholsen and Anderson, Cell. Signaling 14,381-395 (2002)). Further, AKT activation in human cancers has been demonstrated to occur by other means, including mutation of the tumor suppressor PTEN (Di Cristofano and Pandolfi, Cell 100:387-390 (2000); Sun et al., Proc. Natl. Acad. Sci. USA 96:6199-6204 (1999)). One consequence of PTEN loss is hyperactivation of AKT and phosphorylation of downstream AKT substrates, including BAD, FOXO proteins and GSK3. Deletion of AKT1 has been shown to reverse the aggressive growth phenotype of PTEN null mouse embryonic stem cells (Stiles et al., Mol. Cell. Biol. 22:3842-3851 (2002) Loss-of function mutations in the PTEN gene are extremely common among sporadic glioblastomas, melanoma, prostate cancers and endometrial carcinomas, and a significant percentage of breast tumors, lung cancers, and lymphomas have PTEN mutations (Cantley and Neel, Proc. Natl. Acad Sci. USA 96,4240-4245 (1999); Luo et al. Cancer Cell, 4, 257-262 (2003)). Mutations of PIK3CA which encodes p110α catalytic subunit of class 1A PI3Ks results in activating mutations of PI3K (Samuels et al., Cancer Cell 7:561-573 (2005)). PIK3CA appears to be one of the most highly mutated oncogenes, with somatic mutations seen in colorectal, gastric, breast, and certain brain tumors (Samuels et al., Cancer Cell 7,561-573 (2005) and references therein). Together, these data indicate that AKTs play a key role in tumor biology and that the three AKT isoforms may serve different functions; therefore, selective inhibition of one or more AKT isoenzyme may be a productive approach to cancer therapeutics.

Blocking of the PI3K/AKT pathway could inhibit the proliferation of tumor cells and sensitize them toward apoptosis. The resistance of many types of cancer to conventional chemotherapies is a major factor undermining successful cancer treatment, and targeting the PI3K/AKT pathway for inhibition is being investigated as a strategy to overcome chemotherapeutic resistance (McCormick, Nature, 428, 267-269 (2004); Bellacosa et al., Canc. Biol. Therapy, 3, 268-275 (2004); West et al., Drug Resistance Update 5, 234-248 (2002); Bianco et al., Oncogene 22, 2812-2822 (2003)). Therefore, conventional targeted and cytotoxic anti-proliferative and targeted anti-angiogenic therapeutics would complement the pro-apoptotic mechanism of an AKT inhibitor.

A number of cancers are associated with activation of the PI3K/AKT pathway, including, but not limited to, glioblastoma, ovarian, breast, endometrial, hepatocellular carcinoma, melanoma, digestive tract, lung, renal-cell carcinoma, thyroid, lymphoid, prostate and pancreatic cancer (Vivanco and Sawyer, Nature Rev. Drug Disc., 2, 489-501 (2002); Graff, Expert Opin. Ther. Targets, 6, 103-113 (2002); Bondar et al., Mol. Canc. Therapies 1, 989-997 (2002)).

Inappropriate activation of the phosphatidylinositol 3-kinase (PI3K)/AKT pathway has also been associated with the development of diseases such as diabetes and autoimmunity.

The PI3K/AKT pathway also functions in the growth and survival of normal tissues and may be regulated during normal physiology to control cell and tissue function. Thus the undesirable proliferation and survival of normal cells and tissues may result in a number of disorders, such as disorders of immune cells associated with prolonged expansion and survival of cell population leading to prolonged or up regulated immune response. For example, T and B lymphocytes response to cognate antigens or growth factors such as Il-2 activates the PI3K/AKT pathway and is responsible for maintaining the survival of the antigen specific lymphocyte clones during the immune response. Under conditions in which lymphocytes and other immune cells are responding to inappropriate self or foreign antigens, or in which other abnormalities lead to prolonged activation, the PI3K/AKT pathway contributes an important survival signal preventing normal mechanism by which the immune response is terminated via apoptosis of the activated cell population. There is a considerable amount of evidence demonstrating the expansion of lymphocyte populations responding to self antigens in autoimmune conditions such as multiple sclerosis and arthritis. Expansion of lymphocyte populations responding to inappropriately to foreign antigens is a feature of another set of conditions such as allergic response and asthma.

Other examples of inappropriate expansion, growth, proliferation, hyperplasi and survival of normal cells in which the PI3K/AKT pathway may play a role include, but are not limited to, atherosclerosis, cardiac myopathy and glomerulonephritis.

In addition to the role in cell growth and survival, the PI3K/AKT pathway functions in the control of glucose metabolism by insulin. As a consequence, modulators of PI3K/AKT activity may also find utility in disease in which there is a dysfunction of glucose metabolism and energy storage such as diabetes, metabolic disease and obesity.

AKT was first identified as a viral oncogene (Bellacosa et al. 1991 Science 254, 274-277). A number of studies have demonstrated the role of PI3K/AKT pathway in the life cycle of numerous viruses. Some viral proteins have been shown to activate the PI3K/AKT pathway, thus providing an environment favorable for viral replication. These include the Tat protein of HIV (Borgatti et al. 1997, Eur. J. immunol. 27,2805-2811), protein X of hepatitis B virus (Lee et al. 2001 J. Biol. Chem. 276,16969-16977), NS5A of hepatitis C virus (He et al. 2002 J. Virol. 76,9207-9217), human cyctomegalovirus (Johnson et al. 2001 J. Virol. 75,6022-6032), and Epstein-Barr virus (Moody et al. 2005 J. Virol. 79,5499-5506).

ATP-utilizing enzymes, such as protein kinases, therefore, represent a broad class of pharmacological targets of interest for the treatment of human disease. The identification and development of compounds that selectively inhibit the functioning of ATP-utilizing enzymes is therefore of considerable interest.

Provided is at least one chemical entity chosen from compounds of Formula I:

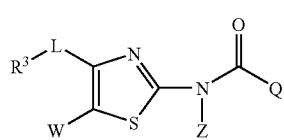

(Formula I)

and pharmaceutically acceptable salts, solvates, chelates, non-covalent complexes, prodrugs, and mixtures thereof, wherein $R^3$ is chosen from hydroxy, alkoxy, amino, substituted amino, and Ar;

Ar is chosen from cycloalkyl, substituted cycloalkyl, aryl, substituted aryl, heteroaryl, and substituted heteroaryl;

L is chosen from $C_0$-$C_4$alkylene, substituted $C_1$-$C_4$alkylene, —($C_0$-$C_4$alkylene)-NH—(C=O)—; and —($C_0$-$C_4$alkylene)(C=O)—;

W is chosen from hydrogen, halo, alkyl, substituted alkyl, cycloalkyl, substituted cycloalkyl, heterocycloalkyl, substituted heterocycloalkyl, aryl, substituted aryl, heteroaryl, and substituted heteroaryl;

Q is chosen from alkyl, substituted alkyl, cycloalkyl, substituted cycloalkyl, cycloheteroalkyl, substituted cycloheteroalkyl, aryl, substituted aryl, heteroaryl, and substituted heteroaryl; and Z is chosen from alkyl, and substituted alkyl, with the provisos that when Q is optionally substituted pyridin-3-yl, L is a covalent bond, W is 3-methylphenyl, $R^3$ is optionally substituted pyridin-4-yl, then Z is not methyl;

when Ar is pyridin-4-yl, W is hydrogen, and Q is chosen from benzyl, substituted benzyl, phenethyl, and substituted phenethyl, then Z is not chosen from lower alkyl and substituted lower alkyl;

when Ar is 2-oxo-(3-hydroquinolyl), W is hydrogen, Z is methyl, then Q is not phenyl;

when W is chosen from 2-(cyclohexylamino)pyridin-4-yl and 2-(cyclopentylamino)pyridin-4-yl, Ar is 3-methylphenyl, Z is methyl, then Q is not pyridin-3-yl or 6-methylpyridin-3-yl;

Ar is not substituted pyridone or benzoyloxypyridine;

when either $R^1$ or $R^2$ is hydrogen, then Ar is not 4-pivaloyloxyphenyl;

Q is not a heteroaryl, substituted heteroaryl, heterocycloalkyl or substituted heterocycloalkyl comprising one or more heteroatoms chosen from S and N, fused with an aryl, substituted aryl, heteroaryl, or substituted heteroaryl ring;

when Z is lower alkyl or 3-morpholinopropyl, then Ar is not phenyl, 4-methoxyphenyl, or 2,5-dimethoxyphenyl;

when Ar is pyridinyl, L is a covalent bond, Z is hydrogen or methyl, and W is phenyl substituted with one methoxy, methyl, chloro, fluoro, chloroor t-butyl, then Q is not methyl; and when Ar is 4-t-butylphenyl, L is a covalent bond, Z is propyl and Q is 1-cyano-2-hydroxy-prop-1-enyl, then W is not hydrogen.

Also provided is a pharmaceutical composition comprising at least one pharmaceutically acceptable vehicle, and a therapeutically effective amount of at least one chemical entity of the present disclosure.

Also provided is a packaged pharmaceutical formulation comprising a pharmaceutical composition comprising at least one pharmaceutically acceptable vehicle and a therapeutically effective amount of at least one chemical entity of the present disclosure; and instructions for using the composition to treat a mammal.

Also provided is a method of treating at least one disease in a patient in need of such treatment comprising administering to the patient a therapeutically effective amount of at least one chemical entity of the present disclosure.

Additional embodiments of the invention are set forth in the description which follows, or may be learned by practice of the invention.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements. At the very least, and not as an attempt to limit the application of the doctrine of equivalents to the scope of the claims, each numerical parameter as set forth in the claims should at least be construed in light of the number of reported significant digits and by applying ordinary rounding techniques.

"Acyl" refers to a radical —C(O)R, where R is hydrogen, alkyl, substituted alkyl, substituted cycloalkyl, substituted heterocycloalkyl, substituted aryl, or substituted heteroaryl group as defined herein. Representative examples include, but are not limited to, formyl, acetyl, cylcohexylcarbonyl, cyclohexylmethylcarbonyl, benzoyl, benzylcarbonyl, and the like.

"Alkanyl" refers to a saturated branched, straight-chain or cyclic alkyl group derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl; butanyls such as butan-1-yl, butan-2-yl (sec-butyl), 2-methyl-propan-1-yl (isobutyl), 2-methyl-propan-2-yl (t-butyl), cyclobutan-1-yl; and the like.

"Alkenyl" refers to an unsaturated branched, straight-chain or cyclic alkyl group having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. In certain embodiments, an alkenyl group has from 2 to 20 carbon atoms and in other embodiments, from 2 to 6 carbon atoms.

"Alkoxy" refers to a radical —OR where R represents an alkyl, substituted alkyl, substituted cycloalkyl, substituted heterocycloalkyl, substituted aryl, or substituted heteroaryl group as defined herein. Representative examples include, but are not limited to, methoxy, ethoxy, propoxy, butoxy, cyclohexyloxy, and the like.

"Alkoxycarbonyl" refers to a radical —C(O)— alkoxy where alkoxy is as defined herein.

"Alkyl" refers to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl; and the like.

The term "alkyl" is specifically intended to include groups having any degree or level of saturation, i.e., groups having exclusively single carbon-carbon bonds, groups having one or more double carbon-carbon bonds and groups having mixtures of single, double and triple carbon-carbon bonds. Where a specific level of saturation is intended, the expressions "alkanyl," "alkenyl," and "alkynyl" are used. In certain embodiments, an alkyl group comprises from 1 to 20 carbon atoms. In other embodiments, an alkyl group comprises from 1 to 6 carbon atoms, and is referred to as a lower alkyl group.

The term "substituted amino" refers to the group —NHR$^d$ or —NR$^d$R$^d$ where each R$^d$ is independently chosen from: alkyl, substituted alkyl, cycloalkyl, substituted cycloalkyl, acyl, substituted acyl, aryl, substituted aryl, heteroaryl, substituted heteroaryl, heterocycloalkyl, substituted heterocycloalkyl, alkoxycarbonyl, and sulfonyl. Representative examples include, but are not limited to, dimethylamino, methylethylamino, di-(1-methylethyl)amino, (cyclohexyl)(methyl)amino, (cyclohexyl)(ethyl)amino, (cyclohexyl)(propyl)amino, and the like.

"Sulfonyl" refers to a radical —S(O)$_2$R where R is an alkyl, substituted alkyl, substituted cycloalkyl, substituted heterocycloalkyl, substituted aryl, or substituted heteroaryl group as defined herein. Representative examples include, but are not limited to methylsulfonyl, ethylsulfonyl, propylsulfonyl, butylsulfonyl, and the like.

"Sulfinyl" refers to a radical —S(O)R where R is an alkyl, substituted alkyl, substituted cycloalkyl, substituted heterocycloalkyl, substituted aryl, or substituted heteroaryl group as defined herein. Representative examples include, but are not limited to, methylsulfinyl, ethylsulfinyl, propylsulfinyl, butylsulfinyl, and the like.

"Sulfanyl" refers to a radical —SR where R is an alkyl, substituted alkyl, substituted cycloalkyl, substituted heterocycloalkyl, substituted aryl, or substituted heteroaryl group as defined herein. Representative examples include, but are not limited to, methylthio, ethylthio, propylthio, butylthio, and the like.

"Alkynyl" refers to an unsaturated branched, straight-chain or cyclic alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms.

"Amino" refers to the radical —NH$_2$.

"Aminocarbonyl" refers to the group —C(O)NRR' where R and R' are independently chosen from hydrogen, alkyl, substituted alkyl, substituted cycloalkyl, substituted heterocycloalkyl, substituted aryl, or substituted heteroaryl group as defined herein, or optionally R' and R" together with the nitrogen atom to which R and R' are attached form one or more heterocyclic or substituted heterocyclic rings.

"Aryl" encompasses:
5- and 6-membered carbocyclic aromatic rings, for example, benzene;
bicyclic ring systems wherein at least one ring is carbocyclic and aromatic, for example, naphthalene, indane, and tetralin; and
tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

"Arylalkyl" or "aralkyl" refers to an acyclic alkyl group in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl, and/or arylalkynyl is used. In certain embodiments, an arylalkyl group can be $(C_{6-30})$ arylalkyl, e.g., the alkanyl, alkenyl or alkynyl moiety of the arylalkyl group can be $(C_{1-10})$ and the aryl moiety can be $(C_{6-20})$.

"Aryloxycarbonyl" refers to a radical —C(O)—O—R wherein R is chosen from aryl and substituted aryl as defined herein.

"Carbonyl" refers to the radical —C(O).

"Carboxy" refers to the radical —C(O)OH.

"Cleave" refers to breakage of chemical bonds and is not limited to chemical or enzymatic reactions or mechanisms unless clearly indicated by the context.

When the chemical structure and chemical name conflict, the chemical structure is determinative of the identity of the compound. The chemical entities of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

Compounds of Formula I include, but are not limited to optical isomers of compounds of Formula I, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula I include Z- and E-forms (or cis- and trans-forms) of compounds with double bonds. Where compounds of Formula I exists in various tautomeric forms, chemical entities of the present disclosure include all tautomeric forms of the compound.

Chemical entities of the present disclosure include, but are not limited to compounds of Formula 1 and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. Hence, the terms "chemical entity" and "chemical entities" also encompass pharmaceutically acceptable salts, solvates, chelates, non-covalent complexes, prodrugs, and mixtures.

The term "chelate" refers to the chemical entity formed by the coordination of a compound to a metal ion at two (or more) points.

The term "non-covalent complex" refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

As noted above, prodrugs also fall within the scope of chemical entities, for example ester or amide derivatives of the compounds of Formula I. The term "prodrugs" includes any compounds that become compounds of Formula I when administered to a patient, e.g., upon metabolic processing of the prodrug. Examples of prodrugs include, but are not limited to, acetate, formate, and benzoate and like derivatives of functional groups (such as alcohol or amine groups) in the compounds of Formula I.

The term "solvate" refers to the compound formed by the interaction of a solvent and a compound. Suitable solvates are pharmaceutically acceptable solvates, such as hydrates, including monohydrates and hemi-hydrates.

"Bond" refers to a covalent attachment between two atoms.

"Cyano" refers to the radical —CN.

"Cycloalkyl" refers to a saturated or unsaturated (although not aromatic) cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In certain embodiments, the cycloalkyl group can be $C_{3-10}$ cycloalkyl, such as, for example, $C_{3-6}$ cycloalkyl.

"Disease" refers to any disease, disorder, condition, symptom, or indication.

"Enzyme" refers to any naturally occurring or synthetic macromolecular substance composed wholly or largely of protein, that catalyzes, more or less specifically, one or more biochemical reactions. The substances upon which the enzyme acts are referred to "substrates," for which the enzyme possesses a specific binding or "active site," or "catalytic domain." Enzymes can also act on macromolecular structures such as muscle fibers.

"Extended release" refers to dosage forms that provide for the delayed, slowed, over a period of time, continuous, discontinuous, or sustained release of the chemical entities of the present disclosure.

"Halogen" or "halo" refers to a fluoro, chloro, bromo, or iodo group.

"Heteroaryl" encompasses:
5- to 7-membered aromatic, monocyclic rings containing one or more, for example, from 1 to 4, or in certain embodiments, from 1 to 3, heteroatoms chosen from N, O, and S, with the remaining ring atoms being carbon; and
bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heterocycloalkyl aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above. In certain embodiments, heteroaryl groups can be those derived from thiophene, pyrrole, benzothiophene, benzofuran, indole, pyridine, quinoline, imidazole, oxazole, pyrazine, benzothiazole, isoxazole, thiadiaxole, and thiazole.

"Heteroarylalkyl" or "heteroaralkyl" refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl, and/or heteroarylalkynyl is used. In certain embodiments, the heteroarylalkyl group can be a 6 to 30 membered heteroarylalkyl, e.g., the alkanyl, alkenyl or alkynyl moiety of the heteroarylalkyl can be 1 to 10 membered and the heteroaryl moiety can be a 5 to 20-membered heteroaryl.

By "heterocycloalkyl" is meant a single aliphatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. Suitable heterocycloalkyl groups include, for example (as numbered from the linkage position assigned priority 1), 2-pyrrolinyl, 2,4-imidazolidinyl, 2,3-pyrazolidinyl, 2-piperidyl, 3-piperidyl, 4-piperdyl, and 2,5-piperzinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo (=O) or oxide (—O⁻) substituents, such as piperidinyl N-oxide, morpholinyl-N-oxide, 1-oxo-1-thiomorpholinyl and 1,1-dioxo-1-thiomorpholinyl.

"Leaving group" refers to an atom or a group capable of being displaced by a nucleophile and includes halogen, such as chloro, bromo, fluoro, and iodo, alkoxycarbonyl (e.g., acetoxy), aryloxycarbonyl, mesyloxy, tosyloxy, trifluoromethanesulfonyloxy, aryloxy (e.g., 2,4-dinitrophenoxy), methoxy, N,O-dimethylhydroxylamino, and the like.

"Optional" or "optionally" means that the subsequently described event or circumstance may but need not occur, and that the description includes instances where the event or circumstance occurs and instances in which the event does not.

"Pharmaceutically acceptable" refers to approved or approvable by a regulatory agency of the Federal or a state government or listed in the U.S. Pharmacopeia or other generally recognized pharmacopeia for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient, carrier or adjuvant" refers to an excipient, carrier or adjuvant that can be administered to a subject, together with at least one chemical entity of the present disclosure, and which does not destroy the pharmacological activity thereof and is nontoxic when administered in doses sufficient to deliver a therapeutic amount of the compound.

"Pharmaceutically acceptable vehicle" refers to a diluent, adjuvant, excipient or carrier with which at least one chemical entity of the present disclosure is administered.

"Prodrug" refers to a derivative of a therapeutically effective compound that requires a transformation within the body to produce the therapeutically effective compound. Prodrugs can be pharmacologically inactive until converted to the parent compound.

"Promoiety" refers to a form of protecting group that when used to mask a functional group within a drug molecule converts the drug into a prodrug. For example, the promoiety can be attached to the drug via bond(s) that are cleaved by enzymatic or non-enzymatic means in vivo.

"Protecting group" refers to a grouping of atoms that when attached to a reactive group in a molecule masks, reduces or prevents that reactivity. Examples of protecting groups can be found in Green et al., "Protective Groups in Organic Chemistry," (Wiley, $2^{nd}$ ed. 1991) and Harrison et al., "Compendium of Synthetic Organic Methods," Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC"), and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Protein kinase," "kinase," and "human protein kinase" refer to any enzyme that phosphorylates one or more hydroxyl or phenolic groups in proteins, ATP being the phosphoryl-group donor.

"Stereoisomer" refers to an isomer that differs in the arrangement of the constituent atoms in space. Stereoisomers that are mirror images of each other and optically active are termed "enantiomers," and stereoisomers that are not mirror images of one another are termed "diastereoisomers."

"Subject" includes mammals, such as humans. The terms "human" and "subject" are used interchangeably herein.

"Substituted" refers to a group in which one or more hydrogen atoms are each independently replaced with the same or different substituent(s). Typical substituents include, but are not limited to, —X, —$R^{33}$, —O$^-$, =O, —O$R^{33}$, —S$R^{33}$, —S$^-$, =S, —N$R^{33}R^{34}$, =N$R^{33}$, —C$X_3$, —C$F_3$, —CN, —OCN, —SCN, —NO, —N$O_2$, =$N_2$, —$N_3$, —S(O)$_2$O$^-$, —S(O)$_2$OH, —S(O)$_2R^{33}$, —OS(O)$_2$O$^-$, —OS(O)$_2R^{33}$, —P(O)(O$^-$)$_2$, —P(O)(O$R^{33}$)(O$^-$), —OP(O)(O$R^{33}$)(O$R^{34}$), —C(O)$R^{33}$, —C(S)$R^{33}$, —C(O)O$R^{33}$, —C(O)N$R^{33}R^{34}$, —C(O)O$^-$, —C(S)O$R^{33}$, —N$R^{35}$C(O)N$R^{33}R^{34}$, —N$R^{35}$(S)N$R^{33}R^{34}$, —N$R^{35}$C(N$R^{33}$)N$R^{33}R^{34}$, —C(N$R^{33}$)N$R^{33}R^{34}$, —S(O)$_2$N$R^{33}R^{34}$, —N$R^{35}$S(O)$_2R^{33}$, —N$R^{35}$C(O)$R^{33}$, and —S(O)$R^{33}$ where each X is independently a halogen; each $R^{33}$ and $R^{34}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, —N$R^{35}R^{36}$, —C(O)$R^{35}$ or —S(O)$_2R^{35}$ or optionally $R^{33}$ and $R^{34}$ together with the atom to which $R^{33}$ and $R^{34}$ are attached form one or more cycloheteroalkyl, substituted cycloheteroalkyl, heteroaryl, or substituted heteroaryl rings; and $R^{35}$ and $R^{36}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl or substituted heteroarylalkyl, or optionally $R^{35}$ and $R^{36}$ together with the nitrogen atom to which $R^{35}$ and $R^{36}$ are attached form one or more cycloheteroalkyl, substituted cycloheteroalkyl, heteroaryl, or substituted heteroaryl rings. In certain embodiments, a tertiary amine or aromatic nitrogen may be substituted with one or more oxygen atoms to form the corresponding nitrogen oxide.

In certain embodiments, substituted aryl and substituted heteroaryl include one or more of the following substituent groups: F, Cl, Br, $C_{1-3}$ alkyl, substituted alkyl, $C_{1-3}$ alkoxy, —S(O)$_2$N$R^{33}R^{34}$, —N$R^{33}R^{34}$, —C$F_3$, —OC$F_3$, —CN, —N$R^{35}$S(O)$_2R^{33}$, —N$R^{35}$C(O)$R^{33}$, $C_{5-10}$ aryl, substituted $C_{5-10}$ aryl, $C_{5-10}$ heteroaryl, substituted $C_{5-10}$ heteroaryl, —C(O)O$R^{33}$, —N$O_2$, —C(O)$R^{33}$, —C(O)N$R^{33}R^{34}$, —OCH$F_2$, $C_{1-3}$ acyl, —S$R^{33}$, —S(O)$_2$OH, —S(O)$_2R^{33}$, —S(O)$R^{33}$, —C(S)$R^{33}$, —C(O)O$^-$, —C(S)O$R^{33}$, —N$R^{35}$C(O)N$R^{33}R^{34}$, —N$R^{35}$C(S)N$R^{33}R^{34}$, and —C(N$R^{35}$)N$R^{33}R^{34}$, $C_{3-8}$ cycloalkyl, and substituted $C_{3-8}$ cycloalkyl, $C_{3-8}$ heterocycloalkyl, and substituted $C_{3-8}$ heterocycloalkyl, as defined herein.

In certain embodiments, substituted arylalkyl, and substituted heteroarylalkyl include one or more of the following substitute groups: F, Cl, Br, $C_{1-3}$ alkyl, $C_{1-3}$ alkoxy, —S(O)$_2$N$R^{33}R^{34}$, —N$R^{33}R^{34}$, —C$F_3$, —OC$F_3$, CN, —N$R^{35}$S(O)$_2R^{33}$, —N$R^{35}$C(O)$R^{33}$, $C_{5-10}$ aryl, substituted alkyl, substituted $C_{5-10}$ aryl, $C_{5-10}$ heteroaryl, substituted $C_{5-10}$ heteroaryl, —C(O)O$R^{33}$, —N$O_2$, —C(O)$R^{33}$, —C(O)N$R^{33}R^{34}$, —OCH$F_2$, $C_{1-3}$ acyl, —S$R^{33}$, —S(O)$_2$OH, —S(O)$_2R^{33}$, —S(O)$R^{33}$, —C(S)$R^{33}$, —C(O)O$^-$, —C(S)O$R^{33}$, —N$R^{35}$C(O)N$R^{33}R^{34}$, and —C(N$R^{35}$)N$R^{33}R^{34}$, $C_{3-8}$ cycloalkyl, and substituted $C_{3-8}$ cycloalkyl, as defined herein.

In certain embodiments, substituted alkyl includes one or more of the following substitute groups: $C_{1-3}$ alkoxy, —N$R^{33}R^{34}$, substituted $C_{5-10}$ heteroaryl, —S$R^{33}$, $C_{1-3}$ alkoxy, —S(O)$_2$N$R^{33}R^{34}$, CN, F, Cl, —C$F_3$, —OC$F_3$, —N$R^{35}$S(O)$_2R^{33}$, —N$R^{35}$C(O)$R^{33}$, $C_{5-10}$ aryl, substituted $C_{5-10}$ aryl, $C_{5-10}$ heteroaryl, substituted $C_{5-10}$ heteroaryl, —C(O)O$R^{33}$, —N$O_2$, —C(O)$R^{33}$, —C(O)N$R^{33}R^{34}$, —OCH$F_2$, $C_{1-3}$ acyl, —S(O)$_2$OH, —S(O)$_2R^{33}$, —S(O)$R^{33}$, —C(S)R, —C(O)O$^-$, —C(S)O$R^{33}$, —N$R^{35}$C(O)N$R^{33}R^{34}$, —N$R^{35}$C(S)N$R^{33}R^{34}$, and —C(N$R^{35}$)N$R^{33}R^{34}$, $C_{3-8}$ cycloalkyl, and substituted $C_{3-8}$ cycloalkyl, as defined herein.

In certain embodiments, substituted alkenyl includes one or more of the following substitute groups: $C_{1-8}$ alkyl, substituted $C_{1-8}$ alkyl, $C_{5-10}$ aryl, substituted $C_{5-10}$ aryl, $C_{5-10}$ heteroaryl, substituted $C_{5-10}$ heteroaryl, $C_{3-8}$ cycloalkyl, substituted $C_{3-8}$ cycloalkyl, cycloheteroalkylalkyl, and substituted cycloheteroalkylalkyl, as defined herein.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, and inhibit at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

In the specification and the appended claims, the singular forms "a," "an," and "the" include plural reference unless the context clearly dictates otherwise.

The compounds of Formula I can be named and numbered in the manner (e.g., using ChemDraw Ultra 9.0 Struct=Name algorithm) described below. For example, the compound:

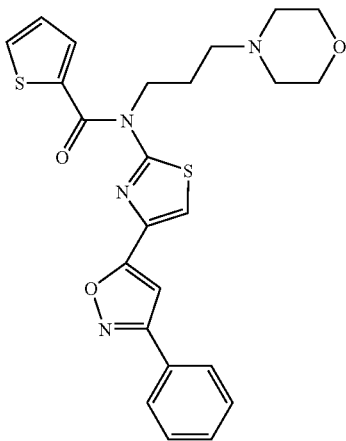

i.e., the compound according to Formula I where $R^3$ is 3-phenylisoxazol-5-yl, L is $C_0$ alkylene (i.e., a covalent bond), W is hydrogen, Z is 3-morpholinopropyl, and Q is thiophen-2-yl can be named N-(3-morpholinopropyl)-N-(4-(3-phenylisoxazol-5-yl)thiazol-2-yl)thiophene-2-carboxamide.

Likewise, the compound:

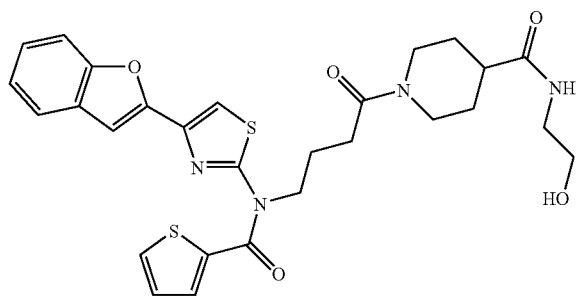

i.e., the compound according to Formula I where $R^3$ is benzofuran-2-yl, L is $C_0$ alkylene (i.e., a covalent bond), W is hydrogen, Z is 4-(4-(2-hydroxyethylcarbamoyl)piperidin-1-yl)-4-oxobutyl-, and Q is thiophen-2-yl can be named 1-(4-(N-(4-(benzofuran-2-yl)thiazol-2-yl)thiophene-2-carboxamido)butanoyl)-N-(2-hydroxyethyl)piperidine-3-carboxamide.

Provided is at least one chemical entity chosen from compounds of Formula I:

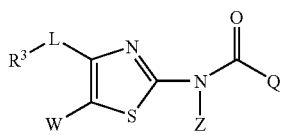
(Formula I)

and pharmaceutically acceptable salts, solvates, chelates, non-covalent complexes, prodrugs, and mixtures thereof, wherein
$R^3$ is chosen from hydroxy, alkoxy, amino, substituted amino, and Ar;
Ar is chosen from cycloalkyl, substituted cycloalkyl, aryl, substituted aryl, heteroaryl, and substituted heteroaryl;
L is chosen from $C_0$-$C_4$alkylene, substituted $C_1$-$C_4$alkylene, —($C_0$-$C_4$alkylene)-NH—(C=O)—; and —($C_0$-$C_4$alkylene)(C=O)—;
W is chosen from hydrogen, halo, alkyl, substituted alkyl, cycloalkyl, substituted cycloalkyl, heterocycloalkyl, substituted heterocycloalkyl, aryl, substituted aryl, heteroaryl, and substituted heteroaryl;
Q is chosen from alkyl, substituted alkyl, cycloalkyl, substituted cycloalkyl, cycloheteroalkyl, substituted cycloheteroalkyl, aryl, substituted aryl, heteroaryl, and substituted heteroaryl; and
Z is chosen from alkyl and substituted alkyl,
with the provisos that
when Q is optionally substituted pyridin-3-yl, L is a covalent bond, W is 3-methylphenyl, $R^3$ is optionally substituted pyridin-4-yl, then Z is not methyl;
when Ar is pyridin-4-yl, W is hydrogen, and Q is chosen from benzyl, substituted benzyl, phenethyl, and substituted phenethyl, then Z is not chosen from lower alkyl and substituted lower alkyl;
when Ar is 2-oxo-(3-hydroquinolyl), W is hydrogen, Z is methyl, then Q is not phenyl;
when W is chosen from 2-(cyclohexylamino)pyridin-4-yl and 2-(cyclopentylamino)pyridin-4-yl, Ar is 3-methylphenyl, Z is methyl, then Q is not pyridin-3-yl or 6-methylpyridin-3-yl;
Ar is not substituted pyridone or benzoyloxypyridine;
when either $R^1$ or $R^2$ is hydrogen, then Ar is not 4-pivaloyloxyphenyl;
Q is not a heteroaryl, substituted heteroaryl, heterocycloalkyl or substituted heterocycloalkyl comprising one or more heteroatoms chosen from S and N, fused with an aryl, substituted aryl, heteroaryl, or substituted heteroaryl ring;
when Z is lower alkyl or 3-morpholinopropyl, then Ar is not phenyl, 4-methoxyphenyl, or 2,5-dimethoxyphenyl;
when Ar is pyridinyl, L is a covalent bond, Z is hydrogen or methyl, and W is phenyl substituted with one methoxy, methyl, chloro, fluoro, chloroor t-butyl, then Q is not methyl; and
when Ar is 4-t-butylphenyl, L is a covalent bond, Z is propyl and Q is 1-cyano-2-hydroxy-prop-1-enyl, then W is not hydrogen.

In certain embodiments, $R^3$ is $C_{1-8}$ alkoxy.

In certain embodiments, $R^3$ is Ar wherein Ar is chosen from cycloalkyl, substituted cycloalkyl, aryl, substituted aryl, heteroaryl, and substituted heteroaryl.

In certain embodiments, Ar is chosen from substituted aryl and substituted heteroaryl.

In certain embodiments, Ar is chosen from phenyl, substituted phenyl, benzo[b]thiophen-3-yl, substituted benzo[bPthiophen-3-yl, pyridin-2-yl, substituted pyridin-2-yl, pyridin-3-yl, substituted pyridin-3-yl, pyridin-4-yl, substituted pyridin-4-yl, thiophen-2-yl, substituted thiophen-2-yl, thiophen-3-yl, substituted thiophen-3-yl, 4-isoxazolyl, substituted 4-isoxazolyl, 5-isoxazolyl, substituted 5-isoxazolyl, 3-pyrazolyl, substituted 3-pyrazolyl, 4-pyrazolyl, substituted 4-pyrazolyl, naphthalene-2-yl, substituted napthalen-2-yl, 2,3-dihydro-1,4-benzodioxin-6-yl, substituted 2,3-dihydro-1,4-benzodioxin-6-yl, 3,4-dihydro-2H-1,5-benzodioxepin- 7-yl, substituted 3,4-dihydro-2H-1,5-benzodioxepin-7-yl, benzothiazol-2-yl, substituted benzothiazol-2-yl, benzofuran-2-yl, and substituted benzofuran-2-yl.

In certain embodiments, Ar is chosen from phenyl, substituted phenyl, 4-isoxazolyl, substituted 4-isoxazolyl, 5-isoxazolyl, substituted 5-isoxazolyl, 3-pyrazolyl, substituted 3-pyrazolyl, 4-pyrazolyl, substituted 4-pyrazolyl, benzofuran-2-yl, and substituted benzofuran-2-yl.

In certain embodiments, when Ar is a substituted radical (for example, substituted phenyl, substituted 4-isoxazolyl, substituted 5-isoxazolyl, substituted benzofuran-2-yl, or substituted pyridin-2-yl, substituted 3-pyrazolyl, substituted 4-pyrazolyl, etc.), the radical is substituted with at least one substituent, such as one, two, or three substitutents, independently chosen from halogen, —CN, —OH, —COOH, —NO$_2$, $C_{1-8}$ alkoxy, substituted $C_{1-8}$ alkoxy, $C_{1-8}$ alkyl, substituted $C_{1-8}$ alkyl, $C_{5-10}$ aryl, substituted $C_{5-10}$ aryl, $C_{5-10}$ cycloalkyl, substituted $C_{5-10}$ cycloalkyl, $C_{1-8}$ sulfanyl, substituted $C_{1-8}$ sulfanyl, $C_{1-8}$ sulfinyl, substituted $C_{1-8}$ sulfinyl, substituted amino, $C_{1-8}$ aminocarbonyl, substituted $C_{1-8}$ aminocarbonyl, $C_{1-8}$ alkylcarbonylamino, substituted $C_{1-8}$ alkylcarbonylamino, $C_{1-8}$ sulfonyl, substituted $C_{1-8}$ sulfonyl, $C_{1-8}$ alkylcarbonyl, substituted $C_{1-8}$ alkylcarbonyl, $C_{5-10}$ heteroaryl, $C_{5-10}$ cycloheteroalkyl, and $C_{1-8}$ alkoxycarbonyl.

In certain embodiments, when Ar is a substituted radical (for example, substituted phenyl, substituted 4-isoxazolyl, substituted 5-isoxazolyl, substituted 3-pyrazolyl, substituted 4-pyrazolyl, substituted benzofuran-2-yl, or substituted pyridin-2-yl, etc.), the radical is substituted with at least one substituent, such as one, two, or three substitutents, independently chosen from methoxy, Cl, F, Br, nitro, methyl, pentyl, cyano, difluoromethoxy, trifluoromethyl, trifluoromethoxy, diethylamino, phenyl, substituted phenyl, morpholin-4-yl, methanesulfonyl, and —CO—O—CH$_3$.

In certain embodiments, L is a covalent bond. In certain embodiments, L is —NH—(C═O)— (wherein the carbonyl is attached to the thiazole core).

In certain embodiments, W is chosen from hydrogen, alkyl, and substituted alkyl. In certain embodiments, W is hydrogen.

In certain embodiments, Q is chosen from alkyl, substituted alkyl, cycloalkyl, substituted cycloalkyl, aryl, substituted aryl, heteroaryl, and substituted heteroaryl.

In certain embodiments, Q is chosen from monocyclic cycloalkyl, substituted monocyclic cycloalkyl, monocyclic aryl, substituted monocyclic aryl, heteroaryl, and substituted monocyclic heteroaryl.

In certain embodiments, Q is chosen from monocyclic $C_{5-10}$ cycloalkyl, substituted monocyclic $C_{5-10}$ cycloalkyl, monocyclic $C_{5-10}$ aryl, substituted monocyclic $C_{5-10}$ aryl, monocyclic $C_{5-10}$ heteroaryl, and substituted monocyclic $C_{5-10}$ heteroaryl.

In certain embodiments, Q is chosen from $C_{5-10}$ monocyclic heteroaryl, and substituted monocyclic $C_{5-10}$ heteroaryl.

In certain embodiments, Q is chosen from phenyl, substituted phenyl, furanyl, substituted furanyl, cyclohexyl, substituted cyclohexyl, cyclopentenyl, substituted cyclopentenyl, 4-isoxazolyl, substituted 4-isoxazolyl, 5-isoxazolyl, substituted 5-isoxazolyl, thiophene-2-yl, substituted thiophene-2-yl, pyrimidin-2-yl, substituted pyrimidin-2-yl, 5-thiadiazolyl, substituted 5-thiadiazolyl, imidazolyl, substituted imidazolyl, 3-isothiazolyl, substituted thiazolyl, 3-pyrrolyl, and substituted 3-pyrrolyl.

In certain embodiments, Q is chosen from thiophene, and substituted thiophene.

In certain embodiments, when Q is a substituted radial (e.g., substituted thiophene, substituted phenyl, etc.) the radical is substituted with at least one substituent, such as one, two, or three substituents, independently chosen from $C_{1-4}$ alkyl, halo, nitro, $C_{1-4}$ acyl, $C_{1-4}$ sulfanyl, and $C_{1-4}$ sulfonyl. In certain embodiments, when Q is a substituted radial (e.g., substituted thiophene, substituted phenyl, etc.) the radical is substituted with at least one substituent, such as one, two, or three substituents, independently chosen from F, Cl, methyl, cyano, Br, nitro, methanesulfonyl, acetyl, and thiomethyl.

In certain embodiments, Z is substituted alkyl. In certain embodiments, Z is substituted lower alkyl.

Provided is at least one chemical entity chosen from compounds of Formula II:

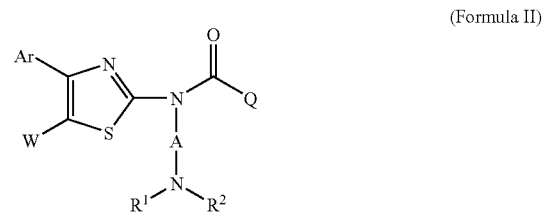

(Formula II)

and pharmaceutically acceptable salts, solvates, chelates, non-covalent complexes, prodrugs, and mixtures thereof, wherein Ar, W, and Q are as described for compounds of Formula I and A is chosen from alkylene, substituted alkylene, alkenylene, and substituted alkenylene; and $R^1$ and $R^2$ are independently selected from hydrogen, alkyl, substituted alkyl, cycloalkyl, substituted cycloalkyl, heterocycloalkyl, substituted heterocycloalkyl, aryl, substituted aryl, heteroaryl, and substituted heteroaryl, or $R^1$ and $R^2$ together with the nitrogen to which $R^1$ and $R^2$ are attached form a ring chosen from cycloheteroalkyl, substituted cycloheteroalkyl, heteroaryl, and substituted heteroaryl.

In certain embodiments, A is chosen from alkylene, and substituted alkylene. In certain embodiments, A is chosen from 1,3-propylene, 1,4-butylene, or —(CH$_2$)$_m$—(C═O)— wherein the carbonyl is attached to —NR$^1$R$^2$ and wherein m is 2 or 3.

In certain embodiments, $R^1$ and $R^2$ are independently chosen from alkyl, and substituted alkyl, or $R^1$ and $R^2$, together with the nitrogen to which $R^1$ and $R^2$ are attached form a monocyclic cycloheteroalkyl ring.

In certain embodiments, $R^1$ and $R^2$ are independently chosen from $C_{1-8}$ alkyl, and substituted $C_{1-8}$ alkyl, or $R^1$ and $R^2$, together with the nitrogen to which $R^1$ and $R^2$ are attached form a monocyclic $C_{5-10}$ cycloheteroalkyl ring.

In certain embodiments, $R^1$ and $R^2$ are independently chosen from $C_{1-4}$ alkyl.

In certain embodiments, $R^1$ and $R^2$, together with the nitrogen atom to which $R^1$ and $R^2$ are attached form a pyrrolidine, substituted pyrrolidine, piperidine, substituted piperidine, azepane, substituted azepane, piperazine, substituted piperazine, morpholine, or substituted morpholine ring.

In certain embodiments, $R^1$ and $R^2$ together with the nitrogen atom to which $R^1$ and $R^2$ are attached form a morpholin-4-yl ring.

Provided is at least one chemical entity chosen from compounds of Formula III:

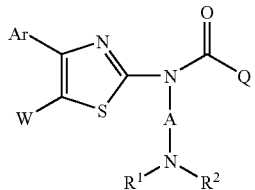

(Formula III)

and pharmaceutically acceptable salts, solvates, chelates, non-covalent complexes, prodrugs, and mixtures thereof, wherein Ar, W, and Q are as described for compounds of Formula I and A is chosen from alkylene, substituted alkylene, alkenylene, and substituted alkenylene; and $R^1$ and $R^2$ together with the nitrogen to which $R^1$ and $R^2$ are attached form an optionally substituted 5- to 7-membered cycloheteroalkyl ring which optionally includes 1 or 2 additional heteroatoms chosen from O, S, and N in the ring.

In certain embodiments, $R^1$ and $R^2$, together with the nitrogen atom to which $R^1$ and $R^2$ are attached form a pyrrolidine, substituted pyrrolidine, piperidine, substituted piperidine, azepane, substituted azepane, piperazine, substituted piperazine, morpholine, or substituted morpholine ring.

In certain embodiments, $R^1$ and $R^2$ together with the nitrogen atom to which $R^1$ and $R^2$ are attached form a morpholin-4-yl ring.

Provided is at least one chemical entity chosen from compounds of Formula III:

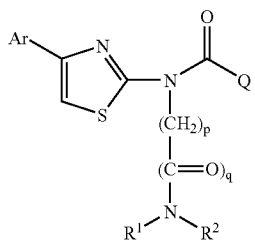

(Formula IV)

and pharmaceutically acceptable salts, solvates, chelates, non-covalent complexes, prodrugs, and mixtures thereof, wherein Ar and Q are as described for compounds of Formula I and $R^1$ and $R^2$ are as described for compounds of Formula II and wherein p is chosen from 2, 3, and 4 and q is chosen from 0 and 1.

In certain embodiments, p is chosen from 2, 3 and 4 and q is 0. In certain embodiments, p is chosen from 2 and 3 and q is 0.

In certain embodiments, p is chosen from 2 and 3 and q is 1. In certain embodiments, p is 2 and q is 1.

In certain embodiments, the compound of Formula I is chosen from any of compounds listed in Table 1 and/or Table 2.

Provided is at least one chemical entity chosen from compounds of Formula V:

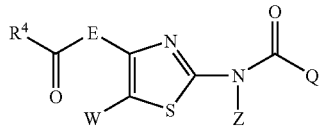

(Formula V)

and pharmaceutically acceptable salts, solvates, chelates, non-covalent complexes, prodrugs, and mixtures thereof, wherein W, Z, and Q are as described for compounds of Formula I and wherein E is chosen from $C_0$-$C_4$alkylene and substituted $C_1$-$C_4$alkylene; and $R^4$ is chosen from hydroxy, alkoxy, amino, and substituted amino.

In certain embodiments, $R^4$ is alkoxy.

As used herein, the chemical entities of the present disclosure can include pharmaceutically acceptable derivatives or prodrugs thereof. A "pharmaceutically acceptable derivative or prodrug" refers to any appropriate pharmaceutically acceptable salt, ester, salt of an ester, hydrate, solvate, or other derivative of a compound of this present disclosure that, upon administration to a subject, is capable of providing, directly or indirectly, a compound of the present disclosure. Particularly favored derivatives and prodrugs include those that increase the bioavailability of the chemical entities of the present disclosure when such chemical entities are administered to a subject, for example by allowing an orally administered compound to be more readily absorbed into the blood, or which enhance delivery of the parent compound to a biological compartment, such as the brain or lymphatic system, relative to the parent species. Prodrugs can include derivatives where a group that enhances aqueous solubility or active transport through the gut membrane is appended to the structure of Formulae (I)-(V). Other prodrugs can include a promoiety that modifies the ADME (absorption, distribution, metabolism and excretion) of the parent compound and thereby enhances the therapeutic effectiveness of the parent compound.

In certain embodiments, chemical entities of the present disclosure can be modified by appending appropriate functionalities to enhance selective biological properties. Such modifications are known in the art and include those which can increase biological penetration into a given biological compartment, such as blood, lymphatic system, central nervous system, to increase oral availability, increase solubility to allow administration by injection, alter metabolism, and alter the rate of excretion.

In some embodiments, chemical entities of the present disclosure can be modified to facilitate use in biological assay, screening, and analysis protocols. Such modifications can include, for example, derivatizing to effect or enhance binding to physical surfaces such as beads or arrays, or modifying to facilitate detection such as by radiolabeling, affinity labeling, or fluorescence labeling.

Chemical entities of the present disclosure possess inhibitory activity with at least one ATP-utilizing enzyme. An ATP-utilizing enzyme refers to an enzyme that catalyzes the transfer of a phosphate group from an ATP molecule to a biomolecule such as a protein or carbohydrate. Examples of ATP-utilizing enzymes include, but are not limited to, synthetases, ligases, and kinases. The kinases can be animal kinases, including mammalian protein kinases, and human protein kinases.

Without being limited by theory, ATP-utilizing enzymes can be inhibited by compounds structurally similar to the phosphoryl-containing compounds that serve as the substrate for the phosphorylation reaction. For example, structurally similar compounds can bind to the active site or catalytic domain of an ATP-utilizing enzyme and thereby prevent substrate binding.

In certain embodiments, chemical entities of the present disclosure exhibited human protein kinase inhibitory activity.

Protein kinases are among the largest and most functionally diverse gene families. Most of the over 500 human protein kinases belong to a single superfamily of enzymes in which the catalytic domains are related in sequence and structure. Most human protein kinases can further be grouped into seven major groups based on the deoxyribonucleic acid (DNA) sequence homologies identified as CAMK (calcium/calmodulin-dependent protein kinases), AGC (including PKA (protein kinase A), PKG (protein kinase G), PKC (protein kinase C) kinases), CK1 (casein kinases), CMGC (containing CDK (cyclin-dependent), MAPK (mitogen activated), GSK3 (glycogen synthase) and CLK (CDC2-like) kinases), STE (homologs of yeast Sterile 7, Sterile 11, and Sterile 20 kinases), TK (tyrosine kinases), and TKL (tyrosine-kinase like).

The AGC protein kinase family includes AKT1, AKT2, AKT3, AURORA-A, MSK1, MSK2, P70S6K, PAK1, PKA, and SGK1 protein kinases. The CMGC protein kinase family includes the CDK1, CDK2/cyclinA, CDK2/cyclinE, CDK5, DYRK2, GSK3-α, GSK3-β, P38-α, P38-β, P38-δ, and P38-γ, and MAPK1 protein kinases. The CAMK protein kinase family includes the DAPK1, MAPKAPK2, CHEK1, CHEK2, PRAK, and c-TAK1 protein kinases. The TK protein kinase family includes the ABL1, CSK, FLT3, FYN, HCK, INSR, KIT, LCK, PDGFR-α, LYNA, SYK, and SRC protein kinases. The STE protein kinase family includes PAK2 protein kinase.

Certain chemical entities of the present disclosure exhibited selectivity for one or more protein kinases, where selectivity is as defined herein. Certain chemical entities of the present disclosure exhibited selective activity for at least one of the following protein kinases: AKT1, AKT2, AMP kinase, AXL, AURORA-A, BMX, CDK2/cyclinA, CDK2/cyclinE, CHEK1, CHEK2, CK2, DYRK2, EGFR, EPHB4, FLT3, GSK3-α, GSK3-β, IGF1R, INSR, KDR, KIT, MAPKAPK2, MAPKAPK3, MET, MSK2, NEK2, P70S6K1, PAK2, PDGFR-α, PDK1, PIM1 kinase, PLK1, ROCK2, RSK2, SYK, TIE2, TRKB, and ZAP70. Certain chemical entities of the present disclosure exhibited selective activity for AKT1.

Chemical entities of the present disclosure can be prepared by methods well known in the art.

Chemical entities of the present disclosure can be prepared from readily available starting materials using the flowing general methods and procedures. It will be appreciated that where typical or preferred process conditions, such as, reaction temperatures, times, mole ratios of reactants, solvents, pressures, are given, other process conditions can also be used unless otherwise stated. Reaction conditions may vary with the reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, 3$^{rd}$ Edition, John Wiley & Sons, 1999, and references cited therein.

Furthermore, chemical entities of the present disclosure can contain one or more chiral centers. Accordingly, if desired, such compounds can be prepared or isolated as pure stereoisomers, i.e., as individual enantiomers or diastereomers, or as stereoisomer-enriched mixtures. All such stereoisomers, and enriched mixtures thereof, are included within the scope of the present disclosure, unless otherwise indicated. Pure stereoisomers, and enriched mixtures thereof, can be prepared using, for example, optically active starting materials or stereoselective reagents well-known in the art. Alternatively, racemic mixtures of such compounds can be separated using, for example, chiral column chromatography, chiral resolving agents and the like.

General synthetic schemes and specific reaction protocols used to prepare chemical entities of the present disclosure are presented in the reaction schemes and Examples provided herein.

Chemical entities of the present disclosure can be prepared as illustrated in Scheme 1 below. Reaction of an appropriately substituted α-bromoketone 4 with a thiourea 5 can provide aminothiazoles 6 or 7 via known procedures (e.g. Hantzsch, A. R., et al., Ber. 1887, 20, 3118; Metzger, J. V., Thiazole and Its Derivatives, Wiley, 1979 and references cited therein). Bromoketones of structure 4 can be prepared by bromination of the appropriate α-methylene ketones also via known procedures (e.g. Langley, W. D. Org. Syn. 1932, 122; Corey, E. J. J. Am. Chem. Soc. 1954, 75, 2301; King, L. C., et al. J. Org. Chem. 1964, 3459). Thioureas of structure 5 can be prepared from the corresponding amine via known procedures, such as reaction with thiophosgene followed by treatment of the resulting chloride with ammonia, reaction with FMOC-isothiocyanate followed by deprotection with piperidine, reaction with TMS-isocyanate followed by deprotection and thionation with Lawesson's reagent, or reaction with benzoyl isothiocyanate followed by acidic hydrolysis. Preparation of compounds of structure 7 may also be accomplished by alkylation of 6 with the appropriate reagent, with e.g. Z-X (where X is a leaving group such as Cl, Br, I, mesylate, or triflate) or via reductive alkylation with the appropriate aldehyde under reductive amination conditions. Aminothiazoles 6 and 7 may be acylated under standard conditions with the appropriate acid chloride, carboxylic acid, or carboxylic acid anhydride to provide the amidothiazoles 8 or compounds of Formula I. Alkylation of 8 with an appropriate Z-X alkylating agent is also capable of providing compounds of Formula I.

Solid phase reaction methodology has been developed for synthesis of aminothiazoles such as 7 and can be applied for the preparation of chemical entities of the disclosure (see, for example, Kearney, P. C., et al. J. Org. Chem. 1998, 63, 196).

Scheme 1

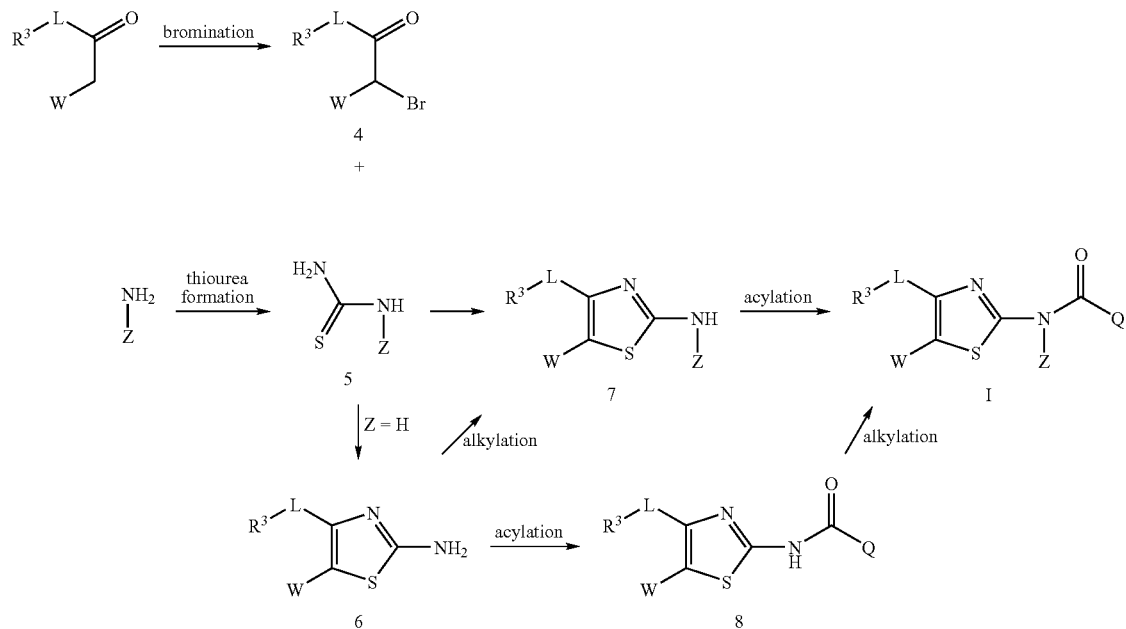

Chemical entities of the present disclosure may be prepared by the procedures in Scheme 1. The requisite diamine starting materials are either known or can be prepared by methods known in the art. Alternatively, chemical entities of the present disclosure may be prepared by routes described in Scheme 2. Alcohols 7a may be prepared via the procedures in Scheme 1. Compounds of structure 7a (where L is a substituted or unsubstituted alkylene or alkenylene group) can be protected with an alcohol protecting group, such as trimethylsilyl, then acylated to provide compounds where G is —C(=O)Q or protected with an amine protecting group, such as 4-methoxybenzyl or tert-butyloxycarbonyl, or the protecting group may be a solid phase polymer resin containing a readily cleavable linker. Removal of the alcohol protecting group, can provide compounds 9. Alcohols 9 can be oxidized to provide carbonyl compounds 10, or can be transformed into the alkylating agents 11. Alternatively, acetals/ketals of structure 7b can be acylated or protected, followed by acid hydrolysis, to provide compounds 10. Alkylating agents 11 can also be prepared via alkylation of aminothiazoles 12. Preparation of amines 13 can be accomplished by reductive amination of the appropriate amine with carbonyl compounds 10 or by alkylation of the appropriate amine with compounds 11. Amines 13 can be transformed into amides, carbamates, or ureas by acylation with the appropriate acylating agents to provide compounds of Formula 2a, or into sulfonamides via sulfonylation to provide compounds of Formula 2b. Reductive amination using the appropriate aldehyde or ketone, or alkylation with the appropriate alkyl halide, for example, can provide amines of Formula II. Alternatively, chemical entities of the present disclosure can be prepared by reductive alkylation of the appropriate amine with compounds 10 or reaction of the appropriate amine with alkylating agents 11. In reactions of compounds 10, 11, and 13 when G is a protecting group, an additional deprotection followed by acylation sequence to attach the —C(=O)Q group to the aminothiazole core is required to provide compounds of Formula 2a, 2b, and II.

Scheme 2

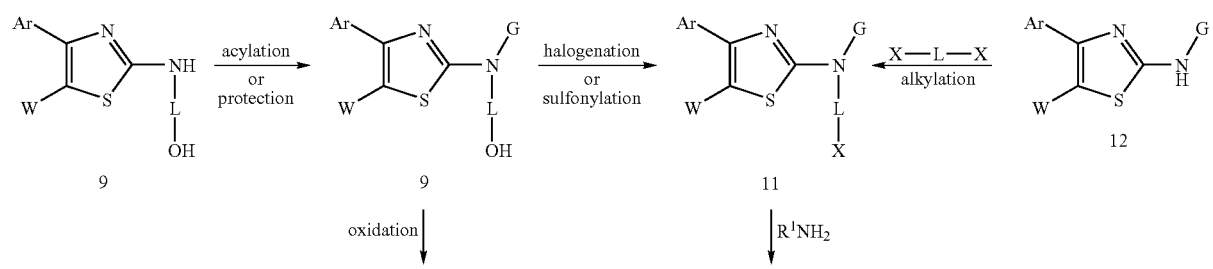

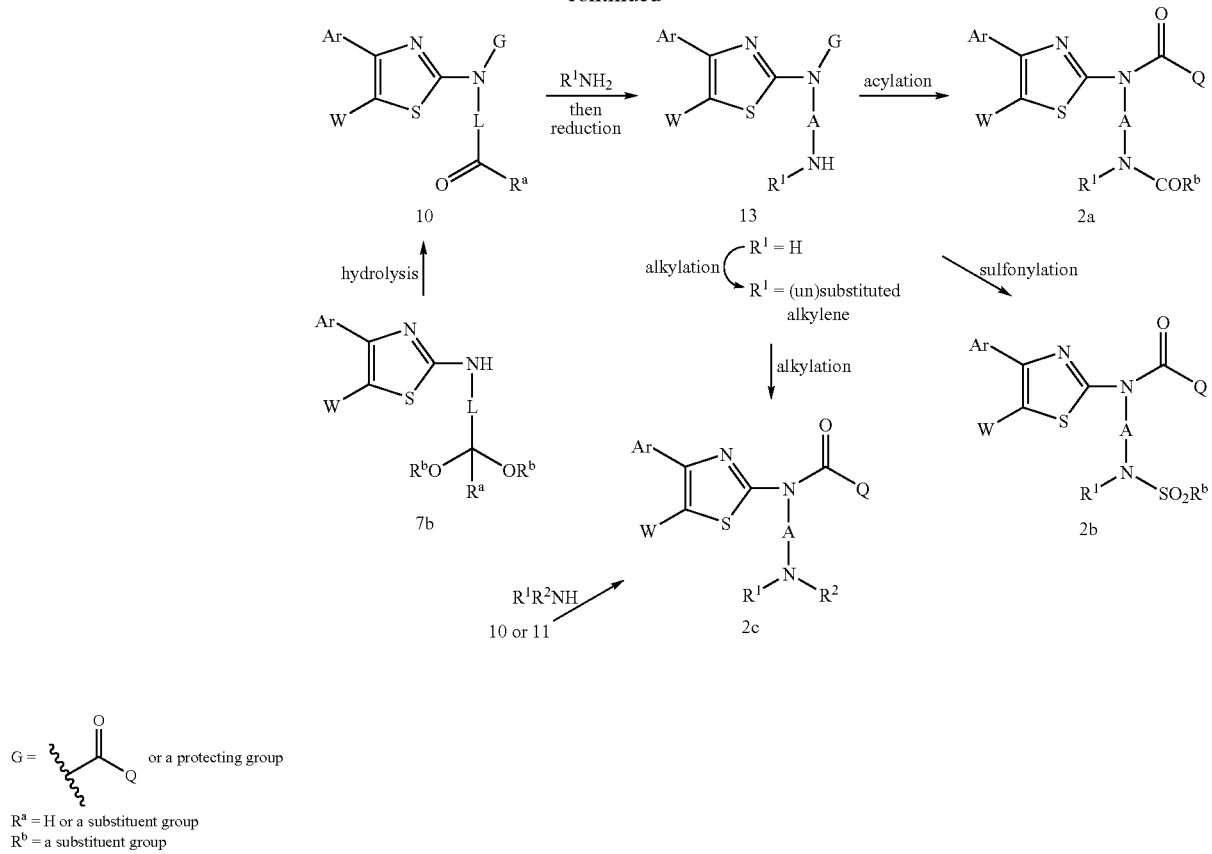

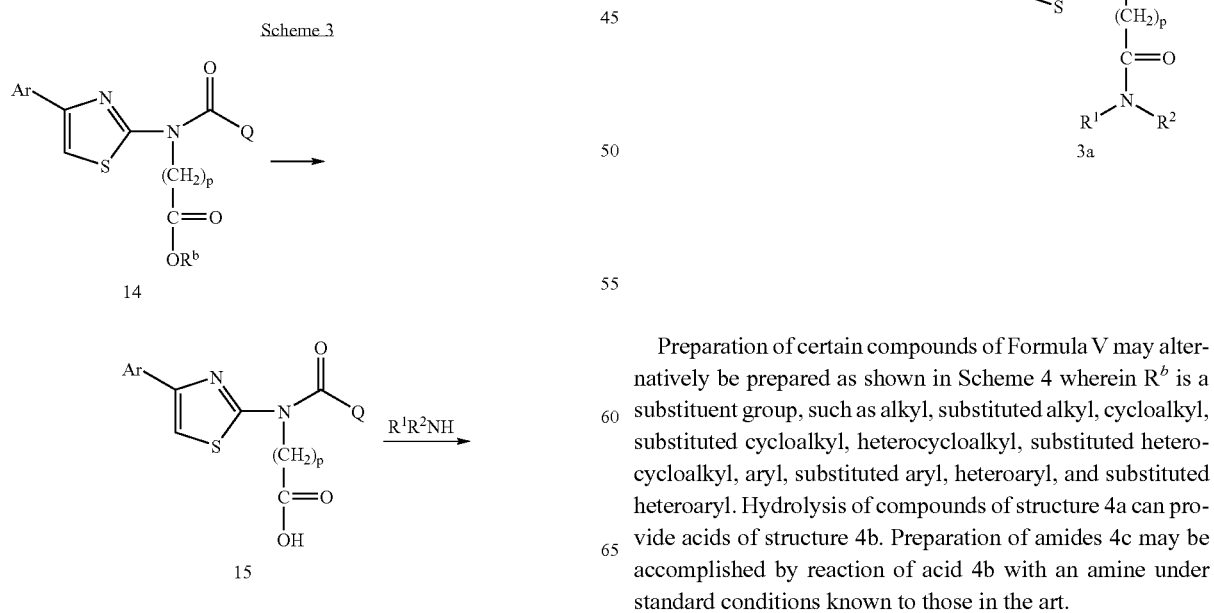

Certain amides of Formula IV can alternatively be prepared as shown in Scheme 3. Esters of structure 14 can be transformed into the carboxylic acids 15 by, for example, acid or base hydrolysis. Amide coupling, using methods known to those skilled in the art, and utilizing the appropriate amine can provide amides of Formula 3a.

Preparation of certain compounds of Formula V may alternatively be prepared as shown in Scheme 4 wherein $R^b$ is a substituent group, such as alkyl, substituted alkyl, cycloalkyl, substituted cycloalkyl, heterocycloalkyl, substituted heterocycloalkyl, aryl, substituted aryl, heteroaryl, and substituted heteroaryl. Hydrolysis of compounds of structure 4a can provide acids of structure 4b. Preparation of amides 4c may be accomplished by reaction of acid 4b with an amine under standard conditions known to those in the art.

Scheme 4

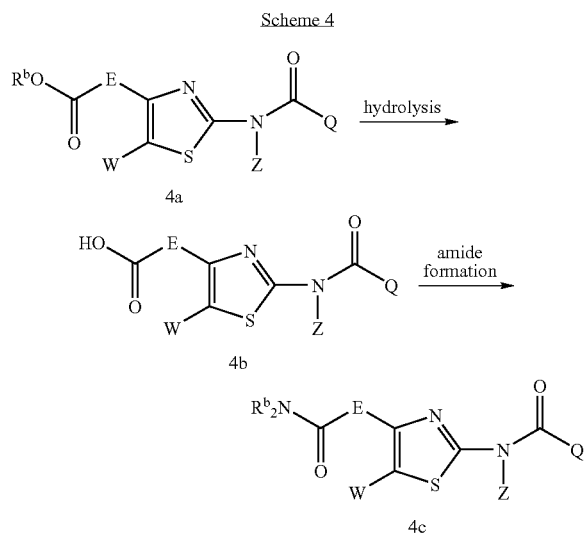

In accordance with certain embodiments, chemical entities of the present disclosure exhibit ATP-utilizing enzyme inhibitory activity. Thus, one important use of the chemical entities of the present present disclosure includes the administration of at least one chemical entity of the present disclosure to a subject, such as a human. This administration serves to arrest, ameliorate, reduce the risk of acquiring, reduce the development of or at least one of the clinical symptoms of, or reduce the risk of developing or at least one of the clinical symptoms of diseases or conditions regulated by ATP-utilizing enzymes, such as, protein kinases.

For example, unregulated or inappropriately high protein kinase activity has been implicated in many diseases resulting from abnormal cellular function. Unregulated or inappropriately high protein kinase activity can arise either directly or indirectly, for example, by failure of the proper control mechanisms of a protein kinase, related, for example, to mutation, over-expression or inappropriate activation of the enzyme; or by over- or under-production of cytokines or growth factors also participating in the transduction of signal upstream or downstream of the protein kinase. In all of these instances, selective inhibition of the action of a protein kinase can be expected to have a beneficial effect.

According to certain embodiments, the present disclosure relates to methods of treating a disease regulated by at least one ATP-utilizing enzyme in a subject. ATP-utilizing enzyme regulated diseases include, for example, those where the ATP-utilizing enzyme participates in the signaling, mediation, modulation, control or otherwise involved in the biochemical processes affecting the manifestation of a disease. In certain embodiments, the methods are useful in treating diseases regulated by protein kinase enzymes. Protein kinase regulated diseases include, for example, the following general disease classes: cancer, autoimmunological, metabolic, inflammatory, infection, diseases of the central nervous system, degenerative neural disease, allergy/asthma, angiogenesis, neovascularization, vasucolgenesis, cardiovascular, and the like. Without being limited by theory, specific examples of diseases that are known or believed to be regulated by protein kinase enzymes, include, transplant rejection, osteoarthritis, rheumatoid arthritis, multiple sclerosis, diabetes, diabetic retinopathy, asthma, inflammatory bowel disease such as Crohn's disease, and ulcerative colitis, renal disease cachexia, septic shock, lupus, diabetes mellitus, myasthenia gravis, psoriasis, dermatitis, eczema, seborrhea, Alzheimer's disease, Parkinson's disease, stem cell protection during chemotherapy, ex vivo selection or ex vivo purging for autologous or allogeneic bone marrow transplantation, leukemia including, but not limited to, acute myeloid leukemia, chronic myeloid leukemia, and acute lymphoblastic leukemia, cancer including but not limited to, breast cancer, lung cancer, colorectal cancer, ovarian cancer, prostate cancer, renal cancer, squamous cell cancer, glioblastoma, melanoma, pancreatic cancer, and Kaposi's sarcoma, ocular disease, corneal disease, glaucoma, bacterial infections, viral infections, fungal infections, heart disease, stroke, obesity, endometriosis, atherosclerosis, vein graft stenosis, peri-anastomatic prosthetic graft stenosis, prostate hyperplasia, chronic obstructive pulmonary disease, inhibition of neurological damage due to tissue repair, scar tissue formation, wound healing, pulmonary disease, neoplasm, macular degeneration.

Chemical entities of the present disclosure are particularly useful for the treatment of cancer including, but are not limited to, glioblastoma, ovarian cancer, breast cancer, endometrial carcinoma, hepatocellular carcinoma, melanoma, colorectal cancer, colon cancer, digestive tract, lung cancer, renal-cell carcinoma, thyroid, lymphoid, prostate cancer and pancreatic cancer, advanced tumors, hairy cell leukemia, melanoma, chronic myelygenous leukemia, advanced head and neck, squamous cell cancer, metastatic renal cell, non-Hodgkin's lymphoma, metastatic breast, breast adenocarcinoma, advanced melanoma, pancreatic, gastric, non-small cell lung, small cell lung, renal cell carcinoma, various solid tumors, multiple myeloma, metastatic prostate, malignant glioma, renal cancer, lymphoma, refractory metastatic disease, refractory multiple myeloma, cervical cancer, Kaposi's sarcoma, recurrent anaplastic glioma, and metastatic colon cancer.

More particularly, cancers that may be treated by chemical entities of the present disclosure, include, but are not limited to: Cardiac: sarcoma (angiosarcoma, fibrosarcoma, rhabdomyosarcoma, liposarcoma), myxoma, rhabdomyoma, fibroma, lipoma, teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous, cell carcinoma, adenocarcinoma, leiomyosarcoma, lymphoma) stomach (carcinoma, lymphoma, leiomyosarcoma), pancreas (ductal adenocarcinoma, insulinoma, glucagonoma, gastrinoma, carcinoid tumors, Karposi's sarcoma, leiomyoma, hemangioma, lipoma, neurofibroma, fibroma), large bowel (adenocarcinomas, tubular adenoma, villous adenoma, hamartoma, leiomyoma); Genitourinary tract: kidney (adenocarcinoma, Wilm's tumor[nephroblastoma], lymphoma, leukemia), bladder and uretha (squamous cell carcinoma, transitional cell carcinoma, adenocarcinoma), prostate (adenocarcinoma, sarcoma), testis (seminoma, teratoma, embroyonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma(osteocartilaginous exostoses), benign chrodroma, chondroblastoma, chondromyxofibroma, osteoid osteoma and giant cell tumors; Nervous system: skull (osteoma, hemangioma, granuloma, xanthoma, osteitis deformans, meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenitial tumors), spinal cord, neurofibroma, meningioma, glioma, sarcoma); Gynecological: uterus (endometrial carcinoma), cervix (cervical carcinoma, pre-tumor cervical dsplasia), ovaries (ovarian carcinoma [serous cystadenocarcinoma, mucinous cystadenocarcinoma], granulose-thecal cell tumors, Sertoli-Leydig cell tumors, dysgerminoma, malignant teratoma), vulva (squamous cell carcinoma, intraepithelial carcinoma, adenocarcinoma, firosarcoma, melanoma) vagina (clear cell carcinoma, squamous cell carcinoma, botryoid sarcoma (embryonal rhabdomyosarcoma), fallopian tubes carcinoma); Hematologic: blood (myeloid leukemia (acute and chronic], acute lymphoblastic leukemia, chronic lymphocytic leukemia, myeloproliferative diseases, multiple myeloma, myelodysplastic syndrome), Hodgkin's disease, non-Hodgkins's lymphoma [malignant lymphoma]; Skin: malignant melanoma, basel cell carcinoma, squamous cell carcinoma, Karposi's sarcoma, moles dysplastic nevi, lipoma, angioma, dermatofibroma, keloids, psoriasis; and Adrenal glands: neuroblastoma.

Chemical entities of the present disclosure may also be useful for the treatment of tuberous sclerosis complex.

Chemical entities of the present disclosure may also be useful for the treatment of other conditions (e.g., inflammatory disease), including, but are not limited to, rheumatoid arthritis, osteoarthritis, endometriosis, atherosclerosis, vein graft stenosis, peri-anastomatic prosthetic graft stenosis, prostate hyperplasia, chronic obstructive pulmonary disease, psoriasis, inhibition of neurological damage due to tissue repair, scar tissue formation, wound healing, multiple sclerosis, inflammatory bowel disease, infections, particularly bacterial, viral, retroviral or parasitic infections (by increasing apoptosis), pulmonary disease, neoplasm, Parkinson's disease, transplant rejection (as an immunosuppressant), macular degeneration and septic shock.

Chemical entities of the present disclosure may also be useful for the treatment of diseases mediated by, but not limited to, modulation or regulation of AKT protein kinases, tyrosine kinases, additional serine/threonine kinases, and/or dual specificity kinases.

In certain embodiments, a pharmaceutical composition can include at least one chemical entity of the present disclosure and at least one additional therapeutic agent appropriate for effecting combination therapy. Chemical entities of the present disclosure are also useful in combination with known therapeutic agents and anti-cancer agents. A person skilled in the art would be able to discern which combinations of agents would be useful based on the particular characteristics of the drugs and the cancer involved. Many chemotherapeutics are presently known in the art. Such anti-cancer agents include, but are not limited to, estrogen receptor modulators, cytostatic/cytotoxic agents, anti-proliferative agents, cell cycle checkpoint inhibitors, angiogenesis inhibitors, monoclonal antibody targeted therapeutic agents, tyrosine kinase inhibitors, serine-threonine kinase inhibitors, histone deacetylase inhibitors, heat shock protein inhibitors, and farnesyl transferase inhibitors. Chemical entities of the present disclosure are also useful in combination with radiation therapy.

Examples of cytostatic/cytotoxic agents, anti-proliferative agents and cell cycle checkpoint inhibitors include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX1OO, (trans, trans, trans)-bis-mu-(hexane-1,6-diamine)-mu[diamine-platinum(II)]bis[diamine(chloro)platinum (II) ]tetrachloride, diarizidinylspermine, arsenic trioxide,1-(11-dodecylamino-10-hydroxyundecyl)-3,7-dimethylxanthine, zocubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elioafide, MENI0755, and 4-demetboxy-3-deamino-3-aziridinyl-4-methylsulphonyl-daunoruhicin.

An example of a hypoxia activatable compound is tirapazamine.

Examples of proteosome inhibitors include but are not limited to lactacystin and MLN-341 (Velcade).

Examples of microtubule inhibitors/microtubule-stabilizing agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPRI09881, BMS184476, vinflunine, and BMS188797.

Some examples of topoisomerase inhibitors are topotecan, bycaptamine, irinotecan, robitecan, 6-ethoxypropionyl-3',4'-O-exo-benzylidene-chartreusin.

"Inhibitors of kinases" involved in mitotic progression include, but are not limited to, inhibitors of aurora kinases, inhibitors of Polo-like kinases (PLK; in particular inhibitors of PLK-1), inhibitors of bub-1 and inhibitors of bub-R1.

"Antiproliferative agents" includes antisense RNA and DNA oligonucleotides such a.s G3139, ODN698, RVASK-RAS, GEM231, and INX3001, and antimetabolites such as enocitabine, carmofur, tegafur, pentostatin, doxiflu ridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pem-etrexed, nelzarabine.

Examples of monoclonal antibody targeted therapeutic agents include those therapeutic agents which have cytotoxic agents or radioisotopes attached to a cancer cell specific or target cell specific monoclonal antibody. Examples can be found in a number of references (Krause and Van Etten, 2005 New Eng. J. Med. 353,172184) and include, but are not limited to, Bexxar, trastuzumab (herceptin), cetuximab (erbitux), ABX-EGF, 2C4, bevacizumab (avastin), bortezomib, rituxan.

Some specific examples of tyrosine inhibitors can be found in a number of references (Krause and Van Etten, 2005 New Eng. J. Med. 353,172184; Brown and Small 2004 Eur. J. Cancer 40,707-721; Fabian et al. 2005 Nat. Biotech. 23,329-336) and include imatinib (Gleevec, STI571), gefitnib (Iressa), BMS-354825, PKC412, PD 0173074, SU5402, MLN-518, CEP-701, SU5416, erlotinib (tarceva), CI-1033, CT2923, sunitinib (SU11248), GW-2016, EKB-569, ZD-6474, vatalanib (PTK-787), AMN107, ZD6474, CHIR-258, OSI-930, AZD0530, AEE788.

Some specific examples of serine/threonine kinase inhibitors can be found in a number of references (Jackman et al. 2004 Drug Disc Today:Ther Strategies 1,445-454; Fabian et al. 2005 Nat. Biotech. 23,329-336; Pearson and Fabbro 2004, Expert Rev. Anticancer Ther. 4, 1113-1124) and include but are not limited to, LY-333531, sorafenib (BAY-43-9006), roscovitine (CYC202), CI-1040, ZM447439, CCI-779, RAD001, UNC01, VX680, AP23573.

Examples of heat shock protein inhibitors include, but are not limited to, 17-AAG and 17-DMAG.

Examples of histone deacetylase inhibitors include, but are not limited to, MS-275, AN-9, apicidin derivatives, Baceca, CBHA, CHAPs, chlamydocin, CS-00028, CS-055, EHT-0205, FK-228, FR-135313, G2M-777, HDAC-42, LBH-589, MGCD-0103, NSC-3852, PXD-101, pyroxamide, SAHA derivatives, suberanilohydroxamic acid, tacedinaline, VX-563, and zebularine.

Examples of farnesyl transferase inhibitors include, but are not limited to, lonafarnib.

Certain embodiments of the present disclosure are directed to methods of treating disease in a subject comprising the step of administering to a subject, in need of such treatment, a therapeutically effective amount of at least one chemical entity of the present disclosure. In some embodiments, a disease can be regulated by at least one ATP-utilizing enzyme such as a protein kinase. Certain diseases can be regulated by one or more ATP-utilizing enzymes. In such cases, treatment of the disease or disorder can include administering a therapeutically effective amount of at least one chemical entity of the present disclosure that inhibits the activity of one or more ATP-utilizing enzymes, or more than one compound of the present disclosure, wherein each compound inhibits at least one different ATP-utilizing enzyme.

Other embodiments of the present disclosure are related to methods of inhibiting at least one ATP-utilizing enzyme, including for example, a protein kinase. In certain embodiments, the ATP-utilizing enzyme can be inhibited by the method of administering to a subject, at least one chemical entity of the present disclosure, or a composition comprising at least one chemical entity of the present disclosure.

In certain embodiments, the present disclosure relates to methods of inhibiting ATP-utilizing enzyme activity by contacting at least one ATP-utilizing enzyme with at least one chemical entity of the present disclosure. ATP-utilizing enzymes include phosphotransferase enzymes that catalyze the phosphorylation of a biological molecule by transferring a phosphate group from an ATP substrate. ATP-utilizing enzymes include for example, synthetases, ligases, and kinases. Certain methods of the present disclosure are useful in inhibiting protein kinase enzymes, including, for example, the following protein kinase enzymes: AKT1, AKT2, AMP kinase, AXL, AURORA-A, BMX, CDK2/cyclinA, CDK2/cyclinE, CHEK1, CHEK2, CK2, DYRK2, EGFR, EPHB4, FLT3, GSK3-α, GSK3-β, IGF1R, INSR, KDR, KIT, MAPKAPK2, MAPKAPK3, MET, MSK2, NEK2, P70S6K1, PAK2, PDGFR-α, PDK1, PIM1 kinase, PLK1, ROCK2, RSK2, SYK, TIE2, TRKB, and ZAP70. Certain methods of the present disclosure are useful in inhibiting AKT1.

Some methods of the present disclosure can be used to inhibit ATP-utilizing enzymes that are present in a living organism, such as a mammal; contained in a biological sample such as a cell, cell culture, or extract thereof, biopsied material obtained from a mammal or extracts thereof, and blood, saliva, feces, semen, tears or other body fluids or extracts thereof; contained within a reagent, or bound to a physical support. In certain embodiments, an ATP-utilizing enzyme can regulate a disease or disorder and in other embodiments, the ATP-utilizing enzyme may not regulate a disease or disorder.

According to the methods of the present disclosure, at least one ATP-utilizing enzyme can be inhibited by contact with at least one chemical entity of the present disclosure. In vivo ATP-utilizing enzymes can be inhibited by administration through routes and using compositions comprising at least one chemical entity of the present disclosure. For in vitro systems, contacting an ATP-utilizing enzyme with at least one chemical entity of the present disclosure can include, for example, combining liquid reagents or combining a reagent and an ATP-utilizing enzyme and/or compound of the present disclosure attached to a solid support. The ATP-utilizing enzyme and compound of the present disclosure can be contacted in any appropriate device such as an affinity chromatography column, a microarray, a microfluidic device, assay plate, or other appropriate chemical or biotechnology apparatus used to perform biochemical analysis, assay, screening, and the like.

In certain embodiments, pharmaceutical compositions of the present disclosure may be administered orally, parenterally, by inhalation spray, topically, rectally, nasally, buccally, vaginally, via an implanted reservoir, or by any other appropriate route. Pharmaceutical compositions of the present disclosure can contain one or more pharmaceutically acceptable vehicles. In some embodiments, the pH of the formulation can be adjusted with pharmaceutically acceptable acids, bases or buffers to enhance the stability of the formulated compound or the delivery form. The term parenteral as used herein includes subcutaneous, intracutaneous, intravenous, intramuscular, intra-articular, intra-arterial, interasynovial, intrasternal, interathecal, intralesional, and intracranial injection or infusion techniques.

In certain embodiments, compounds disclosed herein can be delivered orally. Suitable dosage ranges for oral administration can depend on the potency of the compounds, but generally can range from 0.1 mg to 20 mg of a compound per kilogram of body weight. Appropriate dosages can be in the range of 25 to 500 mg/day and the dose of compounds administered can be adjusted to provide an equivalent molar quantity of compound in the plasma of a subject. Dosage ranges can be readily determined by methods known to those skilled in the art.

A dosage can be delivered in a composition by a single administration, by multiple applications, by sustained release or by controlled sustained release, or any other appropriate intervals and/or rates of release.

Chemical entities of the present disclosure can be assayed in vitro and in vivo, for the desired therapeutic or prophylactic activity prior to therapeutic use in mammals. For example, in vitro assays can be used to determine whether administration of a specific compound of the present disclosure or a combination of such compounds is effective for inhibiting the activity of certain ATP-utilizing enzymes or treating at least one disease. Chemical entities of the present disclosure can also be demonstrated to be effective and safe using animal model systems. A therapeutically effective dose of at least one chemical entity of the present disclosure can, in certain embodiments, provide therapeutic benefit without causing substantial toxicity. Toxicity of chemical entities of the present disclosure can be determined using standard pharmaceutical procedures and can be readily ascertained by the skilled artisan. The dose ratio between toxic and therapeutic effect is the therapeutic index. Chemical entities of the present disclosure can exhibit high therapeutic indices in treating diseases and disorders. The dosage of a compound of the present present disclosure can be within a range of circulating concentrations that include an effective dose with little or no toxicity.

When employed as pharmaceuticals, chemical entities of the present disclosure can be administered in the form of pharmaceutical compositions. Such compositions can be prepared in a manner well known in the pharmaceutical art and can comprise at least one chemical entity of the present disclosure.

Pharmaceutical compositions of the present disclosure can comprise a therapeutically effective amount of at least one chemical entity of the present disclosure, and at least one pharmaceutically acceptable vehicle. Pharmaceutical compositions of the present disclosure can additionally comprise at least addional compound that enhances the therapeutic efficacy of one or more chemical entities of the present disclosure. For example, such compounds can enhance the therapeutic efficacy of chemical entities of the present disclosure by effectively increasing the plasma concentration of the compounds. Without being limited by theory, certain compound can decrease the degradation of the chemical entities of the present disclosure prior to administration or during transport to the plasma, or within the plasma. Certain compounds can increase the plasma concentration by increasing the absorption of compounds in the gastrointestinal tract. Pharmaceutical compositions of the present disclosure can also include additional therapeutic agents that are normally administered to treat a disease or disorder.

In certain embodiments, a pharmaceutical composition can include at least one chemical entity of the present disclosure and at least one additional therapeutic agent appropriate for effecting combination therapy.

In some embodiments, chemical entities and compositions of the present disclosure can be administered by oral routes. The compositions can be prepared in a manner well known in the pharmaceutical art and can comprise at least one chemical entity of the present disclosure. In some embodiments, compositions of the present disclosure contain a therapeutically effective amount of at least one chemical entity of the present disclosure, which can be in purified form, together with a therapeutically effective amount of at least one additional therapeutic agent, and a suitable amount of at least one pharmaceutically acceptable excipient, so as to provide the form for proper administration to a subject Some embodiments of the present disclosure are directed to compositions that contain, as the active ingredient, of one or more chemical entities of the present disclosure associated with pharmaceutically acceptable excipients. In making certain compositions of the present disclosure, the active ingredient can be mixed with an excipient, diluted by an excipient, or enclosed within such a carrier that can be in the form of a capsule, sachet, paper or other container. When the excipient serves as a diluent, the excipient can be a solid, semi-solid, or liquid material, which acts as a vehicle, carrier or medium for the active ingredient. Thus, for example, the compositions can be in the form of tablets, pills, powders, lozenges, sachets, cachets, elixirs, suspensions, emulsions, solutions, and syrups containing, for example, from 1% to 90% by weight of at least one chemical entities of the present disclosure using, for example, soft and hard gelatin capsules.

In preparing a composition, it can be necessary to mill the active compound to provide the appropriate particle size prior to combining with other ingredients. If the active compound is insoluble, the active component ordinarily can be milled to a particle size of less than 200 mesh. If the active compound is water soluble, the particle size can be adjusted by milling to provide a uniform distribution in the formulation, e.g. 40 mesh.

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, modified cyclodextrins, cellulose, water, syrup, and methyl cellulose. Some compositions can additionally include, lubricating agents such as talc, magnesium stearate, and mineral oil, wetting agents, emulsifying and suspending agents, preserving agents such as methyl- and propylhydroxy-benzoates, sweetening agents, and flavoring agents. Compositions of the present disclosure can be formulated so as to provide quick, sustained or delayed release of the active ingredient after administration to the subject by employing procedures known in the art.

Some compositions of the present disclosure can be formulated in unit dosage form, each dosage containing, for example, 0.1 mg to 2 g of the active ingredient. As used herein, "unit dosage forms" refers to physically discrete units suitable as unitary dosages for human subjects and other mammals, each unit containing a predetermined quantity of active material calculated to produce the desired therapeutic effect, in association with a suitable pharmaceutical excipient, diluent, carrier and/or adjuvant. In certain embodiments, compositions of the present disclosure can be formulated in multiple dosage forms. The amount of the chemical entities of the present disclosure that can be combined with other materials and therapeutic agents to produce compositions of the present disclosure in a single dosage form will vary depending upon the subject and the particular mode of administration.

In the treatment of disease, chemical entities of the present disclosure can be administered in a therapeutically effective amount. It will be understood, however, that the amount of the compound administered will be determined by a physician, in the light of the relevant circumstances, including the condition to be treated, the chosen route of administration, the actual compound administered, the age, weight, and response of the individual subject, the severity of the subject's symptoms, and the like.

For preparing solid compositions such as tablets, the principal active ingredient can be mixed with a pharmaceutical excipient to form a solid preformulation composition containing a homogeneous mixture of a compound of the present present disclosure. When referring to these preformulation compositions as homogeneous, it is meant that the active ingredient is dispersed evenly throughout the composition so that the composition may be readily subdivided into equally effective unit dosage forms such as tablets, pills and capsules. The solid preformulation can then subdivided into unit dosage forms of the type described above containing from, for example, 0.1 mg to 2 g of the therapeutically effective compound of the present present disclosure.

The tablets or pills comprising certain compositions of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials include a number of polymeric acids and mixtures of polymeric acids with such materials as shellac, cetyl alcohol, and cellulose acetate.

The liquid forms in which the compositions of the present disclosure may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

As used herein, a "pharmaceutically acceptable derivative or prodrug" refers to any pharmaceutically acceptable salt, ester, salt of an ester or other derivative of a compound of the present disclosure that, upon administration to a recipient, is capable of providing, either directly or indirectly, a compound of the present disclosure or an inhibitory active metabolite or residue thereof. Examples of such derivates or prodrugs include those that increase the bioavailability of the chemical entities of the present disclosure when such compounds are administered to a mammal, e.g., by allowing an orally administered compound to be more readily absorbed into the blood, or which enhance delivery of the parent compound to a biological compartment, e.g., the brain or lymphatic system, relative to the parent species.

In certain embodiments, acceptable formulation materials can be nontoxic to recipients at the dosages and concentrations employed.

In certain embodiments, a pharmaceutical composition of the present disclosure can contain formulation materials for modifying, maintaining, or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids such as glycine, glutamine, asparagine, arginine or lysine; antimicrobials; antioxidants such as ascorbic acid, sodium sulfite, or sodium hydrogen-sulfite; buffers such as borate, bicarbonate, Tris-HCl, citrates, phosphates or other organic acids; bulking agents such as mannitol or glycine; chelating agents such as ethylenediamine tetraacetic acid (EDTA); complexing agents such as caffeine, polyvinylpyrrolidone, beta-cyclodextrin, hydroxypropyl-beta-cyclodextrin, or sulfobutyl ether β-cyclodextrin; fillers; monosaccharides; disaccharides; and other carbohydrates such as glucose, mannose, or dextrins; proteins such as serum albumin, gelatin or immunoglobulins; coloring, flavoring and diluting agents; emulsifying agents; hydrophilic polymers such as polyvinylpyrrolidone; low molecular weight polypeptides; salt-forming counterions such as sodium; preservatives such as benzalkonium chloride, benzoic acid, salicylic acid, thimerosal, phenethyl alcohol, methylparaben, propylparaben, chlorhexidine, sorbic acid or hydrogen peroxide; solvents such as glycerin, propylene glycol or polyethylene glycol; sugar alcohols such as mannitol or sorbitol; suspending agents; surfactants or wetting agents such as pluronics, PEG, sorbitan esters, polysorbates such as polysorbate 20, polysorbate 80, triton, tromethamine, lecithin, cholesterol, tyloxapal; stability enhancing agents such as sucrose or sorbitol; tonicity enhancing agents such as alkali metal halides, such as sodium or potassium chloride, mannitol, sorbitol; delivery vehicles; diluents; excipients and/or pharmaceutical adjuvants (Remington's Pharmaceutical Sciences, 18$^{th}$ Edition, A.R. Gennaro, ed., Mack Publishing Company (1990)).

In certain embodiments, the optimal pharmaceutical composition can be determined by one skilled in the art depending upon, for example the intended route of administration, delivery format, and desired dosage. See, for example, Remington's Pharmaceutical Sciences, supra. In certain embodiments, such compositions may influence the physical state, stability, rate of in vivo release, and rate of in vivo clearance of the antibodies of the present disclosure.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, neutral buffered saline or saline mixed with serum albumin are further exemplary vehicles. In certain embodiments, pharmaceutical compositions comprise Tris buffer of pH 7 to 8.5, or acetate buffer of pH 4 to 5.5, which can further comprise sorbitol or a suitable substitute thereof. In certain embodiments, buffers are used to maintain the composition at physiological pH or at a slightly lower pH, typically within a pH range of from 5 to 8.

In certain embodiments, pharmaceutical compositions of the present disclosure can be selected for parenteral delivery. In other embodiments, compositions can be selected for inhalation or for delivery through the digestive tract, such as orally. The preparation of such pharmaceutically acceptable compositions is within the skill of the art.

In certain embodiments, composition components can be present in concentrations that are acceptable to the site of administration. In certain embodiments, when parenteral administration is contemplated, a therapeutic composition can be in the form of a pyrogen-free, parenterally acceptable aqueous solution comprising at least one chemical entity of the present disclosure, with or without additional therapeutic agents, in a pharmaceutically acceptable vehicle. In other embodiments, a vehicle for parenteral injection can be sterile distilled water in which at least one chemical entity of the present disclosure, with or without at least one additional therapeutic agent, is formulated as a sterile, isotonic solution, properly preserved. In still other embodiments, the pharmaceutical composition can include encapsulation of at least one chemical entity of the present disclosure with an agent, such as injectable microspheres, bio-erodible particles, polymeric compounds such as polyacetic acid or polyglycolic acid, beads or liposomes, that can provide the controlled or sustained release of the compound of the present disclosure which can then be delivered via a depot injection. In certain embodiments, implantable drug delivery devices can be used to introduce a compound of the present disclosure to the plasma of a subject, within a target organ, or to a specific site within the subject's body.

In certain embodiments, a pharmaceutical composition can be formulated for inhalation. In certain embodiments, a compound of the present disclosure, with or without at least one additional therapeutic agent, can be formulated as a dry powder for inhalation. In certain embodiments, an inhalation solution comprising a compound of the present disclosure with or without at least one additional therapeutic agent can be formulated with a propellant for aerosol delivery. In other embodiments, solutions can be nebulized. In still other embodiments, solutions, powders or dry films of chemical entities of the present disclosure can be aerosolized or vaporized for pulmonary delivery.

In certain embodiments, it is contemplated that formulations can be administered orally. In certain embodiments, a compound of the present disclosure, with or without at least one additional therapeutic agent that can be administered orally, can be formulated with or without carriers customarily used in the compounding of solid dosage forms such as tablets and capsules. In other embodiments, a capsule may be designed to release the active portion of the formulation in the region of the gastrointestinal tract where bioavailability can be maximized and pre-systemic degradation minimized. In still other embodiments, at least one additional agent can be included in the formulation to facilitate absorption of the compound of the present disclosure and/or any additional therapeutic agents into the systemic circulation. In certain embodiments, diluents, flavorings, low melting point waxes, vegetable oils, lubricants, suspending agents, tablet disintegrating agents, and binders can be employed.

In certain embodiments, a pharmaceutical composition of the present disclosure can include an effective quantity of chemical entities of the present disclosure, with or without at least one additional therapeutic agent, in a mixture with at least one pharmaceutically acceptable vehicle suitable for the manufacture of tablets. In certain embodiments, by dissolving the tablets in sterile water, or other appropriate vehicle, solutions can be prepared in unit-dose form. In certain embodiments, suitable excipients include inert diluents, such as calcium carbonate, sodium carbonate or bicarbonate, lactose, or calcium phosphate; or binding agents, such as starch, gelatin, or acacia; and lubricating agents such as magnesium stearate, stearic acid or talc.

In certain embodiments, the frequency of dosing will take into account the pharmacokinetic parameters of the chemical entities of the present disclosure and/or any additional therapeutic agents in the pharmaceutical composition used. In certain embodiments, a clinician can administer the composition until a dosage is reached that achieves the desired effect. The composition can be administered as a single dose, or as two or more doses, which may or may not contain the same amount of the therapeutically active compound time, or as a continuous infusion via an implantation device or catheter. Further refinement of an appropriate dosage can be routinely made by those of ordinary skill in the art. For example, therapeutically effective amounts and regimens can be determined through use of appropriate dose-response data.

In certain embodiments, the route of administration of the pharmaceutical composition can be in accord with known methods, e.g. orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions can be administered by bolus injection or continuously by infusion, or by an implantation device.

In certain embodiments, the composition can be administered locally via implantation of a membrane, sponge or another appropriate material onto which the desired compound of the present disclosure has been absorbed or encapsulated. In certain embodiments, where an implantation device is used, the device can be implanted into any suitable tissue or organ, and delivery of the desired molecule via diffusion, timed-release bolus, or continuous administration.

In certain embodiments, it can be desirable to use a pharmaceutical composition comprising a compound of the present disclosure, with or without at least one additional therapeutic agent, in an ex vivo manner. For example, cells, tissues and/or organs that have been removed from a subject are exposed to a pharmaceutical composition comprising a compound of the present disclosure, with or without at least one additional therapeutic agent, after which the cells, tissues and/or organs are subsequently implanted back into the subject.

Pharmaceutical compositions according to the present disclosure can take a form suitable for oral, buccal, parenteral, nasal, topical or rectal administration, or a form suitable for administration by inhalation or insufflation.

The compositions of the present disclosure can, if desired, be presented in a pack or dispenser device that can contain one or more unit dosage forms containing the active ingredient. The pack or dispensing device can be accompanied by instructions for administration.

The quantity of a compound of the present disclosure required for the treatment of a particular condition can vary depending on the compound, and the condition of the subject to be treated. In general, daily dosages can range from 100 ng/kg to 100 mg/kg, e.g., 0.01 mg/kg to 40 mg/kg body weight, for oral or buccal administration; from 10 ng/kg to 50 mg/kg body weight, e.g., 0.001 mg/kg to 20 mg/kg body weight, for parenteral administration; and from 0.05 mg to 1,000 mg for nasal administration or administration by inhalation or insufflation.

Certain chemical entities of the present disclosure and/or compositions of the present disclosure can be administered as sustained release systems. In certain embodiments, the chemical entities of the present disclosure can be delivered by oral sustained release administration. In this embodiment, the chemical entities of the present disclosure can be administered, for example, twice per day and, once per day.

The chemical entities of the present disclosure can be practiced with a number of different dosage forms, which can be adapted to provide sustained and/or extended release of a compound upon oral administration. Examples of sustained and/or extended release dosage forms include, but are not limited to, beads comprising a dissolution or diffusion release compositon and/or structure, an oral sustained release pump, enteric-coated preparations, compound-releaseing lipid matrices, compound releasing waxes, osmotic delivery systems, bioerodible polymer matrices, diffusible polymer matrices, a plurality of time-release pellets, and osmitic dosage forms.

Regardless of the specific form of sustained release oral dosage form used, the compounds and composition of the present disclosure can be released from the dosage form over an extended period of time. In certain embodiments, sustained release oral dosage forms can provide a therapeutically effective amount of a compound of the present disclosure over a period of at least several hours. In certain embodiments the extended release dosage form can provide a constant therapeutically effective concentration of a compound of the present disclosure in the plasma of a subject for a prolonged period of time, such as at least several hours. In other embodiments, the sustained release oral dosage form can provide a controlled and constant concentration of a therapeutically effective amount of a compound of the present disclosure in the plasma of a subject.

Dosage forms comprising compositions and chemical entities of the present disclosure can be administered at certain intervals such as, for example, twice per day or once per day.

Exemplary dosage ranges for oral administration are dependent on the potency of the compound of the present disclosure, but can range from 0.1 mg to 20 mg of the compound per kilogram of body weight. Dosage ranges may be readily determined by methods known to those skilled in the art.

Also provided are packaged pharmaceutical formulations. Such packaged formulations include a pharmaceutical composition comprising at least one chemical entity of the present disclosure, and instructions for using the composition to treat a mammal (typically a human patient). In some embodiments, the instructions are for using the pharmaceutical composition to treat a patient suffering from a disease responsive to inhibition at least one ATP-utilizing enzyme, such as a human protein kinase, for example AKT1, AKT2, AMP kinase, AXL, AURORA-A, BMX, CDK2/cyclinA, CDK2/cyclinE, CHEK1, CHEK2, CK2, DYRK2, EGFR, EPHB4, FLT3, GSK3-α, GSK3-β, IGF1R, INSR, KDR, KIT, MAPKAPK2, MAPKAPK3, MET, MSK2, NEK2, P70S6K1, PAK2, PDGFR-α, PDK1, PIM1 kinase, PLK1, ROCK2, RSK2, SYK, TIE2, TRKB, and ZAP70. Also provided is prescribing information; for example, to a patient or health care provider, or as a label in a packaged pharmaceutical formulation. Prescribing information may include for example efficacy, dosage and administration, contraindication and adverse reaction information pertaining to the pharmaceutical formulation.

Chemical entities of the present disclosure can be assayed in vitro and in vivo, to determine and optimize therapeutic or prophylactic activity prior to use in subjects. For example, in vitro assays can be used to determine whether administration of a specific compound of the present disclosure or a combination of such compounds exhibits therapeutic efficacy. Chemical entities of the present disclosure can also be demonstrated to be effective and safe using animal model systems.

It is desirable that a therapeutically effective dose of a compound of the present disclosure provide therapeutic benefit without causing substantial toxicity. Toxicity of chemical entities of the present disclosure can be determined using standard pharmaceutical procedures and can be readily ascertained by the skilled artisan. The dose ratio between toxic and therapeutic effect is the therapeutic index. In certain embodiments, chemical entities of the present disclosure can exhibit particularly high therapeutic indices in treating diseases and disorders. In certain embodiments, the dosage of a compound of the present disclosure can be within a range of circulating concentration that exhibits therapeutic efficacy with limited or no toxicity.

EXAMPLES

Embodiments of the present disclosure can be further defined by reference to the following examples, which describe in detail preparation of chemical entities of the present disclosure and assays for using chemical entities of the present disclosure. It will be apparent to those skilled in the art that many modifications, both to materials and methods, may be practiced without departing from the scope of the present disclosure.

In the examples below, the following abbreviations have the following meanings. If an abbreviation is not defined, it has its generally accepted meaning.

AcOH=acetic acid
Atm=atmosphere
ATP=adenosine triphosphate
Boc=tert-butyloxycarbonyl
br=broad
BSA=bovine serum albumin
d=doublet
Da=Dalton
dd=doublet of doublets
DMF=N,N-dimethylformamide
DMSO=dimethylsulfoxide
DTT=(R,R)-dithiothreitol
EDTA=ethylenediaminetetraacetic acid
ESI=electrospray ionization
EtOAc=ethyl acetate
EtOH=ethanol
FMOC=fluorenylmethoxycarbonyl
g=gram
HCl=hydrochloric acid
h=hour
HEPES=[4-(2-hydroxyethyl)-1-piperazineethanesulfonic acid
HPLC=high performance liquid chromatography
HTS=high throughput screen
Hz=hertz
i-PrOH=isopropanol
J=coupling constant
kDa=kilodalton
$K_2CO_3$=potassium carbonate
L=liter
LC/MS=liquid chromatography/mass spectroscopy
M=molar
MeOH=methanol
$MgSO_4$=magnesium sulfate
MHz=megahertz
mg=milligram
min=minute
mL=milliliter
mm=millimeter
mmol=millimoles
mM=millimolar
MS=mass spectroscopy
m/z=mass to charge ratio
nM=nanomolar
NMR=nuclear magnetic resonance
$NaHCO_3$=sodium bicarbonate
NaOH=sodium hydroxide
NMP=N-methylpyrrolidinone
psi=pounds per square inch
RT=room temperature
s=singlet
t=triplet
TCB=trough circulating buffer
THF=tetrahydrofuran
TFA=trifluoroacetic acid
TLC=thin layer chromatography
TMS=trimethylsilyl
UV=ultraviolet
v/v=volume to volume
w=watt
μL=microliter
μM=micromolar Method 1

General Procedure for Solid Phase Parallel Synthesis

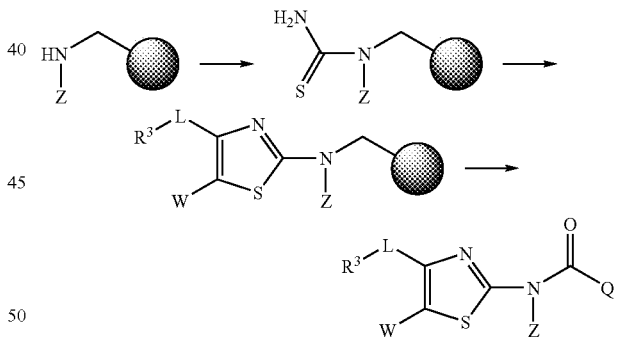

SynPhase™ aminomethylated (TFA salt) lanterns (60 units, 2.28 mmol) were placed in a plastic container (100 mL) with a cap and allowed to swell in NMP (50 mL) for 30 min. A mixture of benzotriazole-1-yloxy-tris(dimethylamino) phosphonium hexafluorophosphate (1512 mg, 3.42 mmol), (3-formyl-1-indolyl)acetic acid (720 mg, 3.42 mmol) and 1-hydroxybenzotriazole (280 mg, 5.7 mmol) was added, followed by N,N-diisopropylethylamine (1190 μL, 6.84 mmol). The container was shaken overnight at room temperature, and then the liquid was removed. The lanterns were washed with DMF (2×100 mL), MeOH (100 mL), and dichloromethane (3×100 mL), then dried under vacuum at room temperature.

The lanterns were split into 6 sets with 9 units (0.342 mmol) in each set. Each set was placed in a plastic syringe (20 mL) with a plastic frit and allowed to swell in a mixture of DMF/EtOH (3:1, 10 mL). The appropriate amine (3.42 mmol) and borane-pyridine complex (318 mg, 3.42 mmol) were added to each syringe. Syringes were equipped with plungers and caps, and were shaken overnight at room temperature. The liquid was removed, and the lanterns were washed with DMF (2×10 mL), MeOH (10 mL), and dichloromethane (3×10 mL), then allowed to swell in dichloromethane (10 mL). FMOC-isothiocyanate (578 mg, 2.05 mmol) was added to each syringe. Syringes were equipped with plungers and caps, and were shaken overnight at room temperature. The liquid was removed, and the lanterns were washed with DMF (2×10 mL), MeOH (10 mL), and dichloromethane (3×10 mL), then treated with a solution of 20% piperidine in DMF (10 mL) for 20 min at room temperature. The liquid was removed, and the lanterns were treated again with a solution of 20% piperidine in DMF (10 mL) for 20 min at room temperature. The liquid was removed, and the lanterns were washed with DMF (2×10 mL), MeOH (10 mL), and dichloromethane (3×10 mL), then dried under vacuum at room temperature.

Each set was split into 3 subsets with 3 units (0.114 mmol) in each subset. Each subset was placed in a plastic syringe (50 mL) with a plastic frit and allowed to swell in dioxane (10 mL). The appropriate bromomethyl ketone (6.84 mmol) was added to each syringe. Syringes were equipped with plungers and caps, and were shaken overnight at room temperature. The liquid was removed, and the lanterns were washed with DMF (2×10 mL), MeOH (10 mL), and dichloromethane (3×10 mL), then dried under vacuum at room temperature.

The lanterns were distributed into a 96-deep well polypropylene plate (one unit per well) and treated with 60% TFA/dichloromethane (400 μL per well) for 2 h at room temperature, and the solvents were removed under vacuum. The well content was extracted with N,N-dimethylacetamide (500 μL per well) by agitation for 16 h at room temperature. The resulting solution from each well was transferred to a 96-deep well polypropylene plate and concentrated under vacuum. The residue from each well was dissolved in MeOH (100 μL) and treated with 1M HCl/ether (500 μL). The plate was centrifuged, the liquids were removed, and the precipitated solid residues were dried in vacuum to give hydrochloric salts of the crude intermediate amines.

The crude intermediate amines were dissolved in a mixture of dichloromethane/N,N-dimethylacetamide (2:1, 150 μL) followed by addition of N,N-diisopropylethylamine (13 μL, 0.076 mmol) and the appropriate acid chloride (0.057 mmol). The reaction mixture was maintained for 2 h at room temperature then concentrated under vacuum. The resulting residue was dissolved in DMSO (200 μL) and subjected to HPLC purification (Method Z) to provide the desired acylated products.

Example 1

N-(4-(3,4-Dimethoxyphenyl)thiazol-2-yl)-N-(3-morpholinopropyl)thiophene-2-carboxamide A mixture of 2-bromo-1-(3,4-dimethoxyphenyl)ethanone (259 mg, 1 mmol) and (3-morpholin-4-yl-propyl)-thiourea (203 mg, 1 mmol) in dry dioxane (10 mL) was heated at reflux for 1 h, and then cooled to room temperature. Evaporation of solvent provided the crude aminothiazole as a colorless oil.

A mixture of the crude aminothiazole, N,N-diisopropylethylamine (522 μL, 3 mmol) and 2-thiophenecarbonyl chloride (220 μL, 1.5 mmol) in dichloromethane (3 mL) was maintained at room temperature for 16 h. The reaction mixture was concentrated in vacuo, the resulting residue was dissolved in DMSO (2 mL), and purified by HPLC (Method Y). Fractions containing the desired product were combined and concentrated in vacuo. The residue was dissolved in MeOH (1 mL) and 1M HCl/ether (50 mL) was added. The resulting precipitate was filtered and dried in vacuo to provide the title compound (382 mg, 75%) as an off-white solid as the hydrochloride salt. LC/MS (ESI) m/z 474.3 [M+H]. HPLC retention time (Method A)=2.59 min. $^1$H NMR (DMSO-$d_6$) δ 2.36 (m, 2H), 3.04 (m, 2H), 3.23 (m, 2H), 3.40 (m, 3H), 3.76 (m, 1H), 3.79 (s, 3H), 3.85 (s, 3H), 3.91 (br d, J=12.1 Hz, 2H), 4.44 (t, J=7.3 Hz, 2H), 7.00 (d, J=8.4 Hz, 1H), 7.23 (dd, J=4.7, 4.0 Hz, 1H), 7.49 (d, J=1.8 Hz, 1H), 7.53 (dd, J=8.2, 1.8 Hz, 1H), 7.68 (d, J=3.4 Hz, 1H), 7.73 (s, 1H), 7.98 (d, J=4.9 Hz, 1H).

Example 2

N-(4-(Benzofuran-2-yl)thiazol-2-yl)-N-(3-morpholinopropyl)thiophene-2-carboxamide A mixture of 1-(benzofuran-2-yl)-2-bromoethanone (239 mg, 1 mmol) and (3-morpholin-4-yl-propyl)-thiourea (203 mg, 1 mmol) in dry dioxane (10 mL) was heated at reflux for 1 h, and then cooled to room temperature. Evaporation of solvent provided the crude aminothiazole as a colorless oil.

A mixture of the crude intermediate, N,N-diisopropylethylamine (522 μL, 3 mmol) and 2-thiophenecarbonyl chloride (220 μL, 1.5 mmol) in dichloromethane (3 mL) was maintained at room temperature for 16 h. The reaction mixture was concentrated in vacuo, and the resulting residue was dissolved in DMSO (2 mL), and purified by HPLC (Method Y). Fractions containing the desired product were combined and concentrated in vacuo. The residue was dissolved in MeOH (1 mL) and 1M HCl/ether (50 mL) was added. The resulting precipitate was filtered and dried in vacuo to provide the title compound (303 mg, 62%) as an off-white solid as the hydrochloride salt. LC/MS (ESI) m/z 454.3 [M+H]. HPLC retention time (Method A)=3.02 min. $^1$H NMR (500 MHz, $CD_3OD$) δ 2.39 (m, 2H), 3.17-3.95 (br m, 10H), 4.54 (t, J=7.2 Hz, 2H), 7.18 (dd, J=5.0, 3.8 Hz, 1H), 7.37 (m, 2H), 7.57 (m, 2H), 7.67 (s, 1H), 7.80 (dd, J=5.0, 1.0 Hz, 1H), 8.02 (dd, J=7.0, 1.4 Hz, 1H), 8.29 (s, 1H).

Example 3

N-(3-Morpholinopropyl)-N-(4-phenylthiazol-2-yl) thiophene-2-carboxamide

A mixture of 2-bromoacetophenone (60 mg, 0.3 mmol) and (3-morpholin-4-yl-propyl)-thiourea (61 mg, 0.3 mmol) in dry ethanol (3 mL) was heated at reflux for 10 min, cooled to room temperature, and concentrated in vacuo. The resulting residue was suspended in dichloromethane (3 mL) followed by the addition of N,N-diisopropylethylamine (105 μL, 0.6 mmol) and thiophene-2-carbonyl chloride (34 μL, 0.32 mmol). The reaction mixture was maintained at room temperature overnight, then concentrated in vacuo. The resulting residue was dissolved in DMSO (1.5 mL) and subjected to HPLC purification (Method Y). The resulting free amine was dissolved in MeOH (1 mL) and 1M HCl/ether (50 mL) was added. The precipitate was filtered and dried in vacuo to provide the title compound (67 mg) as an off-white solid as the hydrochloride salt. LC/MS (ESI) m/z 413.9 [M+H]. HPLC retention time (Method A)=2.78 min.

Example 4

N-(4-(3-Chlorophenyl)thiazol-2-yl)-N-(3-morpholinopropyl)thiophene-2-carboxamide A mixture of 3-chlorophenacyl bromide (467 mg, 2 mmol) and (3-morpholin-4-yl-propyl)-thiourea (407 mg, 2 mmol) in dry ethanol (4 ml) was heated at reflux for 2 min, cooled to room temperature, and concentrated in vacuo. The resulting residue was suspended in dichloromethane (5 mL) followed by the addition of N,N-diisopropylethylamine (554 µL, 3 mmol) and thiophene-2-carbonyl chloride (160 µL, 1.5 mmol). The reaction mixture was maintained at room temperature overnight, then concentrated in vacuo. The resulting residue was dissolved in DMSO (3 mL) and subjected to HPLC purification (Method Y). The resulting free amine was dissolved in MeOH (2 mL) and 1M HCl/ether (75 mL) was added. The precipitate was filtered and dried in vacuo to provide the title compound (367 mg) as an off-white solid as the hydrochloride salt. LC/MS (ESI) m/z 447.9 [M+H]. HPLC retention time (Method A)=2.95 min.

Example 5

N-(4-(5-Chlorothiophen-2-yl)thiazol-2-yl)-N-(3-morpholinopropyl)thiophene-2-carboxamide A mixture of 2-bromo-1-(5-chloro-thiophen-2-yl)-ethanone (72 mg, 0.3 mmol) and (3-morpholin-4-yl-propyl)-thiourea (61 mg, 0.3 mmol) in dry ethanol (3 ml) was heated at reflux for 10 min, cooled to room temperature, and concentrated in vacuo. The resulting residue was suspended in dichloromethane (3 mL) followed by the addition of N,N-diisopropylethylamine (105 µL, 0.6 mmol) and thiophene-2-carbonyl chloride (34 µL, 0.32 mmol). The reaction mixture was maintained at room temperature overnight, then concentrated in vacuo. The resulting residue was dissolved in DMSO (1.5 mL) and subjected to HPLC purification (Method Y). The resulting free amine was dissolved in MeOH (1 mL) and 1M HCl/ether (50 mL) was added. The precipitate was filtered and dried in vacuo to provide the title compound (61 mg) as an yellow solid as the hydrochloride salt. LC/MS (ESI) m/z 453.9 [M+H]. HPLC retention time (Method A)=2.93 min.

Example 6

Methyl 4-(2-(N-(3-morpholinopropyl)thiophene-2-carboxamido)thiazol-4-yl)benzoate A mixture of 4-(2-bromo-acetyl)-benzoic acid methyl ester (77 mg, 0.3 mmol) and (3-morpholin-4-yl-propyl)-thiourea (61 mg, 0.3 mmol) in dry ethanol (3 mL) was heated at reflux for 10 min, cooled to room temperature, and concentrated in vacuo. The resulting residue was suspended in dichloromethane (3 mL) followed by the addition of N,N-diisopropylethylamine (105 µL, 0.6 mmol) and thiophene-2-carbonyl chloride (34 µL, 0.32 mmol). The reaction mixture was maintained at room temperature overnight, then concentrated in vacuo. The resulting residue was dissolved in DMSO (1.5 mL) and subjected to HPLC purification (Method Y). The resulting free amine was dissolved in MeOH (1 mL) and 1M HCl/ether (50 mL) was added. The precipitate was filtered and dried in vacuo to provide the title compound (52 mg) as an off-white solid as the hydrochloride salt. LC/MS (ESI) m/z 472.3 [M+H]. HPLC retention time (Method A)=2.80 min.

Example 7

N-(4-(2,3-Dihydrobenzo[b][1,4]dioxin-6-yl)thiazol-2-yl)-N-(3-morpholinopropyl)thiophene-2-carboxamide A mixture of 3,4-(ethylenedioxy)phenacyl bromide (77 mg, 0.3 mmol) and (3-morpholin-4-yl-propyl)-thiourea (61 mg, 0.3 mmol) in dry ethanol (3 mL) was heated at reflux for 10 min, cooled to room temperature, and concentrated in vacuo. The resulting residue was suspended in dichloromethane (3 mL) followed by the addition of N,N-diisopropylethylamine (105 µL, 0.6 mmol) and thiophene-2-carbonyl chloride (34 µL, 0.32 mmol). The reaction mixture was maintained at room temperature overnight, then concentrated in vacuo. The resulting residue was dissolved in DMSO (1.5 mL) and subjected to HPLC purification (Method Y). The resulting free amine was dissolved in MeOH (1 mL) and 1M HCl/ether (50 mL) was added. The precipitate was filtered and dried in vacuo to provide the title compound (72 mg) as an off-white solid as the hydrochloride salt. LC/MS (ESI) m/z 472.3 [M+H]. HPLC retention time (Method A)=2.72 min.

Example 8

N-(4-(2,4-Dimethoxyphenyl)thiazol-2-yl)-N-(3-morpholinopropyl)thiophene-2-carboxamide A mixture of 2-bromo-2',4'-dimethoxyacetophenone (156 mg, 0.6 mmol) and (3-morpholin-4-yl-propyl)-thiourea (122 mg, 0.6 mmol) in dry dioxane (5 ml) was heated at 80° C. for 2 h, cooled to room temperature, and concentrated in vacuo. The resulting residue was suspended in dichloromethane (5 mL) followed by the addition of N,N-diisopropylethylamine (209 µL, 1.2 mmol) and thiophene-2-carbonyl chloride (96 µL, 0.9 mmol). The reaction mixture was maintained at room temperature overnight, then concentrated in vacuo. The resulting residue was dissolved in DMSO (2.5 mL) and subjected to HPLC purification (Method Y). The resulting free amine was dissolved in MeOH (1 mL) and 2M HCl/ether (50 mL) was added. The precipitate was filtered and dried in vacuo to provide the title compound (207 mg) as an yellow solid as the hydrochloride salt. LC/MS (ESI) m/z 474.3 [M+H]. HPLC retention time (Method A)=2.81 min.

Example 9

N-(3-Morpholinopropyl)-N-(4-(3-phenylisoxazol-5-yl)thiazol-2-yl)thiophene-2-carboxamide A mixture of 2-bromo-1-(3-phenylisoxazol-5-yl)ethan-1-one (160 mg, 0.6 mmol) and (3-morpholin-4-yl-propyl)-thiourea (122 mg, 0.6 mmol) in dry dioxane (5 ml) was heated at 80° C. for 2 h, cooled to room temperature, and concentrated in vacuo. The resulting residue was suspended in dichloromethane (5 mL) followed by the addition of N,N-diisopropylethylamine (209 µL, 1.2 mmol) and thiophene-2-carbonyl chloride (96 µL, 0.9 mmol). The reaction mixture was maintained at room temperature overnight, then concentrated in vacuo. The resulting residue was dissolved in DMSO (2.5 mL) and subjected to HPLC purification (Method Y). The resulting free amine was dissolved in MeOH (1 mL) and 1M HCl/ether (50 mL) was added. The precipitate was filtered and dried in vacuo to provide the title compound (155 mg) as an off-white solid as the hydrochloride salt. LC/MS (ESI) m/z 481.1 [M+H]. HPLC retention time (Method B)=2.94 min.

Example 10

N-(4-(5-Methyl-1-phenyl-1H-pyrazol-4-yl)thiazol-2-yl)-N-(3-morpholinopropyl)thiophene-2-carboxamide A mixture of 2-bromo-1-(5-methyl-1-phenyl-1H-pyrazol-4-yl)-1-ethanone (167 mg, 0.6 mmol) and (3-morpholin-4-yl-propyl)-thiourea (122 mg, 0.6 mmol) in dry dioxane (5 ml) was heated at 80° C. for 2 h, cooled to room temperature, and concentrated in vacuo. The resulting residue was suspended in dichloromethane (5 mL) followed by the addition of N,N-diisopropylethylamine (209 μL, 1.2 mmol) and thiophene-2-carbonyl chloride (96 μL, 0.9 mmol). The reaction mixture was maintained at room temperature overnight, then concentrated in vacuo. The resulting residue was dissolved in DMSO (2.5 mL) and subjected to HPLC purification (Method Y). The resulting free amine was dissolved in MeOH (1 mL) and 1M HCl/ether (50 mL) was added. The precipitate was filtered and dried in vacuo to provide the title compound (193 mg) as an yellow solid as the hydrochloride salt. LC/MS (ESI) m/z 494.3 [M+H]. HPLC retention time (Method B)=2.72 min.

Example 11

N-(3-Morpholinopropyl)-N-(4-(5-(pyridin-2-yl)thiophen-2-yl)thiazol-2-yl)thiophene-2-carboxamide A mixture of 2-bromo-1-[5-(2-pyridinyl)-2-thienyl]-1-ethanone (169 mg, 0.6 mmol) (167 mg, 0.6 mmol) and (3-morpholin-4-yl-propyl)-thiourea (122 mg, 0.6 mmol) in dry dioxane (5 ml) was heated at 80° C. for 2 h, cooled to room temperature, and concentrated in vacuo. The resulting residue was suspended in dichloromethane (5 mL) followed by the addition of N,N-diisopropylethylamine (209 μL, 1.2 mmol) and thiophene-2-carbonyl chloride (96 μL, 0.9 mmol). The reaction mixture was maintained at room temperature overnight, then concentrated in vacuo. The resulting residue was dissolved in DMSO (2.5 mL) and subjected to HPLC purification (Method Y). The resulting free amine was dissolved in MeOH (1 mL) and 1M HCl/ether (50 mL) was added. The precipitate was filtered and dried in vacuo to provide the title compound (320 mg) as an off-white solid as the hydrochloride salt. LC/MS (ESI) m/z 497.5 [M+H]. HPLC retention time (Method B)=2.55 min.

Example 12

2-(N-(3-Morpholinopropyl)thiophene-2-carboxamido)-N-(1,3,4-thiadiazol-2-yl)thiazole-4-carboxamide According to the procedure in Example 1, 3-bromopyruvic acid was utilized to give 2-(N-(3-morpholinopropyl)thiophene-2-carboxamido)thiazole-4-carboxylic acid.

A mixture of the acid (990 mg, 2 mmol) and pentafluorophenol (368 mg, 2 mmol) was dissolved in NMP (8 mL) followed by N,N'-diisopropylcarbodiimide (314 μL, 2 mmol). The reaction mixture was maintained at room temperature for 20 min. A portion of the aforementioned mixture (100 μL, 0.02 mmol) was added to a solution of 2-amino-1,3,4-thiazole (2 mg, 0.02 mmol) in NMP (100 μL) and reaction mixture was maintained at room temperature overnight. The resulting reaction mixture was subjected to HPLC purification (Method Z) to provide the desired coupled product (1.1 mg) as a brownish oil as the trifluroacetate salt. LC/MS (ESI) m/z 465.1 [M+H]. HPLC retention time (Method B)=2.22 min.

Example 13

N-(4-(3,4-Dimethoxyphenyl)thiazol-2-yl)-N-(5-morpholinopentyl)thiophene-2-carboxamide A mixture of N-(5-bromopentyl)phthalimide (1.49 g, 5 mmol) and N,N-diisopropylethylamine (870 μL, 5 mmol) was dissolved in NMP (2 mL) followed by morpholine (870 μL, 5.5 mmol). The reaction mixture was stirred at room temperature overnight, the formed precipitate was filtered, and the filtrate evaporated. The crude product was triturated from EtOAc, filtered, and dried in vacuo to provide the alkylated morpholine intermediate (939 mg) as a white solid. The intermediate was dissolved in ethanol (20 mL) then treated with hydrazine hydrate (155 μL, 3.1 mmol). The reaction mixture was heated at reflux for 2 h, cooled to room temperature, and the formed precipitate was filtered. The filtrate was concentrated in vacuo, and the resulting residue was dissolved in chloroform (5 mL) followed by treatment with N-(9-fluorenylmethoxycarbonyl)-isothiocyanate (872 mg, 3.1 mmol) The reaction mixture was maintained at room temperature for 2 h, then concentrated in vacuo. The resulting oil was dissolved in EtOAc (5 mL), treated with piperidine (614 μL, 6.2 mmol), stirred at room temperature for 30 min, and concentrated in vacuo. The resulting residue was dissolved in dichloromethane (10 mL), and the formed precipitate was filtered and dried in vacuo to provide 1-(5-morpholinopentyl)thiourea (287 mg, 58%) as a yellowish amorphous solid.

According to the procedure in Example 1, 2-bromo-1-(3,4-dimethoxyphenyl)ethanone was reacted with 1-(5-morpholinopentyl)thiourea to provide the title compound (1.5 mg) as a colorless thin film. LC/MS (ESI) m/z 502.3 [M+H]. HPLC retention time (Method B)=2.75 min.

Example 14

N-(3-(2-Oxopyrrolidin-1-yl)propyl)-N-(4-(3-phenylisoxazol-5-yl)thiazol-2-yl)thiophene-2-carboxamide A mixture of 1-(3-aminopropyl)-2-pyrrolidinone (560 μL, 4 mmol) and benzoyl isothiocyanate (536 μL, 4 mmol) was dissolved in chloroform (3 mL), stirred at room temperature for 30 min, then concentrated in vacuo. The resulting residue was dissolved in concentrated HCl (3 mL), heated at 95° C. for 2 h, then concentrated in vacuo. The resulting residue was dissolved in water and washed with dichloromethane (2×30 mL), then basified with 2 M NaOH and extracted with dichloromethane (2×30 mL). The combined extracts were dried over $MgSO_4$ and concentrated to provide 1-(3-(2-oxopyrrolidin-1-yl)propyl)thiourea (638 mg) as a pale yellow oil.

According to the procedure in Example 1, 5-(bromoacetyl)-3-phenylisoxazole was reacted with 1-(3-(2-oxopyrrolidin-1-yl)propyl)thiourea to provide the title compound (1.5 mg) as a colorless thin film. LC/MS (ESI) m/z 479.1 [M+H]. HPLC retention time (Method C)=3.59 min.

Example 15

N-(4-(2,6-Dimethoxypyridin-3-yl)thiazol-2-yl)-N-(3-morpholinopropyl)thiophene-2-carboxamide A mixture of 2,6-dimethoxynicotinic acid (1.1 g, 6 mmol) and N,N-diisopropylethylamine (1.01 mL, 6.3 mmol) was dissolved in 1,2-dichloroethane (10 mL), treated with thionyl chloride (460 µL, 6.3 mmol), and stirred at room temperature for 2 h. The reaction mixture was concentrated in vacuo, and the resulting oil was extracted with ether (10 mL). The supernatant was separated and utilized in the next step without any further purification.

The aforementioned ethereal solution of acid chloride was cooled to −30° C., and an ethereal solution of diazomethane (25 mL, 25 mmol) was added dropwise. The reaction mixture was stirred at −30° C. for additional 30 min, and then at 0° C. for 3 h. The reaction mixture was concentrated in vacuo, and the resulting oil was dissolved in THF (5 mL), cooled to 0° C., and treated with 48% HBr (2 mL) dropwise. The reaction mixture was stirred at 0° C. for 20 min., neutralized with saturated aqueous $NaHCO_3$, then extracted with dichloromethane (2×50 mL). The combined organic layers were dried over $Na_2SO_4$ and concentrated in vacuo to provide 2-bromo-1-(2,6-dimethoxypyridin-3-yl)ethanone (1.1 g) as a yellow solid.

According to the procedure in Example 1, 2-bromo-1-(2,6-dimethoxypyridin-3-yl)ethanone was reacted with (3-morpholin-4-yl-propyl)-thiourea to provide the title compound (1.9 mg) as a colorless thin film. LC/MS (ESI) m/z 475.1 [M+H]. HPLC retention time (Method B)=2.87 min.

Example 16

N-(4-(4-(2-(Dimethylamino)ethylcarbamoyl)phenyl)thiazol-2-yl)-N-(3-morpholinopropyl)thiophene-2-carboxamide A mixture of 4-(2-bromoacetyl)benzoic acid (100 mg, 0.41 mmol) and pentafluorophenol (75 mg, 0.41 mmol) was dissolved in THF (1 mL), and cooled to 0° C. N,N'-diisopropylcarbodiimide (64 µL, 0.41 mmol) was added, and the reaction mixture was stirred for 10 min at 0° C., then for an additional 30 min at room temperature. N,N-dimethylethylenediamine (36 mg, 0.41 mmol) was added, and the reaction mixture was stirred at room temperature for 3 h, then concentrated in vacuo. The resulting 4-(2-bromoacetyl)-N-(2-(dimethylamino)ethyl)benzamide was dissolved in dry ethanol (4 mL) and used immediately in the next reaction.

According to the procedure in Example 1, 4-(2-bromoacetyl)-N-(2-(dimethylamino)ethyl)benzamide was reacted with (3-morpholin-4-yl-propyl)-thiourea to provide the title compound (0.3 mg) as a colorless thin film. LC/MS (ESI) m/z 528.3 [M+H]. HPLC retention time (Method B)=2.08 min.

Example 17

2-(3-(2-(N-(3-Morpholinopropyl)thiophene-2-carboxamido)thiazol-4-yl)phenoxy)acetic acid A mixture of methyl bromoacetate (690 µL, 7.3 mmol) and 4-hydroxyacetophenone (1 g, 7.3 mmol) was dissolved in acetone (100 mL), followed by addition of anhydrous $K_2CO_3$ (10 g, 73 mmol). The reaction mixture was stirred at room temperature overnight, filtered, and the filtrate was concentrated in vacuo. The resulting residue was dissolved in dioxane (21 mL), and a portion of the obtained solution (3.2 mL, 1.03 mmol) was combined with a solution of NaOH (64 mg, 1.6 mmol) in water (3 mL). The reaction mixture was maintained at room temperature for 1 h, then concentrated in vacuo. The residue was dissolved in water (3 mL) and neutralized with 1M HCl. The mixture was extracted with EtOAc (10 mL), and the organic layer was dried over $MgSO_4$ and concentrated in vacuo. The crude acid was dissolved in THF (36 mL) and a portion of the obtained solution (5.2 mL, 0.14 mmol) was combined with phenyltrimethylammonium tribromide (93 mg, 0.14 mmol). The reaction mixture was heated at reflux for 1 h, cooled and stirred at room temperature overnight, then concentrated in vacuo. The resulting residue was dissolved in water (15 mL) and extracted with dichloromethane (2×30 mL). The combined organic extracts were dried over $MgSO_4$ and concentrated in vacuo. The crude bromoketone was dissolved in dry dioxane (1 mL) followed by the addition of (3-morpholin-4-yl-propyl)-thiourea (28 mg, 0.14 mmol). The reaction mixture was heated at 80° C. for 1 h, cooled to room temperature, then concentrated in vacuo. The resulting crude aminothiazole was suspended in dry chloroform (600 µL) followed by addition of N,N-diisopropylethylamine (52 µL, 0.3 mmol) and thiophene-2-carbonyl chloride (24 µL, 0.22 mmol). The reaction mixture was stirred at room temperature for 30 min, then concentrated in vacuo. The resulting residue was dissolved in AcOH/water (1:1, 5 mL), heated at reflux for 30 min, cooled to room temperature, then concentrated in vacuo. The resulting crude product was dissolved in DMSO (800 µL) and a portion of the obtained solution (200 µL, 0.035 mmol) was subjected to HPLC purification (Method Z) to provide the title compound (2.4 mg) as a colorless amorphous solid. LC/MS (ESI) m/z 488.3 [M+H]. HPLC retention time (Method B)=2.58 min.

Example 18

N-(4-(4-(2-(Dimethylamino)ethoxy)phenyl)thiazol-2-yl)-N-(3-morpholinopropyl)thiophene-2-carboxamide A mixture of 2-(dimethylamino)ethyl chloride hydrochloride (1.05 g, 7.3 mmol) and 4-hydroxyacetophenone (1 g, 7.3 mmol) was dissolved in acetone (100 mL) followed by addition of anhydrous $K_2CO_3$ (10 g, 73 mmol). The reaction mixture was stirred at room temperature overnight, filtered, and the filtrate was concentrated in vacuo. The resulting residue was dissolved in THF (20 mL) and a portion of the obtained solution (7.4 mL, 2.7 mmol) was mixed with phenyltrimethylammonium tribromide (1.05 g, 2.7 mmol). The reaction mixture was heated at reflux for 1 h, cooled, and stirred at room temperature overnight, then concentrated in vacuo. The resulting residue was dissolved in water (15 mL) and extracted with dichloromethane (2×30 mL). The combined organic layers were dried over $MgSO_4$ and concentrated in vacuo. The resulting crude bromoketone was dissolved in dry dioxane (25 mL), and a portion of the solution (1 mL, 0.11 mmol) was combined with (3-morpholin-4-yl-propyl)-thiourea (21 mg, 0.11 mmol). The reaction mixture was heated at 80° C. for 1 h, cooled, and stirred at room temperature overnight, then concentrated in vacuo. The resulting residue was suspended in dry chloroform (600 µL) followed by addition of N,N-diisopropylethylamine (52 µL, 0.3 mmol) and thiophene-2-carbonyl chloride (24 µL, 0.22 mmol). The reaction mixture was maintained for 30 min at room temperature, then concentrated in vacuo. The resulting residue was dissolved in AcOH (5 mL) and heated at reflux for 30 min, cooled, and concentrated in vacuo. The residue was dissolved in DMSO (600 μL) and portion of the solution (200 μL, 0.035 mmol) was subjected to HPLC purification (Method Z) to provide the title compound (0.8 mg) as a yellowish amorphous solid. LC/MS (ESI) m/z 501.1 [M+H]. HPLC retention time (Method B)=2.21 min.

Example 19

1-(3-(N-(4-(Benzofuran-2-yl)thiazol-2-yl)thiophene-2-carboxamido)propanoyl)piperidine-3-carboxamide A mixture of β-alanine t-butyl ester hydrochloride (1.09 g, 6 mmol) and N,N-diisopropylethylamine (1.04 mL, 6 mmol) was dissolved in chloroform (6 mL) followed by the addition of N-(9-fluorenylmethoxycarbonyl)-isothiocyanate (1.67 g, 6 mmol). The reaction mixture was stirred at room temperature for 2 h, concentrated, and the resulting residue was dissolved in EtOAc (10 mL) followed by addition of piperidine (1.1 mL, 11 mmol). The reaction mixture was maintained at room temperature for 30 min, then concentrated in vacuo. The resulting residue was dissolved in dichloromethane (3 mL), and hexane (30 mL) was added. The formed precipitate was filtered and dried in vacuo to provide the thiourea (1.1 g) as a yellow solid.

A mixture of 1-(1-benzofuran-2-yl)-2-bromoethan-1-one (360 mg, 1.5 mmol) and the thiourea prepared above (300 mg, 1.5 mmol) was dissolved in dry dioxane (3 mL), followed by addition of N,N-diisopropylethylamine (261 μL, 1.5 mmol). The reaction mixture was heated at 80° C. for 1 h, cooled, then concentrated in vacuo. The resulting residue was dissolved in chloroform (3 mL) and purified by flash chromatography (Teledyne Isco CombiFlash®) eluting with a mixture of chloroform/AcOH (95:3) and MeOH. Product fractions were combined, concentrated in vacuo, dissolved in EtOAc (25 mL), washed with 5% aqueous NaHCO₃ and brine, then dried over MgSO₄. Concentration in vacuo provided the aminothiazole (400 mg) as an off-white solid.

A mixture of compound the aminothiazole prepared above (140 mg, 0.41 mmol) and N,N-diisopropylethylamine (710 μL, 4.1 mmol) was dissolved in dry chloroform (1 mL) followed by addition of 2-thiophenecarbonyl chloride (430 μL, 4.1 mmol). The reaction mixture was irradiated in a microwave oven (max. power 250 W, 140° C.) for 10 min., cooled to room temperature, and concentrated in vacuo. The resulting residue was dissolved in DMSO (500 μL) and subjected to HPLC purification (Method Y). Fractions containing the desired product were combined and concentrated in vacuo. The resulting ester was dissolved in the mixture of TFA/dichloromethane (60:40, 10 mL), stirred at room temperature for 30 min, concentrated in vacuo, then the resulting residue was dried in vacuo to provide the carboxylic acid (163 mg) as a yellowish solid.

A mixture of the acid prepared above (159 mg, 0.4 mmol) and pentafluorophenol (74 mg, 0.4 mmol) was dissolved in chloroform (4 mL) followed by addition of N,N'-diisopropylcarbodiimide (63 μL, 0.4 mmol). The reaction mixture was maintained at room temperature for 20 min, then a portion (200 μL, 0.02 mmol) was added to a solution of nipecotamide (2.6 mg, 0.02 mmol) in chloroform (100 μL). The reaction mixture was maintained at room temperature overnight, then concentrated in vacuo. The resulting residue was dissolved in DMSO (200 μL) and subjected to HPLC purification (Method Z) to provide the title compound (1.8 mg) as a yellowish solid. LC/MS (ESI) m/z 509.1 [M+H]. HPLC retention time (Method C)=3.40 min.

Example 20

1-Acetyl-N-(3-(N-(4-(benzofuran-2-yl)thiazol-2-yl) thiophene-2-carboxamido)propyl)piperidine-4-carboxamide According to the procedure in Example 19, (3-amino-propyl)carbamic acid tert-butyl ester was transformed into tert-butyl 3-(N-(4-(benzofuran-2-yl)thiazol-2-yl)thiophene-2-carboxamido)propylcarbamate, which was reacted with TFA/dichoromethane (3:2), stirred at room temperature for 30 min, concentrated in vacuo, then dissolved in MeOH and treated with 1M HCl/ether. The resulting precipitate was filtered and dried in vacuo to provide N-(3-aminopropyl)-N-(4-(benzofuran-2-yl)thiazol-2-yl)thiophene-2-carboxamide (220 mg) as a white solid.

A mixture of the amine prepared above (77 mg, 0.2 mmol) and N,N-diisopropylethylamine (139 μL, 0.8 mmol) was dissolved in chloroform (2 mL), and a portion of the solution (200 μL, 0.02 mmol) was added to a solution of 1-acetyl-isonipecotoyl chloride (7.6 mg, 0.04 mmol) in chloroform (200 μL). The reaction mixture was maintained at room temperature overnight.). The reaction mixture was maintained at room temperature overnight, then concentrated in vacuo. The resulting residue was dissolved in DMSO (200 μL) and subjected to HPLC purification (Method Z) to provide the title compound (4.5 mg) as a yellowish solid. LC/MS (ESI) m/z 537.1 [M+H]. HPLC retention time (Method C)=3.44 min.

Example 21

N-(4-(Benzofuran-2-yl)thiazol-2-yl)-N-(3-(3-(piperidin-1-yl)propanamido)propyl)thiophene-2-carboxamide A mixture of 1-piperidinepropionic acid (3 mg, 0.02 mmol) and tris(dimethylamino)chlorophosphonium perchlorate (7 mg, 0.02 mmol) was dissolved in NMP (200 μL) followed by the addition of N,N-diisopropylethylamine (17 μL, 0.1 mmol). The reaction mixture was maintained at room temperature for 20 min, then N-(3-aminopropyl)-N-(4-(benzofuran-2-yl)thiazol-2-yl)thiophene-2-carboxamide (7.7 mg, 0.02 mmol) was added, and the reaction mixture was stirred at room temperature overnight. The resulting mixture was subjected to HPLC purification (Method Z) to provide the title compound (3.2 mg) as a pale yellow solid. LC/MS (ESI) m/z 523.5 [M+H]. HPLC retention time (Method C)=3.15 min.

Example 22

N-(4-(Benzofuran-2-yl)thiazol-2-yl)-N-(3-(4,4-dihydroxypiperidin-1-yl)propyl)thiophene-2-carboxamide According to the procedure in Example 19, 3-amino-1-propanol was transformed into the aminotriazole, which was dissolved in i-PrOH and treated with 1M HCl/ether to provide 3-(4-(benzofuran-2-yl)thiazol-2-ylamino)propan-1-ol (437 mg) as a white solid as the hydrochloride salt.

A mixture of the aminotriazole hydrochloride prepared above (423 mg, 1.36 mmol) and N,O-bis(trimethylsilyl)acetamide (674 µL, 2.73 mmol) was dissolved in dry chloroform (32 mL). The reaction mixture was heated in a pressure vessel at 80° C. for 30 min and cooled to room temperature. N,N-Diisopropylethylamine (1.07 mL, 6.12 mmol) was added, followed by addition of 2-thiophenecarbonyl chloride (945 µL, 8.84 mmol). The reaction mixture was irradiated in a microwave oven (max. power 250 W, 120° C.) for 45 min, then cooled to room temperature. The resulting solution was washed with water (2×30 mL) and concentrated in vacuo. The resulting residue was dissolved in DMSO (2 mL) and purified by HPLC (Method X) to provide the amide (347 mg) as an off-white solid.

A mixture of the amide (318 mg, 0.83 mmol) and N,N-diisopropylethylamine (432 µL, 2.48 mmol) was dissolved in dichloromethane (28 mL), cooled to 0° C., and treated with methanesulfonyl chloride (192 µL, 2.48 mmol). The ice bath was removed, and the reaction mixture was stirred at room temperature for 2 h, washed with water (2×30 mL), then azeotroped with toluene (2×20 mL) to provide the desired mesylate. The residual oil was used in the next step without further purification.

In a glove box under nitrogen, a mixture of 4-piperidone monohydrate hydrochloride (3 mg, 0.2 mmol) and N,N-diisopropylethylamine (35 µL, 0.2 mmol) was dissolved in NMP (200 µL) followed by the addition of 4 Å molecular sieves. The reaction mixture was maintained at room temperature overnight. The solution was decanted, and a solution of the mesylate prepared above (0.2 mmol) in NMP (100 µL) was added. The reaction mixture was maintained at room temperature overnight, then purified by HPLC (Method Z) to provide the desired coupled product (0.4 mg) as an off-white solid. LC/MS (ESI) m/z 484.3 [M+H]. HPLC retention time (Method C)=2.95 min.

Example 23

N-(4-(Benzofuran-2-yl)thiazol-2-yl)-N-(3-(2-(hydroxymethyl)pyrrolidin-1-yl)propyl)thiophene-2-carboxamide According to the procedure in Example 19, 1-amino-3,3-diethoxypropane was utilized, replacing the HPLC purification with flash chromatography eluting with EtOAc/hexane mixtures containing 1% triethylamine, to provide N-(4-(benzofuran-2-yl)thiazol-2-yl)-N-(3,3-diethoxypropyl)thiophene-2-carboxamide as an off-white solid.

A solution of the acetal (880 mg, 1.93 mmol) in dioxane (5 mL) was cooled to 0° C., and 1 M HCl/ether (8 mL) was added. The ice bath was removed and the reaction mixture was stirred at room temperature for 30 min, diluted with ether (100 mL) and extracted with water. The aqueous layer was neutralized with saturated aqueous $NaHCO_3$ and extracted with ether (3×30 mL). The combined organic layers were dried over $Na_2SO_4$ and concentrated to provide the aldehyde (735 mg, 99%) as an off-white solid.

A mixture of the aldehyde (8 mg, 0.024 mmol) and (S)-(+)-2-pyrrolidinemethanol (12 mg, 0.12 mmol) was dissolved in 1,2-dichloroethane (500 µL) followed by treatment with sodium borohydride (1.1 mg, 0.029 mmol). The reaction mixture was maintained at room temperature for 1 h, then concentrated in vacuo. The resulting residue was extracted with DMSO (250 µL) and filtered. The resulting filtrate was subjected to HPLC purification (Method Z) to provide the title compound (1 mg) as a pale yellow solid. LC/MS (ESI) m/z 468.3 [M+H]. HPLC retention time (Method B)=3.08 min.

Example 24

The following compounds listed in Table 1 were prepared by the General Procedure for Solid Phase Parallel Synthesis (Method 1) or by the general procedures as exemplified in the examples, utilizing the appropriate starting materials.

TABLE 1

| Compound Name | LC/MS m/z [M + H] | HPLC retention time (min) | HPLC Method | Synthesis Method |
|---|---|---|---|---|
| N-(4-(4-methoxyphenyl)thiazol-2-yl)-3,3-dimethyl-N-(3-morpholinopropyl)butanamide | 432.3 | 3.05 | A | Example 1 or Method 1 |
| 2-(2-chlorophenyl)-N-(4-(4-methoxyphenyl)thiazol-2-yl)-N-(3-morpholinopropyl)acetamide | 486.3 | 2.96 | A | Example 1 or Method 1 |
| 2-(3-chlorophenyl)-N-(4-(4-methoxyphenyl)thiazol-2-yl)-N-(3-morpholinopropyl)acetamide | 486.3 | 3.08 | A | Example 1 or Method 1 |
| N-(3-(diethylamino)propyl)-N-(4-(2,5-dimethoxyphenyl)thiazol-2-yl)benzamide | 454.3 | 3.02 | A | Example 1 or Method 1 |
| N-(3-(diethylamino)propyl)-N-(4-(2,5-dimethoxyphenyl)thiazol-2-yl)thiophene-2-carboxamide | 460.3 | 2.99 | A | Example 1 or Method 1 |
| N-(4-phenylthiazol-2-yl)-N-(3-(pyrrolidin-1-yl)propyl)thiophene-2-carboxamide | 397.9 | 2.88 | A | Example 1 or Method 1 |
| N-(4-(4-methoxyphenyl)thiazol-2-yl)-N-(3-(pyrrolidin-1-yl)propyl)benzamide | 421.9 | 2.96 | A | Example 1 or Method 1 |
| N-(4-(4-methoxyphenyl)thiazol-2-yl)-N-(3-(pyrrolidin-1-yl)propyl)thiophene-2-carboxamide | 428.3 | 2.92 | A | Example 1 or Method 1 |

TABLE 1-continued

| Compound Name | LC/MS m/z [M + H] | HPLC retention time (min) | HPLC Method | Synthesis Method |
|---|---|---|---|---|
| N-(4-(4-methoxyphenyl)thiazol-2-yl)-N-(3-(pyrrolidin-1-yl)propyl)furan-2-carboxamide | 411.9 | 2.86 | A | Example 1 or Method 1 |
| N-(4-(2,5-dimethoxyphenyl)thiazol-2-yl)-N-(3-(pyrrolidin-1-yl)propyl)benzamide | 452.3 | 3.00 | A | Example 1 or Method 1 |
| N-(4-(2,5-dimethoxyphenyl)thiazol-2-yl)-N-(3-(pyrrolidin-1-yl)propyl)thiophene-2-carboxamide | 458.3 | 2.98 | A | Example 1 or Method 1 |
| N-(4-(2,5-dimethoxyphenyl)thiazol-2-yl)-N-(3-(pyrrolidin-1-yl)propyl)furan-2-carboxamide | 442.3 | 2.92 | A | Example 1 or Method 1 |
| N-(4-(4-methoxyphenyl)thiazol-2-yl)-N-(3-(piperidin-1-yl)propyl)thiophene-2-carboxamide | 442.3 | 2.95 | A | Example 1 or Method 1 |
| N-(4-(2,5-dimethoxyphenyl)thiazol-2-yl)-N-(3-(piperidin-1-yl)propyl)benzamide | 466.3 | 3.06 | A | Example 1 or Method 1 |
| N-(4-(2,5-dimethoxyphenyl)thiazol-2-yl)-N-(3-(piperidin-1-yl)propyl)thiophene-2-carboxamide | 472.3 | 3.03 | A | Example 1 or Method 1 |
| N-(4-(2,5-dimethoxyphenyl)thiazol-2-yl)-N-(3-(piperidin-1-yl)propyl)furan-2-carboxamide | 456.3 | 2.98 | A | Example 1 or Method 1 |
| N-(3-(azepan-1-yl)propyl)-N-(4-phenylthiazol-2-yl)benzamide | 420.3 | 3.12 | A | Example 1 or Method 1 |
| N-(3-(azepan-1-yl)propyl)-N-(4-phenylthiazol-2-yl)thiophene-2-carboxamide | 426.3 | 3.11 | A | Example 1 or Method 1 |
| N-(3-(azepan-1-yl)propyl)-N-(4-phenylthiazol-2-yl)furan-2-carboxamide | 410.3 | 3.03 | A | Example 1 or Method 1 |
| N-(3-(azepan-1-yl)propyl)-N-(4-(4-methoxyphenyl)thiazol-2-yl)benzamide | 450.3 | 3.11 | A | Example 1 or Method 1 |
| N-(3-(azepan-1-yl)propyl)-N-(4-(4-methoxyphenyl)thiazol-2-yl)thiophene-2-carboxamide | 456.3 | 3.06 | A | Example 1 or Method 1 |
| N-(3-(azepan-1-yl)propyl)-N-(4-(4-methoxyphenyl)thiazol-2-yl)furan-2-carboxamide | 440.3 | 3.02 | A | Example 1 or Method 1 |
| N-(3-(azepan-1-yl)propyl)-N-(4-(2,5-dimethoxyphenyl)thiazol-2-yl)benzamide | 480.3 | 3.18 | A | Example 1 or Method 1 |
| N-(3-(azepan-1-yl)propyl)-N-(4-(2,5-dimethoxyphenyl)thiazol-2-yl)thiophene-2-carboxamide | 486.3 | 3.12 | A | Example 1 or Method 1 |
| N-(3-(azepan-1-yl)propyl)-N-(4-(2,5-dimethoxyphenyl)thiazol-2-yl)furan-2-carboxamide | 470.3 | 3.06 | A | Example 1 or Method 1 |
| N-(3-(4-methylpiperazin-1-yl)propyl)-N-(4-phenylthiazol-2-yl)benzamide | 421.1 | 2.53 | A | Example 1 or Method 1 |
| N-(3-(4-methylpiperazin-1-yl)propyl)-N-(4-phenylthiazol-2-yl)thiophene-2-carboxamide | 427.1 | 2.49 | A | Example 1 or Method 1 |
| N-(3-(4-methylpiperazin-1-yl)propyl)-N-(4-phenylthiazol-2-yl)furan-2-carboxamide | 411.1 | 2.42 | A | Example 1 or Method 1 |
| N-(4-(4-methoxyphenyl)thiazol-2-yl)-N-(3-(4-methylpiperazin-1-yl)propyl)benzamide | 451.1 | 2.55 | A | Example 1 or Method 1 |
| N-(4-(4-methoxyphenyl)thiazol-2-yl)-N-(3-(4-methylpiperazin-1-yl)propyl)thiophene-2-carboxamide | 457.1 | 2.50 | A | Example 1 or Method 1 |
| N-(4-(4-methoxyphenyl)thiazol-2-yl)-N-(3-(4-methylpiperazin-1-yl)propyl)furan-2-carboxamide | 441.1 | 2.45 | A | Example 1 or Method 1 |
| N-(4-(2,5-dimethoxyphenyl)thiazol-2-yl)-N-(3-(4-methylpiperazin-1-yl)propyl)benzamide | 481.1 | 2.61 | A | Example 1 or Method 1 |

TABLE 1-continued

| Compound Name | LC/MS m/z [M + H] | HPLC retention time (min) | HPLC Method | Synthesis Method |
|---|---|---|---|---|
| N-(4-(2,5-dimethoxyphenyl)thiazol-2-yl)-N-(3-(4-methylpiperazin-1-yl)propyl)thiophene-2-carboxamide | 487.1 | 2.55 | A | Example 1 or Method 1 |
| N-(4-(2,5-dimethoxyphenyl)thiazol-2-yl)-N-(3-(4-methylpiperazin-1-yl)propyl)furan-2-carboxamide | 471.5 | 2.50 | A | Example 1 or Method 1 |
| N-(4-(4-methoxyphenyl)thiazol-2-yl)-N-(3-morpholinopropyl)cyclopent-1-enecarboxamide | 428.3 | 2.73 | A | Example 1 or Method 1 |
| 4-chloro-N-(4-(4-methoxyphenyl)thiazol-2-yl)-N-(3-morpholinopropyl)benzamide | 472.3 | 2.90 | A | Example 1 or Method 1 |
| 3-fluoro-N-(4-(4-methoxyphenyl)thiazol-2-yl)-N-(3-morpholinopropyl)benzamide | 456.3 | 2.81 | A | Example 1 or Method 1 |
| N-(4-(4-methoxyphenyl)thiazol-2-yl)-3-methyl-N-(3-morpholinopropyl)benzamide | 452.3 | 2.88 | A | Example 1 or Method 1 |
| 2-fluoro-N-(4-(4-methoxyphenyl)thiazol-2-yl)-N-(3-morpholinopropyl)benzamide | 456.3 | 2.81 | A | Example 1 or Method 1 |
| N-(4-(4-methoxyphenyl)thiazol-2-yl)-4-methyl-N-(3-morpholinopropyl)benzamide | 452.3 | 2.85 | A | Example 1 or Method 1 |
| 2-cyano-N-(4-(4-methoxyphenyl)thiazol-2-yl)-N-(3-morpholinopropyl)benzamide | 463.1 | 2.69 | A | Example 1 or Method 1 |
| N-(4-(4-methoxyphenyl)thiazol-2-yl)-5-methyl-N-(3-morpholinopropyl)furan-2-carboxamide | 442.3 | 2.78 | A | Example 1 or Method 1 |
| N-(4-(4-methoxyphenyl)thiazol-2-yl)-3-methyl-N-(3-morpholinopropyl)furan-2-carboxamide | 442.3 | 2.84 | A | Example 1 or Method 1 |
| N-(4-(4-methoxyphenyl)thiazol-2-yl)-N-(3-morpholinopropyl)thiophene-2-carboxamide | 444.3 | 2.79 | A | Example 1 or Method 1 |
| N-(4-(4-chlorophenyl)thiazol-2-yl)-N-(3-morpholinopropyl)thiophene-2-carboxamide | 447.9 | 2.98 | A | Example 1 or Method 1 |
| N-(3-morpholinopropyl)-N-(4-p-tolylthiazol-2-yl)thiophene-2-carboxamide | 428.3 | 2.88 | A | Example 1 or Method 1 |
| N-(4-(2,3-dihydrobenzo[b][1,4]dioxin-6-yl)thiazol-2-yl)-N-(3-morpholinopropyl)thiophene-2-carboxamide | 472.3 | 2.72 | A | Example 1 or Method 1 |
| N-(4-(4-chloro-3-nitrophenyl)thiazol-2-yl)-N-(3-morpholinopropyl)thiophene-2-carboxamide | 493.1 | 3.03 | A | Example 1 or Method 1 |
| N-(4-(2-methoxyphenyl)thiazol-2-yl)-N-(3-morpholinopropyl)thiophene-2-carboxamide | 444.3 | 2.78 | A | Example 1 or Method 1 |
| N-(4-(2,4-dimethylphenyl)thiazol-2-yl)-N-(3-morpholinopropyl)thiophene-2-carboxamide | 442.3 | 2.95 | A | Example 1 or Method 1 |
| N-(4-(4-cyanophenyl)thiazol-2-yl)-N-(3-morpholinopropyl)thiophene-2-carboxamide | 439.1 | 2.73 | A | Example 1 or Method 1 |
| methyl 4-(2-(N-(3-morpholinopropyl)thiophene-2-carboxamido)thiazol-4-yl)benzoate | 472.3 | 2.80 | A | Example 1 or Method 1 |
| N-(4-(4-(methylsulfonyl)phenyl)thiazol-2-yl)-N-(3-morpholinopropyl)thiophene-2-carboxamide | 492.3 | 2.48 | A | Example 1 or Method 1 |
| N-(4-(2,4-dimethoxyphenyl)thiazol-2-yl)-N-(3-morpholinopropyl)thiophene-2-carboxamide | 474.3 | 2.81 | A | Example 1 or Method 1 |
| N-(4-(benzofuran-3-yl)thiazol-2-yl)-N-(3-morpholinopropyl)thiophene-2-carboxamide | 454.3 | 2.93 | A | Example 1 or Method 1 |
| N-(4-(2-chlorophenyl)thiazol-2-yl)-N-(3-morpholinopropyl)thiophene-2-carboxamide | 447.9 | 2.83 | A | Example 1 or Method 1 |

TABLE 1-continued

| Compound Name | LC/MS m/z [M + H] | HPLC retention time (min) | HPLC Method | Synthesis Method |
|---|---|---|---|---|
| N-(4-(3-chlorophenyl)thiazol-2-yl)-N-(3-morpholinopropyl)thiophene-2-carboxamide | 447.9 | 2.95 | A | Example 1 or Method 1 |
| N-(4-(benzo[b]thiophen-3-yl)thiazol-2-yl)-N-(3-morpholinopropyl)thiophene-2-carboxamide | 470.3 | 2.99 | A | Example 1 or Method 1 |
| N-(3-morpholinopropyl)-N-(4-(pyridin-2-yl)thiazol-2-yl)thiophene-2-carboxamide | 415.1 | 1.92 | A | Example 1 or Method 1 |
| N-(3-morpholinopropyl)-N-(4-(pyridin-3-yl)thiazol-2-yl)thiophene-2-carboxamide | 415.1 | 1.92 | A | Example 1 or Method 1 |
| N-(3-morpholinopropyl)-N-(4-(pyridin-4-yl)thiazol-2-yl)thiophene-2-carboxamide | 415.1 | 1.93 | A | Example 1 or Method 1 |
| N-(3-morpholinopropyl)-N-(4-(thiophen-2-yl)thiazol-2-yl)thiophene-2-carboxamide | 420.3 | 2.69 | A | Example 1 or Method 1 |
| N-(4-(5-chlorothiophen-2-yl)thiazol-2-yl)-N-(3-morpholinopropyl)thiophene-2-carboxamide | 453.9 | 2.93 | A | Example 1 or Method 1 |
| N-(4-(5-chlorothiophen-2-yl)thiazol-2-yl)-N-(3-morpholinopropyl)thiophene-2-carboxamide | 420.3 | 2.65 | A | Example 1 or Method 1 |
| N-(4-(3,4-dichlorophenyl)thiazol-2-yl)-N-(3-morpholinopropyl)thiophene-2-carboxamide | 482.3 | 3.13 | A | Example 1 or Method 1 |
| N-(4-(4-fluorophenyl)thiazol-2-yl)-N-(3-morpholinopropyl)thiophene-2-carboxamide | 432.3 | 2.78 | A | Example 1 or Method 1 |
| N-(4-(4-(difluoromethoxy)phenyl)thiazol-2-yl)-N-(3-morpholinopropyl)thiophene-2-carboxamide | 479.9 | 2.93 | A | Example 1 or Method 1 |
| N-(3-morpholinopropyl)-N-(4-(2-(trifluoromethyl)phenyl)thiazol-2-yl)thiophene-2-carboxamide | 482.3 | 2.89 | A | Example 1 or Method 1 |
| N-(4-(2-fluorophenyl)thiazol-2-yl)-N-(3-morpholinopropyl)thiophene-2-carboxamide | 432.3 | 2.83 | A | Example 1 or Method 1 |
| N-(4-(3,4-difluorophenyl)thiazol-2-yl)-N-(3-morpholinopropyl)thiophene-2-carboxamide | 450.3 | 2.90 | A | Example 1 or Method 1 |
| N-(4-(3-bromophenyl)thiazol-2-yl)-N-(3-morpholinopropyl)thiophene-2-carboxamide | 491.9 | 3.00 | A | Example 1 or Method 1 |
| N-(3-morpholinopropyl)-N-(4-(4-(trifluoromethoxy)phenyl)thiazol-2-yl)thiophene-2-carboxamide | 498.3 | 3.15 | A | Example 1 or Method 1 |
| N-(4-(3-fluorophenyl)thiazol-2-yl)-N-(3-morpholinopropyl)thiophene-2-carboxamide | 432.3 | 2.80 | A | Example 1 or Method 1 |
| N-(4-(3-methylbenzo[b]thiophen-2-yl)thiazol-2-yl)-N-(3-morpholinopropyl)thiophene-2-carboxamide | 484.3 | 3.16 | A | Example 1 or Method 1 |
| N-(4-(3-cyanophenyl)thiazol-2-yl)-N-(3-morpholinopropyl)thiophene-2-carboxamide | 439.1 | 2.72 | A | Example 1 or Method 1 |
| N-(3-morpholinopropyl)-N-(4-(4-pentylphenyl)thiazol-2-yl)thiophene-2-carboxamide | 484.3 | 3.56 | A | Example 1 or Method 1 |
| N-(4-(4-(diethylamino)phenyl)thiazol-2-yl)-N-(3-morpholinopropyl)thiophene-2-carboxamide | 485.5 | 2.15 | A | Example 1 or Method 1 |
| N-(3-morpholinopropyl)-N-(4-(4-(pyrrolidin-1-yl)phenyl)thiazol-2-yl)thiophene-2-carboxamide | 483.5 | 2.72 | A | Example 1 or Method 1 |
| N-(4-(3,4-dimethoxyphenyl)thiazol-2-yl)-N-(3-morpholinopropyl)thiophene-2-carboxamide | 474.3 | 2.59 | A | Example 1 or Method 1 |
| N-(4-(benzo[d][1,3]dioxol-5-yl)thiazol-2-yl)-N-(3-morpholinopropyl)thiophene-2-carboxamide | 458.3 | 2.73 | A | Example 1 or Method 1 |

TABLE 1-continued

| Compound Name | LC/MS m/z [M + H] | HPLC retention time (min) | HPLC Method | Synthesis Method |
|---|---|---|---|---|
| N-(4-(benzo[d]thiazol-2-yl)thiazol-2-yl)-N-(3-morpholinopropyl)thiophene-2-carboxamide | 471.5 | 2.80 | A | Example 1 or Method 1 |
| N-(4-(3-methoxyphenyl)thiazol-2-yl)-N-(3-morpholinopropyl)thiophene-2-carboxamide | 444.3 | 2.75 | A | Example 1 or Method 1 |
| N-(3-morpholinopropyl)-N-(4-(2-nitrophenyl)thiazol-2-yl)thiophene-2-carboxamide | 459.1 | 2.69 | A | Example 1 or Method 1 |
| N-(3-morpholinopropyl)-N-(4-(naphthalen-2-yl)thiazol-2-yl)thiophene-2-carboxamide | 464.3 | 3.06 | A | Example 1 or Method 1 |
| N-(4-(benzofuran-2-yl)thiazol-2-yl)-N-(3-morpholinopropyl)thiophene-2-carboxamide | 454.3 | 3.02 | A | Example 1 or Method 1 |
| N-(4-(4-morpholinophenyl)thiazol-2-yl)-N-(3-morpholinopropyl)thiophene-2-carboxamide | 499.1 | 2.46 | A | Example 1 or Method 1 |
| N-(4-(3,4-dihydro-2H-benzo[b][1,4]dioxepin-7-yl)thiazol-2-yl)-N-(3-morpholinopropyl)thiophene-2-carboxamide | 486.3 | 2.76 | A | Example 1 or Method 1 |
| N-(4-(2-chloropyridin-4-yl)thiazol-2-yl)-N-(3-morpholinopropyl)thiophene-2-carboxamide | 449.1 | 2.59 | A | Example 1 or Method 1 |
| N-(4-(4-methoxyphenyl)thiazol-2-yl)-3-methyl-N-(3-morpholinopropyl)thiophene-2-carboxamide | 458.3 | 2.81 | A | Example 1 or Method 1 |
| 2,5-dichloro-N-(4-(4-methoxyphenyl)thiazol-2-yl)-N-(3-morpholinopropyl)thiophene-3-carboxamide | 512.3 | 3.06 | A | Example 1 or Method 1 |
| 3-bromo-N-(4-(4-methoxyphenyl)thiazol-2-yl)-N-(3-morpholinopropyl)thiophene-2-carboxamide | 522.3 | 2.86 | A | Example 1 or Method 1 |
| N-(4-(4-methoxyphenyl)thiazol-2-yl)-N-(3-morpholinopropyl)-5-nitrothiophene-2-carboxamide | 489.1 | 2.86 | A | Example 1 or Method 1 |
| 5-chloro-N-(4-(4-methoxyphenyl)thiazol-2-yl)-N-(3-morpholinopropyl)thiophene-2-carboxamide | 477.9 | 2.95 | A | Example 1 or Method 1 |
| 5-acetyl-N-(4-(4-methoxyphenyl)thiazol-2-yl)-N-(3-morpholinopropyl)thiophene-2-carboxamide | 486.3 | 2.69 | A | Example 1 or Method 1 |
| 5-bromo-N-(4-(4-methoxyphenyl)thiazol-2-yl)-N-(3-morpholinopropyl)thiophene-2-carboxamide | 522.3 | 2.96 | A | Example 1 or Method 1 |
| N-(4-(4-methoxyphenyl)thiazol-2-yl)-5-(methylthio)-N-(3-morpholinopropyl)thiophene-2-carboxamide | 490.3 | 2.96 | A | Example 1 or Method 1 |
| N-(3-morpholinopropyl)-N-(4-(3-(trifluoromethyl)phenyl)thiazol-2-yl)thiophene-2-carboxamide | 482.3 | 3.06 | A | Example 1 or Method 1 |
| N-(4-(4-methoxyphenyl)thiazol-2-yl)-1-methyl-N-(3-morpholinopropyl)-1H-pyrrole-2-carboxamide | 441.1 | 2.72 | A | Example 1 or Method 1 |
| N-(4-(4-methoxyphenyl)thiazol-2-yl)-N-(3-morpholinopropyl)isoxazole-5-carboxamide | 429.1 | 2.58 | A | Example 1 or Method 1 |
| N-(4-(4-methoxyphenyl)thiazol-2-yl)-3,5-dimethyl-N-(3-morpholinopropyl)isoxazole-4-carboxamide | 457.5 | 2.62 | A | Example 1 or Method 1 |
| N-(4-(4-methoxyphenyl)thiazol-2-yl)-4-methyl-N-(3-morpholinopropyl)-1,2,3-thiadiazole-5-carboxamide | 460.3 | 2.60 | A | Example 1 or Method 1 |
| N-(4-(4-methoxyphenyl)thiazol-2-yl)-2,4-dimethyl-N-(3-morpholinopropyl)thiazole-5-carboxamide | 473.1 | 2.59 | A | Example 1 or Method 1 |
| 4-chloro-N-(4-(4-methoxyphenyl)thiazol-2-yl)-N-(3-morpholinopropyl)picolinamide | 473.1 | 2.83 | A | Example 1 or Method 1 |
| N-(4-(4-methoxyphenyl)thiazol-2-yl)-3-methyl-N-(3-morpholinopropyl)isoxazole-4-carboxamide | 443.5 | 2.59 | A | Example 1 or Method 1 |

TABLE 1-continued

| Compound Name | LC/MS m/z [M + H] | HPLC retention time (min) | HPLC Method | Synthesis Method |
|---|---|---|---|---|
| 6-chloro-N-(4-(4-methoxyphenyl)thiazol-2-yl)-N-(3-morpholinopropyl)picolinamide | 473.1 | 2.80 | A | Example 1 or Method 1 |
| N-(4-(4-methoxyphenyl)thiazol-2-yl)-1-methyl-N-(3-morpholinopropyl)-1H-imidazole-2-carboxamide | 442.3 | 2.62 | A | Example 1 or Method 1 |
| 4,5-dichloro-N-(4-(4-methoxyphenyl)thiazol-2-yl)-N-(3-morpholinopropyl)isothiazole-3-carboxamide | 513.1 | 3.01 | A | Example 1 or Method 1 |
| N-(4-(4-methoxyphenyl)thiazol-2-yl)-1,2,5-trimethyl-N-(3-morpholinopropyl)-1H-pyrrole-3-carboxamide | 469.5 | 2.83 | A | Example 1 or Method 1 |
| ethyl 2-(N-(3-morpholinopropyl)thiophene-2-carboxamido)thiazole-4-carboxylate | 410.3 | 2.39 | A | Example 1 or Method 1 |
| ethyl 3-methyl-3-(2-(N-(3-morpholinopropyl)thiophene-2-carboxamido)thiazol-4-yl)butanoate | 466.3 | 2.69 | A | Example 1 or Method 1 |
| N-(4-(biphenyl-4-yl)thiazol-2-yl)-N-(3-morpholinopropyl)thiophene-2-carboxamide | 490.3 | 3.20 | B | Example 1 or Method 1 |
| N-(4-(5-methyl-1-phenyl-1H-pyrazol-4-yl)thiazol-2-yl)-N-(3-morpholinopropyl)thiophene-2-carboxamide | 494.3 | 2.72 | B | Example 1 or Method 1 |
| N-(4-(2,4-dichlorophenyl)thiazol-2-yl)-N-(3-morpholinopropyl)thiophene-2-carboxamide | 481.9 | 3.08 | B | Example 1 or Method 1 |
| 3-(2-(N-(3-morpholinopropyl)thiophene-2-carboxamido)thiazol-4-yl)benzoic acid | 458.3 | 2.50 | B | Example 1 or Method 1 |
| N-(3-morpholinopropyl)-N-(4-(3-oxo-3,4-dihydro-2H-benzo[b][1,4]oxazin-6-yl)thiazol-2-yl)thiophene-2-carboxamide | 485.1 | 2.42 | B | Example 1 or Method 1 |
| N-(3-morpholinopropyl)-N-(4-(3-phenylisoxazol-5-yl)thiazol-2-yl)thiophene-2-carboxamide | 481.1 | 2.94 | B | Example 1 or Method 1 |
| N-(3-morpholinopropyl)-N-(4-(5-(pyridin-2-yl)thiophen-2-yl)thiazol-2-yl)thiophene-2-carboxamide | 497.5 | 2.55 | B | Example 1 or Method 1 |
| N-(4'-methyl-2'-(pyrazin-2-yl)-4,5'-bithiazol-2-yl)-N-(3-morpholinopropyl)thiophene-2-carboxamide | 513.1 | 2.72 | B | Example 1 or Method 1 |
| 2-(5-(2-(N-(3-morpholinopropyl)thiophene-2-carboxamido)thiazol-4-yl)thiophen-2-yl)acetic acid | 477.9 | 2.48 | B | Example 1 or Method 1 |
| N-(4-(4-chloro-3-methylphenyl)thiazol-2-yl)-N-(3-morpholinopropyl)thiophene-2-carboxamide | 462.3 | 3.06 | B | Example 1 or Method 1 |
| N-(4-(3,4-dimethoxyphenyl)thiazol-2-yl)-N-(3-morpholinopropyl)benzamide | 468.3 | 2.58 | B | Example 1 or Method 1 |
| N-(4-(3,4-dimethoxyphenyl)thiazol-2-yl)-N-(3-morpholinopropyl)furan-2-carboxamide | 458.3 | 2.48 | B | Example 1 or Method 1 |
| N-(4-(benzofuran-2-yl)thiazol-2-yl)-N-(3-morpholinopropyl)furan-2-carboxamide | 438.3 | 2.89 | B | Example 1 or Method 1 |
| N-(4-(benzofuran-2-yl)thiazol-2-yl)-N-(3-morpholinopropyl)nicotinamide | 449.1 | 2.55 | B | Example 1 or Method 1 |
| N-(4-(3,4-dimethoxyphenyl)thiazol-2-yl)-N-(3-morpholinopropyl)cyclopentanecarboxamide | 460.3 | 2.73 | B | Example 1 or Method 1 |
| N-(4-(3,4-dimethoxyphenyl)thiazol-2-yl)-N-(3-morpholinopropyl)cyclobutanecarboxamide | 446.3 | 2.60 | B | Example 1 or Method 1 |
| N-(4-(benzofuran-2-yl)thiazol-2-yl)-N-(3-morpholinopropyl)cyclobutanecarboxamide | 426.4 | 3.08 | A | Example 1 or Method 1 |
| N-(4-(3,4-dimethoxyphenyl)thiazol-2-yl)-N-(3-morpholinopropyl)picolinamide | 469.5 | 2.44 | B | Example 1 or Method 1 |

TABLE 1-continued

| Compound Name | LC/MS m/z [M + H] | HPLC retention time (min) | HPLC Method | Synthesis Method |
|---|---|---|---|---|
| N-(4-(benzofuran-2-yl)thiazol-2-yl)-N-(3-morpholinopropyl)picolinamide | 449.1 | 2.83 | B | Example 1 or Method 1 |
| N-(4-(3-(4-chlorophenyl)isoxazol-5-yl)thiazol-2-yl)-N-(3-morpholinopropyl)thiophene-2-carboxamide | 515.1 | 3.20 | C | Example 1 or Method 1 |
| N-(3-morpholinopropyl)-N-(4-(3-phenylisoxazol-5-yl)thiazol-2-yl)furan-2-carboxamide | 465.1 | 2.85 | C | Example 1 or Method 1 |
| 1-methyl-N-(3-morpholinopropyl)-N-(4-(3-phenylisoxazol-5-yl)thiazol-2-yl)-1H-pyrrole-2-carboxamide | 478.3 | 2.94 | C | Example 1 or Method 1 |
| 4-(2-(N-(3-morpholinopropyl)thiophene-2-carboxamido)thiazol-4-yl)benzoic acid | 458.3 | 2.47 | B | Example 1 or Method 1 |
| N-(3-morpholinopropyl)-N-(4-(trifluoromethyl)thiazol-2-yl)thiophene-2-carboxamide | 406.3 | 2.51 | B | Example 1 or Method 1 |
| ethyl 5-(2-(N-(3-morpholinopropyl)thiophene-2-carboxamido)thiazol-4-yl)isoxazole-3-carboxylate | 477.1 | 2.67 | B | Example 1 or Method 1 |
| 2-(N-(3-morpholinopropyl)thiophene-2-carboxamido)-N-(1,3,4-thiadiazol-2-yl)thiazole-4-carboxamide | 465.1 | 2.22 | B | Example 12 |
| 2-(N-(3-morpholinopropyl)thiophene-2-carboxamido)-N-(thiazol-2-yl)thiazole-4-carboxamide | 463.9 | 2.38 | B | Example 12 |
| N-(3-methoxyphenyl)-2-(N-(3-morpholinopropyl)thiophene-2-carboxamido)thiazole-4-carboxamide | 487.1 | 2.49 | B | Example 12 |
| N-(3-methoxybenzyl)-2-(N-(3-morpholinopropyl)thiophene-2-carboxamido)thiazole-4-carboxamide | 501.1 | 2.39 | B | Example 12 |
| N-(3-chlorobenzyl)-2-(N-(3-morpholinopropyl)thiophene-2-carboxamido)thiazole-4-carboxamide | 505.1 | 2.59 | B | Example 12 |
| N-(2,3-dihydrobenzo[b][1,4]dioxin-6-yl)-2-(N-(3-morpholinopropyl)thiophene-2-carboxamido)thiazole-4-carboxamide | 515.1 | 2.46 | B | Example 12 |
| N-(5-ethyl-1,3,4-thiadiazol-2-yl)-2-(N-(3-morpholinopropyl)thiophene-2-carboxamido)thiazole-4-carboxamide | 493.1 | 2.46 | B | Example 12 |
| N-(benzo[d]thiazol-6-yl)-2-(N-(3-morpholinopropyl)thiophene-2-carboxamido)thiazole-4-carboxamide | 514.3 | 2.42 | B | Example 12 |
| N-(3-carbamoylphenyl)-2-(N-(3-morpholinopropyl)thiophene-2-carboxamido)thiazole-4-carboxamide | 500.3 | 2.15 | B | Example 12 |
| ethyl 2-(2-(2-(N-(3-morpholinopropyl)thiophene-2-carboxamido)thiazole-4-carboxamido)thiazol-4-yl)acetate | 550.3 | 2.62 | B | Example 12 |
| N-(3-(methylsulfonamido)phenyl)-2-(N-(3-morpholinopropyl)thiophene-2-carboxamido)thiazole-4-carboxamide | 550.3 | 2.30 | B | Example 12 |
| N-(4-(benzofuran-2-yl)thiazol-2-yl)-N-(3-(2-oxopyrrolidin-1-yl)propyl)furan-2-carboxamide | 436.3 | 3.65 | C | Example 13 or 14 |
| N-(4-(benzofuran-2-yl)thiazol-2-yl)-N-(3-(2-oxopyrrolidin-1-yl)propyl)thiophene-2-carboxamide | 451.9 | 3.69 | C | Example 13 or 14 |
| N-(4-(benzofuran-2-yl)thiazol-2-yl)-1-methyl-N-(3-(2-oxopyrrolidin-1-yl)propyl)-1H-pyrrole-2-carboxamide | 449.1 | 3.69 | C | Example 13 or 14 |
| N-(3-(2-oxopyrrolidin-1-yl)propyl)-N-(4-(3-phenylisoxazol-5-yl)thiazol-2-yl)furan-2-carboxamide | 463.1 | 3.56 | C | Example 13 or 14 |
| N-(3-(2-oxopyrrolidin-1-yl)propyl)-N-(4-(3-phenylisoxazol-5-yl)thiazol-2-yl)thiophene-2-carboxamide | 479.1 | 3.59 | C | Example 13 or 14 |
| 1-methyl-N-(3-(2-oxopyrrolidin-1-yl)propyl)-N-(4-(3-phenylisoxazol-5-yl)thiazol-2-yl)-1H-pyrrole-2-carboxamide | 476.3 | 3.56 | C | Example 13 or 14 |
| N-(3-(4-methylpiperazin-1-yl)propyl)-N-(4-(3-phenylisoxazol-5-yl)thiazol-2-yl)furan-2-carboxamide | 478.3 | 2.55 | C | Example 13 or 14 |

TABLE 1-continued

| Compound Name | LC/MS m/z [M + H] | HPLC retention time (min) | HPLC Method | Synthesis Method |
|---|---|---|---|---|
| N-(4-morpholinobutyl)-N-(4-(3-phenylisoxazol-5-yl)thiazol-2-yl)furan-2-carboxamide | 479.1 | 2.92 | C | Example 13 or 14 |
| N-(4-morpholinobutyl)-N-(4-(3-phenylisoxazol-5-yl)thiazol-2-yl)thiophene-2-carboxamide | 495.1 | 2.98 | C | Example 13 or 14 |
| N-(3-(diethylamino)propyl)-N-(4-(3,4-dimethoxyphenyl)thiazol-2-yl)thiophene-2-carboxamide | 460.3 | 2.61 | B | Example 13 or 14 |
| N-(4-(3,4-dimethoxyphenyl)thiazol-2-yl)-N-(3-(2-oxopyrrolidin-1-yl)propyl)thiophene-2-carboxamide | 472.3 | 3.11 | B | Example 13 or 14 |
| N-(4-(3,4-dimethoxyphenyl)thiazol-2-yl)-N-(3-(4-methylpiperazin-1-yl)propyl)thiophene-2-carboxamide | 487.1 | 2.32 | B | Example 13 or 14 |
| N-(4-(3,4-dimethoxyphenyl)thiazol-2-yl)-N-(3-(piperidin-1-yl)propyl)thiophene-2-carboxamide | 472.3 | 2.66 | B | Example 13 or 14 |
| N-(4-(3,4-dimethoxyphenyl)thiazol-2-yl)-N-(5-morpholinopentyl)thiophene-2-carboxamide | 502.3 | 2.75 | B | Example 13 or 14 |
| N-(4-(3,4-dimethoxyphenyl)thiazol-2-yl)-N-(2-morpholinoethyl)thiophene-2-carboxamide | 460.3 | 2.41 | B | Example 13 or 14 |
| N-(4-(3,4-dimethoxyphenyl)thiazol-2-yl)-N-(3-phenylpropyl)thiophene-2-carboxamide | 465.1 | 4.04 | B | Example 13 or 14 |
| N-(4-(benzofuran-2-yl)thiazol-2-yl)-N-(3-(diethylamino)propyl)thiophene-2-carboxamide | 440.3 | 3.05 | B | Example 13 or 14 |
| N-(3-(1H-imidazol-1-yl)propyl)-N-(4-(benzofuran-2-yl)thiazol-2-yl)thiophene-2-carboxamide | 435.1 | 2.79 | B | Example 13 or 14 |
| N-(4-(benzofuran-2-yl)thiazol-2-yl)-N-(3-(4-methylpiperazin-1-yl)propyl)thiophene-2-carboxamide | 467.1 | 2.68 | B | Example 13 or 14 |
| N-(4-(benzofuran-2-yl)thiazol-2-yl)-N-(3-(piperidin-1-yl)propyl)thiophene-2-carboxamide | 451.9 | 3.07 | B | Example 13 or 14 |
| N-(4-(benzofuran-2-yl)thiazol-2-yl)-N-(4-morpholinobutyl)thiophene-2-carboxamide | 468.3 | 3.01 | B | Example 13 or 14 |
| N-(4-(benzofuran-2-yl)thiazol-2-yl)-N-(5-morpholinopentyl)thiophene-2-carboxamide | 482.3 | 3.16 | B | Example 13 or 14 |
| N-(4-(benzofuran-2-yl)thiazol-2-yl)-N-(3-phenylpropyl)thiophene-2-carboxamide | 445.1 | 4.60 | B | Example 13 or 14 |
| N-(4-(benzofuran-2-yl)thiazol-2-yl)-N-propylthiophene-2-carboxamide | 369.1 | 4.34 | B | Example 13 or 14 |
| N-(4-(5-methylthiophen-2-yl)thiazol-2-yl)-N-(3-morpholinopropyl)thiophene-2-carboxamide | 434.3 | 2.78 | B | Example 15 |
| N-(4-(6-methoxypyridin-3-yl)thiazol-2-yl)-N-(3-morpholinopropyl)thiophene-2-carboxamide | 445.1 | 2.42 | B | Example 15 |
| N-(4-(2,6-dimethoxypyridin-3-yl)thiazol-2-yl)-N-(3-morpholinopropyl)thiophene-2-carboxamide | 475.1 | 2.87 | B | Example 15 |
| N-(4-cyclopentylthiazol-2-yl)-N-(3-morpholinopropyl)thiophene-2-carboxamide | 406.3 | 2.63 | B | Example 15 |
| N-(4-cyclohexylthiazol-2-yl)-N-(3-morpholinopropyl)thiophene-2-carboxamide | 420.3 | 2.80 | B | Example 15 |
| methyl 6-(2-(N-(3-morpholinopropyl)thiophene-2-carboxamido)thiazol-4-yl)nicotinate | 473.1 | 2.50 | B | Example 15 |
| N-(4-(1H-indol-2-yl)thiazol-2-yl)-N-(3-morpholinopropyl)thiophene-2-carboxamide | 453.1 | 2.93 | C | Example 15 |
| N-(4-(7-methoxybenzofuran-2-yl)thiazol-2-yl)-N-(3-morpholinopropyl)thiophene-2-carboxamide | 484.3 | 2.94 | C | Example 15 |
| N-(4-(5-methoxybenzofuran-2-yl)thiazol-2-yl)-N-(3-morpholinopropyl)thiophene-2-carboxamide | 484.3 | 3.03 | C | Example 15 |
| N-(3-morpholinopropyl)-N-(4-(5-nitrobenzofuran-2-yl)thiazol-2-yl)thiophene-2-carboxamide | 499.1 | 3.09 | C | Example 15 |
| N-(4-(4-(2-hydroxyethylcarbamoyl)phenyl)thiazol-2-yl)-N-(3-morpholinopropyl)thiophene-2-carboxamide | 501.1 | 2.17 | B | Example 16 |
| N-(4-(4-(2-morpholinoethylcarbamoyl)phenyl)thiazol-2-yl)-N-(3-morpholinopropyl)thiophene-2-carboxamide | 570.4 | 2.09 | B | Example 16 |
| N-(4-(4-(methylcarbamoyl)phenyl)thiazol-2-yl)-N-(3-morpholinopropyl)thiophene-2-carboxamide | 471.5 | 2.29 | B | Example 16 |

TABLE 1-continued

| Compound Name | LC/MS m/z [M + H] | HPLC retention time (min) | HPLC Method | Synthesis Method |
|---|---|---|---|---|
| N-(4-(4-(2-(dimethylamino)ethylcarbamoyl)phenyl)thiazol-2-yl)-N-(3-morpholinopropyl)thiophene-2-carboxamide | 528.3 | 2.08 | B | Example 16 |
| N-(4-(4-(3-(dimethylamino)propylcarbamoyl)phenyl)thiazol-2-yl)-N-(3-morpholinopropyl)thiophene-2-carboxamide | 542.3 | 2.09 | B | Example 16 |
| N-(4-(4-(3-hydroxypropylcarbamoyl)phenyl)thiazol-2-yl)-N-(3-morpholinopropyl)thiophene-2-carboxamide | 515.1 | 2.21 | B | Example 16 |
| N-(4-(4-carbamoylphenyl)thiazol-2-yl)-N-(3-morpholinopropyl)thiophene-2-carboxamide | 457.1 | 2.22 | B | Example 16 |
| N-(4-(4-(dimethylcarbamoyl)phenyl)thiazol-2-yl)-N-(3-morpholinopropyl)thiophene-2-carboxamide | 485.5 | 2.38 | B | Example 16 |
| 2-(4-(2-(N-(3-morpholinopropyl)thiophene-2-carboxamido)thiazol-4-yl)benzamido)acetic acid | 515.1 | 2.22 | B | Example 16 |
| N-(4-(4-(4-methylpiperazine-1-carbonyl)phenyl)thiazol-2-yl)-N-(3-morpholinopropyl)thiophene-2-carboxamide | 540.3 | 2.01 | B | Example 16 |
| N-(4-(4-(morpholine-4-carbonyl)phenyl)thiazol-2-yl)-N-(3-morpholinopropyl)thiophene-2-carboxamide | 527.1 | 2.37 | B | Example 16 |
| 2-(3-(2-(N-(3-morpholinopropyl)thiophene-2-carboxamido)thiazol-4-yl)phenoxy)acetic acid | 488.3 | 2.58 | B | Example 17 |
| 3-(3-(2-(N-(3-morpholinopropyl)thiophene-2-carboxamido)thiazol-4-yl)phenoxy)propanoic acid | 502.3 | 2.64 | B | Example 17 |
| 2-(4-(2-(N-(3-morpholinopropyl)thiophene-2-carboxamido)thiazol-4-yl)phenoxy)acetic acid | 488.3 | 2.58 | B | Example 17 |
| 3-(4-(2-(N-(3-morpholinopropyl)thiophene-2-carboxamido)thiazol-4-yl)phenoxy)propanoic acid | 502.3 | 2.60 | B | Example 17 |
| N-(4-(3-(3-(dimethylamino)propoxy)phenyl)thiazol-2-yl)-N-(3-morpholinopropyl)thiophene-2-carboxamide | 515.5 | 2.30 | B | Example 18 |
| N-(4-(3-(2-(dimethylamino)ethoxy)phenyl)thiazol-2-yl)-N-(3-morpholinopropyl)thiophene-2-carboxamide | 501.1 | 2.22 | B | Example 18 |
| N-(4-(4-(3-(dimethylamino)propoxy)phenyl)thiazol-2-yl)-N-(3-morpholinopropyl)thiophene-2-carboxamide | 515.5 | 2.31 | B | Example 18 |
| N-(4-(4-(2-(dimethylamino)ethoxy)phenyl)thiazol-2-yl)-N-(3-morpholinopropyl)thiophene-2-carboxamide | 501.1 | 2.21 | B | Example 18 |
| N-(4-(benzofuran-2-yl)thiazol-2-yl)-N-(3-(2-hydroxyethylamino)-3-oxopropyl)thiophene-2-carboxamide | 442.3 | 3.23 | B | Example 19 |
| N-(4-(benzofuran-2-yl)thiazol-2-yl)-N-(3-(2-(hydroxymethyl)pyrrolidin-1-yl)-3-oxopropyl)thiophene-2-carboxamide | 482.3 | 3.62 | B | Example 19 |
| N-(4-(benzofuran-2-yl)thiazol-2-yl)-N-(3-(2-(dimethylamino)ethylamino)-3-oxopropyl)thiophene-2-carboxamide | 469.1 | 2.93 | B | Example 19 |
| N-(4-(benzofuran-2-yl)thiazol-2-yl)-N-(3-(3-hydroxypiperidin-1-yl)-3-oxopropyl)thiophene-2-carboxamide | 482.3 | 3.54 | B | Example 19 |
| N-(4-(benzofuran-2-yl)thiazol-2-yl)-N-(3-((2-hydroxyethyl)(methyl)amino)-3-oxopropyl)thiophene-2-carboxamide | 456.3 | 3.43 | B | Example 19 |
| N-(4-(benzofuran-2-yl)thiazol-2-yl)-N-(3-(bis(2-hydroxyethyl)amino)-3-oxopropyl)thiophene-2-carboxamide | 486.3 | 3.06 | B | Example 19 |
| N-(4-(benzofuran-2-yl)thiazol-2-yl)-N-(3-oxo-3-(piperazin-1-yl)propyl)thiophene-2-carboxamide | 467.1 | 2.95 | B | Example 19 |
| N-(4-(benzofuran-2-yl)thiazol-2-yl)-N-(3-((2-(dimethylamino)ethyl)(methyl)amino)-3-oxopropyl)thiophene-2-carboxamide | 483.1 | 3.04 | B | Example 19 |
| N-(4-(benzofuran-2-yl)thiazol-2-yl)-N-(3-(methyl(2-(methylamino)ethyl)amino)-3-oxopropyl)thiophene-2-carboxamide | 469.1 | 3.04 | B | Example 19 |

TABLE 1-continued

| Compound Name | LC/MS m/z [M + H] | HPLC retention time (min) | HPLC Method | Synthesis Method |
|---|---|---|---|---|
| N-(4-(benzofuran-2-yl)thiazol-2-yl)-N-(3-(3-hydroxypyrrolidin-1-yl)-3-oxopropyl)thiophene-2-carboxamide | 468.3 | 3.36 | B | Example 19 |
| N-(4-(benzofuran-2-yl)thiazol-2-yl)-N-(3-(3-(dimethylamino)pyrrolidin-1-yl)-3-oxopropyl)thiophene-2-carboxamide | 495.1 | 2.95 | B | Example 19 |
| N-(4-(benzofuran-2-yl)thiazol-2-yl)-N-(3-((2,3-dihydroxypropyl)(methyl)amino)-3-oxopropyl)thiophene-2-carboxamide | 486.3 | 3.23 | C | Example 19 |
| methyl 2-(3-(N-(4-(benzofuran-2-yl)thiazol-2-yl)thiophene-2-carboxamido)propanamido)acetate | 470.3 | 3.62 | C | Example 19 |
| 1-(3-(N-(4-(benzofuran-2-yl)thiazol-2-yl)thiophene-2-carboxamido)propanoyl)piperidine-3-carboxamide | 509.1 | 3.40 | C | Example 19 |
| N-(4-(benzofuran-2-yl)thiazol-2-yl)-N-(3-oxo-3-(thiazolidin-3-yl)propyl)thiophene-2-carboxamide | 470.3 | 3.98 | C | Example 19 |
| N-(4-(benzofuran-2-yl)thiazol-2-yl)-N-(3-morpholino-3-oxopropyl)thiophene-2-carboxamide | 468.3 | 3.75 | C | Example 19 |
| N-(4-(benzofuran-2-yl)thiazol-2-yl)-N-(3-((2-cyanoethyl)(methyl)amino)-3-oxopropyl)thiophene-2-carboxamide | 465.1 | 3.76 | C | Example 19 |
| N-(4-(benzofuran-2-yl)thiazol-2-yl)-N-(3-(3-(hydroxymethyl)piperidin-1-yl)-3-oxopropyl)thiophene-2-carboxamide | 496.3 | 3.66 | C | Example 19 |
| 1-(3-(N-(4-(benzofuran-2-yl)thiazol-2-yl)thiophene-2-carboxamido)propanoyl)piperidine-3-carboxylic acid | 510.3 | 3.62 | C | Example 19 |
| N-(3-(3-acetamidopyrrolidin-1-yl)-3-oxopropyl)-N-(4-(benzofuran-2-yl)thiazol-2-yl)thiophene-2-carboxamide | 509.1 | 3.28 | C | Example 19 |
| 1-(3-(N-(4-(benzofuran-2-yl)thiazol-2-yl)thiophene-2-carboxamido)propanoyl)pyrrolidine-2-carboxamide | 495.1 | 3.34 | C | Example 19 |
| N-(4-(benzofuran-2-yl)thiazol-2-yl)-N-(3-oxo-3-(3-oxopiperazin-1-yl)propyl)thiophene-2-carboxamide | 481.1 | 3.25 | C | Example 19 |
| 1-(3-(N-(4-(benzofuran-2-yl)thiazol-2-yl)thiophene-2-carboxamido)propanoyl)piperidine-2-carboxamide | 509.1 | 3.59 | C | Example 19 |
| N-(4-(benzofuran-2-yl)thiazol-2-yl)-N-(3-oxo-3-(2-phenoxyethylamino)propyl)thiophene-2-carboxamide | 517.9 | 4.11 | C | Example 19 |
| 1-(3-(N-(4-(benzofuran-2-yl)thiazol-2-yl)thiophene-2-carboxamido)propanoyl)-N-(2-hydroxyethyl)piperidine-3-carboxamide | 553.2 | 3.29 | C | Example 19 |
| N-(4-(benzofuran-2-yl)thiazol-2-yl)-N-(3-(isobutyl(1,1-dioxo-tetrahydrothiophen-3-yl)amino)-3oxopropyl)thiophene-2-carboxamide | 572.4 | 4.10 | C | Example 19 |
| N-(4-(benzofuran-2-yl)thiazol-2-yl)-N-(4-(4-(2-(dimethylamino)ethyl)piperazin-1-yl)-4-oxobutyl)thiophene-2-carboxamide | 552.3 | 2.83 | C | Example 19 |
| N-(4-(benzofuran-2-yl)thiazol-2-yl)-N-(4-((2,3-dihydroxypropyl)(methyl)amino)-4-oxobutyl)thiophene-2-carboxamide | 500.3 | 3.32 | C | Example 19 |
| methyl 2-(4-(N-(4-(benzofuran-2-yl)thiazol-2-yl)thiophene-2-carboxamido)butanamido)acetate | 484.3 | 3.67 | C | Example 19 |
| N-(4-(benzofuran-2-yl)thiazol-2-yl)-N-(4-((5-methylpyrazin-2-yl)methylamino)-4-oxobutyl)thiophene-2-carboxamide | 517.9 | 3.57 | C | Example 19 |
| N-(4-(benzofuran-2-yl)thiazol-2-yl)-N-(4-(1-hydroxypropan-2-ylamino)-4-oxobutyl)thiophene-2-carboxamide | 470.3 | 3.42 | C | Example 19 |
| N-(4-(benzofuran-2-yl)thiazol-2-yl)-N-(4-oxo-4-(piperidin-1-yl)butyl)thiophene-2-carboxamide | 479.9 | 4.26 | C | Example 19 |
| 1-(4-(N-(4-(benzofuran-2-yl)thiazol-2-yl)thiophene-2-carboxamido)butanoyl)piperidine-4-carboxamide | 523.5 | 3.37 | C | Example 19 |

TABLE 1-continued

| Compound Name | LC/MS m/z [M + H] | HPLC retention time (min) | HPLC Method | Synthesis Method |
|---|---|---|---|---|
| N-(4-(benzofuran-2-yl)thiazol-2-yl)-N-(4-((2-hydroxyethyl)(phenyl)amino)-4-oxobutyl)thiophene-2-carboxamide | 531.9 | 3.97 | C | Example 19 |
| N-(4-(benzofuran-2-yl)thiazol-2-yl)-N-(4-oxo-4-(2-(pyridin-4-yl)ethylamino)butyl)thiophene-2-carboxamide | 517.1 | 3.01 | C | Example 19 |
| tert-butyl 4-(4-(N-(4-(benzofuran-2-yl)thiazol-2-yl)thiophene-2-carboxamido)butanoyl)piperazine-1-carboxylate | 581.2 | 4.30 | C | Example 19 |
| N-(4-(benzofuran-2-yl)thiazol-2-yl)-N-(4-oxo-4-(pyridin-3-ylmethylamino)butyl)thiophene-2-carboxamide | 503.1 | 3.04 | C | Example 19 |
| N-(4-(benzofuran-2-yl)thiazol-2-yl)-N-(4-(5-(methylsulfonyl)indolin-1-yl)-4-oxobutyl)thiophene-2-carboxamide | 592.4 | 4.06 | C | Example 19 |
| tert-butyl 1-(4-(N-(4-(benzofuran-2-yl)thiazol-2-yl)thiophene-2-carboxamido)butanoyl)pyrrolidin-3-ylcarbamate | 581.2 | 4.07 | C | Example 19 |
| N-(4-(3-acetamidopyrrolidin-1-yl)-4-oxobutyl)-N-(4-(benzofuran-2-yl)thiazol-2-yl)thiophene-2-carboxamide | 523.5 | 3.39 | C | Example 19 |
| methyl 1-(4-(N-(4-(benzofuran-2-yl)thiazol-2-yl)thiophene-2-carboxamido)butanoyl)piperidine-4-carboxylate | 538.3 | 4.02 | C | Example 19 |
| 1-(4-(N-(4-(benzofuran-2-yl)thiazol-2-yl)thiophene-2-carboxamido)butanoyl)-N-methylpiperidine-4-carboxamide | 537.1 | 3.46 | C | Example 19 |
| N-(4-(benzofuran-2-yl)thiazol-2-yl)-N-(4-(4-(N,N-dimethylsulfamoyl)piperazin-1-yl)-4-oxobutyl)thiophene-2-carboxamide | 588.4 | 3.92 | C | Example 19 |
| ethyl 2-(1-(4-(N-(4-(benzofuran-2-yl)thiazol-2-yl)thiophene-2-carboxamido)butanoyl)piperidin-3-yl)acetate | 566.4 | 4.31 | C | Example 19 |
| ethyl 2-(1-(4-(N-(4-(benzofuran-2-yl)thiazol-2-yl)thiophene-2-carboxamido)butanoyl)piperidin-4-yl)acetate | 566.4 | 4.24 | C | Example 19 |
| N-(4-(benzofuran-2-yl)thiazol-2-yl)-N-(4-(4-(diethylamino)piperidin-1-yl)-4-oxobutyl)thiophene-2-carboxamide | 551.5 | 3.18 | C | Example 19 |
| 1-(4-(N-(4-(benzofuran-2-yl)thiazol-2-yl)thiophene-2-carboxamido)butanoyl)pyrrolidine-2-carboxamide | 509.1 | 3.43 | C | Example 19 |
| methyl 1-(4-(N-(4-(benzofuran-2-yl)thiazol-2-yl)thiophene-2-carboxamido)butanoyl)pyrrolidine-2-carboxylate | 524.3 | 3.98 | C | Example 19 |
| N-(4-(benzofuran-2-yl)thiazol-2-yl)-N-(4-oxo-4-(3-oxopiperazin-1-yl)butyl)thiophene-2-carboxamide | 495.1 | 3.34 | C | Example 19 |
| N-(4-(2-amino-2-oxoethylamino)-4-oxobutyl)-N-(4-(benzofuran-2-yl)thiazol-2-yl)thiophene-2-carboxamide | 469.1 | 3.21 | C | Example 19 |
| 1-(4-(N-(4-(benzofuran-2-yl)thiazol-2-yl)thiophene-2-carboxamido)butanoyl)-N-(2-hydroxyethyl)piperidine-3-carboxamide | 567.2 | 3.35 | C | Example 19 |
| 1-(4-(N-(4-(benzofuran-2-yl)thiazol-2-yl)thiophene-2-carboxamido)butanoyl)-N-(2-hydroxyethyl)piperidine-4-carboxamide | 567.2 | 3.25 | C | Example 19 |
| N-(4-(benzofuran-2-yl)thiazol-2-yl)-N-(4-(2-(methylsulfinyl)ethylamino)-4-oxobutyl)thiophene-2-carboxamide | 502.3 | 3.24 | C | Example 19 |
| N-(4-(benzofuran-2-yl)thiazol-2-yl)-N-(4-((2-hydroxyethyl)(pyridin-4-ylmethyl)amino)-4-oxobutyl)thiophene-2-carboxamide | 547.1 | 2.98 | C | Example 19 |
| N-(4-(benzofuran-2-yl)thiazol-2-yl)-N-(4-(cyclohexyl(4-hydroxybutyl)amino)-4-oxobutyl)thiophene-2-carboxamide | 566.4 | 4.25 | C | Example 19 |
| N-(4-(benzofuran-2-yl)thiazol-2-yl)-N-(4-((2-cyanoethyl)((tetrahydrofuran-2-yl)methyl)amino)-4-oxobutyl)thiophene-2-carboxamide | 549.1 | 4.02 | C | Example 19 |
| N-(4-(benzofuran-2-yl)thiazol-2-yl)-N-(4-oxo-4-(2-(pyridin-3-yl)pyrrolidin-1-yl)butyl)thiophene-2-carboxamide | 543.1 | 3.21 | C | Example 19 |

TABLE 1-continued

| Compound Name | LC/MS m/z [M + H] | HPLC retention time (min) | HPLC Method | Synthesis Method |
|---|---|---|---|---|
| N-(4-(benzofuran-2-yl)thiazol-2-yl)-N-(3-(1-hydroxypropan-2-ylamino)-3-oxopropyl)thiophene-2-carboxamide | 456.3 | 3.34 | C | Example 19 |
| N-(4-(benzofuran-2-yl)thiazol-2-yl)-N-(3-(2-methoxyethylamino)-3-oxopropyl)thiophene-2-carboxamide | 456.3 | 3.59 | C | Example 19 |
| N-(4-(benzofuran-2-yl)thiazol-2-yl)-N-(3-(furan-3-ylmethylamino)-3-oxopropyl)thiophene-2-carboxamide | 477.9 | 3.84 | C | Example 19 |
| methyl 1-(3-(N-(4-(benzofuran-2-yl)thiazol-2-yl)thiophene-2-carboxamido)propanoyl)pyrrolidine-2-carboxylate | 510.3 | 3.95 | C | Example 19 |
| N-(4-(benzofuran-2-yl)thiazol-2-yl)-N-(3-(isoindolin-2-yl)-3-oxopropyl)thiophene-2-carboxamide | 500.3 | 4.27 | C | Example 19 |
| N-(3-((1,4-dioxan-2-yl)methylamino)-3-oxopropyl)-N-(4-(benzofuran-2-yl)thiazol-2-yl)thiophene-2-carboxamide | 498.3 | 3.53 | C | Example 19 |
| N-(4-(benzofuran-2-yl)thiazol-2-yl)-N-(3-(cyclohexyl(4-hydroxybutyl)amino)-3-oxopropyl)thiophene-2-carboxamide | 552.3 | 3.55 | C | Example 19 |
| N-(4-(benzofuran-2-yl)thiazol-2-yl)-N-(3-(methyl(pyridin-4-yl)amino)-3-oxopropyl)thiophene-2-carboxamide | 489.1 | 3.20 | C | Example 19 |
| 1-(4-(N-(4-(benzofuran-2-yl)thiazol-2-yl)thiophene-2-carboxamido)butanoyl)piperidine-3-carboxamide | 523.5 | 3.47 | C | Example 19 |
| N-(4-(benzofuran-2-yl)thiazol-2-yl)-N-(4-oxo-4-(pyridin-2-ylmethylamino)butyl)thiophene-2-carboxamide | 503.1 | 3.08 | C | Example 19 |
| N-(4-(benzofuran-2-yl)thiazol-2-yl)-N-(4-oxo-4-(thiazolidin-3-yl)butyl)thiophene-2-carboxamide | 484.3 | 4.03 | C | Example 19 |
| tert-butyl 2-(4-(N-(4-(benzofuran-2-yl)thiazol-2-yl)thiophene-2-carboxamido)butanamido)ethylcarbamate | 555.2 | 3.91 | C | Example 19 |
| (S)-N-(4-(benzofuran-2-yl)thiazol-2-yl)-N-(4-(2-(hydroxymethyl)indolin-1-yl)-4-oxobutyl)thiophene-2-carboxamide | 544.3 | 3.85 | C | Example 19 |
| N-(4-(benzofuran-2-yl)thiazol-2-yl)-N-(4-(isoindolin-2-yl)-4-oxobutyl)thiophene-2-carboxamide | 514.3 | 4.28 | C | Example 19 |
| N-(3-acetamidopropyl)-N-(4-(benzofuran-2-yl)thiazol-2-yl)thiophene-2-carboxamide | 426.3 | 3.50 | B | Example 20 or 21 |
| 1-acetyl-N-(3-(N-(4-(benzofuran-2-yl)thiazol-2-yl)thiophene-2-carboxamido)propyl)piperidine-4-carboxamide | 537.1 | 3.44 | C | Eample 20 or 21 |
| N-(4-(benzofuran-2-yl)thiazol-2-yl)-N-(3-(3-(piperidin-1-yl)propanamido)propyl)thiophene-2-carboxamide | 523.5 | 3.15 | C | Example 20 or 21 |
| N-(4-(benzofuran-2-yl)thiazol-2-yl)-N-(3-(4-(dimethylamino)butanamido)propyl)thiophene-2-carboxamide | 497.5 | 3.04 | C | Example 20 or 21 |
| N-(3-(N-(4-(benzofuran-2-yl)thiazol-2-yl)thiophene-2-carboxamido)propyl)isonicotinamide | 489.1 | 3.12 | C | Example 20 or 21 |
| N-(3-(4-acetamidobutanamido)propyl)-N-(4-(benzofuran-2-yl)thiazol-2-yl)thiophene-2-carboxamide | 511.5 | 3.29 | C | Example 20 or 21 |
| N-(4-(benzofuran-2-yl)thiazol-2-yl)-N-(3-(3-hydroxy-2-(hydroxymethyl)-2-methylpropanamido)propyl)thiophene-2-carboxamide | 500.3 | 3.30 | C | Example 20 or 21 |
| N-(4-(benzofuran-2-yl)thiazol-2-yl)-N-(3-(2-(2,5-dioxoimidazolidin-4-yl)acetamido)propyl)thiophene-2-carboxamide | 524.3 | 3.57 | C | Example 20 or 21 |
| N-(4-(benzofuran-2-yl)thiazol-2-yl)-N-(3-(3-morpholinopropanamido)propyl)thiophene-2-carboxamide | 525.1 | 3.03 | C | Example 20 or 21 |
| N-(3-(N-(4-benzofuran-2-yl)thiazol-2-yl)thiophene-2-carboxamido)propyl)-1,5-dimethyl-1H-pyrazole-3-carboxamide | 505.9 | 3.75 | C | Example 20 or 21 |

TABLE 1-continued

| Compound Name | LC/MS m/z [M + H] | HPLC retention time (min) | HPLC Method | Synthesis Method |
|---|---|---|---|---|
| N-(4-(benzofuran-2-yl)thiazol-2-yl)-N-(3-(2-morpholinoacetamido)propyl)thiophene-2-carboxamide | 511.5 | 3.02 | C | Example 20 or 21 |
| (S)-tert-butyl 1-(3-(N-(4-(benzofuran-2-yl)thiazol-2-yl)thiophene-2-carboxamido)propyl)pyrrolidine-2-carboxylate | 538.3 | 3.53 | C | Example 22 or 23 |
| 1-(3-(N-(4-(benzofuran-2-yl)thiazol-2-yl)thiophene-2-carboxamido)propyl)piperidine-3-carboxamide | 495.1 | 3.02 | C | Example 22 or 23 |
| ethyl 1-(3-(N-(4-(benzofuran-2-yl)thiazol-2-yl)thiophene-2-carboxamido)propyl)piperidine-2-carboxylate | 524.3 | 3.40 | C | Example 22 or 23 |
| N-(4-(benzofuran-2-yl)thiazol-2-yl)-N-(3-(3-hydroxypiperidin-1-yl)propyl)thiophene-2-carboxamide | 468.3 | 3.03 | C | Example 22 or 23 |
| N-(4-(benzofuran-2-yl)thiazol-2-yl)-N-(3-(4-(2-(2-hydroxyethoxy)ethyl)piperazin-1-yl)propyl)thiophene-2-carboxamide | 541.1 | 2.73 | C | Example 22 or 23 |
| N-(4-(benzofuran-2-yl)thiazol-2-yl)-N-(3-(4-(2-hydroxyethyl)piperidin-1-yl)propyl)thiophene-2-carboxamide | 496.3 | 3.04 | C | Example 22 or 23 |
| N-(4-(benzofuran-2-yl)thiazol-2-yl)-N-(3-(4-(2-cyanoethyl)piperazin-1-yl)propyl)thiophene-2-carboxamide | 505.9 | 3.11 | C | Example 22 or 23 |
| N-(4-(benzofuran-2-yl)thiazol-2-yl)-N-(3-(4-(hydroxymethyl)piperidin-1-yl)propyl)thiophene-2-carboxamide | 482.3 | 3.00 | C | Example 22 or 23 |
| N-(4-(benzofuran-2-yl)thiazol-2-yl)-N-(3-(3-(dimethylamino)pyrrolidin-1-yl)propyl)thiophene-2-carboxamide | 481.1 | 2.73 | C | Example 22 or 23 |
| ethyl 1-(3-(N-(4-(benzofuran-2-yl)thiazol-2-yl)thiophene-2-carboxamido)propyl)piperidine-3-carboxylate | 524.3 | 3.36 | C | Example 22 or 23 |
| N-(4-(benzofuran-2-yl)thiazol-2-yl)-N-(3-(4-hydroxypiperidin-1-yl)propyl)thiophene-2-carboxamide | 468.3 | 3.01 | C | Example 22 or 23 |
| N-(4-(benzofuran-2-yl)thiazol-2-yl)-N-(3-(3-(N-ethylacetamido)pyrrolidin-1-yl)propyl)thiophene-2-carboxamide | 523.5 | 3.24 | C | Example 22 or 23 |
| N-(4-(benzofuran-2-yl)thiazol-2-yl)-N-(3-(3-(N-methylacetamido)pyrrolidin-1-yl)propyl)thiophene-2-carboxamide | 509.1 | 3.10 | C | Example 22 or 23 |
| tert-butyl 1-(3-(N-(4-(benzofuran-2-yl)thiazol-2-yl)thiophene-2-carboxamido)propyl)pyrrolidin-3-ylcarbamate | 553.2 | 3.44 | C | Example 22 or 23 |
| (S)-N-(4-(benzofuran-2-yl)thiazol-2-yl)-N-(3-(2-(methoxymethyl)pyrrolidin-1-yl)propyl)thiophene-2-carboxamide | 482.3 | 3.28 | C | Example 22 or 23 |
| N-(3-(3-acetamidopyrrolidin-1-yl)propyl)-N-(4-(benzofuran-2-yl)thiazol-2-yl)thiophene-2-carboxamide | 495.1 | 2.99 | C | Example 22 or 23 |
| ethyl 4-(3-(N-(4-(benzofuran-2-yl)thiazol-2-yl)thiophene-2-carboxamido)propyl)piperazine-1-carboxylate | 525.1 | 3.23 | C | Example 22 or 23 |
| N-(4-(benzofuran-2-yl)thiazol-2-yl)-N-(3-(4-(morpholine-4-carbonyl)piperazin-1-yl)propyl)thiophene-2-carboxamide | 566.4 | 3.02 | C | Example 22 or 23 |
| N-(4-(benzofuran-2-yl)thiazol-2-yl)-N-(3-(4,4-dihydroxypiperidin-1-yl)propyl)thiophene-2-carboxamide | 484.3 | 2.95 | C | Example 22 or 23 |
| N-(4-(benzofuran-2-yl)thiazol-2-yl)-N-(3-(4-(tetrahydrofuran-2-carbonyl)piperazin-1-yl)propyl)thiophene-2-carboxamide | 551.5 | 3.05 | C | Example 22 or 23 |
| (R)-1-(3-(N-(4-(benzofuran-2-yl)thiazol-2-yl)thiophene-2-carboxamido)propyl)-N-methylpyrrolidine-2-carboxamide | 495.1 | 3.12 | C | Example 22 or 23 |
| 1-(3-(N-(4-(benzofuran-2-yl)thiazol-2-yl)thiophene-2-carboxamido)propyl)pyrrolidine-2-carboxamide | 481.1 | 3.04 | C | Example 22 or 23 |
| methyl 1-(3-(N-(4-(benzofuran-2-yl)thiazol-2-yl)thiophene-2-carboxamido)propyl)pyrrolidine-2-carboxylate | 496.3 | 3.26 | C | Example 22 or 23 |

TABLE 1-continued

| Compound Name | LC/MS m/z [M + H] | HPLC retention time (min) | HPLC Method | Synthesis Method |
|---|---|---|---|---|
| methyl 1-(3-(N-(4-(benzofuran-2-yl)thiazol-2-yl)thiophene-2-carboxamido)propyl)piperidine-2-carboxylate | 510.3 | 3.31 | C | Example 22 or 23 |
| (S)-1-(3-(N-(4-(benzofuran-2-yl)thiazol-2-yl)thiophene-2-carboxamido)propyl)-N,N-dimethylpyrrolidine-2-carboxamide | 509.1 | 3.20 | C | Example 22 or 23 |
| N-(4-(benzofuran-2-yl)thiazol-2-yl)-N-(3-(2-(pyrrolidin-1-ylmethyl)piperidin-1-yl)propyl)thiophene-2-carboxamide | 535.1 | 2.85 | C | Example 22 or 23 |
| N-(4-(benzofuran-2-yl)thiazol-2-yl)-N-(3-(3-oxopiperazin-1-yl)propyl)thiophene-2-carboxamide | 467.1 | 2.91 | C | Example 22 or 23 |
| 1-(3-(N-(4-(benzofuran-2-yl)thiazol-2-yl)thiophene-2-carboxamido)propyl)piperidine-2-carboxamide | 495.1 | 3.05 | C | Example 22 or 23 |
| ethyl 2-(4-(3-(N-(4-(benzofuran-2-yl)thiazol-2-yl)thiophene-2-carboxamido)propyl)piperazin-1-yl)acetate | 539.1 | 3.21 | C | Example 22 or 23 |
| tert-butyl 4-(3-(N-(4-(benzofuran-2-yl)thiazol-2-yl)thiophene-2-carboxamido)propyl)piperazine-1-carboxylate | 553.2 | 3.43 | C | Example 22 or 23 |
| N-(4-(benzofuran-2-yl)thiazol-2-yl)-N-(3-(4-morpholinopiperidin-1-yl)propyl)thiophene-2-carboxamide | 537.1 | 2.72 | C | Example 22 or 23 |
| N-(4-(benzofuran-2-yl)thiazol-2-yl)-N-(3-(4-(2-(dimethylamino)ethyl)piperazin-1-yl)propyl)thiophene-2-carboxamide | 524.3 | 2.71 | C | Example 22 or 23 |
| N-(4-(benzofuran-2-yl)thiazol-2-yl)-N-(3-(2-(hydroxymethyl)pyrrolidin-1-yl)propyl)thiophene-2-carboxamide | 468.3 | 3.08 | B | Example 22 or 23 |
| N-(4-(benzofuran-2-yl)thiazol-2-yl)-N-(3-(2-(2-hydroxyethyl)piperidin-1-yl)propyl)thiophene-2-carboxamide | 496.3 | 3.14 | B | Example 22 or 23 |
| N-(4-(benzofuran-2-yl)thiazol-2-yl)-N-(3-(3-(hydroxymethyl)piperidin-1-yl)propyl)thiophene-2-carboxamide | 482.3 | 3.05 | B | Example 22 or 23 |
| N-(4-(benzofuran-2-yl)thiazol-2-yl)-N-(3-(2-(hydroxymethyl)piperidin-1-yl)propyl)thiophene-2-carboxamide | 482.3 | 3.13 | B | Example 22 or 23 |
| N-(4-(benzofuran-2-yl)thiazol-2-yl)-N-(3-(3-hydroxypyrrolidin-1-yl)propyl)thiophene-2-carboxamide | 454.3 | 3.00 | B | Example 22 or 23 |
| (S)-N-(4-(benzofuran-2-yl)thiazol-2-yl)-N-(3-(2-(hydroxymethyl)pyrrolidin-1-yl)propyl)thiophene-2-carboxamide | 468.3 | 3.09 | B | Example 22 or 23 |
| N-(3-(4-acetylpiperazin-1-yl)propyl)-N-(4-(benzofuran-2-yl)thiazol-2-yl)thiophene-2-carboxamide | 495.5 | 2.98 | B | Example 22 or 23 |
| 1-(3-(N-(4-(benzofuran-2-yl)thiazol-2-yl)thiophene-2-carboxamido)propyl)-N,N-diethylpiperidine-3-carboxamide | 551.5 | 3.39 | B | Example 22 or 23 |
| N-(4-(benzofuran-2-yl)thiazol-2-yl)-N-(3-(4-(2-hydroxyethyl)piperazin-1-yl)propyl)thiophene-2-carboxamide | 497.5 | 2.70 | B | Example 22 or 23 |
| N-(4-(benzofuran-2-yl)thiazol-2-yl)-N-(3-(4-(2-methoxyethyl)piperazin-1-yl)propyl)thiophene-2-carboxamide | 511.5 | 2.82 | B | Example 22 or 23 |
| N-(4-(benzofuran-2-yl)thiazol-2-yl)-N-(3-(3-(diethylamino)pyrrolidin-1-yl)propyl)thiophene-2-carboxamide | 509.5 | 2.82 | B | Example 22 or 23 |
| 1-(3-(N-(4-(benzofuran-2-yl)thiazol-2-yl)thiophene-2-carboxamido)propyl)-N-methylpiperidine-4-carboxamide | 509.1 | 2.93 | C | Example 22 or 23 |
| N-(4-(benzofuran-2-yl)thiazol-2-yl)-N-(3-(4-(diethylamino)piperidin-1-yl)propyl)thiophene-2-carboxamide | 523.5 | 2.72 | C | Example 22 or 23 |
| (R)-1-(3-(N-(4-(benzofuran-2-yl)thiazol-2-yl)thiophene-2-carboxamido)propyl)pyrrolidine-2-carboxylic acid | 482.3 | 3.06 | B | Example 22 or 23 |
| 1-(3-(N-(4-(benzofuran-2-yl)thiazol-2-yl)thiophene-2-carboxamido)propyl)piperidine-4-carboxamide | 495.5 | 2.88 | C | Example 22 or23 |

TABLE 1-continued

| Compound Name | LC/MS m/z [M + H] | HPLC retention time (min) | HPLC Method | Synthesis Method |
|---|---|---|---|---|
| N-(4-(benzofuran-2-yl)thiazol-2-yl)-N-(3-(4-(2-(dimethylamino)-2-oxoethyl)piperazin-1-yl)propyl)thiophene-2-carboxamide | 538.3 | 2.84 | B | Example 22 or 23 |
| N-(4-(benzofuran-2-yl)thiazol-2-yl)-N-(3-(4-(methylsulfonyl)piperazin-1-yl)propyl)thiophene-2-carboxamide | 531.1 | 3.13 | B | Example 22 or 23 |

Example 25

Characterization of Compounds

The following analytical HPLC conditions were used for characterizing chemical entities of the present disclosure. MS ions were detected using a Sciex API-100 electrospray single quadrupole mass spectrometer interfaced to the HPLC system.

Method A: Phenomenex Chromolith SpeedRod RP-18e C18 analytical column (4.6 mm×50 mm); flow rate=1.5 mL/min; injection volume=15-20 µL; mobile phase A: 100% water, 0.1% trifluoroacetic acid (TFA); mobile phase B: 100% acetonitrile, 0.1% trifluoroacetic acid (TFA); gradient elution from 5% B to 100% B over 4.4 min, with a stay at 100% B for 1 min, then equilibration to 5% B over 0.6 min.

Method B: Phenomenex Chromolith SpeedRod RP-18e C18 analytical column (4.6 mm×50 mm); flow rate=1.5 mL/min; injection volume=15-20 µL; mobile phase A: 100% water, 0.1% trifluoroacetic acid (TFA); mobile phase B: 100% acetonitrile, 0.1% trifluoroacetic acid (TFA); gradient elution from 5% B to 100% B over 4.3 min, with a stay at 100% B for 1 min, then equilibration to 5% B over 0.7 min.

Method C: Phenomenex Chromolith SpeedRod RP-18e C18 analytical column (4.6 mm×50 mm); flow rate=1.5 mL/min; injection volume=15-20 µL; mobile phase A: 100% water, 0.1% trifluoroacetic acid (TFA); mobile phase B: 100% acetonitrile, 0.1% trifluoroacetic acid (TFA); gradient elution from 5% B to 100% B over 4.2 min, with a stay at 100% B for 1 min, then equilibration to 5% B over 0.8 min.

The following preparative HPLC methods were used for purifying chemical entities of the present disclosure:

Method X: YMC-Pack ODS-A C-18 column (30 mm×100 mm); flow rate=45 mL/min; injection volume=2 mL; mobile phase A: 100% water, 0.1% trifluoroacetic acid (TFA); mobile phase B: 100% acetonitrile, 0.1% TFA; gradient elution from 0% B to 90% B over 90 min.

Method Y: YMC-Pack ODS-A C-18 column (30 mm×100 mm); flow rate=36 mL/min; injection volume=1.5-2.5 mL; mobile phase A: 100% water, 0.1% trifluoroacetic acid (TFA); mobile phase B: 100% acetonitrile, 0.1% TFA; gradient elution from 0% B to 70% B over 70 min.

Method Z: Phenomenex Synergi 4 µm Max-RP column (10 mm×50 mm); flow rate=6 mL/min; injection volume=100 µL; mobile phase A: 100% water, 0.1% trifluoroacetic acid (TFA); mobile phase B: 100% acetonitrile, 0.1% trifluoroacetic acid (TFA); gradient elution from 5% B to 100% B over 6 min.

Example 26

HTS ATP-Utilizing Enzyme Assays

The following procedures describe the reagent and plate preparation for a HTS of an ATP-utilizing enzyme, such as a protein kinase, run in an off-chip mobility-shift assay format. The following provides an HTS protocol for running a protein kinase HTS screen on a Caliper HTS 250 microfluidics system. The following parameters are dependent on the protein kinase used and can be determined by one skilled in the art as part of a typical assay development process. For example, the peptide substrate used can be identified from the current literature, by screening a peptide library of potential protein kinase substrates, or by other applicable means accepted in the field.

The following table provides typical screen assay parameters appropriate for a Caliper HTS 250 microfluidics system used to assay AKT1. Parameters used to assay other protein kinases can be determined by one skilled in the art.

| | | |
|---|---|---|
| Reaction Concentration | | |
| Inhibitor concentration | 10 | µM |
| Enzyme concentration | 0.9 | nM |
| Substrate/Peptide Conc. | 1 | µM |
| ATP | 50 | µM |
| Reaction Properties | | |
| Inhibitor Volume | 5 | µL |
| Enzyme Volume | 10 | µL |
| Substrate Volume | 10 | µL |
| Termination Volume | 45 | µL |
| Reaction Time | 3 | h |
| Reaction Temperature | 20–25 | ° C. |
| Sipper Properties | | |
| Initial Delay | 20 | sec |
| Buffer | 20 | sec |
| Sample | 0.2 | sec |
| Final Delay | 120 | sec |
| Dye Well | | |
| Dye | 0.2 | sec |
| Script Properties | | |
| Electrode 1 | −250 | Volts |
| Electrode 2 | −2000 | Volts |
| Electrode 3 | −2000 | Volts |
| Electrode 4 | −250 | Volts |
| Laser Properties | yes/no | |
| UV | no | |
| Blue | yes | |
| Red | no | |
| Data Collection | yes/no | |
| CCD1 | no | |

-continued

| | | |
|---|---|---|
| CCD2 | yes | |
| CCD3 | no | |
| Inhibitor Concentrations | | |
| Inhibitor: EDTA | | |
| 100% | 20 | mM |
| Inhibitor Staurosporine | | |
| 50% | 32 | nM |
| Pressure Driven Flow | | |
| Pressure | −2 | psi |
| Base Pressure | −2 | psi |

The reagents and buffers listed in the following table are generally applicable for developing and running an HTS screen on a human protein kinase using the Caliper HTS 250 system.

| Reagent | Reagent Name | Manufacturer | Catalog # | MW | Storage |
|---|---|---|---|---|---|
| 4 sipper LABCHIP | FS266 | Caliper Tech. Inc. | 760077-0266 | — | 2–8° C. |
| Enzyme | Akt1/PKBalpha, active | Upstate | 14-276 | — | −20° C. |
| Substrate | Peptide 2 | BioPeptide | — | 1528 Da | −20° C. |
| Control Inhibitor | Staurosporine | Calbiochem | 569397 | 466.5 | 20° C. |
| Buffer Components | HEPES (free acid) | Calbiochem | 391338 | 238.3 | RT |
| | HEPES (Na Salt) | Calbiochem | 391333 | 260.3 | RT |
| | DMSO | Sigma | D8418 | — | RT |
| | Triton X-100 | Sigma | T8787 | — | RT |
| | BSA | Sigma | A8806 | — | 2–8° C. |
| | DTT (Cleland's Reagent) | Calbiochem | 233153 | 154.2 | 2–8° C. |
| | EDTA (0.5 M) | Sigma | E7889 | n/a | RT |
| | Coating Reagent 3 | Caliper Tech. Inc. | 760050 | n/a | 2–8° C. |
| | 6N HCl | VWR | JT5619-2 | n/a | RT |
| | ATP disodium salt | Sigma | A7699 | 551.1 | −20° C. |
| | $Na_3VO_4$ | Calbiochem | 567540 | 183.9 | −20° C. |
| | β-Glycerophosphate | Calbiochem | 35675 | 306.1 | −20° C. |
| | $MgCl_2 \cdot 6H_2O$ | Sigma | M2670 | 203.3 | RT |

The following reagents were prepared using the previously described buffers.

A 2X Master Buffer solution was prepared by combining 200 mL of 1 M HEPES, pH 7.5, 2 mL of 10% Triton X-100, 20 mL of 10% BSA, and 778 mL of $H_2O$.

A 2.5X Enzyme Buffer solution was prepared by combining 177.408 mL of 2X Master Buffer, 0.887 mL of 1 M DTT, 0.089 mL of 100 mM ATP, 8.870 mL of 1 M $MgCl_2$, 0.089 mL of 100 mM β-glycerophosphate, 0.089 mL of 100 mM $Na_3VO_4$, 0.254 mL of 62.8 μM enzyme, and 167.13 mL $H_2O$.

A 2.5X Substrate Buffer solution was prepared by combining 177.408 mL of 2X Master Buffer, 0.887 mL of 1 mM peptide-X, and 176.521 mL of $H_2O$.

A 1.55X Termination Buffer solution was prepared by combining 762.05 mL of 2X Master Buffer, 95.1 mL of 0.5 M EDTA, and 666.94 mL of $H_2O$.

A TCB Buffer solution was prepared by combining 125 mL of 2X Master Buffer, 10 mL of 0.5 M EDTA, 6.25 mL of 4% coating reagent, 1.01 mL of 100% DMSO, and 107.74 mL $H_2O$.

A Dye Trough solution was prepared by combining 0.5 μL of peptide-X, and 2,999.5 μL of 1X Master Buffer.

A 1.06X Assay Buffer solution was prepared by combining 205.15 mL of 2X Master Buffer, and 181.92 mL of $H_2O$.

Assays to determine the kinase inhibitory activity of chemical entities of the present disclosure were performed using a Caliper HTS 250 microfluidics device, Greiner U-bottom assay plates, a Multidrop for transfer of reagents, and Biomek FX (AMNCBM03) software. Initially, 2.4 μL of a 1 mM solution of a test compound in 100% DMSO was added to a well of the Greiner U-bottom plate. A single Greiner U-bottom plate having 24×16 wells could include multiple test compounds. Next, 40 μL of 1.06X Assay Buffer was added to each well of the assay plate. Using the Biomek FX, 10 μL of 0.5 M EDTA was added by the span-8 to wells, indicated as 100% Control and 2.4 μL of 100% DMSO was added by the span-8 to wells, indicated as 0% Control. Using the Multidrop, 10 μL of 2.5X Enzyme Buffer, followed by 10 μL of 2.5X Substrate Buffer was added to each well of the assay plate. The total reaction volume in each well was 25 μL, and the concentration of the test compound was 10 μM. The assay plate was incubated for 2.5 hrs at 20° C. to 22° C. After the incubation period, using the Multidrop, 45 μL of 1.55X Termination Buffer was added to each well of the assay plate to stop the reaction. The inhibition of the ATP-utilizing enzyme, such as a particular protein kinase, was determined by measuring the ratio of the peptide substrate to phosphorylated product for each well of the assay plate using the Caliper HTS 250 system.

Compounds exhibiting an activity for a particular target ATP-utilizing enzyme greater than three-sigma from the mean activity for the population of predominately inactive compounds for the same target ATP-utilizing enzyme were considered to be active. The use of three-sigma statistical limits represents a conservative method for declaring potential hits among targets. The three-sigma activity, as well as the mean population activity, can be different for each target enzyme. This method has an expected false positive rate, from an in-control measurement process, of one in one million. Compounds were considered to show selectivity between a primary target and one or more other targets if the activity (e.g. % inhibition, $IC_{50}$, $K_i$, $EC_{50}$, etc.) for that compound against the primary target was significantly different than that for the other target(s) within the error of the activity measurement.

Each chemical entity listed in Table 2 was tested for protein kinase inhibitory activity according to the biological assays and definitions of protein kinase inhibitory activity as described herein. For each exemplary compound listed in Table 2, the inhibitory activity for at least one protein kinase according to the biological assays and definitions of protein kinase inhibitory activity as described herein is indicated. The human protein kinase or kinases for which a compound exhibited selectivity as defined herein, is also presented in Table 2.

TABLE 2

| Compound | Activity |
| --- | --- |
| N-(4-(2,5-dimethoxyphenyl)thiazol-2-yl)-N-(3-(dimethylamino)propyl)acetamide | GSK-3-α |
| 4-((4-(4-methoxyphenyl)thiazol-2-yl)((tetrahydrofuran-2-yl)methyl)amino)-4-oxobutanoic acid | DYRK2 |
| N-(3-morpholinopropyl)-N-(4-phenylthiazol-2-yl)acetamide | GSK-3-α |
| 4-((4-(2,5-dimethoxyphenyl)thiazol-2-yl)(furan-2-ylmethyl)amino)-4-oxobutanoic acid | AURORA-A GSK-3-α |
| 4-(butyl(4-(2,5-dimethoxyphenyl)thiazol-2-yl)amino)-4-oxobutanoic acid | AURORA-A GSK-3-α |
| N-(furan-2-ylmethyl)-N-(4-(4-methoxyphenyl)thiazol-2-yl)thiophene-2-carboxamide | AKT1 |
| N-ethyl-N-(4-(4-methoxyphenyl)thiazol-2-yl)propionamide | DYRK2 |
| 4-(ethyl(4-(4-methoxyphenyl)thiazol-2-yl)amino)-4-oxobutanoic acid | DYRK2 |
| 4-((3,4-dimethoxyphenethyl)(4-(4-methoxyphenyl)thiazol-2-yl)amino)-4-oxobutanoic acid | DYRK2 |
| N-(4-(4-methoxyphenyl)thiazol-2-yl)-N-((tetrahydrofuran-2-yl)methyl)propionamide | DYRK2 |
| 4-(benzyl(4-(4-methoxyphenyl)thiazol-2-yl)amino)-4-oxobutanoic acid | DYRK2 |
| 4-((3,4-dimethoxyphenethyl)(4-(2,5-dimethoxyphenyl)thiazol-2-yl)amino)-4-oxobutanoic acid | GSK-3-α |
| 4-((furan-2-ylmethyl)(4-(4-methoxyphenyl)thiazol-2-yl)amino)-4-oxobutanoic acid | DYRK2 |
| 4-(benzyl(4-(2,5-dimethoxyphenyl)thiazol-2-yl)amino)-4-oxobutanoic acid | AURORA-A |
| 4-((4-(4-methoxyphenyl)thiazol-2-yl)(3-methoxypropyl)amino)-4-oxobutanoic acid | DYRK2 |
| 4-((2-methoxyethyl)(4-(4-methoxyphenyl)thiazol-2-yl)amino)-4-oxobutanoic acid | DYRK2 |
| 4-(isobutyl(4-(4-methoxyphenyl)thiazol-2-yl)amino)-4-oxobutanoic acid | DYRK2 AURORA-A |
| 4-((4-(4-methoxyphenyl)thiazol-2-yl)(methyl)amino)-4-oxobutanoic acid | DYRK2 |
| N-(3-(diethylamino)propyl)-N-(4-(4-methoxyphenyl)thiazol-2-yl)-2-(p-tolyloxy)acetamide | DYRK2 |
| 4-((4-(4-methoxyphenyl)thiazol-2-yl)(phenethyl)amino)-4-oxobutanoic acid | DYRK2 |
| N-(2-methoxyethyl)-N-(4-(4-methoxyphenyl)thiazol-2-yl)acetamide | DYRK2 |
| N-(4-(4-methoxyphenyl)thiazol-2-yl)-N-methylacetamide | DYRK2 |
| N-(4-(4-methoxyphenyl)thiazol-2-yl)-N-(3-methoxypropyl)propionamide | DYRK2 |
| N-(4-(4-methoxyphenyl)thiazol-2-yl)-N-(3-morpholinopropyl)-2-phenoxyacetamide | DYRK2 GSK-3-α |
| N-(4-(4-methoxyphenyl)thiazol-2-yl)-N-(3-morpholinopropyl)acetamide | DYRK2 |
| N-(4-(4-methoxyphenyl)thiazol-2-yl)-3,3-dimethyl-N-(3-morpholinopropyl)butanamide | DYRK2 |
| 2-(2-chlorophenyl)-N-(4-(4-methoxyphenyl)thiazol-2-yl)-N-(3-morpholinopropyl)acetamide | BMX |
| 2-(3-chlorophenyl)-N-(4-(4-methoxyphenyl)thiazol-2-yl)-N-(3-morpholinopropyl)acetamide | DYRK2 |
| N-(4-(2,5-dimethoxyphenyl)thiazol-2-yl)-N-(3-(dimethylamino)propyl)benzamide | CASPASE-7 CHEK2 |
| N-(3-(dimethylamino)propyl)-2-fluoro-N-(4-phenylthiazol-2-yl)benzamide | AKT1 CHEK2 |
| N-(3-(diethylamino)propyl)-N-(4-phenylthiazol-2-yl)furan-2-carboxamide | AKT1 |
| N-(4-(2,5-dimethoxyphenyl)thiazol-2-yl)-N-(3-(dimethylamino)propyl)-2-fluorobenzamide | CHEK2 AKT1 |
| N-(4-(2,5-dimethoxyphenyl)thiazol-2-yl)-N-(3-(dimethylamino)propyl)thiophene-2-carboxamide | CHEK2 AKT1 |
| N-(3-(diethylamino)propyl)-N-(4-phenylthiazol-2-yl)thiophene-2-carboxamide | AKT1 |
| 2-chloro-N-(3-(diethylamino)propyl)-N-(4-(2,5-dimethoxyphenyl)thiazol-2-yl)benzamide | CHEK2 |
| N-(3-(diethylamino)propyl)-N-(4-(2,5-dimethoxyphenyl)thiazol-2-yl)furan-2-carboxamide | AKT1 |

TABLE 2-continued

| Compound | Activity |
|---|---|
| N-(3-(diethylamino)propyl)-N-(4-(4-methoxyphenyl)thiazol-2-yl)benzamide | AKT1 |
| N-(3-(diethylamino)propyl)-N-(4-(2,5-dimethoxyphenyl)thiazol-2-yl)-2-fluorobenzamide | CHEK2 AKT1 |
| N-(3-(diethylamino)propyl)-N-(4-(2,5-dimethoxyphenyl)thiazol-2-yl)benzamide | AKT1 |
| N-(3-(diethylamino)propyl)-N-(4-(2,5-dimethoxyphenyl)thiazol-2-yl)thiophene-2-carboxamide | AKT1 |
| N-(4-phenylthiazol-2-yl)-N-(3-(pyrrolidin-1-yl)propyl)thiophene-2-carboxamide | AKT1 |
| N-(4-(4-methoxyphenyl)thiazol-2-yl)-N-(3-(pyrrolidin-1-yl)propyl)benzamide | AKT1 |
| N-(4-(4-methoxyphenyl)thiazol-2-yl)-N-(3-(pyrrolidin-1-yl)propyl)thiophene-2-carboxamide | AKT1 |
| N-(4-(4-methoxyphenyl)thiazol-2-yl)-N-(3-(pyrrolidin-1-yl)propyl)furan-2-carboxamide | AKT1 |
| N-(4-(2,5-dimethoxyphenyl)thiazol-2-yl)-N-(3-(pyrrolidin-1-yl)propyl)benzamide | AKT1 |
| N-(4-(2,5-dimethoxyphenyl)thiazol-2-yl)-N-(3-(pyrrolidin-1-yl)propyl)thiophene-2-carboxamide | AKT1 |
| N-(4-(2,5-dimethoxyphenyl)thiazol-2-yl)-N-(3-(pyrrolidin-1-yl)propyl)furan-2-carboxamide | AKT1 |
| N-(4-(4-methoxyphenyl)thiazol-2-yl)-N-(3-(piperidin-1-yl)propyl)thiophene-2-carboxamide | AKT1 |
| N-(4-(2,5-dimethoxyphenyl)thiazol-2-yl)-N-(3-(piperidin-1-yl)propyl)benzamide | AKT1 |
| N-(4-(2,5-dimethoxyphenyl)thiazol-2-yl)-N-(3-(piperidin-1-yl)propyl)thiophene-2-carboxamide | AKT1 |
| N-(4-(2,5-dimethoxyphenyl)thiazol-2-yl)-N-(3-(piperidin-1-yl)propyl)furan-2-carboxamide | AKT1 |
| N-(3-(azepan-1-yl)propyl)-N-(4-phenylthiazol-2-yl)benzamide | AKT1 |
| N-(3-(azepan-1-yl)propyl)-N-(4-phenylthiazol-2-yl)thiophene-2-carboxamide | AKT1 |
| N-(3-(azepan-1-yl)propyl)-N-(4-phenylthiazol-2-yl)furan-2-carboxamide | AKT1 |
| N-(3-(azepan-1-yl)propyl)-N-(4-(4-methoxyphenyl)thiazol-2-yl)benzamide | AKT1 |
| N-(3-(azepan-1-yl)propyl)-N-(4-(4-methoxyphenyl)thiazol-2-yl)thiophene-2-carboxamide | AKT1 |
| N-(3-(azepan-1-yl)propyl)-N-(4-(4-methoxyphenyl)thiazol-2-yl)furan-2-carboxamide | AKT1 |
| N-(3-(azepan-1-yl)propyl)-N-(4-(2,5-dimethoxyphenyl)thiazol-2-yl)benzamide | AKT1 |
| N-(3-(azepan-1-yl)propyl)-N-(4-(2,5-dimethoxyphenyl)thiazol-2-yl)thiophene-2-carboxamide | AKT1 |
| N-(3-(azepan-1-yl)propyl)-N-(4-(2,5-dimethoxyphenyl)thiazol-2-yl)furan-2-carboxamide | AKT1 |
| N-(3-(4-methylpiperazin-1-yl)propyl)-N-(4-phenylthiazol-2-yl)benzamide | AKT1 |
| N-(3-(4-methylpiperazin-1-yl)propyl)-N-(4-phenylthiazol-2-yl)thiophene-2-carboxamide | AKT1 CHEK2 |
| N-(3-(4-methylpiperazin-1-yl)propyl)-N-(4-phenylthiazol-2-yl)furan-2-carboxamidevv | AKT1 |
| N-(4-(4-methoxyphenyl)thiazol-2-yl)-N-(3-(4-methylpiperazin-1-yl)propyl)benzamide | AKT1 CHEK2 |
| N-(4-(4-methoxyphenyl)thiazol-2-yl)-N-(3-(4-methylpiperazin-1-yl)propyl)thiophene-2-carboxamide | AKT1 INSR |
| N-(4-(4-methoxyphenyl)thiazol-2-yl)-N-(3-(4-methylpiperazin-1-yl)propyl)furan-2-carboxamide | AKT1 MAPKAPK-2 CHEK2 |
| N-(4-(2,5-dimethoxyphenyl)thiazol-2-yl)-N-(3-(4-methylpiperazin-1-yl)propyl)benzamide | AKT1 |
| N-(4-(2,5-dimethoxyphenyl)thiazol-2-yl)-N-(3-(4-methylpiperazin-1-yl)propyl)thiophene-2-carboxamide | AKT1 |
| N-(4-(2,5-dimethoxyphenyl)thiazol-2-yl)-N-(3-(4-methylpiperazin-1-yl)propyl)furan-2-carboxamide | AKT1 CHEK2 |
| N-(4-(4-methoxyphenyl)thiazol-2-yl)-N-(3-morpholinopropyl)cyclohexanecarboxamide | AKT1 |
| N-(4-(4-methoxyphenyl)thiazol-2-yl)-N-(3-morpholinopropyl)cyclopent-1-enecarboxamide | AKT1 |
| 4-fluoro-N-(4-(4-methoxyphenyl)thiazol-2-yl)-N-(3-morpholinopropyl)benzamide | AKT1 |
| N-(4-(4-methoxyphenyl)thiazol-2-yl)-N-(3-morpholinopropyl)benzamide | AKT1 |
| 4-methyl-N-(3-morpholinopropyl)-N-(4-phenylthiazol-2-yl)benzamide | AKT1 |
| 4-fluoro-N-(3-morpholinopropyl)-N-(4-phenylthiazol-2-yl)benzamide | AKT1 |
| N-(3-morpholinopropyl)-N-(4-phenylthiazol-2-yl)benzamide | AKT1 |
| 3-methyl-N-(3-morpholinopropyl)-N-(4-phenylthiazol-2-yl)benzamide | AKT1 |
| 4-chloro-N-(4-(4-methoxyphenyl)thiazol-2-yl)-N-(3-morpholinopropyl)benzamide | AKT1 |

TABLE 2-continued

| Compound | Activity |
|---|---|
| 3-fluoro-N-(4-(4-methoxyphenyl)thiazol-2-yl)-N-(3-morpholinopropyl)benzamide | AKT1 |
| N-(4-(4-methoxyphenyl)thiazol-2-yl)-3-methyl-N-(3-morpholinopropyl)benzamide | AKT1 |
| 2-fluoro-N-(4-(4-methoxyphenyl)thiazol-2-yl)-N-(3-morpholinopropyl)benzamide | AKT1 |
| N-(4-(4-methoxyphenyl)thiazol-2-yl)-4-methyl-N-(3-morpholinopropyl)benzamide | FLT-3 |
| 2-cyano-N-(4-(4-methoxyphenyl)thiazol-2-yl)-N-(3-morpholinopropyl)benzamide | ZAP70 |
| N-(3-morpholinopropyl)-N-(4-phenylthiazol-2-yl)furan-2-carboxamide | AKT1 |
| N-(4-(2,5-dimethoxyphenyl)thiazol-2-yl)-N-(3-morpholinopropyl)furan-2-carboxamide | AKT1 |
| N-(4-(4-methoxyphenyl)thiazol-2-yl)-N-(3-morpholinopropyl)furan-2-carboxamide | AKT1 DYRK2 |
| N-(4-(4-methoxyphenyl)thiazol-2-yl)-5-methyl-N-(3-morpholinopropyl)furan-2-carboxamide | AKT1 KIT |
| N-(4-(4-methoxyphenyl)thiazol-2-yl)-3-methyl-N-(3-morpholinopropyl)furan-2-carboxamide | AKT1 |
| N-(3-morpholinopropyl)-N-(4-phenylthiazol-2-yl)thiophene-2-carboxamide | AKT1 |
| N-(4-(2,5-dimethoxyphenyl)thiazol-2-yl)-N-(3-morpholinopropyl)thiophene-2-carboxamide | AKT1 |
| N-(4-(4-methoxyphenyl)thiazol-2-yl)-N-(3-morpholinopropyl)thiophene-2-carboxamide | AKT1 |
| N-(4-(4-chlorophenyl)thiazol-2-yl)-N-(3-morpholinopropyl)thiophene-2-carboxamide | AKT1 |
| N-(3-morpholinopropyl)-N-(4-p-tolylthiazol-2-yl)thiophene-2-carboxamide | AKT1 |
| N-(4-(2,3-dihydrobenzo[b][1,4]dioxin-6-yl)thiazol-2-yl)-N-(3-morpholinopropyl)thiophene-2-carboxamide | AKT1 |
| N-(4-(4-chloro-3-nitrophenyl)thiazol-2-yl)-N-(3-morpholinopropyl)thiophene-2-carboxamide | AKT1 |
| N-(4-(2-methoxyphenyl)thiazol-2-yl)-N-(3-morpholinopropyl)thiophene-2-carboxamide | AKT1 |
| N-(4-(2,4-dimethylphenyl)thiazol-2-yl)-N-(3-morpholinopropyl)thiophene-2-carboxamide | AKT1 |
| N-(4-(4-cyanophenyl)thiazol-2-yl)-N-(3-morpholinopropyl)thiophene-2-carboxamide | AKT1 |
| methyl 4-(2-(N-(3-morpholinopropyl)thiophene-2-carboxamido)thiazol-4-yl)benzoate | AKT1 |
| N-(4-(4-(methylsulfonyl)phenyl)thiazol-2-yl)-N-(3-morpholinopropyl)thiophene-2-carboxamide | AKT1 |
| N-(4-(2,4-dimethoxyphenyl)thiazol-2-yl)-N-(3-morpholinopropyl)thiophene-2-carboxamide | AKT1 |
| N-(4-(benzofuran-3-yl)thiazol-2-yl)-N-(3-morpholinopropyl)thiophene-2-carboxamide | AKT1 |
| N-(4-(2-chlorophenyl)thiazol-2-yl)-N-(3-morpholinopropyl)thiophene-2-carboxamide | AKT1 |
| N-(4-(3-chlorophenyl)thiazol-2-yl)-N-(3-morpholinopropyl)thiophene-2-carboxamide | AKT1 |
| N-(4-(benzo[b]thiophen-3-yl)thiazol-2-yl)-N-(3-morpholinopropyl)thiophene-2-carboxamide | AKT1 |
| N-(3-morpholinopropyl)-N-(4-(pyridin-2-yl)thiazol-2-yl)thiophene-2-carboxamide | AKT1 |
| N-(3-morpholinopropyl)-N-(4-(pyridin-3-yl)thiazol-2-yl)thiophene-2-carboxamide | AKT1 CDK2/cyclin E |
| N-(3-morpholinopropyl)-N-(4-(pyridin-4-yl)thiazol-2-yl)thiophene-2-carboxamide | AKT1 KIT |
| N-(3-morpholinopropyl)-N-(4-(thiophen-2-yl)thiazol-2-yl)thiophene-2-carboxamide | AKT1 |
| N-(4-(5-chlorothiophen-2-yl)thiazol-2-yl)-N-(3-morpholinopropyl)thiophene-2-carboxamide | AKT1 |
| N-(4-(5-chlorothiophen-2-yl)thiazol-2-yl)-N-(3-morpholinopropyl)thiophene-2-carboxamide | AKT1 |
| N-(4-(3,4-dichlorophenyl)thiazol-2-yl)-N-(3-morpholinopropyl)thiophene-2-carboxamide | AKT1 |
| N-(4-(4-fluorophenyl)thiazol-2-yl)-N-(3-morpholinopropyl)thiophene-2-carboxamide | AKT1 |
| N-(4-(4-(difluoromethoxy)phenyl)thiazol-2-yl)-N-(3-morpholinopropyl)thiophene-2-carboxamide | AKT1 |
| N-(3-morpholinopropyl)-N-(4-(2-(trifluoromethyl)phenyl)thiazol-2-yl)thiophene-2-carboxamide | AKT1 |
| N-(4-(2-fluorophenyl)thiazol-2-yl)-N-(3-morpholinopropyl)thiophene-2-carboxamide | AKT1 |
| N-(4-(3,4-difluorophenyl)thiazol-2-yl)-N-(3-morpholinopropyl)thiophene-2-carboxamide | AKT1 |

TABLE 2-continued

| Compound | Activity |
|---|---|
| N-(4-(3-bromophenyl)thiazol-2-yl)-N-(3-morpholinopropyl)thiophene-2-carboxamide | AKT1 |
| N-(3-morpholinopropyl)-N-(4-(4-(trifluoromethoxy)phenyl)thiazol-2-yl)thiophene-2-carboxamide | AKT1 |
| N-(4-(3-fluorophenyl)thiazol-2-yl)-N-(3-morpholinopropyl)thiophene-2-carboxamide | AKT1 |
| N-(4-(3-methylbenzo[b]thiophen-2-yl)thiazol-2-yl)-N-(3-morpholinopropyl)thiophene-2-carboxamide | AKT1 |
| N-(4-(3-cyanophenyl)thiazol-2-yl)-N-(3-morpholinopropyl)thiophene-2-carboxamide | AKT1<br>GSK-3-α<br>KIT |
| N-(3-morpholinopropyl)-N-(4-(4-pentylphenyl)thiazol-2-yl)thiophene-2-carboxamide | AKT1 |
| N-(4-(4-(diethylamino)phenyl)thiazol-2-yl)-N-(3-morpholinopropyl)thiophene-2-carboxamide | AKT1<br>SYK |
| N-(3-morpholinopropyl)-N-(4-(4-(pyrrolidin-1-yl)phenyl)thiazol-2-yl)thiophene-2-carboxamide | AKT1 |
| N-(4-(3,4-dimethoxyphenyl)thiazol-2-yl)-N-(3-morpholinopropyl)thiophene-2-carboxamide | AKT1 |
| N-(4-(benzo[d][1,3]dioxol-5-yl)thiazol-2-yl)-N-(3-morpholinopropyl)thiophene-2-carboxamide | AKT1 |
| N-(4-(benzo[d]thiazol-2-yl)thiazol-2-yl)-N-(3-morpholinopropyl)thiophene-2-carboxamide | AKT1 |
| N-(4-(3-methoxyphenyl)thiazol-2-yl)-N-(3-morpholinopropyl)thiophene-2-carboxamide | AKT1 |
| N-(3-morpholinopropyl)-N-(4-(2-nitrophenyl)thiazol-2-yl)thiophene-2-carboxamide | AKT1 |
| N-(3-morpholinopropyl)-N-(4-(naphthalen-2-yl)thiazol-2-yl)thiophene-2-carboxamide | AKT1 |
| N-(4-(benzofuran-2-yl)thiazol-2-yl)-N-(3-morpholinopropyl)thiophene-2-carboxamide | AKT1 |
| N-(4-(4-morpholinophenyl)thiazol-2-yl)-N-(3-morpholinopropyl)thiophene-2-carboxamide | AKT1 |
| N-(4-(3,4-dihydro-2H-benzo[b][1,4]dioxepin-7-yl)thiazol-2-yl)-N-(3-morpholinopropyl)thiophene-2-carboxamide | AKT1<br>KIT |
| N-(4-(2-chloropyridin-4-yl)thiazol-2-yl)-N-(3-morpholinopropyl)thiophene-2-carboxamide | AKT1<br>KIT |
| N-(4-(4-methoxyphenyl)thiazol-2-yl)-3-methyl-N-(3-morpholinopropyl)thiophene-2-carboxamide | AKT1 |
| 2,5-dichloro-N-(4-(4-methoxyphenyl)thiazol-2-yl)-N-(3-morpholinopropyl)thiophene-3-carboxamide | CDK2 |
| 3-bromo-N-(4-(4-methoxyphenyl)thiazol-2-yl)-N-(3-morpholinopropyl)thiophene-2-carboxamide | AKT1<br>ZAP70 |
| N-(4-(4-methoxyphenyl)thiazol-2-yl)-N-(3-morpholinopropyl)-5-nitrothiophene-2-carboxamide | ZAP70<br>KIT<br>FLT-3 |
| 5-chloro-N-(4-(4-methoxyphenyl)thiazol-2-yl)-N-(3-morpholinopropyl)thiophene-2-carboxamide | AKT1 |
| 5-acetyl-N-(4-(4-methoxyphenyl)thiazol-2-yl)-N-(3-morpholinopropyl)thiophene-2-carboxamide | ZAP70 |
| 5-bromo-N-(4-(4-methoxyphenyl)thiazol-2-yl)-N-(3-morpholinopropyl)thiophene-2-carboxamide | AKT1<br>ZAP70 |
| N-(4-(4-methoxyphenyl)thiazol-2-yl)-5-(methylthio)-N-(3-morpholinopropyl)thiophene-2-carboxamide | KIT<br>ZAP70 |
| N-(3-morpholinopropyl)-N-(4-(3-(trifluoromethyl)phenyl)thiazol-2-yl)thiophene-2-carboxamide | AKT1 |
| N-(4-(4-methoxyphenyl)thiazol-2-yl)-1-methyl-N-(3-morpholinopropyl)-1H-pyrrole-2-carboxamide | AKT1 |
| N-(4-(4-methoxyphenyl)thiazol-2-yl)-N-(3-morpholinopropyl)isoxazole-5-carboxamide | AKT1<br>AURORA-A |
| N-(4-(4-methoxyphenyl)thiazol-2-yl)-3,5-dimethyl-N-(3-morpholinopropyl)isoxazole-4-carboxamide | ZAP70<br>KIT |
| N-(4-(4-methoxyphenyl)thiazol-2-yl)-4-methyl-N-(3-morpholinopropyl)-1,2,3-thiadiazole-5-carboxamide | KIT<br>ZAP70<br>PDGFR-α<br>FLT-3<br>DYRK2 |
| N-(4-(4-methoxyphenyl)thiazol-2-yl)-2,4-dimethyl-N-(3-morpholinopropyl)thiazole-5-carboxamide | PDK1 |
| 4-chloro-N-(4-(4-methoxyphenyl)thiazol-2-yl)-N-(3-morpholinopropyl)picolinamide | AKT1 |
| N-(4-(4-methoxyphenyl)thiazol-2-yl)-3-methyl-N-(3-morpholinopropyl)isoxazole-4-carboxamide | ZAP70<br>DYRK2 |
| 6-chloro-N-(4-(4-methoxyphenyl)thiazol-2-yl)-N-(3-morpholinopropyl)picolinamide | ZAP70<br>AKT1 |
| N-(4-(4-methoxyphenyl)thiazol-2-yl)-1-methyl-N-(3-morpholinopropyl)-1H-imidazole-2-carboxamide | AKT1 |

TABLE 2-continued

| Compound | Activity |
|---|---|
| 4,5-dichloro-N-(4-(4-methoxyphenyl)thiazol-2-yl)-N-(3-morpholinopropyl)isothiazole-3-carboxamide | ZAP70 |
| N-(4-(4-methoxyphenyl)thiazol-2-yl)-1,2,5-trimethyl-N-(3-morpholinopropyl)-1H-pyrrole-3-carboxamide | CDK2/cyclin E |
| ethyl 2-(N-(3-morpholinopropyl)thiophene-2-carboxamido)thiazole-4-carboxylate | AKT1 |
| ethyl 3-methyl-3-(2-(N-(3-morpholinopropyl)thiophene-2-carboxamido)thiazol-4-yl)butanoate | AKT1 |
| N-(4-(biphenyl-4-yl)thiazol-2-yl)-N-(3-morpholinopropyl)thiophene-2-carboxamide | AKT1 |
| N-(4-(5-methyl-1-phenyl-1H-pyrazol-4-yl)thiazol-2-yl)-N-(3-morpholinopropyl)thiophene-2-carboxamide | AKT1 |
| N-(4-(2,4-dichlorophenyl)thiazol-2-yl)-N-(3-morpholinopropyl)thiophene-2-carboxamide | AKT1 |
| 3-(2-(N-(3-morpholinopropyl)thiophene-2-carboxamido)thiazol-4-yl)benzoic acid | AKT1 |
| N-(3-morpholinopropyl)-N-(4-(3-oxo-3,4-dihydro-2H-benzo[b][1,4]oxazin-6-yl)thiazol-2-yl)thiophene-2-carboxamide | AKT1 |
| N-(3-morpholinopropyl)-N-(4-(3-phenylisoxazol-5-yl)thiazol-2-yl)thiophene-2-carboxamide | AKT1 |
| N-(3-morpholinopropyl)-N-(4-(5-(pyridin-2-yl)thiophen-2-yl)thiazol-2-yl)thiophene-2-carboxamide | AKT1 |
| N-(4'-methyl-2'-(pyrazin-2-yl)-4,5'-bithiazol-2-yl)-N-(3-morpholinopropyl)thiophene-2-carboxamide | AKT1 |
| 2-(5-(2-(N-(3-morpholinopropyl)thiophene-2-carboxamido)thiazol-4-yl)thiophen-2-yl)acetic acid | AKT1 |
| N-(4-(4-chloro-3-methylphenyl)thiazol-2-yl)-N-(3-morpholinopropyl)thiophene-2-carboxamide | AKT1 |
| N-(4-(3,4-dimethoxyphenyl)thiazol-2-yl)-N-(3-morpholinopropyl)benzamide | AKT1 |
| N-(4-(3,4-dimethoxyphenyl)thiazol-2-yl)-N-(3-morpholinopropyl)furan-2-carboxamide | AKT1 |
| N-(4-(benzofuran-2-yl)thiazol-2-yl)-N-(3-morpholinopropyl)furan-2-carboxamide | AKT1 |
| N-(4-(benzofuran-2-yl)thiazol-2-yl)-N-(3-morpholinopropyl)nicotinamide | AKT1 |
| N-(4-(3,4-dimethoxyphenyl)thiazol-2-yl)-N-(3-morpholinopropyl)cyclopentanecarboxamide | AKT1 |
| N-(4-(3,4-dimethoxyphenyl)thiazol-2-yl)-N-(3-morpholinopropyl)cyclobutanecarboxamide | AKT1 |
| N-(4-(benzofuran-2-yl)thiazol-2-yl)-N-(3-morpholinopropyl)cyclobutanecarboxamide | AKT1 |
| N-(4-(3,4-dimethoxyphenyl)thiazol-2-yl)-N-(3-morpholinopropyl)picolinamide | AKT1 |
| N-(4-(benzofuran-2-yl)thiazol-2-yl)-N-(3-morpholinopropyl)picolinamide | AKT1 |
| N-(4-(3-(4-chlorophenyl)isoxazol-5-yl)thiazol-2-yl)-N-(3-morpholinopropyl)thiophene-2-carboxamide | AKT1 |
| N-(3-morpholinopropyl)-N-(4-(3-phenylisoxazol-5-yl)thiazol-2-yl)furan-2-carboxamide | AKT1 |
| 1-methyl-N-(3-morpholinopropyl)-N-(4-(3-phenylisoxazol-5-yl)thiazol-2-yl)-1H-pyrrole-2-carboxamide | AKT1 |
| 4-(2-(N-(3-morpholinopropyl)thiophene-2-carboxamido)thiazol-4-yl)benzoic acid | AKT1 |
| N-(3-morpholinopropyl)-N-(4-(trifluoromethyl)thiazol-2-yl)thiophene-2-carboxamide | AKT1 |
| ethyl 5-(2-(N-(3-morpholinopropyl)thiophene-2-carboxamido)thiazol-4-yl)isoxazole-3-carboxylate | AKT1 |
| 2-(N-(3-morpholinopropyl)thiophene-2-carboxamido)-N-(1,3,4-thiadiazol-2-yl)thiazole-4-carboxamide | AKT1 |
| 2-(N-(3-morpholinopropyl)thiophene-2-carboxamido)-N-(thiazol-2-yl)thiazole-4-carboxamide | AKT1 |
| N-(3-methoxyphenyl)-2-(N-(3-morpholinopropyl)thiophene-2-carboxamido)thiazole-4-carboxamide | AKT1 |
| N-(3-methoxybenzyl)-2-(N-(3-morpholinopropyl)thiophene-2-carboxamido)thiazole-4-carboxamide | AKT1 |
| N-(3-chlorobenzyl)-2-(N-(3-morpholinopropyl)thiophene-2-carboxamido)thiazole-4-carboxamide | AKT1 |
| N-(2,3-dihydrobenzo[b][1,4]dioxin-6-yl)-2-(N-(3-morpholinopropyl)thiophene-2-carboxamido)thiazole-4-carboxamide | AKT1 |
| N-(5-ethyl-1,3,4-thiadiazol-2-yl)-2-(N-(3-morpholinopropyl)thiophene-2-carboxamido)thiazole-4-carboxamide | AKT1 |
| N-(benzo[d]thiazol-6-yl)-2-(N-(3-morpholinopropyl)thiophene-2-carboxamido)thiazole-4-carboxamide | AKT1 |
| N-(3-carbamoylphenyl)-2-(N-(3-morpholinopropyl)thiophene-2-carboxamido)thiazole-4-carboxamide | AKT1 |
| ethyl 2-(2-(2-(N-(3-morpholinopropyl)thiophene-2-carboxamido)thiazole-4-carboxamido)thiazol-4-yl)acetate | AKT1 |

TABLE 2-continued

| Compound | Activity |
|---|---|
| N-(3-(methylsulfonamido)phenyl)-2-(N-(3-morpholinopropyl)thiophene-2-carboxamido)thiazole-4-carboxamide | AKT1 |
| N-(4-(benzofuran-2-yl)thiazol-2-yl)-N-(3-(2-oxopyrrolidin-1-yl)propyl)furan-2-carboxamide | AKT1 |
| N-(4-(benzofuran-2-yl)thiazol-2-yl)-N-(3-(2-oxopyrrolidin-1-yl)propyl)thiophene-2-carboxamide | AKT1 |
| N-(4-(benzofuran-2-yl)thiazol-2-yl)-1-methyl-N-(3-(2-oxopyrrolidin-1-yl)propyl)-1H-pyrrole-2-carboxamide | AKT1 |
| N-(3-(2-oxopyrrolidin-1-yl)propyl)-N-(4-(3-phenylisoxazol-5-yl)thiazol-2-yl)furan-2-carboxamide | AKT1 |
| N-(3-(2-oxopyrrolidin-1-yl)propyl)-N-(4-(3-phenylisoxazol-5-yl)thiazol-2-yl)thiophene-2-carboxamide | AKT1 |
| 1-methyl-N-(3-(2-oxopyrrolidin-1-yl)propyl)-N-(4-(3-phenylisoxazol-5-yl)thiazol-2-yl)-1H-pyrrole-2-carboxamide | AKT1 |
| N-(3-(4-methylpiperazin-1-yl)propyl)-N-(4-(3-phenylisoxazol-5-yl)thiazol-2-yl)furan-2-carboxamide | AKT1 |
| N-(4-morpholinobutyl)-N-(4-(3-phenylisoxazol-5-yl)thiazol-2-yl)furan-2-carboxamide | AKT1 |
| N-(4-morpholinobutyl)-N-(4-(3-phenylisoxazol-5-yl)thiazol-2-yl)thiophene-2-carboxamide | AKT1 |
| N-(3-(diethylamino)propyl)-N-(4-(3,4-dimethoxyphenyl)thiazol-2-yl)thiophene-2-carboxamide | AKT1 |
| N-(4-(3,4-dimethoxyphenyl)thiazol-2-yl)-N-(3-(2-oxopyrrolidin-1-yl)propyl)thiophene-2-carboxamide | AKT1 |
| N-(4-(3,4-dimethoxyphenyl)thiazol-2-yl)-N-(3-(4-methylpiperazin-1-yl)propyl)thiophene-2-carboxamide | AKT1 |
| N-(4-(3,4-dimethoxyphenyl)thiazol-2-yl)-N-(3-(piperidin-1-yl)propyl)thiophene-2-carboxamide | AKT1 |
| N-(4-(3,4-dimethoxyphenyl)thiazol-2-yl)-N-(5-morpholinopentyl)thiophene-2-carboxamide | AKT1 |
| N-(4-(3,4-dimethoxyphenyl)thiazol-2-yl)-N-(2-morpholinoethyl)thiophene-2-carboxamide | AKT1 |
| N-(4-(3,4-dimethoxyphenyl)thiazol-2-yl)-N-(3-phenylpropyl)thiophene-2-carboxamide | AKT1 |
| N-(4-(benzofuran-2-yl)thiazol-2-yl)-N-(3-(diethylamino)propyl)thiophene-2-carboxamide | AKT1 |
| N-(3-(1H-imidazol-1-yl)propyl)-N-(4-(benzofuran-2-yl)thiazol-2-yl)thiophene-2-carboxamide | AKT1 |
| N-(4-(benzofuran-2-yl)thiazol-2-yl)-N-(3-(4-methylpiperazin-1-yl)propyl)thiophene-2-carboxamide | AKT1 |
| N-(4-(benzofuran-2-yl)thiazol-2-yl)-N-(3-(piperidin-1-yl)propyl)thiophene-2-carboxamide | AKT1 |
| N-(4-(benzofuran-2-yl)thiazol-2-yl)-N-(4-morpholinobutyl)thiophene-2-carboxamide | AKT1 |
| N-(4-(benzofuran-2-yl)thiazol-2-yl)-N-(5-morpholinopentyl)thiophene-2-carboxamide | AKT1 |
| N-(4-(benzofuran-2-yl)thiazol-2-yl)-N-(3-phenylpropyl)thiophene-2-carboxamide | AKT1 |
| N-(4-(benzofuran-2-yl)thiazol-2-yl)-N-propylthiophene-2-carboxamide | AKT1 |
| N-(4-(5-methylthiophen-2-yl)thiazol-2-yl)-N-(3-morpholinopropyl)thiophene-2-carboxamide | AKT1 |
| N-(4-(6-methoxypyridin-3-yl)thiazol-2-yl)-N-(3-morpholinopropyl)thiophene-2-carboxamide | AKT1 |
| N-(4-(2,6-dimethoxypyridin-3-yl)thiazol-2-yl)-N-(3-morpholinopropyl)thiophene-2-carboxamide | AKT1 |
| N-(4-cyclopentylthiazol-2-yl)-N-(3-morpholinopropyl)thiophene-2-carboxamide | AKT1 |
| N-(4-cyclohexylthiazol-2-yl)-N-(3-morpholinopropyl)thiophene-2-carboxamide | AKT1 |
| methyl 6-(2-(N-(3-morpholinopropyl)thiophene-2-carboxamido)thiazol-4-yl)nicotinate | AKT1 |
| N-(4-(1H-indol-2-yl)thiazol-2-yl)-N-(3-morpholinopropyl)thiophene-2-carboxamide | AKT1 |
| N-(4-(7-methoxybenzofuran-2-yl)thiazol-2-yl)-N-(3-morpholinopropyl)thiophene-2-carboxamide | AKT1 |
| N-(4-(5-methoxybenzofuran-2-yl)thiazol-2-yl)-N-(3-morpholinopropyl)thiophene-2-carboxamide | AKT1 |
| N-(3-morpholinopropyl)-N-(4-(5-nitrobenzofuran-2-yl)thiazol-2-yl)thiophene-2-carboxamide | AKT1 |
| N-(4-(4-(2-hydroxyethylcarbamoyl)phenyl)thiazol-2-yl)-N-(3-morpholinopropyl)thiophene-2-carboxamide | AKT1 |
| N-(4-(4-(2-morpholinoethylcarbamoyl)phenyl)thiazol-2-yl)-N-(3-morpholinopropyl)thiophene-2-carboxamide | AKT1 |
| N-(4-(4-(methylcarbamoyl)phenyl)thiazol-2-yl)-N-(3-morpholinopropyl)thiophene-2-carboxamide | AKT1 |
| N-(4-(4-(2-(dimethylamino)ethylcarbamoyl)phenyl)thiazol-2-yl)-N-(3-morpholinopropyl)thiophene-2-carboxamide | AKT1 |

TABLE 2-continued

| Compound | Activity |
|---|---|
| N-(4-(4-(3-(dimethylamino)propylcarbamoyl)phenyl)thiazol-2-yl)-N-(3-morpholinopropyl)thiophene-2-carboxamide | AKT1 |
| N-(4-(4-(3-hydroxypropylcarbamoyl)phenyl)thiazol-2-yl)-N-(3-morpholinopropyl)thiophene-2-carboxamide | AKT1 |
| N-(4-(4-carbamoylphenyl)thiazol-2-yl)-N-(3-morpholinopropyl)thiophene-2-carboxamide | AKT1 |
| N-(4-(4-(dimethylcarbamoyl)phenyl)thiazol-2-yl)-N-(3-morpholinopropyl)thiophene-2-carboxamide | AKT1 |
| 2-(4-(2-(N-(3-morpholinopropyl)thiophene-2-carboxamido)thiazol-4-yl)benzamido)acetic acid | AKT1 |
| N-(4-(4-(4-methylpiperazine-1-carbonyl)phenyl)thiazol-2-yl)-N-(3-morpholinopropyl)thiophene-2-carboxamide | AKT1 |
| N-(4-(4-(morpholine-4-carbonyl)phenyl)thiazol-2-yl)-N-(3-morpholinopropyl)thiophene-2-carboxamide | AKT1 |
| 2-(3-(2-(N-(3-morpholinopropyl)thiophene-2-carboxamido)thiazol-4-yl)phenoxy)acetic acid | AKT1 |
| 3-(3-(2-(N-(3-morpholinopropyl)thiophene-2-carboxamido)thiazol-4-yl)phenoxy)propanoic acid | AKT1 |
| 2-(4-(2-(N-(3-morpholinopropyl)thiophene-2-carboxamido)thiazol-4-yl)phenoxy)acetic acid | AKT1 |
| 3-(4-(2-(N-(3-morpholinopropyl)thiophene-2-carboxamido)thiazol-4-yl)phenoxy)propanoic acid | AKT1 |
| N-(4-(3-(3-(dimethylamino)propoxy)phenyl)thiazol-2-yl)-N-(3-morpholinopropyl)thiophene-2-carboxamide | AKT1 |
| N-(4-(3-(2-(dimethylamino)ethoxy)phenyl)thiazol-2-yl)-N-(3-morpholinopropyl)thiophene-2-carboxamide | AKT1 |
| N-(4-(4-(3-(dimethylamino)propoxy)phenyl)thiazol-2-yl)-N-(3-morpholinopropyl)thiophene-2-carboxamide | AKT1 |
| N-(4-(4-(2-(dimethylamino)ethoxy)phenyl)thiazol-2-yl)-N-(3-morpholinopropyl)thiophene-2-carboxamide | AKT1 |
| N-(4-(benzofuran-2-yl)thiazol-2-yl)-N-(3-(2-hydroxyethylamino)-3-oxopropyl)thiophene-2-carboxamide | AKT1 |
| N-(4-(benzofuran-2-yl)thiazol-2-yl)-N-(3-(2-(hydroxymethyl)pyrrolidin-1-yl)-3-oxopropyl)thiophene-2-carboxamide | AKT1 |
| N-(4-(benzofuran-2-yl)thiazol-2-yl)-N-(3-(2-(dimethylamino)ethylamino)-3-oxopropyl)thiophene-2-carboxamide | AKT1 |
| N-(4-(benzofuran-2-yl)thiazol-2-yl)-N-(3-(3-hydroxypiperidin-1-yl)-3-oxopropyl)thiophene-2-carboxamide | AKT1 |
| N-(4-(benzofuran-2-yl)thiazol-2-yl)-N-(3-((2-hydroxyethyl)(methyl)amino)-3-oxopropyl)thiophene-2-carboxamide | AKT1 |
| N-(4-(benzofuran-2-yl)thiazol-2-yl)-N-(3-(bis(2-hydroxyethyl)amino)-3-oxopropyl)thiophene-2-carboxamide | AKT1 |
| N-(4-(benzofuran-2-yl)thiazol-2-yl)-N-(3-oxo-3-(piperazin-1-yl)propyl)thiophene-2-carboxamide | AKT1 |
| N-(4-(benzofuran-2-yl)thiazol-2-yl)-N-(3-((2-(dimethylamino)ethyl)(methyl)amino)-3-oxopropyl)thiophene-2-carboxamide | AKT1 |
| N-(4-(benzofuran-2-yl)thiazol-2-yl)-N-(3-(methyl(2-(methylamino)ethyl)amino)-3-oxopropyl)thiophene-2-carboxamide | AKT1 |
| N-(4-(benzofuran-2-yl)thiazol-2-yl)-N-(3-(3-hydroxypyrrolidin-1-yl)-3-oxopropyl)thiophene-2-carboxamide | AKT1 |
| N-(4-(benzofuran-2-yl)thiazol-2-yl)-N-(3-(3-(dimethylamino)pyrrolidin-1-yl)-3-oxopropyl)thiophene-2-carboxamide | AKT1 |
| N-(4-(benzofuran-2-yl)thiazol-2-yl)-N-(3-((2,3-dihydroxypropyl)(methyl)amino)-3-oxopropyl)thiophene-2-carboxamide | AKT1 |
| methyl 2-(3-(N-(4-(benzofuran-2-yl)thiazol-2-yl)thiophene-2-carboxamido)propanamido)acetate | AKT1 |
| 1-(3-(N-(4-(benzofuran-2-yl)thiazol-2-yl)thiophene-2-carboxamido)propanoyl)piperidine-3-carboxamide | AKT1 |
| N-(4-(benzofuran-2-yl)thiazol-2-yl)-N-(3-oxo-3-(thiazolidin-3-yl)propyl)thiophene-2-carboxamide | AKT1 |
| N-(4-(benzofuran-2-yl)thiazol-2-yl)-N-(3-morpholino-3-oxopropyl)thiophene-2-carboxamide | AKT1 |
| N-(4-(benzofuran-2-yl)thiazol-2-yl)-N-(3-((2-cyanoethyl)(methyl)amino)-3-oxopropyl)thiophene-2-carboxamide | AKT1 |
| N-(4-(benzofuran-2-yl)thiazol-2-yl)-N-(3-(3-(hydroxymethyl)piperidin-1-yl)-3-oxopropyl)thiophene-2-carboxamide | AKT1 |
| 1-(3-(N-(4-(benzofuran-2-yl)thiazol-2-yl)thiophene-2-carboxamido)propanoyl)piperidine-3-carboxylic acid | AKT1 |
| N-(3-(3-acetamidopyrrolidin-1-yl)-3-oxopropyl)-N-(4-(benzofuran-2-yl)thiazol-2-yl)thiophene-2-carboxamide | AKT1 |
| 1-(3-(N-(4-(benzofuran-2-yl)thiazol-2-yl)thiophene-2-carboxamido)propanoyl)pyrrolidine-2-carboxamide | AKT1 |
| N-(4-(benzofuran-2-yl)thiazol-2-yl)-N-(3-oxo-3-(3-oxopiperazin-1-yl)propyl)thiophene-2-carboxamide | AKT1 |
| 1-(3-(N-(4-(benzofuran-2-yl)thiazol-2-yl)thiophene-2-carboxamido)propanoyl)piperidine-2-carboxamide | AKT1 |

TABLE 2-continued

| Compound | Activity |
|---|---|
| N-(4-(benzofuran-2-yl)thiazol-2-yl)-N-(3-oxo-3-(2-phenoxyethylamino)propyl)thiophene-2-carboxamide | AKT1 |
| 1-(3-(N-(4-(benzofuran-2-yl)thiazol-2-yl)thiophene-2-carboxamido)propanoyl)-N-(2-hydroxyethyl)piperidine-3-carboxamide | AKT1 |
| N-(4-(benzofuran-2-yl)thiazol-2-yl)-N-(3-(isobutyl(1,1-dioxo-tetrahydrothiophen-3-yl)amino)-3-oxopropyl)thiophene-2-carboxamide | AKT1 |
| N-(4-(benzofuran-2-yl)thiazol-2-yl)-N-(4-(4-(2-(dimethylamino)ethyl)piperazin-1-yl)-4-oxobutyl)thiophene-2-carboxamide | AKT1 |
| N-(4-(benzofuran-2-yl)thiazol-2-yl)-N-(4-((2,3-dihydroxypropyl)(methyl)amino)-4-oxobutyl)thiophene-2-carboxamide | AKT1 |
| methyl 2-(4-(N-(4-(benzofuran-2-yl)thiazol-2-yl)thiophene-2-carboxamido)butanamido)acetate | AKT1 |
| N-(4-(benzofuran-2-yl)thiazol-2-yl)-N-(4-((5-methylpyrazin-2-yl)methylamino)-4-oxobutyl)thiophene-2-carboxamide | AKT1 |
| N-(4-(benzofuran-2-yl)thiazol-2-yl)-N-(4-(1-hydroxypropan-2-ylamino)-4-oxobutyl)thiophene-2-carboxamide | AKT1 |
| N-(4-(benzofuran-2-yl)thiazol-2-yl)-N-(4-oxo-4-(piperidin-1-yl)butyl)thiophene-2-carboxamide | AKT1 |
| 1-(4-(N-(4-(benzofuran-2-yl)thiazol-2-yl)thiophene-2-carboxamido)butanoyl)piperidine-4-carboxamide | AKT1 |
| N-(4-(benzofuran-2-yl)thiazol-2-yl)-N-(4-((2-hydroxyethyl)(phenyl)amino)-4-oxobutyl)thiophene-2-carboxamide | AKT1 |
| N-(4-(benzofuran-2-yl)thiazol-2-yl)-N-(4-oxo-4-(2-(pyridin-4-yl)ethylamino)butyl)thiophene-2-carboxamide | AKT1 |
| tert-butyl 4-(4-(N-(4-(benzofuran-2-yl)thiazol-2-yl)thiophene-2-carboxamido)butanoyl)piperazine-1-carboxylate | AKT1 |
| N-(4-(benzofuran-2-yl)thiazol-2-yl)-N-(4-oxo-4-(pyridin-3-ylmethylamino)butyl)thiophene-2-carboxamide | AKT1 |
| N-(4-(benzofuran-2-yl)thiazol-2-yl)-N-(4-(5-(methylsulfonyl)indolin-1-yl)-4-oxobutyl)thiophene-2-carboxamide | AKT1 |
| tert-butyl 1-(4-(N-(4-(benzofuran-2-yl)thiazol-2-yl)thiophene-2-carboxamido)butanoyl)pyrrolidin-3-ylcarbamate | AKT1 |
| N-(4-(3-acetamidopyrrolidin-1-yl)-4-oxobutyl)-N-(4-(benzofuran-2-yl)thiazol-2-yl)thiophene-2-carboxamide | AKT1 |
| methyl 1-(4-(N-(4-(benzofuran-2-yl)thiazol-2-yl)thiophene-2-carboxamido)butanoyl)piperidine-4-carboxylate | AKT1 |
| 1-(4-(N-(4-(benzofuran-2-yl)thiazol-2-yl)thiophene-2-carboxamido)butanoyl)-N-methylpiperidine-4-carboxamide | AKT1 |
| N-(4-(benzofuran-2-yl)thiazol-2-yl)-N-(4-(4-(N,N-dimethylsulfamoyl)piperazin-1-yl)-4-oxobutyl)thiophene-2-carboxamide | AKT1 |
| ethyl 2-(1-(4-(N-(4-(benzofuran-2-yl)thiazol-2-yl)thiophene-2-carboxamido)butanoyl)piperidin-3-yl)acetate | AKT1 |
| ethyl 2-(1-(4-(N-(4-(benzofuran-2-yl)thiazol-2-yl)thiophene-2-carboxamido)butanoyl)piperidin-4-yl)acetate | AKT1 |
| N-(4-(benzofuran-2-yl)thiazol-2-yl)-N-(4-(4-(diethylamino)piperidin-1-yl)-4-oxobutyl)thiophene-2-carboxamide | AKT1 |
| 1-(4-(N-(4-(benzofuran-2-yl)thiazol-2-yl)thiophene-2-carboxamido)butanoyl)pyrrolidine-2-carboxamide | AKT1 |
| methyl 1-(4-(N-(4-(benzofuran-2-yl)thiazol-2-yl)thiophene-2-carboxamido)butanoyl)pyrrolidine-2-carboxylate | AKT1 |
| N-(4-(benzofuran-2-yl)thiazol-2-yl)-N-(4-oxo-4-(3-oxopiperazin-1-yl)butyl)thiophene-2-carboxamide | AKT1 |
| N-(4-(2-amino-2-oxoethylamino)-4-oxobutyl)-N-(4-(benzofuran-2-yl)thiazol-2-yl)thiophene-2-carboxamide | AKT1 |
| 1-(4-(N-(4-(benzofuran-2-yl)thiazol-2-yl)thiophene-2-carboxamido)butanoyl)-N-(2-hydroxyethyl)piperidine-3-carboxamide | AKT1 |
| 1-(4-(N-(4-(benzofuran-2-yl)thiazol-2-yl)thiophene-2-carboxamido)butanoyl)-N-(2-hydroxyethyl)piperidine-4-carboxamide | AKT1 |
| N-(4-(benzofuran-2-yl)thiazol-2-yl)-N-(4-(2-(methylsulfinyl)ethylamino)-4-oxobutyl)thiophene-2-carboxamide | AKT1 |
| N-(4-(benzofuran-2-yl)thiazol-2-yl)-N-(4-((2-hydroxyethyl)(pyridin-4-ylmethyl)amino)-4-oxobutyl)thiophene-2-carboxamide | AKT1 |
| N-(4-(benzofuran-2-yl)thiazol-2-yl)-N-(4-(cyclohexyl(4-hydroxybutyl)amino)-4-oxobutyl)thiophene-2-carboxamide | AKT1 |
| N-(4-(benzofuran-2-yl)thiazol-2-yl)-N-(4-((2-cyanoethyl)((tetrahydrofuran-2-yl)methyl)amino)-4-oxobutyl)thiophene-2-carboxamide | AKT1 |
| N-(4-(benzofuran-2-yl)thiazol-2-yl)-N-(4-oxo-4-(2-(pyridin-3-yl)pyrrolidin-1-yl)butyl)thiophene-2-carboxamide | AKT1 |
| N-(4-(benzofuran-2-yl)thiazol-2-yl)-N-(3-(1-hydroxypropan-2-ylamino)-3-oxopropyl)thiophene-2-carboxamide | AKT1 |
| N-(4-(benzofuran-2-yl)thiazol-2-yl)-N-(3-(2-methoxyethylamino)-3-oxopropyl)thiophene-2-carboxamide | AKT1 |
| N-(4-(benzofuran-2-yl)thiazol-2-yl)-N-(3-(furan-3-ylmethylamino)-3-oxopropyl)thiophene-2-carboxamide | AKT1 |

TABLE 2-continued

| Compound | Activity |
|---|---|
| methyl 1-(3-(N-(4-(benzofuran-2-yl)thiazol-2-yl)thiophene-2-carboxamido)propanoyl)pyrrolidine-2-carboxylate | AKT1 |
| N-(4-(benzofuran-2-yl)thiazol-2-yl)-N-(3-(isoindolin-2-yl)-3-oxopropyl)thiophene-2-carboxamide | AKT1 |
| N-(3-((1,4-dioxan-2-yl)methylamino)-3-oxopropyl)-N-(4-(benzofuran-2-yl)thiazol-2-yl)thiophene-2-carboxamide | AKT1 |
| N-(4-(benzofuran-2-yl)thiazol-2-yl)-N-(3-(cyclohexyl(4-hydroxybutyl)amino)-3-oxopropyl)thiophene-2-carboxamide | AKT1 |
| N-(4-(benzofuran-2-yl)thiazol-2-yl)-N-(3-(methyl(pyridin-4-yl)amino)-3-oxopropyl)thiophene-2-carboxamide | AKT1 |
| 1-(4-(N-(4-(benzofuran-2-yl)thiazol-2-yl)thiophene-2-carboxamido)butanoyl)piperidine-3-carboxamide | AKT1 |
| N-(4-(benzofuran-2-yl)thiazol-2-yl)-N-(4-oxo-4-(pyridin-2-ylmethylamino)butyl)thiophene-2-carboxamide | AKT1 |
| N-(4-(benzofuran-2-yl)thiazol-2-yl)-N-(4-oxo-4-(thiazolidin-3-yl)butyl)thiophene-2-carboxamide | AKT1 |
| tert-butyl 2-(4-(N-(4-(benzofuran-2-yl)thiazol-2-yl)thiophene-2-carboxamido)butanamido)ethylcarbamate | AKT1 |
| (S)-N-(4-(benzofuran-2-yl)thiazol-2-yl)-N-(4-(2-(hydroxymethyl)indolin-1-yl)-4-oxobutyl)thiophene-2-carboxamide | AKT1 |
| N-(4-(benzofuran-2-yl)thiazol-2-yl)-N-(4-(isoindolin-2-yl)-4-oxobutyl)thiophene-2-carboxamide | AKT1 |
| N-(3-acetamidopropyl)-N-(4-(benzofuran-2-yl)thiazol-2-yl)thiophene-2-carboxamide | AKT1 |
| 1-acetyl-N-(3-(N-(4-(benzofuran-2-yl)thiazol-2-yl)thiophene-2-carboxamido)propyl)piperidine-4-carboxamide | AKT1 |
| N-(4-(benzofuran-2-yl)thiazol-2-yl)-N-(3-(3-(piperidin-1-yl)propanamido)propyl)thiophene-2-carboxamide | AKT1 |
| N-(4-(benzofuran-2-yl)thiazol-2-yl)-N-(3-(4-(dimethylamino)butanamido)propyl)thiophene-2-carboxamide | AKT1 |
| N-(3-(N-(4-(benzofuran-2-yl)thiazol-2-yl)thiophene-2-carboxamido)propyl)isonicotinamide | AKT1 |
| N-(3-(4-acetamidobutanamido)propyl)-N-(4-(benzofuran-2-yl)thiazol-2-yl)thiophene-2-carboxamide | AKT1 |
| N-(4-(benzofuran-2-yl)thiazol-2-yl)-N-(3-(3-hydroxy-2-(hydroxymethyl)-2-methylpropanamido)propyl)thiophene-2-carboxamide | AKT1 |
| N-(4-(benzofuran-2-yl)thiazol-2-yl)-N-(3-(2-(2,5-dioxoimidazolidin-4-yl)acetamido)propyl)thiophene-2-carboxamide | AKT1 |
| N-(4-(benzofuran-2-yl)thiazol-2-yl)-N-(3-(3-morpholinopropanamido)propyl)thiophene-2-carboxamide | AKT1 |
| N-(3-(N-(4-(benzofuran-2-yl)thiazol-2-yl)thiophene-2-carboxamido)propyl)-1,5-dimethyl-1H-pyrazole-3-carboxamide | AKT1 |
| N-(4-(benzofuran-2-yl)thiazol-2-yl)-N-(3-(2-morpholinoacetamido)propyl)thiophene-2-carboxamide | AKT1 |
| (S)-tert-butyl 1-(3-(N-(4-(benzofuran-2-yl)thiazol-2-yl)thiophene-2-carboxamido)propyl)pyrrolidine-2-carboxylate | AKT1 |
| 1-(3-(N-(4-(benzofuran-2-yl)thiazol-2-yl)thiophene-2-carboxamido)propyl)piperidine-3-carboxamide | AKT1 |
| ethyl 1-(3-(N-(4-(benzofuran-2-yl)thiazol-2-yl)thiophene-2-carboxamido)propyl)piperidine-2-carboxylate | AKT1 |
| N-(4-(benzofuran-2-yl)thiazol-2-yl)-N-(3-(3-hydroxypiperidin-1-yl)propyl)thiophene-2-carboxamide | AKT1 |
| N-(4-(benzofuran-2-yl)thiazol-2-yl)-N-(3-(4-(2-(2-hydroxyethoxy)ethyl)piperazin-1-yl)propyl)thiophene-2-carboxamide | AKT1 |
| N-(4-(benzofuran-2-yl)thiazol-2-yl)-N-(3-(4-(2-hydroxyethyl)piperidin-1-yl)propyl)thiophene-2-carboxamide | AKT1 |
| N-(4-(benzofuran-2-yl)thiazol-2-yl)-N-(3-(4-(2-cyanoethyl)piperazin-1-yl)propyl)thiophene-2-carboxamide | AKT1 |
| N-(4-(benzofuran-2-yl)thiazol-2-yl)-N-(3-(4-(hydroxymethyl)piperidin-1-yl)propyl)thiophene-2-carboxamide | AKT1 |
| N-(4-(benzofuran-2-yl)thiazol-2-yl)-N-(3-(3-(dimethylamino)pyrrolidin-1-yl)propyl)thiophene-2-carboxamide | AKT1 |
| ethyl 1-(3-(N-(4-(benzofuran-2-yl)thiazol-2-yl)thiophene-2-carboxamido)propyl)piperidine-3-carboxylate | AKT1 |
| N-(4-(benzofuran-2-yl)thiazol-2-yl)-N-(3-(4-hydroxypiperidin-1-yl)propyl)thiophene-2-carboxamide | AKT1 |
| N-(4-(benzofuran-2-yl)thiazol-2-yl)-N-(3-(3-(N-ethylacetamido)pyrrolidin-1-yl)propyl)thiophene-2-carboxamide | AKT1 |
| N-(4-(benzofuran-2-yl)thiazol-2-yl)-N-(3-(3-(N-methylacetamido)pyrrolidin-1-yl)propyl)thiophene-2-carboxamide | AKT1 |
| tert-butyl 1-(3-(N-(4-(benzofuran-2-yl)thiazol-2-yl)thiophene-2-carboxamido)propyl)pyrrolidin-3-ylcarbamate | AKT1 |
| (S)-N-(4-(benzofuran-2-yl)thiazol-2-yl)-N-(3-(2-(methoxymethyl)pyrrolidin-1-yl)propyl)thiophene-2-carboxamide | AKT1 |
| N-(3-(3-acetamidopyrrolidin-1-yl)propyl)-N-(4-(benzofuran-2-yl)thiazol-2-yl)thiophene-2-carboxamide | AKT1 |

TABLE 2-continued

| Compound | Activity |
|---|---|
| ethyl 4-(3-(N-(4-(benzofuran-2-yl)thiazol-2-yl)thiophene-2-carboxamido)propyl)piperazine-1-carboxylate | AKT1 |
| N-(4-(benzofuran-2-yl)thiazol-2-yl)-N-(3-(4-(morpholine-4-carbonyl)piperazin-1-yl)propyl)thiophene-2-carboxamide | AKT1 |
| N-(4-(benzofuran-2-yl)thiazol-2-yl)-N-(3-(4,4-dihydroxypiperidin-1-yl)propyl)thiophene-2-carboxamide | AKT1 |
| N-(4-(benzofuran-2-yl)thiazol-2-yl)-N-(3-(4-(tetrahydrofuran-2-carbonyl)piperazin-1-yl)propyl)thiophene-2-carboxamide | AKT1 |
| (R)-1-(3-(N-(4-(benzofuran-2-yl)thiazol-2-yl)thiophene-2-carboxamido)propyl)-N-methylpyrrolidine-2-carboxamide | AKT1 |
| 1-(3-(N-(4-(benzofuran-2-yl)thiazol-2-yl)thiophene-2-carboxamido)propyl)pyrrolidine-2-carboxamide | AKT1 |
| methyl 1-(3-(N-(4-(benzofuran-2-yl)thiazol-2-yl)thiophene-2-carboxamido)propyl)pyrrolidine-2-carboxylate | AKT1 |
| methyl 1-(3-(N-(4-(benzofuran-2-yl)thiazol-2-yl)thiophene-2-carboxamido)propyl)piperidine-2-carboxylate | AKT1 |
| (S)-1-(3-(N-(4-(benzofuran-2-yl)thiazol-2-yl)thiophene-2-carboxamido)propyl)-N,N-dimethylpyrrolidine-2-carboxamide | AKT1 |
| N-(4-(benzofuran-2-yl)thiazol-2-yl)-N-(3-(2-(pyrrolidin-1-ylmethyl)piperidin-1-yl)propyl)thiophene-2-carboxamide | AKT1 |
| N-(4-(benzofuran-2-yl)thiazol-2-yl)-N-(3-(3-oxopiperazin-1-yl)propyl)thiophene-2-carboxamide | AKT1 |
| 1-(3-(N-(4-(benzofuran-2-yl)thiazol-2-yl)thiophene-2-carboxamido)propyl)piperidine-2-carboxamide | AKT1 |
| ethyl 2-(4-(3-(N-(4-(benzofuran-2-yl)thiazol-2-yl)thiophene-2-carboxamido)propyl)piperazin-1-yl)acetate | AKT1 |
| tert-butyl 4-(3-(N-(4-(benzofuran-2-yl)thiazol-2-yl)thiophene-2-carboxamido)propyl)piperazine-1-carboxylate | AKT1 |
| N-(4-(benzofuran-2-yl)thiazol-2-yl)-N-(3-(4-morpholinopiperidin-1-yl)propyl)thiophene-2-carboxamide | AKT1 |
| N-(4-(benzofuran-2-yl)thiazol-2-yl)-N-(3-(4-(2-(dimethylamino)ethyl)piperazin-1-yl)propyl)thiophene-2-carboxamide | AKT1 |
| N-(4-(benzofuran-2-yl)thiazol-2-yl)-N-(3-(2-(hydroxymethyl)pyrrolidin-1-yl)propyl)thiophene-2-carboxamide | AKT1 |
| N-(4-(benzofuran-2-yl)thiazol-2-yl)-N-(3-(2-(2-hydroxyethyl)piperidin-1-yl)propyl)thiophene-2-carboxamide | AKT1 |
| N-(4-(benzofuran-2-yl)thiazol-2-yl)-N-(3-(3-(hydroxymethyl)piperidin-1-yl)propyl)thiophene-2-carboxamide | AKT1 |
| N-(4-(benzofuran-2-yl)thiazol-2-yl)-N-(3-(2-(hydroxymethyl)piperidin-1-yl)propyl)thiophene-2-carboxamide | AKT1 |
| N-(4-(benzofuran-2-yl)thiazol-2-yl)-N-(3-(3-hydroxypyrrolidin-1-yl)propyl)thiophene-2-carboxamide | AKT1 |
| (S)-N-(4-(benzofuran-2-yl)thiazol-2-yl)-N-(3-(2-(hydroxymethyl)pyrrolidin-1-yl)propyl)thiophene-2-carboxamide | AKT1 |
| N-(3-(4-acetylpiperazin-1-yl)propyl)-N-(4-(benzofuran-2-yl)thiazol-2-yl)thiophene-2-carboxamide | AKT1 |
| 1-(3-(N-(4-(benzofuran-2-yl)thiazol-2-yl)thiophene-2-carboxamido)propyl)-N,N-diethylpiperidine-3-carboxamide | AKT1 |
| N-(4-(benzofuran-2-yl)thiazol-2-yl)-N-(3-(4-(2-hydroxyethyl)piperazin-1-yl)propyl)thiophene-2-carboxamide | AKT1 |
| N-(4-(benzofuran-2-yl)thiazol-2-yl)-N-(3-(4-(2-methoxyethyl)piperazin-1-yl)propyl)thiophene-2-carboxamide | AKT1 |
| N-(4-(benzofuran-2-yl)thiazol-2-yl)-N-(3-(3-(diethylamino)pyrrolidin-1-yl)propyl)thiophene-2-carboxamide | AKT1 |
| 1-(3-(N-(4-(benzofuran-2-yl)thiazol-2-yl)thiophene-2-carboxamido)propyl)-N-methylpiperidine-4-carboxamide | AKT1 |
| N-(4-(benzofuran-2-yl)thiazol-2-yl)-N-(3-(4-(diethylamino)piperidin-1-yl)propyl)thiophene-2-carboxamide | AKT1 |
| (R)-1-(3-(N-(4-(benzofuran-2-yl)thiazol-2-yl)thiophene-2-carboxamido)propyl)pyrrolidine-2-carboxylic acid | AKT1 |
| 1-(3-(N-(4-(benzofuran-2-yl)thiazol-2-yl)thiophene-2-carboxamido)propyl)piperidine-4-carboxamide | AKT1 |
| N-(4-(benzofuran-2-yl)thiazol-2-yl)-N-(3-(4-(2-(dimethylamino)-2-oxoethyl)piperazin-1-yl)propyl)thiophene-2-carboxamide | AKT1 |
| N-(4-(benzofuran-2-yl)thiazol-2-yl)-N-(3-(4-(methylsulfonyl)piperazin-1-yl)propyl)thiophene-2-carboxamide | AKT1 |

Example 27

Cellular Assays

The cellular activities of the inhibitor compounds described may be assessed in a number of assays by those skilled in the art. Sources for cells include, but are not limited to, human peripheral blood mononuclear cells and transformed cell lines available from standard cell banks such as The American Type Culture Collection (Bethesda, Md.). Cells genetically manipulated to express a particular kinase or kinases are also suitable for use in assaying cellular activity.

The compounds can be tested for activities in cellular proliferation assays using target cells (e.g., LNCaP, HT-29, U87MG, PC3, MV4-11, RS4:11, H1299, H526, K562, and others). The cells are plated into 96-well plates in appropriate cell culture medium from suppliers such as Gibco, BRL at an optimal density for each cell line (typically 1000-2500 cells per well). Cells may be stimulated to proliferate with growth factors and/or cytokines. Cell viability is measured using Alamar Blue™ (Biosource International, Camarillo, Calif.). Typical controls for inhibition of proliferation include but are not limited to paclitaxel and doxorubicin (Calbiochem, San Diego Calif.).

Compounds can be tested for induction of apoptosis in target cells by measuring Caspase 3 induction using the Promega Caspase-Glo 3/7 Assay System (Madison, Wis.). Caspase 3 induction by compound can be compared to Caspase 3 induction by vehicle (1% DMSO) and to known apoptosis inducers such as LY294002 (Calbiochem. San Diego, Calif.).

Intracellular signaling proteins can be assayed for activity by assessing their phosphorylation states using techniques such as Western Blotting and solution bead-based assays. Reagents to measure phosphorylation of Akt (S473), PRAS40 (T246), GSK3beta (S9) and others were from Biosource International (Camarillo, Calif.). Cells at the optimum density can be treated with compound for 2-24 hours then lysed in a standard hypotonic lysis buffer (50 mM Tris, pH 7.4, 250 mM NaCl, 5 mM EDTA, 50 mM NaF, 1 mM NaVO3, 1% Nonidet P40, 1 mM PMSF, Roche Inhibitor Cocktail, Cat #1836170). Lysates can be centrifuged and the supernatant used for either running SDS/PAGE or assessing phosphoproteins using bead-based reagents and detecting on a Luminex 100 assay system (Luminex, Austin, Tex.).

Certain of the chemical entities of the present disclosure are tested in cellular proliferation assays as described herein and exhibit an $IC_{50}$ value less than or equal to 30 micromolar.

Some of the chemical entities of the present disclosure are tested for induction of apoptosis in target cells and exhibit an $EC_{50}$ value less than or equal to 30 micromolar.

Example 28

In vivo Xenograft Tumor Models

Animals: Female athymic nude mice (Harlan) were used. Animals were 9-10 weeks old on Day 1 of the study.

Tumor: HT29, human colon tumor was maintained in athymic nude mice by serial engraftment. Animals implanted subcutaneously with tumor fragment (1 mm$_3$) on the animals right flank. Tumors were monitored twice weekly and then daily as their volumes approached 80-120 mm$^3$. On Day 1, mice were randomized into control and treatment groups with tumor sizes of 62.5-196.0 mm$^3$ and group mean tumor sizes of 91.1-155.3 mm$^3$. Recorded initial tumor size and body weight of animals.

Treatment: Control (no treatment). Vehicle control, (30% CAPTISOL® in water), 0.2 ml/mouse, i.p. twice daily on Days 1-10 (b.i.d.×10). Chemical entities of the present disclosure, 150 mg/kg/inj, i.p., twice daily on Days 1-10 (b.i.d.× 10). Paclitaxel, 30 mg/kg/inj, i.v., once daily on Days 1, 3, 5, 7, and 9 (qod×5). In all groups, the dosing volume of 0.2 or 0.3 mL/20-g mouse was scaled to the body weight of each animal. Animals were weighed daily on Days 1-5, then twice weekly until the completion of the study. Monitored the study daily and made notations on any unusual observations on animals.

Each animal was euthanized when its neoplasm reached the predetermined endpoint size (1,500 mm$^3$). The time to endpoint (TTE) for each mouse was calculated by the following equation:

$$TTE = \frac{\log_{10}(\text{endpoint volume}) - b}{m}$$

where TTE is expressed in days, endpoint volume is in mm$^3$, b is the intercept, and m is the slope of the line obtained by linear regression of a log-transformed tumor growth data set. The data set is comprised of the first observation that exceeded the study endpoint volume and the three consecutive observations that immediately preceded the attainment of the endpoint volume. Animals that do not reach the endpoint are assigned a TTE value equal to the last day of the study (60 days). The logrank test was employed to analyze the significance of the difference between the TTE values of two groups.

Treatment efficacy was determined from tumor growth delay (TGD), which is defined as the increase in the median TTE for a treatment group compared to the control group:

$$TGD = T - C,$$

expressed in days, or as a percentage of the median TTE of the control group:

$$\% \, TGD = \frac{T - C}{C} \times 100$$

where: T=median TTE for a treatment group, C=median TTE for control group.

Treatment may cause partial regression (PR) or complete regression (CR) of the tumor in an animal. In a PR response, the tumor volume is 50% or less of its Day 1 volume for three consecutive measurements during the course of the study, and equal to or greater than 13.5 mm$^3$ for one or more of these three measurements. In a CR response, the tumor volume is less than 13.5 mm$^3$ for three consecutive measurements during the course of the study.

Other embodiments of the present disclosure will be apparent to those skilled in the art from consideration of the specification and practice of the present disclosure disclosed herein. It is intended that the specification and examples be considered as exemplary only, with a true scope and spirit of the present disclosure being indicated by the following claims.

What is claimed is:

1. A compound of Formula IV:

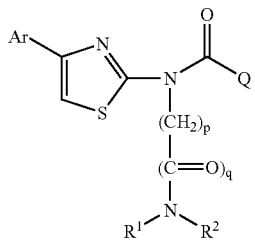

(Formula IV)

and pharmaceutically acceptable salts, solvates, chelates, non-covalent complexes, and mixtures thereof, wherein Ar is selected from aryl, substituted aryl, heteroaryl, and substituted heteroaryl;

Q is selected from cycloalkyl, substituted cycloalkyl, cycloheteroalkyl, substituted cycloheteroalkyl, aryl, substituted aryl, heteroaryl, and substituted heteroaryl;

$R^1$ and $R_2$ are independently selected from hydrogen, alkyl, substituted alkyl, cycloalkyl, substituted cycloalkyl, heterocycloalkyl, substituted heterocycloalkyl, aryl, substituted aryl, heteroaryl, and substituted heteroaryl; or $R^1$ and $R_2$ together with the nitrogen to which $R^1$ and $R_2$ are attached form a ring chosen from cycloheteroalkyl, substituted cycloheteroalkyl, heteroaryl, and substituted heteroaryl;

p is selected from 2, 3, 4, and 5; and q is 0 or 1.

2. The compound of claim 1 wherein p is chosen from 2, 3 and 4 and q is 0.

3. The compound of claim 2 wherein p is chosen from 2 and 3 and q is 0.

4. The compound of claim 1 wherein p is chosen from 2 and 3 and q is 1.

5. The compound of claim 4 wherein p is 2 and q is 1.

6. The compound of claim 1 wherein $R^1$ and $R^2$ are independently chosen from $C_{1-4}$ alkyl.

7. The compound of claim 1 wherein $R^1$ and $R^2$, together with the nitrogen atom to which $R^1$ and $R_2$ are attached form a pyrrolidine, substituted pyrrolidine, piperidine, substituted piperidine, azepane, substituted azepane, piperazine, substituted piperazine, morpholine, or substituted morpholine ring.

8. The compound of claim 7 wherein $R^1$ and $R^2$ together with the nitrogen atom to which $R^1$ and $R^2$ are attached form a morpholin-4-yl ring.

9. The compound of claim 1 wherein Ar is chosen from substituted aryl, and substituted heteroaryl.

10. The compound of claim 9 wherein Ar is chosen from phenyl, substituted phenyl, benzo[b]thiophen-3-yl, substituted benzo[b]thiophen-3-yl, pyridin-2-yl, substituted pyridin-2-yl, pyridin-3-yl, substituted pyridin-3-yl, pyridin-4-yl, substituted pyridin-4-yl, thiophen-2-yl, substituted thiophen-2-yl, thiophen-3-yl, substituted thiophen-3-yl, 4-isoxazolyl, substituted 4-isoxazolyl, 5-isoxazolyl, substituted 5-isoxazolyl, 3-pyrazolyl, substituted 3-pyrazolyl, 4-pyrazolyl, substituted 4-pyrazolyl, naphthalene-2-yl, substituted napthalen-2-yl, 2,3-dihydro-1,4-benzodioxin-6-yl, substituted 2,3-dihydro-1,4-benzodioxin-6-yl, 3,4-dihydro-2H-1,5-benzodioxepin-7-yl, substituted 3,4-dihydro-2H-1,5-benzodioxepin-7-yl, benzothiazol-2-yl, substituted benzothiazol-2-yl, benzofuran-2-yl, and substituted benzofuran-2-yl.

11. The compound of claim 10 wherein Ar is chosen from phenyl, substituted phenyl, 4-isoxazolyl, substituted 4-isoxazolyl, 5-isoxazolyl, substituted 5-isoxazolyl, 3-pyrazolyl, substituted 3-pyrazolyl, 4-pyrazolyl, substituted 4-pyrazolyl, benzofuran-2-yl, and substituted benzofuran-2-yl.

12. The compound of claim 1 wherein Q is chosen from $C_{5-10}$ monocyclic heteroaryl, and substituted monocyclic $C_{5-10}$ heteroaryl.

13. The compound of claim 1 wherein Q is chosen from phenyl, substituted phenyl, furanyl, substituted furanyl, cyclohexyl, substituted cyclohexyl, cyclopentenyl, substituted cyclopentenyl, 4-isoxazolyl, substituted 4-isoxazolyl, 5-isoxazolyl, substituted 5-isoxazolyl, thiophene-2-yl, substituted thiophene-2-yl, pyrimidin-2-yl, substituted pyrimidin-2-yl, 5-thiadiazolyl, substituted 5-thiadiazolyl, imidazolyl, substituted imidazolyl, 3-isothiazolyl, substituted thiazolyl, 3-pyrrolyl, and substituted 3-pyrrolyl.

14. The compound of claim 13 wherein Q is chosen from thiophene, and substituted thiophene.

15. A pharmaceutical composition comprising at least one pharmaceutically acceptable vehicle, and a therapeutically effective amount of a compound of claim 1.

16. The pharmaceutical composition of claim 15 further comprising at least one additional therapeutic agent appropriate for effecting combination therapy.

17. The pharmaceutical composition of claim 16 wherein said at least one additional therapeutic agent appropriate for effecting combination therapy is chosen from estrogen receptor modulators, cytostatic/cytotoxic agents, anti-proliferative agents, cell cycle checkpoint inhibitors, angiogenesis inhibitors, monoclonal antibody targeted therapeutic agents, tyrosine kinase inhibitors, serine-threonine kinase inhibitors, histone deacetylase inhibitors, heat shock protein inhibitors, and farnesyl transferase inhibitors.

18. The compound of claim 8 wherein p is 3 and q is 0.

19. The compound of claim 11 wherein Ar is substituted phenyl.

20. The compound of claim 11 wherein Ar is 3-substituted isoxazol-5-yl.

21. The compound of claim 20 wherein Ar is 3-phenyl isoxazol-5-yl.

22. The compound of claim 21 wherein Q is thiophen 2-yl or substituted thiophen-2-yl.

23. The compound of claim 1 selected from:
N-(3-(diethylamino)propyl)-N-(4-(2,5-dimethoxyphenyl)thiazol-2-yl)benzamide;
N-(3-(diethylamino)propyl)-N-(4-(2,5-dimethoxyphenyl)thiazol-2-yl)thiophene-2-carboxamide;
N-(4-phenylthiazol-2-yl)-N-(3-(pyrrolidin-1-yl)propyl)thiophene-2-carboxamide;
N-(4-(4-methoxyphenyl)thiazol-2-yl)-N-(3-(pyrrolidin-1-yl)propyl)benzamide;
N-(4-(4-methoxyphenyl)thiazol-2-yl)-N-(3-(pyrrolidin-1-yl)propyl)thiophene-2-carboxamide;
N-(4-(4-methoxyphenyl)thiazol-2-yl)-N-(3-(pyrrolidin-1-yl)propyl)furan-2-carboxamide;
N-(4-(2,5-dimethoxyphenyl)thiazol-2-yl)-N-(3-(pyrrolidin-1-yl)propyl)benzamide;
N-(4-(2,5-dimethoxyphenyl)thiazol-2-yl)-N-(3-(pyrrolidin-1-yl)propyl)thiophene-2-carboxanilde;
N-(4-(2,5-dimethoxyphenyl)thiazol-2-yl)-N-(3-(pyrrolidin-1-yl)propyl)furan-2-carboxamide;
N-(4-(4-methoxyphenyl)thiazol-2-yl)-N-(3-(piperidin-1-yl)propyl)thiophene-2-carboxamide;
N-(4-(2,5-dimethoxyphenyl)thiazol-2-yl)-N-(3-(piperidin-1-yl)propyl)benzamide;

N-(4-(2,5-dimethoxyphenyl)thiazol-2-yl)-N-(3-(piperidin-1-yl)propyl)thiophene-2-carboxamide;
N-(4-(2,5-dimethoxyphenyl)thiazol-2-yl)-N-(3-(piperidin-1-yl)propyl)furan-2-carboxamide;
N-(3-(azepan-1-yl)propyl)-N-(4-phenylthiazol-2-yl)benzamide;
N-(3-(azepan-1-yl)propyl)-N-(4-phenylthiazol-2-yl)thiophene-2-carboxamide;
N-(3-(azepan-1-yl)propyl)-N-(4-phenylthiazol-2-yl)furan-2-carboxamide;
N-(3-(azepan-1-yl)propyl)-N-(4-(4-methoxyphenyl)thiazol-2-yl)benzamide;
N-(3-(azepan-1-yl)propyl)-N-(4-(4-methoxyphenyl)thiazol-2-yl)thiophene-2-carboxamide;
N-(3-(azepan-1-yl)propyl)-N-(4-(4-methoxyphenyl)thiazol-2-yl)furan-2-carboxamide;
N-(3-(azepan-1-yl)propyl)-N-(4-(2,5-dimethoxyphenyl)thiazol-2-yl)benzamide;
N-(3-(azepan-1-yl)propyl)-N-(4-(2,5-dimethoxyphenyl)thiazol-2-yl)thiophene-2-carboxamide;
N-(3-(azepan-1-yl)propyl)-N-(4-(2,5-dimethoxyphenyl)thiazol-2-yl)furan-2-carboxamide;
N-(3-(4-methylpiperazin-1-yl)propyl)-N-(4-phenylthiazol-2-yl)benzamide;
N-(3-(4-methylpiperazin-1-yl)propyl)-N-(4-phenylthiazol-2-yl)thiophene-2-carboxamide;
N-(3-(4-methylpiperazin-1-yl)propyl)-N-(4-phenylthiazol-2-yl)furan-2-carboxamide;
N-(4-(4-methoxyphenyl)thiazol-2-yl)-N-(3-(4-methylpiperazin-1-yl)propyl)benzamide;
N-(4-(4-methoxyphenyl)thiazol-2-yl)-N-(3-(4-methylpiperazin-1-yl)propyl)thiophene-2-carboxamide;
N-(4-(4-methoxyphenyl)thiazol-2-yl)-N-(3-(4-methylpiperazin-1-yl)propyl)furan-2-carboxamide;
N-(4-(2,5-dimethoxyphenyl)thiazol-2-yl)-N-(3-(4-methylpiperazin-1-yl)propyl)benzamide;
N-(4-(2,5-dimethoxyphenyl)thiazol-2-yl)-N-(3-(4-methylpiperazin-1-yl)propyl)thiophene-2-carboxamide;
N-(4-(2,5-dimethoxyphenyl)thiazol-2-yl)-N-(3-(4-methylpiperazin-1-yl)propyl)furan-2-carboxamide;
N-(4-(4-methoxyphenyl)thiazol-2-yl)-N-(3-morpholinopropyl)cyclopent-1-enecarboxamide;
4-chloro-N-(4-(4-methoxyphenyl)thiazol-2-yl)-N-(3-morpholinopropyl)benzamide;
3-fluoro-N-(4-(4-methoxyphenyl)thiazol-2-yl)-N-(3-morpholinopropyl)benzamide;
N-(4-(4-methoxyphenyl)thiazol-2-yl)-3-methyl-N-(3-morpholinopropyl)benzamide;
2-fluoro-N-(4-(4-methoxyphenyl)thiazol-2-yl)-N-(3-morpholinopropyl)benzamide;
N-(4-(4-methoxyphenyl)thiazol-2-yl)-4-methyl-N-(3-morpholinopropyl)benzamide;
2-cyano-N-(4-(4-methoxyphenyl)thiazol-2-yl)-N-(3-morpholinopropyl)benzamide;
N-(4-(4-methoxyphenyl)thiazol-2-yl)-5-methyl-N-(3-morpholinopropyl)furan-2-carboxamide;
N-(4-(4-methoxyphenyl)thiazol-2-yl)-3-methyl-N-(3-morpholinopropyl)furan-2-carboxamide;
N-(4-(4-methoxyphenyl)thiazol-2-yl)-N-(3-morpholinopropyl)thiophene-2-carboxamide;
N-(4-(4-chlorophenyl)thiazol-2-yl)-N-(3-morpholinopropyl)thiophene-2-carboxamide;
N-(3-morpholinopropyl)-N-(4-p-tolylthiazol-2-yl)thiophene-2-carboxamide;
N-(4-(2,3-dihydrobenzo [b][1,4]dioxin-6-yl)thiazol-2-yl)-N-(3-morpholinopropyl)thiophene-2-carboxamide;
N-(4-(4-chloro-3-nitrophenyl)thiazol-2-yl)-N-(3-morpholinopropyl)thiophene-2-carboxaniide;
N-(4-(2-methoxyphenyl)thiazol-2-yl)-N-(3-morpholinopropyl)thiophene-2-carboxamide;
N-(4-(2,4-dimethylphenyl)thiazol-2-yl)-N-(3-morpholinopropyl)thiophene-2-carboxamide;
N-(4-(4-cyanophenyl)thiazol-2-yl)-N-(3-morpholinopropyl)thiophene-2-carboxamide;
methyl 4-(2-(N-(3-morpholinopropyl)thiophene-2-carboxamido)thiazol-4-yl)benzoate;
N-(4-(4-(methylsulfonyl)phenyl)thiazol-2-yl)-N-(3-morpholinopropyl)thiophene-2-carboxamide;
N-(4-(2,4-dimethoxyphenyl)thiazol-2-yl)-N-(3-morpholinopropyl)thiophene-2-carboxamide;
N-(4-(benzofuran-3-yl)thiazol-2-yl)-N-(3-morpholinopropyl)thiophene-2-carboxamide;
N-(4-(2-chlorophenyl)thiazol-2-yl)-N-(3-morpholinopropyl)thiophene-2-carboxamide, N-(4-(3-chlorophenyl)thiazol-2-yl)-N-(3-morpholinopropyl)thiophene-2-carboxamide;
N-(4-(benzo[b]thiophen-3-yl)thiazol-2-yl)-N-(3-morpholinopropyl)thiophene-2-carboxamide;
N-(3-morpholinopropyl)-N-(4-(pyridin-2-yl)thiazol-2-yl)thiophene-2-carboxamide;
N-(3-morpholinopropyl)-N-(4-(pyridin-3-yl)thiazol-2-yl)thiophene-2-carboxamide;
N-(3-morpholinopropyl)-N-(4-(pyridin-4-yl)thiazol-2-yl)thiophene-2-carboxamide;
N-(3-morpholinopropyl)-N-(4-(thiophen-2-yl)thiazol-2-yl)thiophene-2-carboxamide;
N-(4-(5-chlorothiophen-2-yl)thiazol-2-yl)-N-(3-morpholinopropyl)thiophene-2-carboxamide;
N-(4-(5-chlorothiophen-2-yl)thiazol-2-yl)-N-(3-morpholinopropyl)thiophene-2-carboxamide;
N-(4-(3,4-dimethoxyphenyl)thiazol-2-yl)-N-(5-morpholinopentyl)thiophene-2-carboxamide;
N-(4-(benzofuran-2-yl)thiazol-2-yl)-N-(5-morpholinopentyl)thiophene-2-carboxamide;
N-(4-(3,4-dichlorophenyl)thiazol-2-yl)-N-(3-morpholinopropyl)thiophene-2-carboxamide;
N-(4-(4-fluorophenyl)thiazol-2-yl)-N-(3-morpholinopropyl)thiophene-2-carboxamide;
N-(4-(4-(difluoromethoxy)phenyl)thiazol-2-yl)-N-(3-morpholinopropyl)thiophene-2-carboxamide;
N-(3-morpholinopropyl)-N-(4-(2-(trifluoromethyl)phenyl)thiazol-2-yl)thiophene-2-carboxamide;
N-(4-(2-fluorophenyl)thiazol-2-yl)-N-(3-morpholinopropyl)thiophene-2-carboxamide;
N-(4-(3,4-difluorophenyl)thiazol-2-yl)-N-(3-morpholinopropyl)thiophene-2-carboxamide;
N-(4-(3-bromophenyl)thiazol-2-yl)-N-(3-morpholinopropyl)thiophene-2-carboxamide;
N-(3-morpholinopropyl)-N-(4-(4-(trifluoromethoxy)phenyl)thiazol-2-yl)thiophene-2-carboxamide;
N-(4-(3-fluorophenyl)thiazol-2-yl)-N-(3-morpholinopropyl)thiophene-2-carboxamide;
N-(4-(3-methylbenzol[b]thiophen-2-yl)thiazol-2-yl)-N-(3-morpholinopropyl)thiophene-2-carboxamide;
N-(4-(3-cyanophenyl)thiazol-2-yl)-N-(3-morpholinopropyl)thiophene-2-carboxamide;
N-(3-.morpholinopropyl)-N-(4-(4-pentylphenyl)thiazol-2-yl)thiophene-2-carboxamide;
N-(4-(4-(diethylamino)phenyl)thiazol-2-yl)-N-(3-morpholinopropyl)thiophene-2-carboxamide;
N-(3-.morpholinopropyl)-N-(4-(4-(pyrrolidin-1-yl)phenyl)thiazol-2-yl)thiophene-2-carboxamide;

N-(4-(3,4-dimethoxyphenyl)thiazol-2-yl)-N-(3-morpholinopropyl)thiophene-2-carboxamide;
N-(4-(benzo[d][1,3]dioxol-5-yl)thiazol-2-yl)-N-(3-morpholinopropyl)thiophene-2-carboxamide;
N-(4-(benzo[d]thiazol-2-yl)thiazol-2-yl)-N-(3-morpholinopropyl)thiophene-2-carboxamide;
N-(4-(3-methoxyphenyl)thiazol-2-yl)-N-(3-morpholinopropyl)thiophene-2-carboxamide;
N-(3-morpholinopropyl)-N-(4-(2-nitrophenyl)thiazol-2-yl)thiophene-2-carboxamide;
N-(3-morpholinopropyl)-N-(4-(naphthalen-2-yl)thiazol-2-yl)thiophene-2-carboxamide;
N-(4-(benzofuran-2-yl)thiazol-2-yl)-N-(3-morpholinopropyl)thiophene-2-carboxamide;
N-(4-(4-morpholinophenyl)thiazol-2-yl)-N-(3-morpholinopropyl)thiophene-2-carboxamide;
N-(4-(3,4-dihydro-2H-benzo[b][1,4]dioxepin-7-yl)thiazol-2-yl)-N-(3-morpholinopropyl)thiophene-2-carboxamide;
N-(4-(2-chloropyridin-4-yl)thiazol-2-yl)-N-(3-morpholinopropyl)tbiophene-2-carboxamide;
N-(4-(4-methoxyphenyl)thiazol-2-yl)-3-methyl-N-(3-morpholinopropyl)thiophene-2-carboxamide;
2,5-dichloro-N-(4-(4-methoxyphenyl)thiazol-2-yl)-N-(3-morpholinopropyl)thiophene-3-carboxamide;
3-bromo-N-(4-(4-methoxyphenyl)thiazol-2-yl)-N-(3-morpholinopropyl)thiophene-2-carboxamide;
N-(4-(4-methoxyphenyl)thiazol-2-yl)-N-(3-morpholinopropyl)-5-nitrothiophene-2-carboxamide;
5-chloro-N-(4-(4-methoxyphenyl)thiazol-2-yl)-N-(3-morpholinopropyl)thiophene-2-carboxamide;
5-acetyl-N-(4-(4-methoxyphenyl)thiazol-2-yl)-N-(3-morpholinopropyl)thiophene-2-carboxamide;
5-bromo-N-(4-(4-methoxyphenyl)thiazol-2-yl)-N-(3-morpholinopropyl)thiophene-2-carboxamide;
N-(4-(4-methoxyphenyl)thiazol-2-yl)-5-(methylthio)-N-(3-morpholinopropyl)thiophene-2-carboxamide;
N-(3-morpholinopropyl)-N-(4-(3-(trifluoromethyl)phenyl)thiazol-2-yl)thiophene-2-carboxamide;
N-(4-(4-methoxyphenyl)thiazol-2-yl)-1-methyl-N-(3-morpholinopropyl)-1H-pyrrole-2-carboxamide;
N-(4-(4-methoxyphenyl)thiazol-2-yl)-N-(3-morpholinopropyl)isoxazole-5-carboxamide;
N-(4-(4-methoxyphenyl)thiazol-2-yl)-3,5-dimethyl-N-(3-morpholinopropyl)isoxazole-4-carboxamide;
N-(4-(4-methoxyphenyl)thiazol-2-yl)-4-methyl-N-(3-morpholinopropyl)-1,2,3-thiadiazole-5-carboxamide;
N-(4-(4-methoxyphenyl)thiazol-2-yl)-2,4-dimethyl-N-(3-morpholinopropyl)thiazole-5-carboxamide;
4-chloro-N-(4-(4-methoxyphenyl)thiazol-2-yl)-N-(3-morpholinopropyl)picolinamide;
N-(4-(4-methoxyphenyl)thiazol-2-yl)-3-methyl-N-(3-morpholinopropyl)isoxazole-4-carboxamide;
6-chloro-N-(4-(4-methoxyphenyl)thiazol-2-yl)-N-(3-morpholinopropyl)picolinamide;
N-(4-(4-methoxyphenyl)thiazol-2-yl)-1-methyl-N-(3-morpholinopropyl)-1H-imidazole-2-carboxamide;
4,5-dichloro-N-(4-(4-rnethoxyphenyl)thiazol-2-yl)-N-(3-morpholinopropyl)isothiazole-3-carboxamide;
N-(4-(4-methoxyphenyl)thiazol-2-yl)-1,2,5-trimethyl-N-(3-morpholinopropyl)-1H-pyrrole-3-carboxamide;
ethyl 2-(N-(3-morpholinopropyl)thiophene-2-carboxamido)thiazole-4-carboxylate;
ethyl 3-methyl-3-(2-(N-(3-morpholinopropyl)thiophene-2-carboxaniido)thiazol-4-yl)butanoate;
N-(4-(biphenyl-4-yl)thiazol-2-yl)-N-(3-morpholinopropyl)thiophene-2-carboxamide;
N-(4-(5-methyl-1-phenyl-1H-pyrazol-4-yl)thiazol-2-yl)-N-(3-morpholinopropyl)thiophene-2-carboxaniide;
N-(4-(2,4-dichlorophenyl)thiazol-2-yl)-N-(3-morpholinopropyl)thiophene-2-carboxamide;
3-(2-(N-(3-morpholinopropyl)thiophene-2-carboxamido)thiazol-4-yl)benzoic acid;
N-(3-morpholinopropyl)-N-(4-(3-oxo-3,4-dihydro-2H-benzo[b][1,4]oxazin-6-yl)thiazol-2-yl)thiophene-2-carboxamide;
N-(3-morpholinopropyl)-N-(4-(3-phenylisoxazol-5-yl)thiazol-2-yl)thiophene-2-carboxamide;
N-(3-morpholinopropyl)-N-(4-(5-(pyridin-2-yl)thiophen-2-yl)thiazol-2-yl)thiophene-2-carboxamide;
N-(4'-methyl-2'-(pyrazin-2-yl)-4,5'-bithiazol-2-yl)-N-(3-morpholinopropyl)thiophene-2-carboxamide;
2-(5-(2-(N-(3-morpholinopropyl)thiophene-2-carboxamido)thiazol-4-yl)thiophen-2-yl)acetic acid;
N-(4-(4-chloro-3-methylphenyl)thiazol-2-yl)-N-(3-morpholinopropyl)thiophene-2-carboxamide;
N-(4-(3,4-dimethoxyphenyl)thiazol-2-yl)-N-(3-morpholinopropyl)benzamide;
N-(4-(3,4-dimethoxyphenyl)thiazol-2-yl)-N-(3-morpholinopropyl)furan-2-carboxamide;
N-(4-(benzofuran-2-yl)thiazol-2-yl)-N-(3-morpholinopropyl)furan-2-carboxamide;
N-(4-(benzofuran-2-yl)thiazol-2-yl)-N-(3-morpholinopropyl)nicotinamide;
N-(4-(3,4-dimethoxyphenyl)thiazol-2-yl)-N-(3-morpholinopropyl)cyclopentanecarboxamide;
N-(4-(3,4-dimethoxyphenyl)thiazol-2-yl)-N-(3-morpholinopropyl)cyclobutanecarboxamide;
N-(4-(benzofuran-2-yl)thiazol-2-yl)-N-(3-morpholinopropyl)cyclobutanecarboxamide;
N-(4-(3,4-dimethoxyphenyl)thiazol-2-yl)-N-(3-morpholinopropyl)picolinamide;
N-(4-(benzofuran-2-yl)thiazol-2-yl)-N-(3-morpholinopropyl)picolinamide;
N-(4-(3-(4-chlorophenyl)isoxazol-5-yl)thiazol-2-yl)-N-(3-morpholinopropyl)thiophene-2-carboxamide;
N-(3-morpholinopropyl)-N-(4-(3-phenylisoxazol-5-yl)thiazol-2-yl)furan-2-carboxamide;
1-methyl-N-(3-morpholinopropyl)-N-(4-(3-phenylisoxazol-5-yl)thiazol-2-yl)-1H-pyrrole-2-carboxamide;
4-(2-(N-(3-morpholinopropyl)thiophene-2-carboxamido)thiazol-4-yl)benzoic acid;
N-(3-morpholinopropyl)-N-(4-(trifluoromethyl)thiazol-2-yl)thiophene-2-carboxaniide;
ethyl 5-(2-(N-(3-morpholinopropyl)thiophene-2-carboxaniido)thiazol-4-yl)isoxazole-3-carboxylate;
2-(N-(3-morpholinopropyl)thiophene-2-carboxamido)-N-(1,3,4-thiadiazol-2-yl)thiazole-4-carboxamide;
2-(N-(3-morpholinopropyl)thiophene-2-carboxamido)-N-(thiazol-2-yl)thiazole-4-carboxamide;
N-(3-methoxyphenyl)-2-(N-(3-morpholinopropyl)thiophene-2-carboxamido)thiazole-4-carboxamide;
N-(3-methoxybenzyl)-2-(N-(3-morpholinopropyl)tbiophene-2-carboxamido)thiazole-4-carboxamide;
N-(3-chlorobenzyl)-2-(N-(3-morpholinopropyl)thiophene-2-carboxamido)thiazole-4-carboxamide;
N-(2,3-dihydrobenzo[b][1,4]dioxin-6-yl)-2-(N-(3-morpholinopropyl)thiophene-2-carboxamido)tbiazole-4-carboxaniide;
N-(5-ethyl-1,3,4-thiadiazol-2-yl)-2-(N-(3-morpholinopropyl)thiophene-2-carboxamido)thiazole-4-carboxamide;
N-(benzo[d]thiazol-6-yl)-2-(N-(3-morpholinopropyl)thiophene-2-carboxamido)thiazole-4-carboxamide;

N-(3-carbamoylphenyl)-2-(N-(3-morpholinopropyl)
thiophene-2-carboxamido)thiazole-4-carboxamide;

ethyl 2-(2-(2-(N-(3-morpholinopropyl)thiophene-2-carboxamido)thiazole-4-carboxamido)thiazol-4-yl)acetate;

N-(3-(methylsulfonamido)phenyl)-2-(N-(3-morpholinopropyl)thiophene-2-carboxamido)thiazole-4-carboxamide;

N-(4-(benzofuran-2-yl)thiazol-2-yl)-N-(3-(2-oxopyrrolidin-1-yl)propyl)furan-2-carboxamide;

N-(4-(benzofuran-2-yl)thiazol-2-yl)-N-(3-(2-oxopyrrolidin-1-yl)propyl)thiophene-2-carboxamide;

N-(4-(benzofuran-2-yl)thiazol-2-yl)-1-methyl-N-(3-(2-oxopyrrolidin-1-yl)propyl)-1H-pyrrole-2-carboxamide;

N-(3-(2-oxopyrrolidin-1-yl)propyl)-N-(4-(3-phenylisoxazol-5-yl)thiazol-2-yl)furan-2-carboxanilde;

N-(3-(2-oxopyrrolidin-1-yl)propyl)-N-(4-(3-phenylisoxazol-5-yl)thiazol)-2-carboxamide;

1-methyl-N-(3-(2-oxopyrrolidin-1-yl)propyl)-N-(4-(3-phenylisoxazol-5-yl)thiazol-2-yl)-1H-pyrrole-2-carboxamide;

N-(3-(4-methylpiperazin-1-yl)propyl)-N-(4-(3-phenylisoxazol-5-yl)thiazol-2-yl)furan-2-carboxamide;

N-(4-morpholinobutyl)-N-(4-(3-phenylisoxazol-5-yl)thiazol-2-yl)furan-2-carboxamide;

N-(4-morpholinobutyl)-N-(4-(3-phenylisoxazol-5-yl)thiazol-2-yl)thiophene-2-carboxamide;

N-(3-(diethylamino)propyl)-N-(4-(3,4-dimethoxyphenyl)thiazol-2-yl)thiophene-2-carboxamide;

N-(4-(3,4-dimethoxyphenyl)thiazol-2-yl)-N-(3-.(2-oxopyrrolidin-1-yl)propyl)thiophene-2-carboxamide;

N-(4-(3,4-dimethoxyphenyl)thiazol-2-yl)-N-(3-(4-methylpiperazin-1-yl)propyl)tbiophene-2-carboxamide;

N-(4-(3,4-dimethoxyphenyl)thiazol-2-yl)-N-(3-(piperidin-1-yl)propyl)thiophene-2-carboxamide;

N-(4-(3,4-dimethoxyphenyl)thiazol-2-yl)-N-(2-morpholinoethyl)thiophene-2-carboxamide;

N-(4-(benzofuran-2-yl)thiazol-2-yl)-N-(3-(diethylamino)propyl)thiophene-2-carboxamide;

N-(3-(1H-imidazol-1-yl)propyl)-N-(4-(benzofuran-2-yl)thiazol-2-yl)thiophene-2-carboxanilde;

N-(4-(benzofuran-2-yl)thiazol-2-yl)-N-(3-(4-methylpiperazin-1-yl)propyl)thiophene-2-carboxamide;

N-(4-(benzofuran-2-yl)thiazol-2-yl)-N-(3-(piperidin-1-yl)propyl)thiophene-2-carboxamide;

N-(4-(benzofuran-2-yl)thiazol-2-yl)-N-(4-morpholinobutyl)thiophene-2-carboxamide;

N-(4-(5-methylthiophen-2-yl)thiazol-2-yl)-N-(3-morpholinopropyl)thiophene-2-carboxamide;

N-(4-(6-methoxypyridin-3-yl)thiazol-2-yl)-N-(3-morpholinopropyl)thiophene-2-carboxamide;

N-(4-(2,6-dimethoxypyridin-3-yl)thiazol-2-yl)-N-(3-morpholinopropyl)thiophene-2-carboxarnide;

N-(4-cyclopentylthiazol-2-yl)-N-(3-morpholinopropyl)thiophene-2-carboxamide;

N-(4-cyclohexylthiazol-2-yl)-N-(3-morpholinopropyl)thiophene-2-carboxamide;

methyl 6-(2-(N-(3-morpholinopropyl)thiophene-2-carboxamido)thiazol-4-yl)nicotinate;

N-(4-(1H-indol-2-yl)thiazol-2-yl)-N-(3-morpholinopropyl)thiophene-2-carboxamide;

N-(4-(7-methoxybenzofuran-2-yl)thiazol-2-yl)-N-(3-morpholinopropyl)thiophene-2-carboxamide;

N-(4-(5-methoxybenzofuran-2-yl)thiazol-2-yl)-N-(3-morpholinopropyl)thiophene-2-carboxamide;

N-(3-morpholinopropyl)-N-(4-(5-nitrobenzofuran-2-yl)thiazol-2-yl)thiophene-2-carboxamide;

N-(4-(4-(2-hydroxyethylcarbamoyl)phenyl)thiazol-2-yl)-N-(3-morpholinopropyl)thiophene-2-carboxamide;

N-(4-(4-(2-morpholinoethylcarbamoyl)phenyl)thiazol-2-yl)-N-(3-morpholinopropyl)thiophene-2-carboxamide;

N-(4-(4-(methylcarbamoyl)phenyl)thiazol-2-yl)-N-(3-morpholinopropyl)thiophene-2-carboxamide;

N-(4-(4-(2-(dimethylamino)ethylcarbamoyl)phenyl)thiazol-2-yl)-N-(3-morpholinopropyl)thiophene-2-carboxamide;

N-(4-(4-(3-(dimethylamino)propylcarbamoyl)phenyl)thiazol-2-yl)-N-(3-morpholinopropyl)thiophene-2-carboxamide;

N-(4-(4-(3-hydroxypropylcarbamoyl)phenyl)thiazol-2-yl)-N-(3-morpholinopropyl)thiophene-2-carboxamide;

N-(4-(4-carbamoylphenyl)thiazol-2-yl)-N-(3-morpholinopropyl)thiophene-2-carboxamide;

N-(4-(4-(dimethylcarbamoyl)phenyl)thiazol-2-yl)-N-(3-morpholinopropyl)thiophene-2-carboxamide;

2-(4-(2-(N-(3-morpholinopropyl)thiophene-2-carboxamido)thiazol-4-yl)benzamido)acetic acid;

N-(4-(4-(4-methylpiperazine-1-carbonyl)phenyl)thiazol-2-yl)-N-(3-morpholinopropyl)thiophene-2-carboxanide;

N-(4-(4-(morpholine-4-carbonyl)phenyl)thiazol-2-yl)-N-(3-morpholinopropyl)thiophene-2-carboxanilde;

2-(3-(2-(N-(3-morpholinopropyl)thiophene-2-carboxamido)thiazol-4-yl)phenoxy)acetic acid;

3-(3-(2-(N-(3-morpholinopropyl)thiophene-2-carboxamido)thiazol-4-yl)phenoxy)propanoic acid;

2-(4-(2-(N-(3-morpholinopropyl)thiophene-2-carboxaniido)thiazol-4-yl)phenoxy)acetic acid;

3-(4-(2-(N-(3-morpholinopropyl)thiophene-2-carboxamido)thiazol-4-yl)phenoxy)propanoic acid;

N-(4-(3-(3-(dimethylamino)propoxy)phenyl)thiazol-2-yl)-N-(3-morpholinopropyl)thiophene-2-carboxamide;

N-(4-(3-(2-(dimethylainino)ethoxy)phenyl)thiazol-2-yl)-N-(3-morpholinopropyl)thiophene-2-carboxamide;

N-(4-(4-(3-(dimethylamino)propoxy)phenyl)thiazol-2-yl)-N-(3-morpholinopropyl)thiophene-2-carboxaniide;

N-(4-(4-(2-(dimethylamino)ethoxy)phenyl)thiazol-2-yl)-N-(3-morpholinopropyl)thiophene-2-carboxamide;

N-(4-(benzofuran-2-yl)thiazol-2-yl)-N-(3-(2-hydroxyethylamino)-3-oxopropyl)thiophene-2-carboxamide;

N-(4-(benzofuran-2-yl)thiazol-2-yl)-N-(3-(2-(hydroxymethyl)pyrrolidin-1-yl)-3-oxopropyl)thiophene-2-carboxaniide;

N-(4-(benzofuran-2-yl)thiazol-2-yl)-N-(3-(2-(dimethylamino)ethylamino)-3-oxopropyl)thiophene-2-carboxamide;

N-(4-(benzofuran-2-yl)thiazol-2-yl)-N-(3-(3-hydroxypiperidin-1-yl)-3-oxopropyl)thiophene-2-carboxamide;

N-(4-(benzofuran-2-yl)thiazol-2-yl)-N-(3-((2-hydroxyethyl)(methyl)amino)-3-oxopropyl)thiophene-2-carboxamide;

N-(4-(benzofuran-2-yl)thiazol-2-yl)-N-(3-(bis(2-hydroxyethyl)amino)-3-oxopropyl)thiophene-2-carboxamide;

N-(4-(benzofuran-2-yl)thiazol-2-yl)-N-(3-oxo-3-(piperazin-1-yl)propyl)thiophene-2-carboxamide;

N-(4-(benzofuran-2-yl)thiazol-2-yl)-N-(3-((2-(dimethylamino)ethyl)(methyl)amino)-3-oxopropyl)thiophene-2-carboxarnide;

N-(4-(benzofuran-2-yl)thiazol-2-yl)-N-(3-(methyl(2-(methylamino)ethyl)amino)-3-oxopropyl)thiophene-2-carboxamide;

N-(4-(benzofuran-2-yl)thiazol-2-yl)-N-(3-(3-hydroxypyrrolidin-1-yl)-3-oxopropyl)thiophene2-carboxanide;
N-(4-(benzofuran-2-yl)thiazol-2-yl)-N-(3-(3-(dimethylamino)pyrrolidin-1-yl)-3-oxopropyl)thiophene-2-carboxamide;
N-(4-(benzofuran-2-yl)thiazol-2-yl)-N-(3-((2,3-dihydroxypropyl)(methyl)amino)-3-oxopropyl)thiophene-2-carboxamide;
1-(3-(N-(4-(benzofuran-2-yl)thiazol-2-yl)thiophene-2-carboxamido)propanoyl)piperidine-3-carboxamide;
N-(4-(benzofuran-2-yl)thiazol-2-yl)-N-(3-oxo-3-(thiazolidin-3-yl)propyl)thiophene-2-carboxamide;
N-(4-(benzofuran-2-yl)thiazol-2-yl)-N-(3-morpholino-3-oxopropyl)thiophene-2-carboxamide;
N-(4-(benzofuran-2-yl)thiazol-2-yl)-N-(3-((2-cyanoethyl)(methyl)amino)-3-oxopropyl)thiophene-2-carboxamide;
N-(4-(benzofuran-2-yl)thiazol-2-yl)-N-(3-(3-(hydroxymethyl)piperidin-1-yl)-3-oxopropyl)thiophene-2-carboxamide;
1-(3-(N-(4-(benzofuran-2-yl)thiazol-2-yl)thiophene-2-carboxamido)propanoyl)piperidine-3-carboxylic acid;
N-(3-(3-acetamidopyrrolidin-1-yl)-3-oxopropyl)-N-(4-(benzofuran-2-yl)thiazol-2-yl)thiophene-2-carboxamide;
1-(3-(N-(4-(benzofuran-2-yl)thiazol-2-yl)thiophene-2-carboxamido)propanoyl)pyrrolidine-2-carboxamide;
N-(4-(benzofuran-2-yl)thiazol-2-yl)-N-(3-oxo-3-(3-oxopiperazin-1-yl)propyl)thiophene-2-carboxamide;
1-(3-(N-(4-(benzofuran-2-yl)thiazol-2-yl)thiophene-2-carboxamido)propanoyl)piperidine-2-carboxamide;
N-(4-(benzofuran-2-yl)thiazol-2-yl)-N-(3-oxo-3-(2-phenoxyethylamino)propyl)thiophene-2-carboxamide;
1-(3-(N-(4-(benzofuran-2-yl)thiazol-2-yl)thiophene-2-carboxamido)propanoyl)-N-(2-hydroxyethyl)piperidine-3-carboxamide;
N-(4-(benzofuran-2-yl)thiazol-2-yl)-N-(3-(isobutyl(1,1-dioxo-tetrahydrothiophen-3-yl)amino)-3oxopropyl)thiophene-2-carboxamid
N-(4-(benzofuran-2-yl)thiazol-2-yl)-N-(4-(4-(2-(dimethylaminO)ethyl)piperaZifl-1-yl)-4-oxobutyl)thiophene-2-carboxamide;
N-(4-(benzofuran-2-yl)thiazol-2-yl)-N-(4-((2,3-dihydroxypropyl)(methyl)amino)-4-oxobutyl)thiophene-2-carboxamide;
N-(4-(benzofuran-2-yl)thiazol-2-yl)-N-(4-((5-methylpyrazin-2-yl)methylamiflO)-4-oxobutyl)thiophene-2-carboxamide;
N-(4-(benzofuran-2-yl)thiazol-2-yl)-N-(4-(1-hydroxypropan-2-ylamino)-4-oxobutyl)thiophene-2-carboxamide;
N-(4-(benzofuran-2-yl)thiazol-2-yl)-N-(4-oxo-4-(piperidin-1-yl)butyl)thiophene-2-carboxamide;
1-(4-(N-(4-(benzofuran-2-yl)thiazol-2-yl)thiophene-2-carboxamido)butanOyl)piperidifle-4-carboxamide;
N-(4-(benzofuran-2-yl)thiazol-2-yl)-N-(4-((2-hydroxyethyl)(pheflyl)anhiflo)-4-oxobutyl)thiophene-2-carboxamide;
N-(4-(benzofuran-2-yl)thiazol-2-yl)-N-(4-oxo-4-(2-(pyridin-4-yl)ethylamino)butyl)thiophene-2-carboxamide;
tert-butyl 4-(4-(N-(4-(benzofuran-2-yl)thiazol-2-yl)thiophene-2-carboxamido)butanoyl)piperazine-1-carboxylate;
N-(4-(benzofuran-2-yl)thiazol-2-yl)-N-(4-oxo-4-(pyridin-3-ylmethylamino)butyl)thiophene-2-carboxamide;
N-(4-(benzofuran-2-yl)thiazol-2-yl)-N-(4-(5-(methylsulfonyl)indolin-1-yl)-4-oxobutyl)thiophene-2-carboxamide;
tert-butyl 1-(4-(N-(4-(benzofuran-2-yl)thiazol-2-yl)thiophene-2-carboxamido)butanoyl)pyrrolidin-3-ylcarbamate;
N-(4-(3-acetamidopyrrolidin-1-yl)-4-oxobutyl)-N-(4-(benzofuran-2-yl)thiazol-2-yl)thiophene-2-carboxamide;
methyl 1-(4-(N-(4-(benzofuran-2-yl)thiazol-2-yl)thiophene-2-carboxamido)butanoyl)piperidine-4-carboxylate;
1-(4-(N-(4-(benzofuran-2-yl)thiazol-2-yl)thiophene-2-carboxamido)butanoyl)-N-methylpiperidine-4-carboxamide;
N-(4-(benzofuran-2-yl)thiazol-2-yl)-N-(4-(4-(N,N-dimethylsulfamoyl)piperazin-1-yl)-4-oxobutyl)thiophene-2-carboxamide;
ethyl 2-(1-(4-(N-(4-(benzofuran-2-yl)thiazol-2-yl)thiophene-2-carboxamido)butanoyl)piperidin-3-yl)acetate;
ethyl 2-(1-(4-(N-(4-(benzofuran-2-yl)thiazol-2-yl)thiophene-2-carboxamido)butanoyl)piperidin-4-yl)acetate;
N-(4-(benzofuran-2-yl)thiazol-2-yl)-N-(4-(4-(diethylamino)piperidin-1-yl)-4-oxobutyl)thiophene-2-carboxamide;
1-(4-(N-(4-(benzofuran-2-yl)thiazol-2-yl)thiophene-2-carboxamido)butanoyl)pyrrolidine-2-carboxamide;
methyl 1-(4-(N-(4-(benzofuran-2-yl)thiazol-2-yl)thiophene-2-carboxamido)butanoyl)pyrrolidine-2-carboxylate;
N-(4-(benzofuran-2-yl)thiazol-2-yl)-N-(4-oxo-4-(3-oxopiperazin-1-yl)butyl)thiophene-2-carboxamide;
N-(4-(2-amino-2-oxoethylamino)-4-oxobutyl)-N-(4-(benzofuran-2-yl)thiazol-2-yl)thiophene-2-carboxamide;
1-(4-(N-(4-(benzofuran-2-yl)thiazol-2-yl)thiophene-2-carboxamido)butanoyl)-N-(2-hydroxyethyl)piperidine-3-carboxamide;
1-(4-(N-(4-(benzofuran-2-yl)thiazol-2-yl)thiophene-2-carboxamido)butanoyl)-N-(2-hydroxyethyl)piperidine-4-carboxamide;
N-(4-(benzofuran-2-yl)thiazol-2-yl)-N-(4-(2-(methylsulfinyl)ethylamino)-4-oxobutyl)thiophene-2-carboxamide;
N-(4-(benzofuran-2-yl)thiazol-2-yl)-N-(4-((2-hydroxyethyl)(pyridin-4-ylmethyl)amino)-4-oxobutyl)thiophene-2-carboxamide;
N-(4-(benzofuran-2-yl)thiazol-2-yl)-N-(4-(cyclohexyl(4-hydroxybutyl)amino)-4-oxobutyl)thiophene-2-carboxamide;
N-(4-(benzofuran-2-yl)thiazol-2-yl)-N-(4-((2-cyanoethyl)((tetrahydrofuran-2-yl)methyl)amino)-4-oxobutyl)thiophene-2-carboxamide;
N-(4-(benzofuran-2-yl)thiazol-2-yl)-N-(4-oxo-4-(2-(pyridin-3-yl)pyrrOlidin-1-yl)butyl)thiophene-2-carboxamide;
N-(4-(benzofuran-2-yl)thiazol-2-yl)-N-(3-(1-hydroxypropan-2-ylamino)-3-oxopropyl)thiophene-2-carboxamide;
N-(4-(benzofuran-2-yl)thiazol-2-yl)-N-(3-(2-methoxyethylamino)-3-oxopropyl)thiophene-2-carboxamide;
N-(4-(benzofuran-2-yl)thiazol-2-yl)-N-(3-(furan-3-ylmethylamino)-3-oxopropyl)thiophene-2-carboxaniide;

methyl 1-(3-(N-(4-(benzofuran-2-yl)thiazol-2-yl)thiophene-2-carboxamido)propanoyl)pyrrolidine-2-carboxylate;
N-(4-(benzofuran-2-yl)thiazol-2-yl)-N-(3-(isoindolin-2-yl)-3-oxopropyl)thiophene-2-carboxamide;
N-(3-((1,4-dioxan-2-yl)methylaniino)-3-oxopropyl)-N-(4-(benzofuran-2-yl)thiazol-2-yl)thiophene-2-carboxamide;
N-(4-(benzofuran-2-yl)thiazol-2-yl)-N-(3-(cyclohexyl(4-hydroxybutyl)amino)-3-oxopropyl)thiophene-2-carboxamide;
N-(4-(benzofuran-2-yl)thiazol-2-yl)-N-(3-(methyl(pyridin-4-yl)amino)-3-oxopropyl)thiophene-2-carboxamide;
1-(4-(N-(4-(benzofuran-2-yl)thiazol-2-yl)thiophene-2-carboxamido)butanOyl)piperidifle-3-carboxamide;
N-(4-(benzofuran-2-yl)thiazol-2-yl)-N-(4-oxo-4-(pyridin-2-ylmethylamino)butyl)thiophene-2-carboxamide;
N-(4-(benzofuran-2-yl)thiazol-2-yl)-N-(4-oxo-4-(thiazolidin-3-yl)butyl)thiophefle-2-carboxamide;
tert-butyl 2-(4-(N-(4-(benzofuran-2-yl)tbiazol-2-yl)thiophene-2-carboxamido)butanamido)ethylcarbamate;
(S)-N-(4-(benzofuran-2-yl)thiazol-2-yl)-N-(4-(2-(hydroxymethyl)indolin-1-yl)-4-oxobutyl)thiophene-2-carboxamide;
N-(4-(benzofuran-2-yl)thiazol-2-yl)-N-(4-(isoindolin-2-yl)-4-oxobutyl)thiophene-2-carboxamide;
N-(3-acetamidopropyl)-N-(4-(benzofuran-2-yl)thiazol-2-yl)thiophene-2-Carboxamide;
1-acetyl-N-(3-(N-(4-(benzofuran-2-yl)thiazol-2-yl)thiophene-2-carboxamido)propyl)piperidine-4-carboxamide;
N-(4-(benzofuran-2-yl)thiazol-2-yl)-N-(3-(3-(piperidin-1-yl)propanamido)propyl)thiophene-2-carboxaniide;
N-(4-(benzofuran-2-yl)thiazol-2-yl)-N-(3-(4-(dimethylamino)butanamido)propyl)thiophene-2-carboxamide;
N-(3-(N-(4-(benzofuran-2-yl)thiazol-2-yl)thiophene-2-carboxamido)propyl)isonicotinamide;
N-(3-(4-acetamidobutanamido)propyl)-N-(4-(benzofuran-2-yl)thiazol-2-yl)thiophene-2-carboxamide;
N-(4-(benzofuran-2-yl)thiazol-2-yl)-N-(3-(3-hydroxy-2-(hydroxymethyl)-2-methylpropanamido)propyl)thiophene-2-carboxamide;
N-(4-(benzofuran-2-yl)thiazol-2-yl)-N-(3-(2-(2,5-dioxoimidazolidin-4-yl)acetamido)propyl)thiophene-2-carboxamide;
N-(4-(benzofuran-2-yl)thiazol-2-yl)-N-(3-(3-morpholinopropananiido)propyl)thiophene-2-carboxamide;
N-(3-(N-(4-(benzofuran-2-yl)thiazol-2-yl)thiophene-2-carboxamido)propyl)-1,5-dimethyl-1H-pyrazole-3-carboxamide;
N-(4-(benzofuran-2-yl)thiazol-2-yl)-N-(3-(2-morpholinoacetamido)propyl)thiophene-2-carboxamide;
(S)-tert-butyl 1-(3-(N-(4-(benzofuran-2-yl)thiazol-2-yl)thiophene-2-carboxamido)propyl)pyrrolidine-2-carboxylate;
1-(3-(N-(4-(benzofuran-2-yl)thiazol-2-yl)thiophene-2-carboxamido)propyl)piperidine-3-carboxamide;
ethyl 1-(3-(N-(4-(benzofuran-2-yl)thiazol-2-yl)thiophene-2-carboxamido)propyl)piperidine-2-carboxylate;
N-(4-(benzofuran-2-yl)thiazol-2-yl)-N-(3-(3-hydroxypiperidin-1-yl)propyl)thiophene-2-carboxamide;
N-(4-(benzofuran-2-yl)thiazol-2-yl)-N-(3-(4-(2-(2-hydroxyethoxy)ethyl)piperazin-1-yl)propyl)thiophene-2-carboxamide;
N-(4-(benzofuran-2-yl)thiazol-2-yl)-N-(3-(4-(2-hydroxyethyl)piperidin-1-yl)propyl)thiophene-2-carboxamide;
N-(4-(benzofuran-2-yl)thiazol-2-yl)-N-(3-(4-(2-cyanoethyl)piperazin-1-yl)propyl)thiophene-2-carboxamide;
N-(4-(benzofuran-2-yl)thiazol-2-yl)-N-(3-(4-(hydroxymethyl)piperidin-1-yl)propyl)thiophene-2-carboxamide;
N-(4-(benzofuran-2-yl)thiazol-2-yl)-N-(3-(3-(dimethylamino)pyrrolidin-1-yl)propyl)thiophene-2-carboxamide;
ethyl 1-(3-(N-(4-(benzofuran-2-yl)thiazol-2-yl)thiophene-2-carboxamido)propyl)piperidine-3-carboxylate;
N-(4-(benzofuran-2-yl)thiazol-2-yl)-N-(3-(4-hydroxypiperidin-1-yl)propyl)thiophene-2-carboxamide;
N-(4-(benzofuran-2-yl)thiazol-2-yl)-N-(3-(3-(N-ethylacetamido)pyrrolidin-1-yl)propyl)thiophene-2-carboxamide;
N-(4-(benzofuran-2-yl)thiazol-2-yl)-N-(3-(3-(N-methylacetamido)pyrrolidin-1-yl)propyl)thiophene-2-carboxamide;
tert-butyl 1-(3-(N-(4-(benzofuran-2-yl)thiazol-2-yl)thiophene-2-carboxamido)propyl)pyrrolidin-3-ylcarbamate;
(S)-N-(4-(benzofuran-2-yl)thiazol-2-yl)-N-(3-(2-(methoxymethyl)pyrrolidin-1-yl)propyl)thiophene-2-carboxamide;
N-(3-(3-acetamidopyrrolidin-1-yl)propyl)-N-(4-(benzofuran-2-yl)thiazol-2-yl)thiophene-2-carboxamide;
ethyl 4-(3-(N-(4-(benzofuran-2-yl)thiazol-2-yl)thiophene-2-carboxamido)propyl)piperazine-1-carboxylate;
N-(4-(benzofuran-2-yl)thiazol-2-yl)-N-(3-(4-(morpholine-4-carbonyl)piperazin-1-yl)propyl)thiophene-2-carboxamide;
N-(4-(benzofuran-2-yl)thiazol-2-yl)-N-(3-(4,4-dihydroxypiperidin-1-yl)propyl)thiophene-2-carboxamide;
N-(4-(benzofuran-2-yl)thiazol-2-yl)-N-(3-(4-(tetrahydrofuran-2-carbonyl)piperazifl-1-yl)propyl)thiophene-2-carboxainide;
(R)-1-(3-(N-(4-(benzofuran-2-yl)thiazol-2-yl)thiophene-2-carboxamido)propyl)-N-methylpyrrolidine-2-carboxamide;
1-(3-(N-(4-(benzofuran-2-yl)thiazol-2-yl)thiophene-2-carboxamido)propyl)pyrrolidine-2-carboxaniide;
methyl 1-(3-(N-(4-(benzofuran-2-yl)thiazol-2-yl)thiophene-2-carboxamido)propyl)pyrrolidine-2-carboxylate;
methyl 1-(3-(N-(4-(benzofuran-2-yl)thiazol-2-yl)thiophene-2-carboxamido)propyl)piperidine-2-carboxylate;
(S)-1-(3-(N-(4-(benzofuran-2-yl)tbiazol-2-yl)thiophene-2-carboxamido)propyl)-N,N-dimethylpyrrolidine-2-carboxamide;
N-(4-(benzofuran-2-yl)thiazol-2-yl)-N-(3-(2-(pyrrolidin-1-ylmethyl)piperidin-1-yl)propyl)thiophene-2-carboxamide;
N-(4-(benzofuran-2-yl)thiazol-2-yl)-N-(3-(3-oxopiperazin-1-yl)propyl)thiophene-2-carboxamide;
1-(3-(N-(4-(benzofuran-2-yl)thiazol-2-yl)thiophene-2-carboxamido)propyl)piperidine-2-carboxamide;
ethyl 2-(4-(3-(N-(4-(benzofuran-2-yl)thiazol-2-yl)thiophene-2-carboxamido)propyl)piperazin-1-yl)acetate;
tert-butyl 4-(3-(N-(4-(benzofuran-2-yl)thiazol-2-yl)thiophene-2-carboxamido)propyl)piperazine-1-carboxylate;

N-(4-(benzofuran-2-yl)thiazol-2-yl)-N-(3-(4-morpholinopiperidin-1-yl)propyl)thiophene-2-carboxamide;
N-(4-(benzofuran-2-yl)thiazol-2-yl)-N-(3-(4-(2-(dimethylamino)ethyl)piperazin-1-yl)propyl)thiophene-2-carboxamide;
N-(4-(benzofuran-2-yl)thiazol-2-yl)-N-(3-(2-(hydroxymethyl)pyrrolidin-1-yl)propyl)thiophene-2-carboxamide;
N-(4-(benzofuran-2-yl)thiazol-2-yl)-N-(3-(2-(2-hydroxyethyl)piperidin-1-yl)propyl)thiophene-2-carboxamide;
N-(4-(benzofuran-2-yl)thiazol-2-yl)-N-(3-(3-(hydroxymethyl)piperidin-1-yl)propyl)thiophene-2-carboxamide;
N-(4-(benzofuran-2-yl)thiazol-2-yl)-N-(3-(2-(hydroxymethyl)piperidin-1-yl)propyl)thiophene-2-carboxamide;
N-(4-(benzofuran-2-yl)thiazol-2-yl)-N-(3-(3-hydroxypyrrolidin-1-yl)propyl)thiophene-2-carboxamide;
(S)-N-(4-(benzofuran-2-yl)thiazol-2-yl)-N-(3-(2-(hydroxymethyl)pyrrolidin-1-yl)propyl)thiophene-2-carboxamide;
N-(3-(4-acetylpiperazin-1-yl)propyl)-N-(4-(benzofuran-2-yl)thiazol-2-yl)thiophene-2-carboxamide;
1-(3-(N-(4-(benzofuran-2-yl)thiazol-2-yl)thiophene-2-carboxamido)propyl)-N,N-diethylpiperidine-3-carboxamide;
N-(4-(benzofuran-2-yl)thiazol-2-yl)-N-(3-(4-(2-hydroxyethyl)piperazin-1-yl)propyl)thiophene-2-carboxaniide;
N-(4-(benzofuran-2-yl)thiazol-2-yl)-N-(3-(4-(2-methoxyethyl)piperazin-1-yl)propyl)thiophene-2-carboxamide;
N-(4-(benzofuran.-2-yl)thiazol-2-yl)-N-(3-(3-(diethylamino)pyrrolidin-1-yl)propyl)thiophene-2-carboxamide;
1-(3-(N-(4-(benzofuran-2-yl)thiazol-2-yl)thiophene-2-carboxamido)propyl)-N-methylpiperidine-4-carboxamide;
N-(4-(benzofuran-2-yl)thiazol-2-yl)-N-(3-(4-(diethylamino)piperidin-1-yl)propyl)thiophene-2-carboxamide;
(R)-1-(3-(N-(4-(benzofuran-2-yl)thiazol-2-yl)thiophene-2-carboxamido)propyl)pyrrolidine-2-carboxylic acid;
1-(3-(N-(4-(benzofuran-2-yl)thiazol-2-yl)thiophene-2-carboxamido)propyl)piperidine-4-carboxamide;
N-(4-(benzofuran-2-yl)thiazol-2-yl)-N-(3-(4-(2-(dimethylamino)-2-oxoethyl)piperazin-1-yl)propyl)thiophene-2-carboxamide; and
N-(4-(benzofuran-2-yl)thiazol-2-yl)-N-(3-(4-(methylsulfonyl)piperazin-1-yl)propyl)thiophene-2-carboxamide.

24. The compound of claim 1 selected from:
N-(4-(2,5-dimethoxyphenyl)thiazol-2-yl)-N-(3-(dimethylamino)propyl)benzamide;
N-(3-(dimethylamino)propyl)-2-fluoro-N-(4-phenylthiazol-2-yl)benzamide;
N-(3-(diethylamino)propyl)-N-(4-phenylthiazol-2-yl)furan-2-carboxamide;
N-(4-(2,5-dimethoxyphenyl)thiazol-2-yl)-N-(3-(dimethylamino)propyl)-2-fluorobenzaniide;
N-(4-(2,5-dimethoxyphenyl)thiazol-2-yl)-N-(3-(dimethylamino)propyl)thiophene-2-carboxamide;
N-(3-(diethylamino)propyl)-N-(4-phenylthiazol-2-yl)thiophene-2-carboxamide;
2-chloro-N-(3-(diethylamino)propyl)-N-(4-(2,5-dimethoxyphenyl)thiazol-2-yl)benzamide;
N-(3-(diethylamino)propyl)-N-(4-(2,5-dimethoxyphenyl)thiazol-2-yl)furan-2-carboxamide;
N-(3-(diethylamino)propyl)-N-(4-(4-methoxyphenyl)thiazol-2-yl)benzan-iide;
N-(3-(diethylamino)propyl)-N-(4-(2,5-dimethoxyphenyl)thiazol-2-yl)-2-fluorobenzamide;
N-(3-(diethylamino)propyl)-N-(4-(2,5-dimethoxyphenyl)thiazol-2-yl)benzaniide;
N-(3-(diethylamino)propyl)-N-(4-(2,5-dimethoxyphenyl)thiazol-2-yl)thiophene-2-carboxamide;
N-(4-phenylthiazol-2-yl)-N-(3-(pyrrolidin-1-yl)propyl)thiophene-2-carboxamide;
N-(4-(4-methoxyphenyl)thiazol-2-yl)-N-(3-(pyrrolidin-1-yl)propyl)benzamide;
N-(4-(4-methoxyphenyl)thiazol-2-yl)-N-(3-(pyrrolidin-1-yl)propyl)thiophene-2-carboxamide;
N-(4-(4-methoxyphenyl)thiazol-2-yl)-N-(3-(pyrrolidin-1-yl)propyl)furan-2-carboxamide;
N-(4-(2,5-dimethoxyphenyl)thiazol-2-yl)-N-(3-(pyrrolidin-1-.yl)propyl)benzamide;
N-(4-(2,5-dimethoxyphenyl)thiazol-2-yl)-N-(3-(pyrrolidin-1-yl)propyl)thiophene-2-carboxamide;
N-(4-(2,5-dimethoxyphenyl)thiazol-2-yl)-N-(3-(pyrrolidin-1-yl)propyl)furan-2-carboxamide;
N-(4-(4-methoxyphenyl)thiazol-2-yl)-N-(3-(piperidin-1-yl)propyl)thiophene-2-carboxamide;
N-(4-(2,5-dimethoxyphenyl)thiazol-2-yl)-N-(3-(piperidin-1-yl)propyl)benzamide;
N-(4-(2,5-dimethoxyphenyl)thiazol-2-yl)-N-(3-(piperidin-1-yl)propyl)thiophene-2-carboxamide;
N-(4-(2,5-dimethoxyphenyl)thiazol-2-yl)-N-(3-(piperidin-1-yl)propyl)furan-2-carboxamide;
N-(3-(azepan-1-yl)propyl)-N-(4-phenylthiazol-2-yl)benzamide;
N-(3-(azepan-1-yl)propyl)-N-(4-phenylthiazol-2-yl)thiophene-2-carboxamide;
N-(3-(azepan-1-yl)propyl)-N-(4-phenylthiazol-2-yl)furan-2-carboxamide;
N-(3-(azepan-1-yl)propyl)-N-(4-(4-methoxyphenyl)thiazol-2-yl)benzamide;
N-(3-(azepan-1-yl)propyl)-N-(4-(4-methoxyphenyl)thiazol-2-yl)thiophene-2-carboxamide;
N-(3-(azepan-1-yl)propyl)-N-(4-(4-methoxyphenyl)thiazol-2-yl)furan-2-carboxamide;
N-(3-(azepan-1-yl)propyl)-N-(4-(2,5-dimethoxyphenyl)thiazol-2-yl)benzamide;
N-(3-(azepan-1-yl)propyl)-N-(4-(2,5-dimethoxyphenyl)thiazol-2-yl)thiophene-2-carboxamide;
N-(3-(azepan-1-yl)propyl)-N-(4-(2,5-dimethoxyphenyl)thiazol-2-yl)furan-2-carboxamide;
N-(3-(4-methylpiperazin-1-yl)propyl)-N-(4-phenylthiazol-2-yl)benzamide;
N-(3-(4-methylpiperazin-1-yl)propyl)-N-(4-phenylthiazol-2-yl)thiophene-2-carboxamide;
N-(3-(4-methylpiperazin-1-yl)propyl)-N-(4-phenylthiazol-2-yl)furan-2-carboxamide;
N-(4-(4-methoxyphenyl)thiazol-2-yl)-N-(3-(4-methylpiperazin-1-yl)propyl)benzamide;
N-(4-(4-methoxyphenyl)thiazol-2-yl)-N-(3-(4-methylpiperazin-1-yl)propyl)thiophene-2-carboxamide;
N-(4-(4-methoxyphenyl)thiazol-2-yl)-N-(3-(4-methylpiperazin-1-yl)propyl)furan-2-carboxamide;
N-(4-(2,5-dimethoxyphenyl)thiazol-2-yl)-N-(3-(4-methylpiperazin-1-yl)propyl)benzamide;
N-(4-(2,5-dimethoxyphenyl)thiazol-2-yl)-N-(3-(4-methylpiperazin-1-yl)propyl)thiophene-2-carboxamide;
N-(4-(2,5-dimethoxyphenyl)thiazol-2-yl)-N-(3-(4-methylpiperazin-1-yl)propyl)furan-2-carboxamide;
N-(4-(4-methoxyphenyl)thiazol-2-yl)-N-(3-morpholinopropyl)cyclohexanecarboxamide;

N-(4-(4-methoxyphenyl)thiazol-2-yl)-N-(3-morpholinopropyl)cyclopent-1-enecarboxamide;
4-fluoro-N-(4-(4-methoxyphenyl)thiazol-2-yl)-N-(3-morpholinopropyl)benzaniide;
N-(4-(4-methoxyphenyl)thiazol-2-yl)-N-(3-morpholinopropyl)benzamide;
4-methyl-N-(3-morpholinopropyl)-N-(4-phenylthiazol-2-yl)benzamide;
4-.fluoro-N-(3-morpholinopropyl)-N-(4-phenylthiazol-2-yl)benzamide;
N-(3-morpholinopropyl)-N-(4-phenylthiazol-2-yl)benzaniide;
3-methyl-N-(3-morpholinopropyl)-N-(4-phenylthiazol-2-yl)benzamide;
4-chloro-N-(4-(4-methoxyphenyl)thiazol-2-yl)-N-(3-morpholinopropyl)benzamide;
3-fluoro-N-(4-(4-methoxyphenyl)thiazol-2-yl)-N-(3-morpholinopropyl)benzamide;
N-(4-(4-methoxyphenyl)thiazol-2-yl)-3-methyl-N-(3-morpholinopropyl)benzamide;
2-fluoro-N-(4-(4-methoxyphenyl)thiazol-2-yl)-N-(3-morpholinopropyl)benzamide;
N-(4-(4.-methoxyphenyl)thiazol-2-yl)-4-methyl-N-(3-morpholinopropyl)benzamide;
2-cyano-N-(4-(4-methoxyphenyl)thiazol-2-yl)-N-(3-morpholinopropyl)benzamide;
N-(3-morpholinopropyl)-N-(4-phenylthiazol-2-yl)furan-2-carboxamide;
N-(4-(2,5-dimethoxyphenyl)thiazol-2-yl)-N-(3-morpholinopropyl)furan-2-carboxamide;
N-(4-(4-methoxyphenyl)thiazol-2-yl)-N-(3-morpholinopropyl)furan-2-carboxamide;
N-(4-(4-methoxyphenyl)thiazol-2-yl)-5-methyl-N-(3-morpholinopropyl)furan-2-carboxamide;
N-(4-(4-methoxyphenyl)thiazol-2-yl)-3-methyl-N-(3-morpholinopropyl)furan-2-carboxamide;
N-(3-morpholinopropyl)-N-(4-phenylthiazol-2-yl)thiophene-2-carboxamide;
N-(4-(2,5-dimethoxyphenyl)thiazol-2-yl)-N-(3-morpholinopropyl)thiophene-2-carboxamide;
N-(4-(4-methoxyphenyl)thiazol-2-yl)-N-(3-morpholinopropyl)thiophene-2-carboxamide;
N-(4-(4-chlorophenyl)thiazol-2-yl)-N-(3-morpholinopropyl)thiophene-2-carboxamide;
N-(3-morpholinopropyl)-N-(4-p-tolylthiazol-2-yl)thiophene-2-carboxamide;
N-(4-(2,3-dihydrobenzo[b][1,4]dioxin-6-yl)thiazol-2-yl)-N-(3-morpholinopropyl)thiophene-2-carboxamide;
N-(4-(4-chloro-3-nitrophenyl)thiazol-2-yl)-N-(3-morpholinopropyl)thiophene-2-carboxamide;
N-(4-(2-methoxyphenyl)thiazol-2-yl)-N-(3-morpholinopropyl)thiophene-2-carboxamide;
N-(4-(2,4-dimethylphenyl)thiazol-2-yl)-N-(3-morpholinopropyl)thiophene-2-carboxamide;
N-(4-(4-cyanophenyl)thiazol-2-yl)-N-(3-morpholinopropyl)thiophene-2-carboxamide;
methyl 4-(2-(N-(3-morpholinopropyl)thiophene-2-carboxamido)thiazol-.4-yl)benzoate;. N-(4-(4-(methylsulfonyl)phenyl)thiazol-2-yl)-N-(3-morpholinopropyl)thiophene-2-carboxamide;
N-(4-(2,4-dimethoxyphenyl)thiazol-2-yl)-N-(3-morpholinopropyl)thiophene-2-carboxamide;
N-(4-(benzofuran-3-yl)thiazol-2-yl)-N-(3-morpholinopropyl)thiophene-2-carboxamide;
N-(4-(2-chlorophenyl)thiazol-2-yl)-N-(3-morpholinopropyl)thiophene-2-carboxamide, N-(4-(3-chlorophenyl)thiazol-2-yl)-N-(3-morpholinopropyl)thiophene-2-carboxamide;
N-(4-(benzo[b]thiophen-3-yl)thiazol-2-yl)-N-(3-morpholinopropyl)thiophene-2-carboxamide;
N-(3-morpholinopropyl)-N-(4-(pyridin-2-yl)thiazol-2-yl)thiophene-2-carboxamide;
N-(3-morpholinopropyl)-N-(4-(pyridin-3-yl)thiazol-2-yl)thiophene-2-carboxamide;
N-(3-morpholinopropyl)-N-(4-(pyridin-4-yl)thiazol-2-yl)thiophene-2-carboxamide;
N-(3-morpholinopropyl)-N-(4-(thiophen-2-yl)thiazol-2-yl)thiophene-2-carboxamide;
N-(4-(5-chlorothiophen-2-yl)thiazol-2-yl)-N-(3-morpholinopropyl)thiophene-2-carboxamide;
N-(4-(5-chlorothiophen-2-yl)thiazol-2-yl)-N-(3-morpholinopropyl)tbiophene-2-carboxamide;
N-(4-(3,4-dichlorophenyl)thiazol-2-yl)-N-(3-morpholinopropyl)thiophene-2-carboxamide;
N-(4-(4-fluorophenyl)thiazol-2-yl)-N-(3-morpholinopropyl)thiophene-2-carboxamide;
N-(4-(4-(difluoromethoxy)phenyl)thiazol-2-yl)-N-(3-.morpholinopropyl)thiophene-2-carboxamide;
N-(3-morpholinopropyl)-N-(4-(2-(trifluoromethyl)phenyl)thiazol-2-yl)thiophene-2-carboxanilde;
N-(4-(2-fluorophenyl)thiazol-2-yl)-N-(3-morpholinopropyl)thiophene-2-carboxamide;
N-(4-(3,4-difluorophenyl)thiazol-2-yl)-N-(3-morpholinopropyl)thiophene-2-carboxanilde;
N-(4-(3-bromophenyl)thiazol-2-yl)-N-(3-morpholinopropyl)thiophene-2-carboxamide;
N-(3-morpholinopropyl)-N-(4-(4-(trifluoromethoxy)phenyl)thiazol-2-yl)thiophene-2-carboxamide;
N-(4-(3-fluorophenyl)thiazol-2-yl)-N-(3-morpholinopropyl)thiophene-2-carboxamide;
N-(4-(3-methylbenzo[b]thiophen-2-yl)thiazol-2-yl)-N-(3-morpholinopropyl)thiophene-2-carboxamide;
N-(4-(3-cyanophenyl)thiazol-2-yl)-N-(3-morpholinopropyl)thiophene-2-carboxamide;
N-(3-morpholinopropyl)-N-(4-(4-pentylphenyl)thiazol-2-yl)thiophene-2-carboxamide;
N-(4-(4-(diethylamino)phenyl)thiazol-2-yl)-N-(3-morpholinopropyl)thiophene-2-carboxamide;
N-(3-morpholinopropyl)-N-(4-(4-(pyrrolidin-1-yl)phenyl)thiazol-2-yl)thiophene-2-carboxamide;
N-(4-(3,4-dimethoxyphenyl)thiazol-2-yl)-N-(3-morpholinopropyl)thiophene-2-carboxamide;
N-(4-(benzo[d][1,3]dioxol-5-yl)thiazol-2-yl)-N-(3-morpholinopropyl)thiophene-2-carboxamide;
N-(4-(benzol[d]thiazol-2-yl)thiazol-2-yl)-N-(3-morpholinopropyl)thiophene-2-carboxamide;
N-(4-(3-methoxyphenyl)thiazol-2-yl)-N-(3-morpholinopropyl)thiophene-2-carboxamide;
N-(3-morpholinopropyl)-N-(4-(2-nitrophenyl)thiazol-2-yl)thiophene-2-carboxanude, N-(3-morpholinopropyl)-N-(4-(naphthalen-2-yl)thiazol-2-yl)thiophene-2-carboxamide;
N-(4-(benzofuran-2-yl)thiazol-2-yl)-N-(3-morpholinopropyl)thiophene-2-carboxamide;
N-(4-(4-morpholinophenyl)thiazol-2-yl)-N-(3-morpholinopropyl)thiophene-2-carboxanilde;
N-(4-(3,4-dihydro-2H-benzo[b][1,4]dioxepin-7-yl)thiazol-2-yl)-N-(3-morpholinopropyl)thiophene-2-carboxamide;
N-(4-(2-chloropyridin-4-yl)thiazol-2-yl)-N-(3-morpholinopropyl)thiophene-2-carboxamide;

N-(4-(4-methoxyphenyl)thiazol-2-yl)-3-methyl-N-(3-morpholinopropyl)thiophene-2-carboxanilde;
2,5-dicliloro-N-(4-(4-methoxyphenyl)thiazol-2-yl)-N-(3-morpholinopropyl)thiophene-3-carboxamide;
3-bromo-N-(4-(4-methoxyphenyl)thiazol-2-yl)-N-(3-morpholinopropyl)thiophene-2-carboxamide;
N-(4-(4-methoxyphenyl)thiazol-2-yl)-N-(3-morpholinopropyl)-5-nitrothiophene-2-carboxamide;
5-chloro-N-(4-(4-methoxyphenyl)thiazol-2-yl)-N-(3-morpholinopropyl)thiophene-2-carboxamide;
5-acetyl-N-(4-(4-methoxyphenyl)thiazol-2-yl)-N-(3-morpholinopropyl)thiophene-2-carboxanilde;
5-bromo-N-(4-(4-methoxyphenyl)thiazol-2-yl)-N-(3-morpholinopropyl)thiophene-2-carboxamide;
N-(4-(4-methoxyphenyl)thiazol-2-yl)-5-(methylthio)-N-(3-morpholinopropyl)thiophene-2-carboxamide;
N-(3-morpholinopropyl)-N-(4-(3-(trifluoromethyl)phenyl)tbiazol-2-yl)thiophene-2-carboxamide;
N-(4-(4-methoxyphenyl)thiazol-2-yl)-1-methyl-N-(3-morpholinopropyl1H-pyrrole-2-carboxamide;
N-(4-(4-methoxyphenyl)thiazol-2-yl)-N-(3-morpholinopropyl)isoxazole-5-carboxamide;
N-(4-(4-methoxyphenyl)thiazol-2-yl)-3,5-dimethyl-N-(3-morpholinopropyl)isoxazole-4-carboxamide;
N-(4-(4-methoxyphenyl)thiazol-2-yl)-4-methyl-N-(3-morpholinopropyl)-1,2,3-thiadiazole-5-carboxamide;
N-(4-(4-methoxyphenyl)thiazol-2-yl)-2,4-dimethyl-N-(3-morpholinopropyl)thiazole-5-carboxamide;
4-chloro-N-(4-(4-methoxyphenyl)thiazol-2-yl)-N-(3-morpholinopropyl)picolinamide;
N-(4-(4-methoxyphenyl)thiazol-2-yl)-3-methyl-N-(3-morpholinopropyl)isoxazole-4-carboxamide;
6-chloro-N-(4-(4-methoxyphenyl)thiazol-2-yl)-N-(3-morpholinopropyl)picolinamide;
N-(4-(4-methoxyphenyl)thiazol-2-yl)-1-methyl-N-(3-morpholinopropyl)-1H-imidazole-2-carboxamide;
4,5-dichloro-N-(4-(4-methoxyphenyl)thiazol-2-yl)-N-(3-morpholinopropyl)isothiazole-3-carboxamide;
N-(4-(4-methoxyphenyl)thiazol-2-yl)-1,2,5-trimethyl-N-(3-morpholinopropyl)-1H-pyrrole-3-carboxamide;
ethyl 2-(N-(3-morpholinopropyl)thiophene-2-carboxamido)thiazole-4-carboxylate;
ethyl 3-methyl-3-(2-(N-(3-morpholinopropyl)thiophene-2-carboxamido)thiazol-4-yl)butanoate;
N-(4-(biphenyl-4-yl)thiazol-2-yl)-N-(3-morpholinopropyl)thiophene-2-carboxamide;
N-(4-(5-methyl-1-phenyl-1H-pyrazol-4-yl)thiazol-2-yl)-N-(3-morpholinopropyl)thiophene-2-carboxamide;
N-(4-(2,4-dichlorophenyl)thiazol-2-yl)-N-(3-morpholinopropyl)thiophene-2-carboxamide;
3-(2-(N-(3-morpholinopropyl)thiophene-2-carboxamido)thiazol-4-yl)benzoic acid;
N-(3-morpholinopropyl)-N-(4-(3-oxo-3,4-dihydro-2H-benzo[b][1,4]6xazin-6-yl)thiazol-2-yl)thiophene-2-carboxamide;
N-(3-morpholinopropyl)-N-(4-(3-phenylisoxazol-5-yl)thiazol-2-yl)thiophene-2-carboxamide;
N-(3-morpholinopropyl)-N-(4-(5-(pyridin-2-yl)thiophen-2-yl)thiazol-2-yl)thiophene-2-carboxamide;
N-(4'-methyl-2'-(pyrazin-2-yl)-4,5'-bithiazol-2-yl)-N-(3-morpholinopropyl)thiophene-2-carboxamide;
2-(5-(2-(N-(3-morpholinopropyl)thiophene-2-carboxamido)thiazol-4-yl)thiophen-2-yl)acetic acid;
N-(4-(4-chloro-3-methylphenyl)thiazol-2-yl)-N-(3-morpholinopropyl)thiophene-2-carboxamide;
N-(4-(3,4-dimethoxyphenyl)thiazol-2-yl)-N-(3-morpholinopropyl)benzamide;
N-(4-(3,4-dimethoxyphenyl)thiazol-2-yl)-N-(3-morpholinopropyl)furan-2-carboxamide;
N-(4-(benzofuran-2-yl)thiazol-2-yl)-N-(3-morpholinopropyl)furan-2-carboxamide;
N-(4-(benzofuran-2-yl)thiazol-2-yl)-N-(3-morpholinopropyl)nicotinamide;
N-(4-(3,4-dimethoxyphenyl)thiazol-2-yl)-N-(3-morpholinopropyl)cyclopentanecarboxamide;
N-(4-(3,4-dimethoxyphenyl)thiazol-2-yl)-N-(3-morpholinopropyl)cyclobutanecarboxamide;
N-(4-(benzofuran-2-yl)thiazol-2-yl)-N-(3-morpholinopropyl)cyclobutanecarboxamide;
N-(4-(3,4-dimethoxyphenyl)thiazol-2-yl)-N-(3-morpholinopropyl)picolinamide;
N-(4-(benzofuran-2-yl)thiazol-2-yl)-N-(3-morpholinopropyl)picolinamide;
N-(4-(3-(4-chlorophenyl)isoxazol-5-yl)thiazol-2-yl)-N-(3-morpholinopropyl)thiophene-2-carboxamide;
N-(3-morpholinopropyl)-N-(4-(3-phenylisoxazol-5-yl)thiazol-2-yl)furan-2-carboxamide;
1-methyl-N-(3-morpholinopropyl)-N-(4-(3-phenylisoxazol-5-yl)thiazol-2-yl)-1H-pyrrole-2-carboxamide;
4-(2-(N-(3-morpholinopropyl)thiophene-2-carboxamido)thiazol-4-yl)benzoic acid;
N-(3-morpholinopropyl)-N-(4-(trifluoromethyl)thiazol-2-yl)thiophene-2-carboxamide;
ethyl 5-(2-(N-(3-morpholinopropyl)thiophene-2-carboxaniido)thiazol-4-yl)isoxazole-3-carboxylate;
2-(N-(3-morpholinopropyl)thiophene-2-carboxamido)-N-(1,3,4-thiadiazol-2-yl)thiazole-4-carboxamide;
2-(N-(3-morpholinopropyl)thiophene-2-carboxamido)-N-(thiazol-2-yl)thiazole-4-carboxamide;
N-(3-methoxyphenyl)-2-(N-(3-morpholinopropyl)thiophene-2-carboxamido)thiazole-4-carboxamide;
N-(3-methoxybenzyl)-2-(N-(3-morpholinopropyl)thiophene-2-carboxamido)thiazole-4-carboxamide;
N-(3-chlorobenzyl)-2-(N-(3-morpholinopropyl)thiophene-2-carboxamido)thiazole-4-carboxamide;
N-(2,3-dihydrobenzo [b][1,4]dioxin-6-yl)-2-(N-(3-morpholinopropyl)thiophene-2-carboxamido)thiazole-4-carboxamide;
N-(5-ethyl-1,3,4-thiadiazol-2-yl)-2-(N-(3-morpholinopropyl)thiophene-2-carboxaniido)thiazole-4-carboxamide;
N-(benzo [d]thiazol-6-yl)-2-(N-(3-morpholinopropyl)thiophene-2-carboxamido)thiazole-4-carboxamide;
N-(3-carbamoylphenyl)-2-(N-(3-morpholinopropyl)thiophene-2-carboxamido)thiazole-4-carboxamide;
ethyl 2-(2-(2-(N.-(3-morpholinopropyl)thiophene-2-carboxamido)thiazole-4-carboxamido)thiazol-4-yl)acetate;
N-(3-(methylsulfonamido)phenyl)-2-(N-(3-morpholinopropyl)thiophene-2-carboxamido)thiazole-4-carboxaniide;
N-(4-(benzofuran-2-yl)thiazol-2-yl)-N-(3-(2-oxopyrrolidin-1-yl)propyl)furan-2-carboxarnide;
N-(4-(benzofuran-2-yl)thiazol-2-yl)-N-(3-(2-oxopyrrolidin-1-yl)propyl)thiophene-2-carboxamide;
N-(4-(benzofuran-2-yl)thiazol-2-yl)-1-methyl-N-(3-(2-oxopyrrolidin-1-yl)propyl)-1H-pyrrole-2-carboxamide;
N-(3-(2-oxopyrrolidin-1-yl)propyl)-N-(4-(3-phenylisoxazol-5-yl)thiazol-2-yl)furan-2-carboxamide;
N-(3-(2-oxopyrrolidin-1-yl)propyl)-N-(4-(3-phenylisoxazol-5-yl)thiazol-2-yl)thiophene-2-carboxamide;

1-methyl-N-(3-(2-oxopyrrolidin-1-yl)propyl)-N-(4-(3-phenylisoxazol-5-yl)thiazol-2-yl)-1H-pyrrole-2-carboxanilde;
N-(3-(4-methylpiperazin-1-yl)propyl)-N-(4-(3-phenylisoxazol-5-yl)thiazol-2-yl)furan-2-carboxamide;
N-(4-morpholinobutyl)-N-(4-(3-phenylisoxazol-5-yl)thiazol-2-yl)furan-2-carboxamide;
N-(4-morpholinobutyl)-N-(4-(3-phenylisoxazol-5-yl)thiazol-2-yl)thiophene-2-carboxamide;
N-(3-(diethylamino)propyl)-N-(4-(3,4-dimethoxyphenyl)thiazol-2-yl)thiophene-2-carboxamide;
N-(4-(3,4-dimethoxyphenyl)thiazol-2-yl)-N-(3-(2-oxopyrrolidin-1-yl)propyl)thiophene-2-carboxamide;
N-(4-(3,4-dimethoxyphenyl)thiazol-2-yl)-N-(3-(4-methylpiperazin-1-yl)propyl)thiophene-2-carboxamide;
N-(4-(3,4-dimethoxyphenyl)thiazol-2-yl)-N-(3-(piperidin-1-yl)propyl)thiophene-2-carboxamide;
N-(4-(3,4-dimethoxyphenyl)thiazol-2-yl)-N-(2-morpholinoethyl)thiophene-2-carboxamide;
N-(4-(benzofuran-2-yl)thiazol-2-yl)-N-(3-(diethylamino)propyl)thiophene-2-carboxamide;
N-(3-(1H-imidazol-1-yl)propyl)-N-(4-(benzofuran-2-yl)thiazol-2-yl)thiophene-2-carboxamide;
N-(4-(benzofuran-2-yl)thiazol-2-yl)-N-(3-(4-methylpiperazin-1-yl)propyl)thiophene-2-carboxamide;
N-(4-(benzofuran-2-yl)thiazol-2-yl)-N-(3-(piperidin-1-yl)propyl)thiophene-2-carboxamide;
N-(4-(benzofuran-2-yl)thiazol-2-yl)-N-(4-morpholinobutyl)thiophene-2-carboxamide;
N-(4-(5-methylthiophen-2-yl)thiazol-2-yl)-N-(3-morpholinopropyl)thiophene-2-carboxamide;
N-(4-(6-methoxypyridin-3-yl)thiazol-2-yl)-N-(3-morpholinopropyl)thiophene-2-carboxamide;
N-(4-(2,6-dimethoxypyridin-3-yl)thiazol-2-yl)-N-(3-morpholinopropyl)thiophene-2-carboxanilde;
N-(4-cyclopentylthiazol-2-yl)-N-(3-morpholinopropyl)thiophene-2-carboxamide;
N-(4-cyclohexylthiazol-2-yl)-N-(3-morpholinopropyl)thiophene-2-carboxamide;
methyl 6-(2-(N-(3-morpholinopropyl)thiophene-2-carboxamido)thiazol-4-yl)nicotinate;
N-(4-(1H-indol-2-yl)thiazol-2-yl)-N-(3-morpholinopropyl)thiophene-2-carboxamide;
N-(4-(7-methoxybenzofuran-2-yl)thiazol-2-yl)-N-(3-morpholinopropyl)thiophene-2-carboxamide;
N-(4-(5-methoxybenzofuran-2-yl)thiazol-2-yl)-N-(3-morpholinopropyl)thiophene-2-carboxamide;
N-(3-morpholinopropyl)-N-(4-(5-nitrobenzofuran-2-yl)thiazol-2-yl)thiophene-2-carboxamide;
N-(4-(4-(2-hydroxyethylcarbamoyl)phenyl)thiazol-2-yl)-N-(3-morpholinopropyl)thiophene-2-carboxarnide;
N-(4-(4-(2-rnorpholinoethylcarbamoyl)phenyl)thiazol-2-yl)-N-(3-morpholinopropyl)thiophene-2-carboxamide;
N-(4-(4-(methylcarbamoyl)phenyl)thiazol-2-yl)-N-(3-morpholinopropyl)thiophene-2-carboxamide;
N-(4-(4-(2-(dimethylamino)ethylcarbamoyl)phenyl)thiazol-2-yl)-N-(3-morpholinopropyl)thiophene-2-carboxamide;
N-(4-(4-(3-(dimethylamino)propylcarbamoyl)phenyl)thiazol-2-yl)-N-(3-morpholinopropyl)thiophene-2-carboxamide;
N-(4-(4-(3-hydroxypropylcarbamoyl)phenyl)thiazol-2-yl)-N-(3-morpholinopropyl)thiophene-2-carboxamide;
N-(4-(4-carbamoylphenyl)thiazol-2-yl)-N-(3-morpholinopropyl)thiophene-2-carboxamide;
N-(4-(4-(dimethylcarbamoyl)phenyl)thiazol-2-yl)-N-(3-morpholinopropyl)thiophene-2-carboxamide;
2-(4-(2-(N-(3-morpholinopropyl)thiophene-2-carboxamido)thiazol-4-yl)benzamido)acetic acid;
N-(4-(4-(4-methylpiperazine-1-carbonyl)phenyl)thiazol-2-yl)-N-(3-morpholinopropyl)thiophene-2-carboxamide;
N-(4-(4-(morpholine-4-carbonyl)phenyl)thiazol-2-yl)-N-(3-morpholinopropyl)thiophene-2-carboxamide;
2-(3-(2-(N-(3-morpholinopropyl)thiophene-2-carboxaniido)thiazol-4-yl)phenoxy)acetic acid;
3-(3-(2-(N-(3-morpholinopropyl)thiophene-2-carboxamido)thiazol-4-yl)phenoxy)propanoic acid;
2-(4-(2-(N-(3-morpholinopropyl)thiophene-2-carboxaniido)thiazol-4-yl)phenoxy)acetic acid;
3-(4-(2-(N-(3-morpholinopropyl)thiophene-2-carboxamido)thiazol-4-yl)phenoxy)propanoic acid;
N-(4-(3-(3-(dimethylamino)propoxy)phenyl)thiazol-2-yl)-N-(3-morpholinopropyl)thiophene-2-carboxamide;
N-(4-(3-(2-(dimethylamino)ethoxy)phenyl)thiazol-2-yl)-N-(3-morpholinopropyl)thiophene-2-carboxamide;
N-(4-(4-(3-(dimethylamino)propoxy)phenyl)thiazol-2-yl)-N-(3-morpholinopropyl)thiophene-2-carboxamide;
N-(4-(4-(2-(dimethylamino)ethoxy)phenyl)thiazol-2-yl)-N-(3-morpholinopropyl)tbiophene-2-carboxamide;
N-(4-(benzofuran-2-yl)thiazol-2-yl)-N-(3-(2-hydroxyethylamino)-3-oxopropyl)thiophene-2-carboxamide;
N-(4-(benzoftiran-2-yl)thiazol-2-yl)-N-(3-(2-(hydroxymethyl)pyrrolidin-1-yl)-3-oxopropyl)thiophene-2-carboxamide;
N-(4-(benzofuran-2-yl)thiazol-2-yl)-N-(3-(2-(dimethylamino)ethylamino)-3-oxopropyl)thiophene-2-carboxamide;
N-(4-(benzofuran-2-yl)thiazol-2-yl)-N-(3-(3-hydroxypiperidin-1-yl)-3-oxopropyl)thiophene-2-carboxamide;
N-(4-(benzofuran-2-yl)thiazol-2-yl)-N-(3-((2-hydroxyethyl)(methyl)amino)-3-oxopropyl)thiophene-2-carboxamide;
N-(4-(benzofuran-2-yl)thiazol-2-yl)-N-(3-(bis(2-hydroxyethyl)amino)-3-oxopropyl)thiophene-2-carboxamide;
N-(4-(benzofuran-2-yl)thiazol-2-yl)-N-(3-oxo-3-(piperazin-1-yl)propyl)thiophene-2-carboxamide;
N-(4-(benzofuran-2-yl)thiazol-2-yl)-N-(3-((2-(dimethylamino)ethyl)(methyl)amino)-3-oxopropyl)thiophene-2-carboxamide;
N-(4-(benzofuran-2-yl)thiazol-2-yl)-N-(3-(methyl(2-(methylamino)ethyl)amino)-3-oxopropyl)thiophene-2-carboxamide;
N-(4-(benzofuran-2-.yl)thiazol-2-yl)-N-(3-(3-hydroxypyrrolidin-1-yl)-3-oxopropyl)thiophene-2-carboxamide;
N-(4-(benzofuran-2-yl)thiazol-2-yl)-N-(3-(3-(dimethylamino)pyrrolidin-1-yl)-3-oxopropyl)thiophene-2-carboxarnide;
N-(4-(benzofuran-2-yl)thiazol-2-yl)-N-(3-((2,3-dihydroxypropyl)(methyl)amino)-3-oxopropyl)thiophene-2-carboxamide;
1-(3-(N-(4-(benzofuran-2-yl)thiazol-2-yl)thiophene-2-carboxamido)propanoyl)piperidine-3-carboxamide;
N-(4-(benzofuran-2-yl)thiazol-2-yl)-N-(3-oxo-3-(thiazolidin-3-yl)propyl)thiophene-2-carboxamide;
N-(4-(benzofuran-2-yl)thiazol-2-yl)-N-(3-morpholino-3-oxopropyl)thiophene-2-carboxamide;
N-(4-(benzofuran-2-yl)thiazol-2-yl)-N-(3-((2-cyanoethyl)(methyl)amino)-3-oxopropyl)thiophene-2-carboxamide;

N-(4-(benzofuran-2-yl)thiazol-2-yl)-N-(3-(3-(hydroxymethyl)piperidin-1-yl)-3-oxopropyl)thiophene-2-carboxaniide;
1-(3-(N-(4-(benzofuran-2-yl)thiazol-2-yl)thiophene-2-carboxamido)propanoyl)piperidine-3-carboxylic acid;
N-(3-(3-acetamidopyrrolidin-1-yl)-3-oxopropyl)-N-(4-(benzofuran-2-yl)thiazol-2-yl)thiophene-2-carboxamide;
1-(3-(N-(4-(benzofuran-2-yl)thiazol-2-yl)thiophene-2-carboxamido)propanoyl)pyrrolidine-2-carboxamide;
N-(4-(benzofuran-2-yl)thiazol-2-yl)-N-(3-oxo-3-(3-oxopiperazin-1-yl)propyl)thiophene-2-carboxamide;
1-(3-(N-(4-(benzofuran-2-yl)thiazol-2-yl)thiophene-2-carboxamido)propanoyl)piperidine-2-carboxamide;
N-(4-(benzofuran-2-yl)thiazol-2-yl)-N-(3-oxo-3-(2-phenoxyethylamino)propyl)thiophene-2-carboxamide;
1-(3-(N-(4-(benzofuran-2-yl)thiazol-2-yl)thiophene-2-carboxamido)propanoyl)-N-(2-hydroxyethyl)piperidine-3-carboxaniide;
N-(4-(benzofuran-2-yl)thiazol-2-yl)-N-(3-(isobutyl(1,1-dioxo-tetrahydrothiophen-3-yl)amino)-3-oxopropyl)thiophene-2-carboxami
N-(4-(benzofuran-2-yl)thiazol-2-yl)-N-(4-(4-(2-(dimethylamino)ethyl)piperazin-1-yl)-4-oxobutyl)thiophene-2-carboxamide;
N-(4-(benzofuran-2-yl)thiazol-2-yl)-N-(4-((2,3-dihydroxypropyl)(methyl)amino)-4-oxobutyl)thiophene-2-carboxamide;
N-(4-(benzofuran-2-yl)thiazol-2-yl)-N-(4-((5-methylpyrazin-2-yl)methylamino)-4-oxobutyl)thiophene-2-carboxamide;
N-(4-(benzofuran-2-yl)thiazol-2-yl)-N-(4-(1-hydroxypropan-2-ylamino)-4-oxobutyl)thiophene-2-carboxamide;
N-(4-(benzofuran-2-yl)thiazol-2-yl)-N-(4-oxo-4-(piperidin-1-yl)butyl)thiophene-2-carboxamide;
1-(4-(N-(4-(benzofuran-2-yl)thiazol-2-yl)thiophene-2-carboxamido)butanoyl)piperidine-4-carboxamide;
N-(4-(benzofuran-2-yl)thiazol-2-yl)-N-(4-((2-hydroxyethyl)(phenyl)amino)-4-oxobutyl)thiophene-2-carboxamide;
N-(4-(benzofuran-2-yl)thiazol-2-yl)-N-(4-oxo-4-(2-(pyridin-4-yl)ethylamino)butyl)thiophene-2-carboxamide;
tert-butyl 4-(4-(N-(4-(benzofuran-2-yl)thiazol-2-yl)thiophene-2-carboxamido)butanoyl)piperazine-1-carboxylate;
N-(4-(benzofuran-2-yl)thiazol-2-yl)-N-(4-oxo-4-(pyridin-3-ylmethylamino)butyl)thiophene-2-carboxamide;
N-(4-(benzofuran-2-yl)thiazol-2-yl)-N-(4-(5-(methylsulfonyl)indolin-1-yl)-4-oxobutyl)thiophene-2-carboxamide;
tert-butyl 1-(4-(N-(4-(benzofuran-2-yl)thiazol-2-yl)thiophene-2-carboxamido)butanoyl)pyrrolidin-3-ylcarbamate;
N-(4-(3-acetamidopyrrolidin-1-yl)-4-oxobutyl)-N-(4-(benzofuran-2-yl)thiazol-2-yl)thiophene-2-carboxamide;
methyl 1-(4-(N-(4-(benzofuran-2-yl)thiazol-2-yl)thiopheue-2-carboxamido)butanoyl)piperidine-4-carboxylate;
1-(4-(N-(4-(benzofuran-2-yl)thiazol-2-yl)thiophene-2-carboxamido)butanoyl)-N-methylpiperidine-4-carboxamide;
N-(4-(benzofuran-2-yl)thiazol-2-yl)-N-(4-(4-(N,N-dimethylsulfamoyl)piperazin-1-yl)-4-oxobutyl)thiophene-2-carboxamide;
ethyl 2-(1-(4-(N-(4-(benzofuran-2-yl)thiazol-2-yl)thiophene-2-carboxamido)butanoyl)piperidin-3-yl)acetate;
ethyl 2-(1-(4-(N-(4-(benzofuran-2-yl)thiazol-2-yl)thiophene-2-carboxamido)butanoyl)piperidin-4-yl)acetate;
N-(4-(benzofuran-2-yl)thiazol-2-yl)-N-.(4-(4-(diethylamino)piperidin-1-yl)-4-oxobutyl)thiophene-2-carboxamide;
1-(4-(N-(4-(benzofuran-2-yl)thiazol-2-yl)thiophene-2-carboxamido)butanoyl)pyrrolidine-2-carboxamide;
methyl 1-(4-(N-(4-(benzofuran-2-yl)thiazol-2-yl)thiophene-2-carboxamido)butanoyl)pyrrolidine-2-carboxylate;
N-(4-(benzofuran-2-yl)thiazol-2-yl)-N-(4-oxo-4-(3-oxopiperazin-1-yl)butyl)thiophene-2-carboxamide;
N-(4-(2-amino-2-oxoethylamino)-4-oxobutyl)-N-(4-(benzofuran-2-yl)thiazol-2-yl)thiophene-2-carboxainide;
1-(4-(N-(4-(benzofuran-2-yl)thiazol-2-yl)thiophene-2-carboxamido)butanoyl)-N-(2-hydroxyethyl)piperidine-3-carboxamide;
1-(4-(N-(4-(benzofuran-2-yl)thiazol-2-yl)thiophene-2-carboxamido)butanoyl)-N-(2-hydroxyethyl)piperidine-4-carboxamide;
N-(4-(benzofuran-2-yl)thiazol-2-yl)-N-(4-(2-(methylsulfinyl)ethylamino)-4-oxobutyl)thiophene-2-carboxamide;
N-(4-(benzofuran-2-yl)thiazol-2-yl)-N-(4-((2-hydroxyethyl)(pyridin-4-ylmethyl)aniino)-4-oxobutyl)thiophene-2-carboxaniide;
N-(4-(benzofuran-2-yl)thiazol-2-yl)-N-(4-(cyclohexyl(4-hydroxybutyl)amino)-4-oxobutyl)thiophene-2-carboxamide;
N-(4-(benzofuran-2-yl)thiazol-2-yl)-N-(4-((2-cyanoethyl)((tetrahydrofuran-2-yl)methyl)amino)-4-oxobutyl)thiophene-2-carboxamid
N-(4-(benzofuran-2-yl)thiazol-2-yl)-N-(4-oxo-4-(2-(pyridin-3-yl)pyrrolidin-1-yl)butyl)thiophene-2-carboxamide;
N-(4-(benzofuran-2-yl)thiazol-2-yl)-N-(3-(1-hydroxypropan-2-ylamino)-3-oxopropyl)thiophene-2-carboxamide;
N-(4-(benzofuran-2-yl)thiazol-2-yl)-N-(3-(2-methoxyethylamino)-3-oxopropyl)thiophene-2-carboxamide;
N-(4-(benzofuran-2-yl)thiazol-2-yl)-N-(3-(furan-3-ylmethylamino)-3-oxopropyl)thiophene-2-carboxamide;
methyl 1-(3-(N-(4-(benzofuran-2-yl)thiazol-2-yl)thiophene-2-carboxamido)propanoyl)pyrrolidine-2-carboxylate;
N-(4-(benzofuran-2-yl)thiazol-2-yl)-N-(3.-(isoindolin-2-yl)-3-oxopropyl)thiophene-2-carboxamide;
N-(3-((1,4-dioxan-2-yl)methylamino)-3-oxopropyl)-N-(4-(benzofuran-2-yl)thiazol-2-yl)thiophene-2-carboxamide;
N-(4-(benzofuran-2-yl)thiazol-2-yl)-N-(3-(cyclohexyl(4-hydroxybutyl)amino)-3-oxopropyl)thiophene-2-carboxamide;
N-(4-(benzofuran-2-yl)thiazol-2-yl)-N-(3-(methyl(pyridin-4-yl)amino)-3-oxopropyl)thiophene-2-carboxamide;
1-(4-(N-(4-(benzofuran-2-yl)thiazol-2-yl)thiophene-2-carboxamido)butanoyl)piperidine-3-carboxaniide;
N-(4-(benzofuran-.2-yl)thiazol-2-yl)-N-(4-oxo-4-(pyridin-2-ylmethylamino)butyl)thiophene-2-carboxamide;
N-(4-(benzofuran-2-yl)thiazol-2-yl)-N-(4-oxo-4-(thiazolidin-3-yl)butyl)thiophene-2-carboxamide;

tert-butyl 2-(4-(N-(4-(benzofuran-2-yl)thiazol-2-yl)thiophene-2-carboxamido)butanamido)ethylcarbamate;
(S)-N-(4-(benzofuran-2-yl)thiazol-2-yl)-N-(4-(2-(hydroxymethyl)indolin-1-yl)-4-oxobutyl)thiophene-2-carboxamide;
N-(4-(benzofuran-2-yl)thiazol-2-yl)-N-(4-(isoindolin-2-yl)-4-oxobutyl)thiophene-2-carboxamide;
N-(3-acetamidopropyl)-N-(4-(benzofuran-2-yl)thiazol-2-yl)thiophene-2-carboxamide;
1-acetyl-N-(3-(N-(4-(benzofuran-2-yl)thiazol-2-yl)thiophene-2-carboxamido)propyl)piperidine-4-carboxamide;
N-(4-(benzofuran-2-yl)thiazol-2-yl)-N-(3-(3-(piperidin-1-yl)propanaxnido)propyl)thiophene-2-carboxamide;
N-(4-(benzofuran-2-yl)thiazol-2-yl)-N-(3-(4-(dimethylamino)butanamido)propyl)thiophene-2-carboxamide;
N-(3-(N-(4-(benzofuran-2-yl)thiazol-2-yl)thiophene-2-carboxamido)propyl)isonicotinamide;
N-(3-(4-acetamidobutanamido)propyl)-N-(4-(benzofuran-2-yl)thiazol-2-yl)thiophene-2-carboxamide;
N-(4-(benzofuran-2-yl)thiazol-2-yl)-N-(3-(3-hydroxy-2-(hydroxymethyl)-2-methylpropanamido)propyl)thiophene-2-carboxamide;
N-(4-(benzofuran-2-yl)thiazol-2-yl)-N-(3-(2-(2,5-dioxoimidazolidin-4-yl)acetamido)propyl)thiophene-2-carboxamide;
N-(4-(benzofuran-2-yl)thiazol-2-yl)-N-(3-(3-morpholinopropanamido)propyl)thiophene-2-carboxamide;
N-(3-(N-(4-(benzofuran-2-yl)thiazol-2-yl)thiophene-2-carboxamido)propyl)-1,5-dimethyl-1H-pyrazole-3-carboxamide;
N-(4-(benzofuran-2-yl)thiazol-2-yl)-N-(3-(2-morpholinoacetamido)propyl)thiophene-2-carboxamide;
(S)-tert-butyl 1-(3-(N-(4-(benzofuran-2-yl)thiazol-2-yl)thiophene-2-carboxamido)propyl)pyrrolidine-2-carboxylate;
1-(3-(N-(4-(benzofuran-2-yl)thiazol-2-yl)thiophene-2-carboxamido)propyl)piperidine-3-carboxamide;
ethyl 1-(3-(N-(4-(benzofuran-2-yl)thiazol-2-yl)thiophene-2-carboxamido)propyl)piperidine-2-carboxylate;
N-(4-(benzofuran-2-yl)thiazol-2-yl)-N-(3-(3-hydroxypiperidin-1-yl)propyl)thiophene-2-carboxamide;
N-(4-(benzofuran-2-yl)thiazol-2-yl)-N-(3-(4-(2-(2-hydroxyethoxy)ethyl)piperazin-1-yl)propyl)thiophene-2-carboxamide;
N-(4-(benzofuran-2-yl)thiazol-2-yl)-N-(3-(4-(2-hydroxyethyl)piperidin-1-yl)propyl)thiophene-2-carboxamide;
N-(4-(benzofuran-2-yl)thiazol-2-yl)-N-(3-(4-(2-cyanoethyl)piperazin-1-yl)propyl)thiophene-2-carboxamide;
N-(4-(benzofuran-2-yl)thiazol-2-yl)-N-(3-(4-(hydroxymethyl)piperidin-1-yl)propyl)thiophene-2-carboxamide;
N-(4-(benzofuran-2-yl)thiazol-2-yl)-N-(3-(3-(dimethylaniino)pyrrolidin-1-yl)propyl)thiophene-2-carboxamide;
ethyl 1-(3-(N-(4-(benzofuran-2-yl)thiazol-2-yl)thiophene-2-carboxamido)propyl)piperidine-3-carboxylate;
N-(4-(benzofuran-2-yl)thiazol-2-yl)-N-(3-(4-hydroxypiperidin-1-yl)propyl)thiophene-2-carboxamide;
N-(4-(benzofuran-2-yl)thiazol-2-yl)-N-(3-(3-(N-ethylacetamido)pyrrolidin-1-yl)propyl)thiophene-2-carboxamide;
N-(4-(benzofuran-2-yl)thiazol-2-yl)-N-(3-(3-(N-methylacetamido)pyrrolidin-1-yl)propyl)thiophene-2-carboxamide;
tert-butyl 1-(3-(N-(4-(benzofuran-2-yl)thiazol-2-yl)thiophene-2-carboxaniido)propyl)pyrrolidin-3-ylcarbamate;
(S)-N-(4-(benzofuran-2-yl)thiazol-2-yl)-N-(3-(2-(methoxymethyl)pyrrolidin-1-yl)propyl)thiophene-2-carboxaniide;
N-(3-(3-acetamidopyrrolidin-1-yl)propyl)-N-(4-(benzofuran-2-yl)thiazol-2-yl)thiophene-2-carboxamide;
ethyl 4-(3-(N-(4-(benzofuran-2-yl)thiazol-2-yl)thiophene-2-carboxamido)propyl)piperazine-1-carboxylate;
N-(4-(benzofuran-2-yl)thiazol-2-yl)-N-(3-(4-(morpholine-4-carbonyl)piperazin-1-yl)propyl)thiophene-2-carboxamide;
N-(4-(benzofuran-2-yl)thiazol-2-yl)-N-(3-(4,4-dihydroxypiperidin-1-yl)propyl)thiophene-2-carboxamide;
N-(4-(benzofuran-2-yl)thiazol-2-yl)-N-(3-(4-(tetrahydrofuran-2-carbonyl)piperazin-1-yl)propyl)thiophene-2-carboxamide;
(R)-1-(3-(N-(4-(benzofuran-2-yl)thiazol-2-yl)thiophene-2-carboxamido)propyl)-N-methylpyrrolidine-2-carboxamide;
1-(3-(N-(4-(benzofuran-2-yl)thiazol-2-yl)thiophene-2-carboxamido)propyl)pyrrolidine-2-carboxamide;
methyl 1-(3-(N-(4-(benzofuran-2-yl)thiazol-2-yl)thiophene-2-carboxamido)propyl)pyrrolidine-2-carboxylate;
methyl 1-(3-(N-(4-(benzofuran-2-yl)thiazol-2-yl)thiophene-2-carboxaniido)propyl)piperidine-2-carboxylate;
(S)-1-(3-(N-(4-(benzofuran-2-yl)thiazol-2-yl)thiophene-2-carboxamido)propyl)-N,N-dimethylpyrrolidine-2-carboxamide;
N-(4-(benzofuran-2-yl)thiazol-2-yl)-N-(3-(2-(pyrrolidin-1-ylmethyl)piperidin-1-yl)propyl)thiophene-2-carboxamide;
N-(4-(benzofuran-2-yl)thiazol-2-yl)-N-(3-(3-oxopiperazin-1-yl)propyl)thiophene-2-carboxamide;
1-(3-(N-(4-(benzofuran-2-yl)thiazol-2-yl)thiophene-2-carboxamido)propyl)piperidine-2-carboxamide;
ethyl 2-(4-(3-(N-(4-(benzofuran-2-yl)thiazol-2-yl)thiophene-2-carboxamido)propyl)piperazin-1.-yl)acetate;
tert-butyl 4-(3-(N-(4-(benzofuran-2-yl)thiazol-2-yl)thiophene-2-carboxamido)propyl)piperazine-1-carboxylate;
N-(4-(benzofuran-2-yl)thiazol-2-yl)-N-(3-(4-morpholinopiperidin-1-yl)propyl)thiophene-2-carboxamide;
N-(4-(benzofuran-2-yl)thiazol-2-yl)-N-(3-(4-(2-(dimethylamino)ethyl)piperazin-1-yl)propyl)thiophene-2-carboxamide;
N-(4-(benzofuran-2-yl)thiazol-2-yl)-N-(3-(2-(hydroxymethyl)pyrrolidin-1-yl)propyl)thiophene-2-carboxamide;
N-(4-(benzofuran-2-yl)thiazol-2-yl)-N-(3-(2-(2-hydroxyethyl)piperidin-1-yl)propyl)thiophene-2-carboxamide;
N-(4-(benzofuran-2-yl)thiazol-2-yl)-N-(3-(3-(hydroxymethyl)piperidin-1-yl)propyl)thiophene-2-carboxamide;
N-(4-(benzofuran-2-yl)thiazol-2-yl)-N-(3-(2-(hydroxymethyl)piperidin-1-yl)propyl)thiophene-2-carboxamide;
N-(4-(benzofuran-2-yl)thiazol-2-yl)-N-(3-(3-hydroxypyrrolidin-1-yl)propyl)thiophene-2-carboxamide;
(S)-N-(4-(benzofuran-2-yl)thiazol-2-yl)-N-(3-(2-(hydroxymethyl)pyrrolidin-1-yl)propyl)thiophene-2-carboxamide;
N-(3-(4-acetylpiperazin-1-yl)propyl)-N-(4-(benzofuran-2-yl)thiazol-2-yl)thiophene-2-carboxamide;

1-(3-(N-(4-(benzofuran-2-yl)thiazol-2-yl)thiophene-2-carboxamido)propyl)-N,N-diethylpiperidine-3-carboxamide;
N-(4-(benzofuran-2-yl)thiazol-2-yl)-N-(3-(4-(2-hydroxyethyl)piperazin-1-yl)propyl)thiophene-2-carboxamide;
N-(4-(benzofuran-2-yl)thiazol-2-yl)-N-(3-(4-(2-methoxyethyl)piperazin-1-yl)propyl)thiophene-2-carboxamide;
N-(4-(benzofuran-2-yl)thiazol-2-yl)-N-(3-(3-(diethylamino)pyrrolidin-1-yl)propyl)thiophene-2-carboxamide;
1-(3-(N-(4-(benzofuran-2-yl)thiazol-2-yl)thiophene-2-carboxaniido)propyl)-N-methylpiperidine-4-carboxamide;
N-(4-(benzofuran-2-yl)thiazol-2-yl)-N-(3-(4-(diethylamino)piperidin-1-yl)propyl)thiophene-2-carboxamide;
(R)-1-(3-(N-(4-(benzofuran-2-yl)thiazol-2-yl)thiophene-2-carboxamido)propyl)pyrrolidine-2-carboxylic acid;
1-(3-(N-(4-(benzofiiran-2-yl)thiazol-2-yl)thiophene-2-carboxamido)propyl)piperidine-4-carboxamide;
N-(4-(benzofuran-2-yl)thiazol-2-yl)-N-(3-(4-(2-(dimethylamino)-2-oxoethyl)piperazin-1-yl)propyl thiophene-2-carboxaniide; an N-(4-(benzofuran-2-yl)thiazol-2-yl)-N-(3-(4-(methylsuifonyl)piperazin-1-yl)propyl)thiophene-2-carboxamide.

25. The compound of claim 1 selected from:
N-(4-(3,4-dimethoxyphenyl)thiazol-2-yl)-N-(3-morpholinopropyl)thiophene-2-carboxamide;
N-(4-(benzofuran-2-yl)thiazol-2-yl)-N-(3-morpholinopropyl)thiophene-2-carboxamide;
N-(3-morpholinopropyl)-N-(4-phenylthiazol-2-yl)thiophene-2-carboxamide;
N-(4-(3-chlorophenyl)thiazol-2-yl)-N-(3-morpholinopropyl)thiophene-2-carboxamide;
N-(4-(5-chlorothiophen-2-yl)thiazol-2-yl)-N-(3-morpholinopropyl)thiophene-2-carboxamide;
methyl 4-(2-(N-(3-morpholinopropyl)thiophene-2-carboxamido)thiazol-4-yl)benzoate;
N-(4-(2,3-dihydrobenzo[b][1,4]dioxin-6-yl)thiazol-2-yl)-N-(3-morpholinopro-pyl)thiophene-2-carboxamide;
N-(4-(2,4-dimethoxyphenyl)thiazol-2-yl)-N-(3-morpholinopropyl)thiophene-2-carboxamide;
N-(3-morpholinopropyl)-N-(4-(3-phenylisoxazol-5-yl)thiazol-2-yl)thiophene-2-carboxamide;
N-(4-(5-methyl-1-phenyl-1H-pyrazol-4-yl)thiazol-2-yl)-N-(3-morpholinopropyl)thiophene-2-carboxamide;
N-(3-morpholinopropyl)-N-(4-(5-(pyridin-2-yl)thiophen-2-yl)thiazol-2-yl)thiophene-2-carboxamide;
2-(N-(3-morpholinopropyl)thiophene-2-carboxamido)-N-(1,3,4-thiadiazol-2-yl)thiazole-4-carboxamide;
N-(4-(3,4-dimethoxyphenyl)thiazol-2-yl)-N-(5-morpholinopentyl)thiophene-2-carboxamide;
N-(3-(2-oxopyrrolidin-1-yl)propyl)-N-(4-(3-phenylisoxazol-5-yl)thiazol-2-y-1)thiophene-2-carboxamide;
N-(4-(2,6-dimethoxypyridin-3-yl)thiazol-2-yl)-N-(3-morpholinopropyl)thiophene-2-carboxaniide;
N-(4-(4-(2-(dimethylaniino)ethylcarbamoyl)phenyl)thiazol-2-yl)-N-(3-morpholinopropyl)thiophene-2-carboxamide;
2-(4-(2-(N-(3-morpholinopropyl)thiophene-2-carboxamido)thiazol-4-yl)phenoxy)acetic acid;
N-(4-(4-(2-(dimethylamino)ethoxy)phenyl)thiazol-2-yl)-N-(3-morpholinopropyl)thiophene-2-carboxamide;
1-(3-(N-(4-(benzofuran-2-yl)thiazol-2-yl)thiophene-2-carboxamido)propanoyl)piperidine-3-carboxamide;
1-acetyl-N-(3-(N-(4-(benzofuran-2-yl)thiazol-2-yl)thiophene-2-carboxaniido)propyl)piperidine-4-carboxamide;
N-(4-(benzofuran-2-yl)thiazol-2-yl)-N-(3-(3-(piperidin-1-yl)propanamido)propyl)thiophene-2-carboxamide;
N-(4-(benzofuran-2-yl)thiazol-2-yl)-N-(3-(4,4-dihydroxypiperidin-1-yl)propyl)thiophene-2-carboxamide; and
N-(4-(benzofuran-2-yl)thiazol-2-yl)-N-(3-(2-(hydroxymethyl)pyrrolidin-1-yl)propyl)thiophene-2-carboxamide.

\* \* \* \* \*